(12) United States Patent
Thompson et al.

(10) Patent No.: US 8,293,734 B2
(45) Date of Patent: Oct. 23, 2012

(54) NITROIMIDAZOOXAZINE AND NITROIMIDAZOOXAZOLE ANALOGUES AND THEIR USES

(75) Inventors: Andrew Mark Thompson, Auckland (NZ); William Alexander Denny, Auckland (NZ); Adrian Blaser, Waitakere City (NZ); Zhenkun Ma, Westfield, NJ (US)

(73) Assignee: Global Alliance for TB Drug Development, New York, NY (US)

( * ) Notice: Subject to any disclaimer, the term of this patent is extended or adjusted under 35 U.S.C. 154(b) by 219 days.

(21) Appl. No.: 12/847,459

(22) Filed: Jul. 30, 2010

(65) Prior Publication Data

US 2011/0028466 A1  Feb. 3, 2011

Related U.S. Application Data

(60) Provisional application No. 61/230,422, filed on Jul. 31, 2009.

(51) Int. Cl.
*C07D 498/04* (2006.01)
*A61K 31/5365* (2006.01)
(52) U.S. Cl. .................................. 514/230.5; 544/91
(58) Field of Classification Search .................. 544/91; 514/230.5, 375; 548/218
See application file for complete search history.

(56) References Cited

U.S. PATENT DOCUMENTS

| | | | |
|---|---|---|---|
| 5,668,127 A | 9/1997 | Baker et al. | |
| 6,087,358 A | 7/2000 | Baker et al. | |
| 7,262,212 B2 | 8/2007 | Tsubouchi et al. | |
| 2006/0063929 A1 | 3/2006 | Otera et al. | |
| 2008/0119478 A1 | 5/2008 | Tsubouchi et al. | |
| 2008/0275035 A1 | 11/2008 | Jiricek et al. | |
| 2009/0281088 A1 | 11/2009 | Ding et al. | |
| 2010/0075994 A1 | 3/2010 | Cao et al. | |

FOREIGN PATENT DOCUMENTS

| | | |
|---|---|---|
| GB | 1420171 | 1/1976 |
| JP | 2005330266 A | 12/2005 |
| JP | 2008195729 A | 8/2008 |

OTHER PUBLICATIONS

Wolff, Manfred E. "Burger's Medicinal Chemistry and Drug Discovery, 5ed, vol. 1" John Wiley & Sons, 1995, pp. 975-977.*
Banker, G.S. et al, "Modern Pharmaceutics, 3ed." Marcel Dekker, New York, 1996, pp. 451 and 596.*
Apparu, Marcel, et al.; Determination of the enantiomeric purity and the configuration of β-aminoalcohols using (R)-2-fluorophenylacetic acid (AFPA) and fluorine-19 NMR: application to β-blockers, Tetrahedron: Asymmetry 11, 2000, pp. 2885-2898.
Ashtekar, Dilip R., et al.; In Vitro and In Vivo Activities of the Nitroimidazole CGI 17341 against *Mycobacterium tuberculosis*, Antimicrobial Agents and Chemotherapy, Feb. 1993, vol. 37, No. 2, pp. 183-186.

Cavalli, Andrea, et al.; Neglected Tropical Diseases: Multi-Target-Directed Ligands in the Search for Novel Lead Candidates against *Trypanosoma* and*Leishmania*, J. Med. Chem., 2009, vol. 52, No. 23, pp. 7339-7359.
Cativiela, Carlos, et al.; Synthesis of 3-Substituted Pentane-2,4-diones: Valuable Intermediates for Liquid Crystals, J. Org. Chem., 1995, vol. 60, No. 10, pp. 3074-3083.
Cunico, Robert F., et al.; The Triisopropylsilyl Group as a Hydroxyl-Protecting Function, J. Org. Chem., 1980, vol. 45, pp. 4797-4798.
Curran, Dennis P., et al.; Stereoselection at the Steady State. Group Selective Radical Cyclizations of Substrates Containing Two Radical Precursors and One Radical Acceptor, J. Am. Chem Soc., 1998, vol. 120, No. 2, pp. 342-351.
Helmboldt, Hannes, et al.; Synthesis of the Norjatrophane Diterpene (−)-15-Acetyl-3-propionyl-17-norcharaciol, Organic Letters, 2006, vol. 8, No. 8, pp. 1573-1576.
Kopka, Klaus, et al.; Design of New β1-Selective Adrenoceptor Ligands as Potential Radioligands for In Vivo Imaging, Bioorganic & Medicinal Chemistry 11, 2003, pp. 3513-3537.
Matsumoto, Makoto, et al.; OPC-67683, a Nitro-Dihydro-Imidazooxazole Derivative with Promising Action against Tuberculosis In Vitro and In Mice, PLoS Medicine, Nov. 2006, vol. 3, Issue 11, pp. 2131-2144.
Nagarajan, Kuppuswamy, et al.; Nitroimidazoles XXI 2,3-dihydro-6-nitroimidazo [2,1-b] oxazoles with antitubercular activity*, Eur. J. Med. Chem. 24, 1989, pp. 631-633.
Sehgal, Raj K., et al.; Potential Radiosensitizing Agents. 2. Synthesis and Biological Activity of Derivatives of Dinitroimidazole with Oxiranes, J. Med. Chem., 1981, vol. 24, No. 5, pp. 601-604.
Wennerberg, Johan, et al.; Zeolite β Induced Rearrangement of Allyl Benzyl Ethers. 6. Variation of the Aromatic Part and Synthesis of Dihydronaphthalene Derivatives, J. Org. Chem., 1999, vol. 64, No. 1, pp. 54-59.
European Patent Office International Search Report and Written Opinion for Application No. PCT/US2010/043908, filed Jul. 30, 2010.
European Patent Office; International Preliminary Report on Patentability; PCT Application No. PCT/US2010/043908; Aug. 1, 2011.
Anderson, Robert F., et al; Intermediates in the reduction of the antituberculosis drug PA-824, (6S)-2-nitro-6-{[4-(trifluoromethoxy)benzyl]oxy}-6,7-dihydro-5H-imidazo[2,1-b][1,3]oxazine, in aqueous solution, Organic & Biomolecular Chemistry, 2008, 6, 1973-1980.
Cho, Sang Hyun; Low-Oxygen-Recovery Assay for High-Throughput Screening of Compounds against Nonreplicating *Mycobaterium tuberculosis*, Antimicrobial Agents and Chemotherapy, Apr. 2007, p. 1380-1385, vol. 51, No. 4.
Collins, Lisa A.; Microplate Alamar Blue Assay versus BACTEC 460 System for High-Throughput Screening of Compounds against *Mycobacterium tuberculosis* and *Mycobacterium avium*, Antimicrobial Agents and Chemotherapy, May 1997, p. 1004-1009, vol. 41, No. 5.

(Continued)

*Primary Examiner* — Kahsay T Habte
(74) *Attorney, Agent, or Firm* — Jackson Walker L.L.P.

(57) ABSTRACT

The current invention pertains to nitroimidazooxazine and nitroimidazooxazole analogues, their methods of preparation, and uses of the compounds as treatment for *Mycobacterium tuberculosis*, for use as anti-tubercular drugs, for use as anti-protozoal agents with unexpectedly high potency against *Trypanosoma cruzi* or *Leishmania donovani*, and for the treatment of other microbial infections.

6 Claims, 21 Drawing Sheets

OTHER PUBLICATIONS

Falzari, Kanakeshwari, et al., In Vitro and In Vivo Activities of Macrolide Derivatives against *Mycobacterium tuberculosis,* Antimicrobial Agents and Chemotherapy, Apr. 2005, p. 1447-1454, vol. 49, No. 4.

Ferrara, Giovanni, et al,; Use in routine clinical practice of two commercial blood tests for diagnosis of infection with *Mycobacterium tuberculosis:* a prospective study, Lancet 2006, vol. 367, p. 1328-1334.

Kim, Pilho, et al., Structure—Activity Relationships of Antitubercular Nitroimidazoles. 1. Structural Features Associated with Aerobic and Anaerobic Activities of 4- and 5-Nitroimidazoles, J. Med Chem, 2009, vol. 52, p. 1317-1328.

Kim, Pilho, et al., Structure—Activity Relationships of Antitubercular Nitroimidazoles. 2. Determinants of Aerobic Activity and Quantitative Structure—Activity Relationships, J. Med. Chem. 2009, vol. 52, p. 1329-1344.

Li, Xiaojin, et al.; Synthesis and antitubercular activity of 7-(R)- and 7-(S)-methyl-2-nitro-6-(S)-(4-(trifluoromethoxy)benzyloxy)-6,7-dihydro-5H-imidazo[2,1-b][1,3]oxazines, analogues of PA-824, Bioorganic & Medicinal Chemistry Letters 18 (2008) 2256-2262.

Manjunatha, Ujjini H., et al.; Identification of a nitroimidazo-oxazine-specific protein involved in PA-824 resistance in *Mycobacterium tuberculosis,* PNAS, Jan. 10, 2006, vol. 103, No. 2, p. 431-436.

Sasaki, Hirofumi, et al.; Synthesis and Antituberculosis Activity of a Novel Series of Optically Active 6-Nitro-2,3-dihydroimidazo[2,1-b]oxazoles, J Med. Chem. 2006, 49, 7854-7860.

Singh, Ramandeep, et al.; PA-824 Kills Nonreplicating *Mycobacterium tuberculosis* by Intracellular NO Release, Science, Nov. 28, 2008, vol. 322, p. 1392-1395.

Stover, C. Kendall; A small-molecule nitroimidazopyran drug candidate for the treatment of tuberculosis, Nature, Jun. 22, 2000, vol. 405, p. 962-966.

Tyagi, Sandeep, et al.; Bactericidal Activity of the Nitroimidazopyran PA-824 in a Murine Model of Tuberculosis, Antibacterial Agents and Chemotherapy, Jun. 2005, vol. 49, No. 6, p. 2289-2293.

European Patent Office; Response to Office Action; European Patent Application No. 10740807.2; Aug. 21, 2012.

Chinese Patent Office; Amendment; Chinese Patent Application No. 201080041655.3; Jul. 31, 2012.

* cited by examiner compounds 8-12 of Table 1

NITROIMIDAZOOXAZINE AND NITROIMIDAZOOXAZOLE ANALOGUES AND THEIR USES

This application claims priority to U.S. Provisional Patent Application Ser. No. 61/230,422, entitled "Nitroimidazooxazine and Nitroimidazooxazole Analogues and Their Uses," filed on Jul. 31, 2009, the entire content of which is hereby incorporated by reference.

BACKGROUND

The present invention relates to nitroimidazooxazine and nitroimidazooxazole analogues, to their preparation, and to their use as drugs effective against *Mycobacterium tuberculosis* and as anti-protozoal agents, either alone or in combination with other treatments.

Tuberculosis remains a leading infectious cause of death worldwide (having a mortality estimated to be 1.3 million in 2008), with a recent resurgence attributable to an enhanced susceptibility in HIV patients, as well as the increasing incidence of multidrug-resistant strains and the emergence of extensively drug resistant strains. Current drug therapy for tuberculosis is long and complex, involving multidrug combinations (usually isoniazid, rifampin, pyrazinamide and ethambutol) given daily for in excess of 6 months. Furthermore, these drugs are relatively ineffective against the persistent form of the disease, which is suggested to occur in a significant proportion of cases (Ferrara et al., 2006). Second-line drugs used in lengthy combination therapies for multi-drug resistant diseases (typically over 2 years) mostly have reduced potency or greater toxicity than existing first-line agents. Frequently, incomplete treatment is administered, leading to high relapse rates and increased drug resistance, underscoring the urgent need for new, more effective drugs.

Chagas disease affects about 9 million people, principally in South America, and results in about 14,000 deaths annually. It is caused by the protozoan parasite *Trypanosoma cruzi*, which is transmitted to humans by blood-sucking bugs. The two drugs currently available for treatment, nifurtimox and benznidazole, show efficacy that is limited to the acute phase of the disease and to only some pathogen strains. These drugs also give serious side effects, and this, together with the lengthy and expensive treatment required, leads to inadequate patient compliance and the development of drug resistance (Cavalli et al., 2009).

Leishmaniases affect almost 12 million people in nearly 90 countries and result in about 51,000 deaths annually. They are particularly prevalent on the Indian subcontinent and in east Africa, where the parasite *Leishmania donovani* is the causative agent. This parasite is transmitted to humans through the bite of female sandflies and is responsible for the most severe form, visceral leishmaniasis (kala-azar), which causes chronic disease in the liver and spleen and is fatal unless treated by chemotherapy. First-line treatments are the antimonials meglumine antimonate (Glucantime) and sodium stibogluconate (Pentostam), discovered more than 50 years ago, which present severe, undesirable side effects. Their administration in low doses over a longer time has resulted in growing drug resistance such that they can no longer be used in India (Cavalli et al., 2009). Second-line agents suffer from similar toxicity concerns, illustrating the real need for safer, more effective treatments.

It is therefore highly desirable to provide new nitroimidazooxazine and nitroimidazooxazole analogues with unexpectedly high potency against both aerobic (replicating) and hypoxic (latent or persistent) cultures of *Mycobacterium tuberculosis*, for use as anti-tubercular drugs, and/or with unexpectedly high potency against *Trypanosoma cruzi* or *Leishmania donovani* for use as anti-protozoal agents, and for the treatment of other microbial infections.

SUMMARY

The current invention pertains to nitroimidazooxazine and nitroimidazooxazole analogues, their methods of preparation, and uses of the compounds as treatment for *Mycobacterium tuberculosis*, for use as anti-tubercular drugs, for use as anti-protozoal agents with unexpectedly high potency against *Trypanosoma cruzi* or *Leishmania donovani*, and for the treatment of other microbial infections.

The recent introduction of the nitroimidazooxazine PA-824 to clinical trial is significant, as this compound shows good in vitro and in vivo activity against *Mycobacterium tuberculosis* in both its active and persistent forms (Tyagi et al., 2005). A related 2-nitroimidazo[2,1-b]oxazole, OPC-67683 is also in clinical trial (Sasaki et al., 2006). The structures of these compounds are shown in FIG. 1. Without wanting to be bound by theory, the mechanism of action of PA-824 is suggested to involve the release of nitric oxide (Singh et al., 2008), following a reductive step, in a process dependent on the bacterial glucose-6-phosphate dehydrogenase (FGD1) and its cofactor F420 (Stover et al., 2000). Microarray studies on mutant strains wild-type for both FGD1 and F420 show that a 151-amino acid (17.37 kDa) protein of unknown function, Rv3547, appears to be critical for this activation (Manjunatha et al., 2006). Recent mechanistic studies of the reductive chemistry of PA-824 support this contention (Anderson et al., 2008). Nitroimidazooxazine analogues and nitroimidazooxazole analogues and their uses in tuberculosis have been previously reported (U.S. Pat. Nos. 5,668,127 and 6,087,358; Jiricek et al., WO 2007075872A2; Li et al., 2008; Kim et al., 2009; Nagarajan et al., 1989; Ashtekar et al., 1993; Sasaki et al., 2006; Matsumoto et al., 2006; Tsubochi et al., WO 2005042542A1 and WO 2004033463A1; JP 2005330266A; EP 1555267A1).

In a first aspect, the present invention pertains to a compound having a general structure of Formula I:

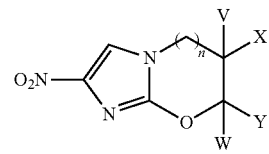

I wherein n is 0 or 1,

V and W independently are H or $CH_3$, and one of X or Y represents H and the other represents one of Formulae IIa or IIb, wherein Formulae IIa and IIb have the general structures:

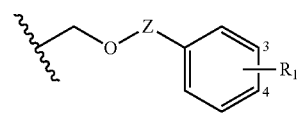

IIa

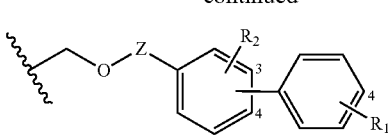

wherein Formula IIb comprises a first ring labeled at a 3-position and a 4-position and having as substituents both $R_2$ and a terminal ring labeled at a 4-position and having $R_1$ as a substituent, Z in Formulae IIa and IIb represents $CH_2$ or a direct bond, and $R_1$ and $R_2$ each represents any one or two of H, F, Cl, I, CN, $CF_3$, $OCF_3$, $OCH_3$, $OCH_2Ph$, aza (—CH= replaced by —N=), or diaza (—CH=CH— replaced by —N=N—, —CH=CH—CH= replaced by —N=CH—N=, or —CH=CH—CH=CH— replaced by —N=CH—CH=N—) at any of the available ring positions;

provided that if n is 0, V, W and X are all H, and Y is Formula IIa wherein Z is either $CH_2$ or a direct bond, then $R_1$ is not H; and provided that if n is 0, V and X are both H, W is $CH_3$, and Y is Formula IIa wherein Z is a direct bond, then $R_1$ is not H, 4-Cl, 4-I, 4-$CF_3$, 4-$OCH_3$, or 4-$OCF_3$;

and provided that if n is 0, V and X are both H, W is $CH_3$, and Y is Formula IIb wherein Z is a direct bond, the terminal ring is located at the 4-position on the first ring, and $R_2$ is H, then $R_1$ is not H, or 4-aza.

A more preferred subclass of compounds includes those having a general structure of Formula I as defined above, wherein:

n is 0 or 1,

V and W independently are H or $CH_3$, and one of X or Y represents H and the other represents one of Formulae IIa or IIb, wherein Formulae IIa and IIb have the general structures:

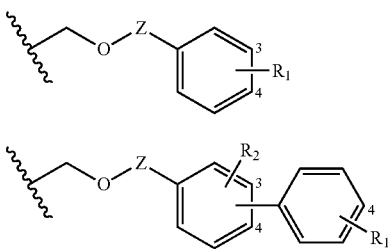

wherein Formula IIb comprises a first ring labeled at a 3-position and a 4-position and having as substituents both $R_2$ and a terminal ring labeled at a 4-position and having $R_1$ as a substituent, Z in Formulae IIa and IIb represents $CH_2$ or a direct bond, $R_1$ represents 4-F, 4-CN, 4-I, 4-$CF_3$, 3-$OCF_3$, 4-$OCF_3$, 4-$OCH_2Ph$, or 3-aza-4-OMe, and $R_2$ represents H, aza (—CH= replaced by —N=), or diaza (—CH=CH— replaced by —N=N—, 13 CH=CH—CH= replaced by —N=CH—N=, or —CH=CH—CH=CH— replaced by —N=CH—CH=N—) at any of the available ring positions;

provided that if n is 0, V, W and X are all H, and Y is Formula IIa wherein Z is either $CH_2$ or a direct bond, then $R_1$ is not H; and provided that if n is 0, V and X are both H, W is $CH_3$, and Y is Formula IIa wherein Z is a direct bond, then $R_1$ is not H, 4-Cl, 4-I, 4-$CF_3$, 4-$OCH_3$, or 4-$OCF_3$;

and provided that if n is 0, V and X are both H, W is $CH_3$, and Y is Formula IIb wherein Z is a direct bond, the terminal ring is located at the 4-position on the first ring, and $R_2$ is H, then $R_1$ is not H, or 4-aza.

These compounds, as well as mixtures thereof, isomers, physiologically functional salt derivatives, and prodrugs thereof, are useful in prevention of or therapy for treating *Mycobacterium tuberculosis*, for use as anti-tubercular drugs, for use as anti-protozoal agents with unexpectedly high potency against *Trypanosoma cruzi* or *Leishmania donovani*, and for the treatment of other microbial infections.

DETAILED DESCRIPTION OF PREFERRED EMBODIMENTS

Figure 1:
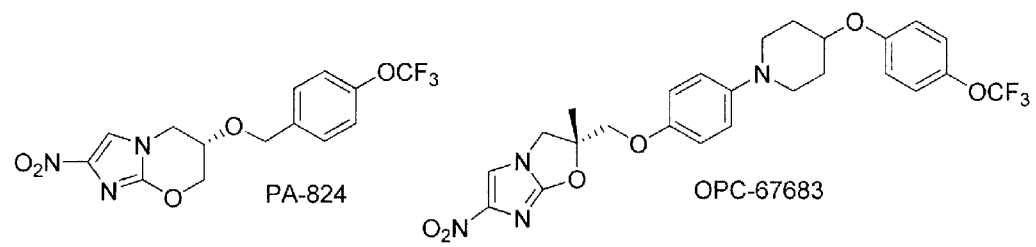
FIG. 1 shows the structures of compounds PA-824 and OPC-67683.

The current invention pertains to nitroimidazooxazine and nitroimidazooxazole analogues, their methods of preparation, and uses of the compounds in prevention of or therapy for treating *Mycobacterium tuberculosis*, for use as anti-tubercular drugs, for use as anti-protozoal agents with unexpectedly high potency against *Trypanosoma cruzi* or *Leishmania donovani*, and for the treatment of other microbial infections.

In a first aspect, the present invention pertains to a compound having a general structure of Formula I:

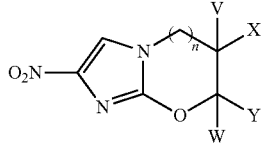

wherein n is 0 or 1,

V and W independently are H or CH₃, and one of X or Y represents H and the other represents one of Formulae IIa or IIb, wherein Formulae IIa and IIb have the general structures:

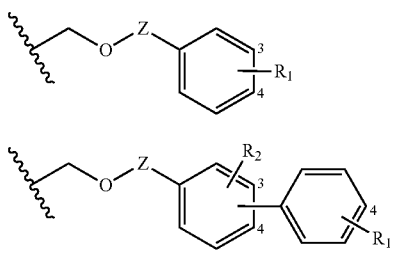

wherein Formula IIb comprises a first ring labeled at a 3-position and a 4-position and having as substituents both R₂ and a terminal ring labeled at a 4-position and having R₁ as a substituent, Z in Formulae IIa and IIb represents CH₂ or a direct bond, and R₁ and R₂ each represents any one or two of H, F, Cl, I, CN, CF₃, OCF₃, OCH₃, OCH₂Ph, aza (—CH═ replaced by —N═), or diaza (—CH═CH— replaced by —N═N—, —CH═CH—CH═ replaced by —N═CH—N═, or —CH═CH—CH═CH— replaced by —N═CH—CH═N—) at any of the available ring positions;

provided that if n is 0, V, W and X are all H, and Y is Formula IIa wherein Z is either CH₂ or a direct bond, then R₁ is not H;

and provided that if n is 0, V and X are both H, W is CH₃, and Y is Formula IIa wherein Z is a direct bond, then R₁ is not H, 4-Cl, 4-I, 4-CF₃, 4-OCH₃, or 4-OCF₃;

and provided that if n is 0, V and X are both H, W is CH₃, and Y is Formula IIb wherein Z is a direct bond, the terminal ring is located at the 4-position on the first ring, and R₂ is H, then R₁ is not H, or 4-aza.

A more preferred subclass of compounds includes those having a general structure of Formula I as defined above, wherein:

n is 0 or 1,

V and W independently are H or C₃, and one of X or Y represents H and the other represents one of Formulae IIa or IIb, wherein Formulae IIa and IIb have the general structures:

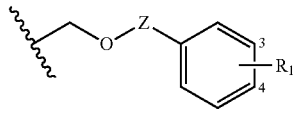

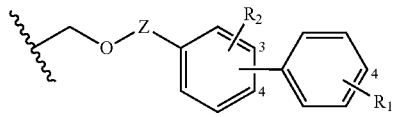

wherein Formula IIb comprises a first ring labeled at a 3-position and a 4-position and having as substituents both R₂ and a terminal ring labeled at a 4-position and having R₁ as a substituent, Z in Formulae IIa and IIb represents CH₂ or a direct bond, R₁ represents 4-F, 4-CN, 4-I, 4-CF₃, 3-OCF₃, 4-OCF₃, 4-OCH₂Ph, or 3-aza-4-OMe, and R₂ represents H, aza (—CH═ replaced by —N═), or diaza (—CH═CH— replaced by —N═N—, —CH═CH—CH═ replaced by —N═CH—N═, or —CH═CH—CH═CH— replaced by —N═CH—CH═N—) at any of the available ring positions;

provided that if n is 0, V, W and X are all H, and Y is Formula IIa wherein Z is either CH₂ or a direct bond, then R₁ is not H;

and provided that if n is 0, V and X are both H, W is CH₃, and Y is Formula IIa wherein Z is a direct bond, then R₁ is not H, 4-Cl, 4-I, 4-CF₃, 4-OCH₃, or 4-OCF₃;

and provided that if n is 0, V and X are both H, W is CH₃, and Y is Formula IIb wherein Z is a direct bond, the terminal ring is located at the 4-position on the first ring, and R₂ is H, then R₁ is not H, or 4-aza.

Figure 18:
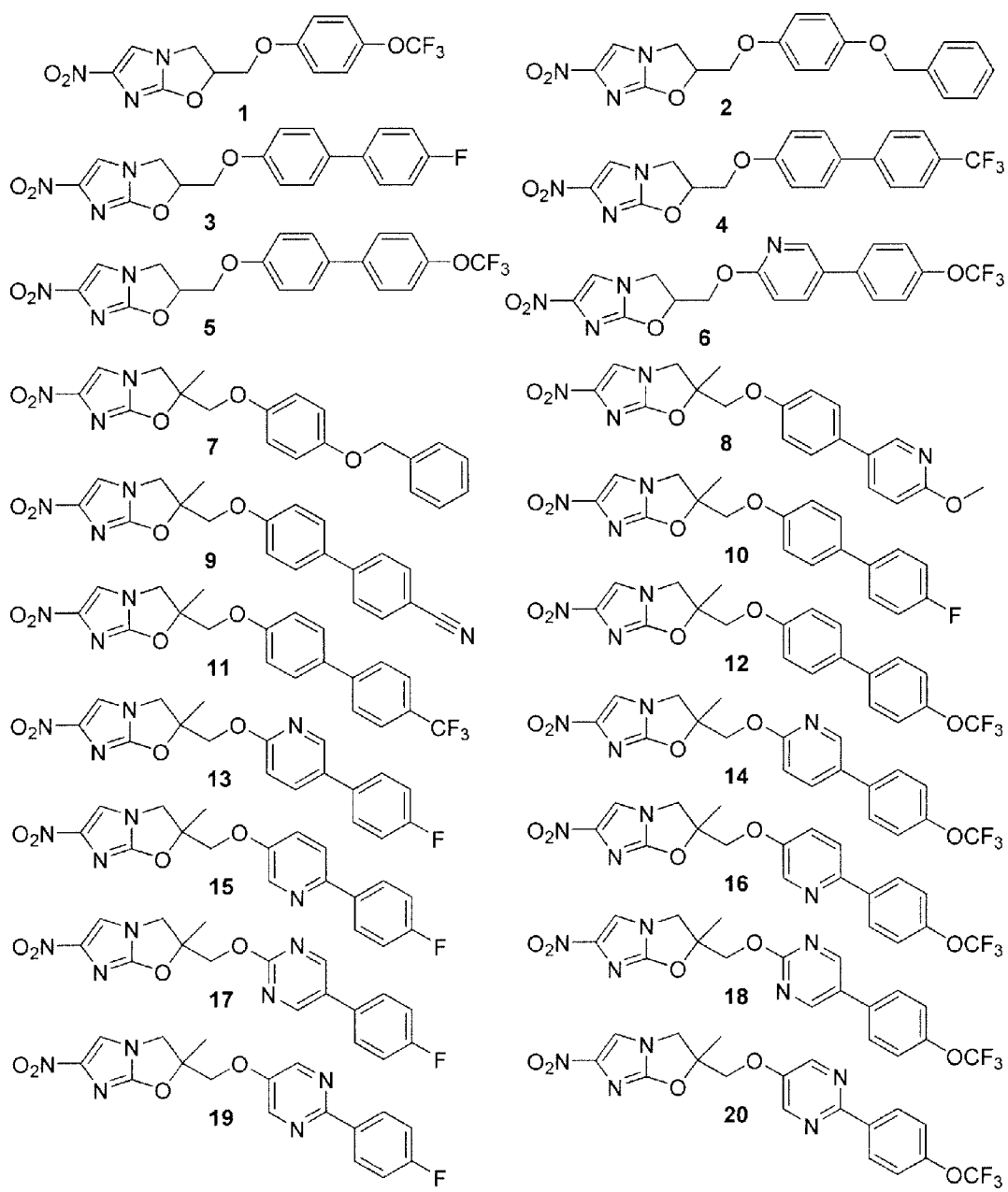
FIG. 18 shows the structures of representative compounds 1-20 referred to in Table 1 and Examples 1-3.
Figure 19:
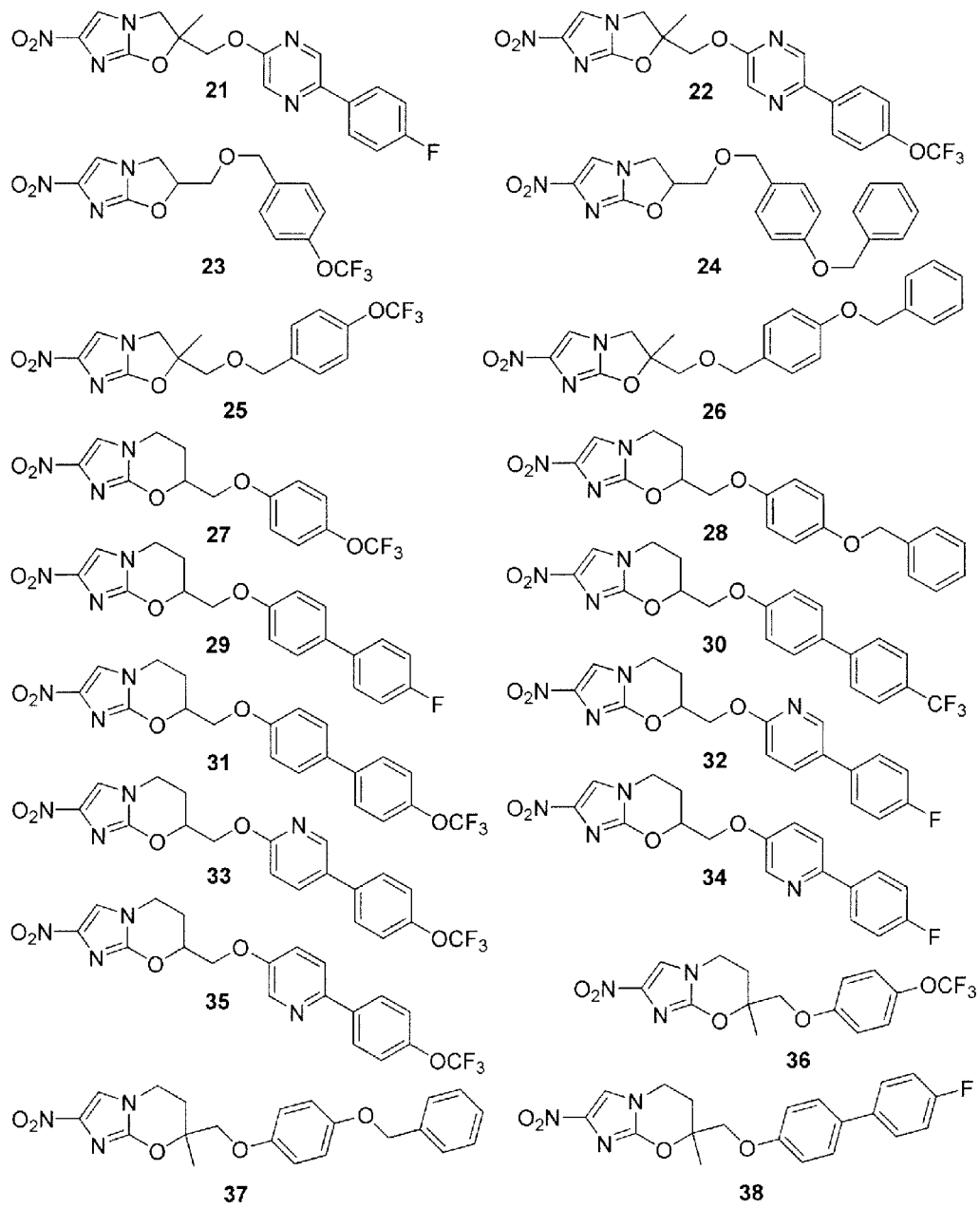
FIG. 19 shows the structures of representative compounds 21-38 referred to in Table 1 and Examples 1-3.
Figure 20:
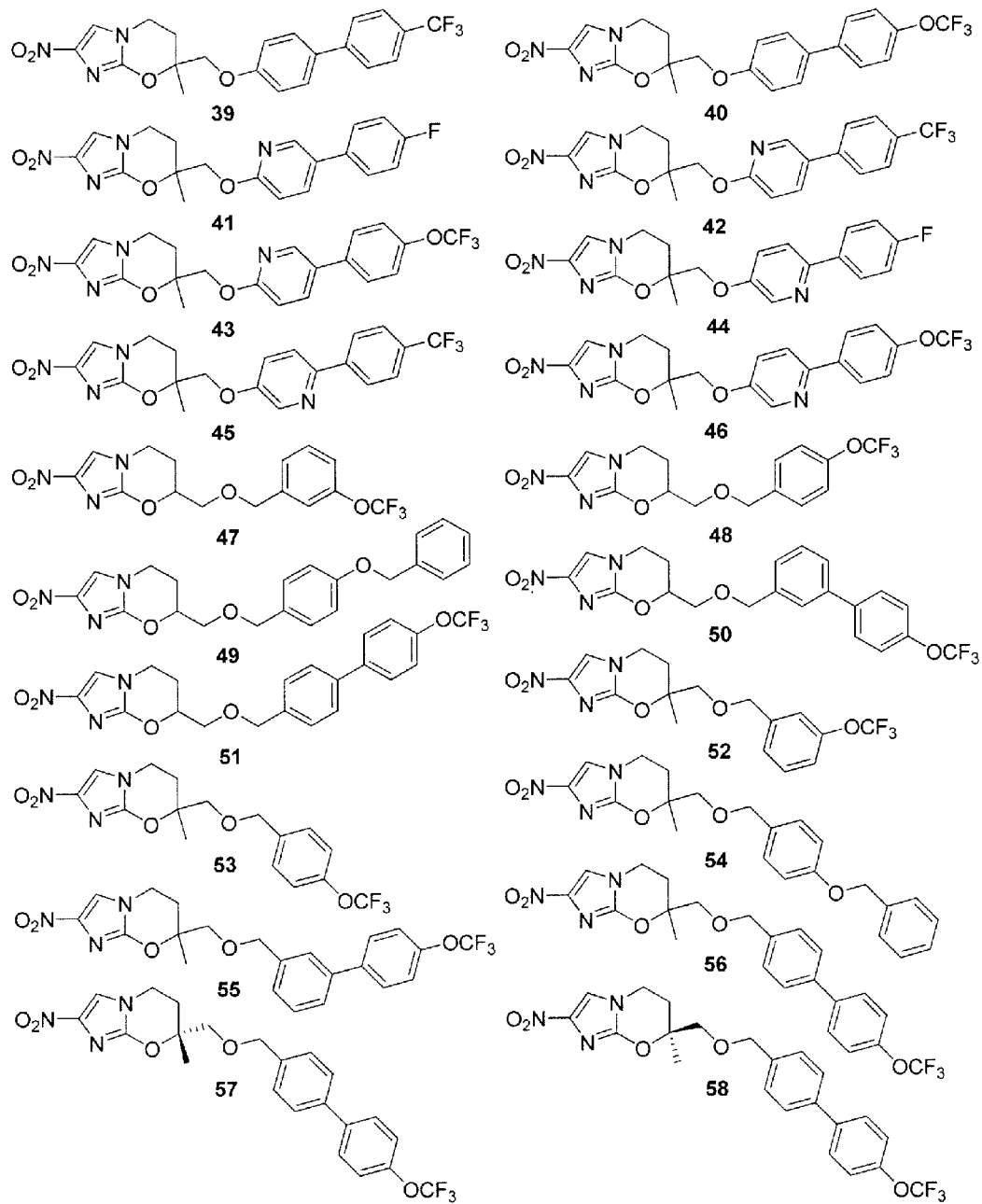
FIG. 20 shows the structures of representative compounds 39-58 referred to in Table 1 and Examples 1-3.
Figure 21:
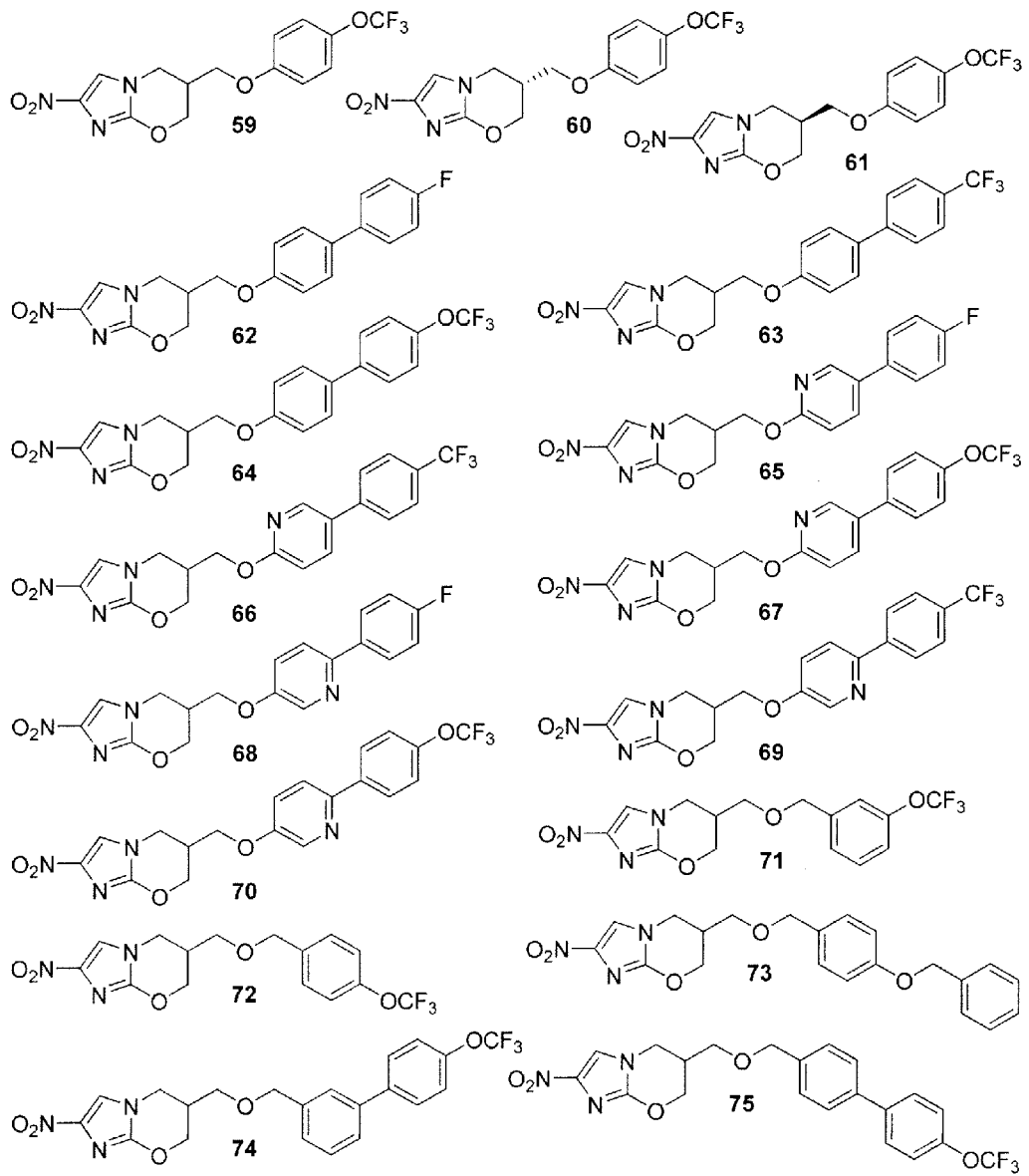
FIG. 21 shows the structures of representative compounds 59-75 referred to in Table 1 and Examples 1-3.

The most highly preferred of the compounds of Formula I are:

A. 6-Nitro-2-{[4-(trifluoromethoxy)phenoxy]methyl}-2,3-dihydroimidazo[2,1-b][1,3]oxazole (compound 1 of Table 1 and FIG. 18);

B. 2-{[4-(Benzyloxy)phenoxy]methyl}-6-nitro-2,3-dihydroimidazo[2,1-b][1,3]oxazole (compound 2 of Table 1 and FIG. 18);

C. 2-{[(4'-Fluoro[1,1'-biphenyl]-4-yl)oxy]methyl}-6-nitro-2,3-dihydroimidazo[2,1-b][1,3]oxazole (compound 3 of Table 1 and FIG. 18);

D. 6-Nitro-2-({[4'-(trifluoromethyl)[1,1'-biphenyl]-4-yl]oxy}methyl)-2,3-dihydroimidazo[2,1-b][1,3]oxazole (compound 4 of Table 1 and FIG. 18);

E. 6-Nitro-2-({[4'-(trifluoromethoxy)[1,1'-biphenyl]-4-yl]oxy}methyl)-2,3-dihydroimidazo[2,1-b][1,3]oxazole (compound 5 of Table 1 and FIG. 18);

F. 6-Nitro-2-[({5-[4-(trifluoromethoxy)phenyl]-2-pyridinyl}oxy)methyl]-2,3-dihydroimidazo[2,1-b][1,3]oxazole (compound 6 of Table 1 and FIG. 18);

G. 2-{[4-(Benzyloxy)phenoxy]methyl}-2-methyl-6-nitro-2,3-dihydroimidazo[2,1-b][1,3]oxazole (compound 7 of Table 1 and FIG. 18);

H. 2-{[4-(6-Methoxy-3-pyridinyl)phenoxy]methyl}-2-methyl-6-nitro-2,3-dihydroimidazo[2,1-b][1,3]oxazole (compound 8 of Table 1 and FIG. 18);

I. 4'-[(2-Methyl-6-nitro-2,3-dihydroimidazo[2,1-b][1,3]oxazol-2-yl)methoxy][1,1'-biphenyl]-4-carbonitrile (compound 9 of Table 1 and FIG. 18);

J. 2-{[(4'-Fluoro[1,1'-biphenyl]-4-yl)oxy]methyl}-2-methyl-6-nitro-2,3-dihydroimidazo[2,1-b][1,3]oxazole (compound 10 of Table 1 and FIG. 18);

K. 2-Methyl-6-nitro-2-({[4'-(trifluoromethyl)[1,1'-biphenyl]-4-yl]oxy}methyl)-2,3-dihydroimidazo[2,1-b][1,3]oxazole (compound 11 of Table 1 and FIG. 18);

L. 2-Methyl-6-nitro-2-({[4'-(trifluoromethoxy)[1,1'-biphenyl]-4-yl]oxy}methyl)-2,3-dihydroimidazo[2,1-b][1,3]oxazole (compound 12 of Table 1 and FIG. 18);

M. 2-({[5-(4-Fluorophenyl)-2-pyridinyl]oxy}methyl)-2-methyl-6-nitro-2,3-dihydroimidazo[2,1-b][1,3]oxazole (compound 13 of Table 1 and FIG. 18);

N. 2-Methyl-6-nitro-2-[({5-[4-(trifluoromethoxy)phenyl]-2-pyridinyl}oxy)methyl]-2,3-dihydroimidazo[2,1-b][1,3]oxazole (compound 14 of Table 1 and FIG. 18);

O. 2-({[6-(4-Fluorophenyl)-3-pyridinyl]oxy}methyl)-2-methyl-6-nitro-2,3-dihydroimidazo[2,1-b][1,3]oxazole (compound 15 of Table 1 and FIG. 18);

P. 2-Methyl-6-nitro-2-[({6-[4-(trifluoromethoxy)phenyl]-3-pyridinyl}oxy)methyl]-2,3-dihydroimidazo[2,1-b][1,3]oxazole (compound 16 of Table 1 and FIG. 18);

Q. 2-({[5-(4-Fluorophenyl)-2-pyrimidinyl]oxy}methyl)-2-methyl-6-nitro-2,3-dihydroimidazo[2,1-b][1,3]oxazole (compound 17 of Table 1 and FIG. 18);

R. 2-Methyl-6-nitro-2-[({5-[4-(trifluoromethoxy)phenyl]-2-pyrimidinyl}oxy)methyl]-2,3-dihydroimidazo[2,1-b][1,3]oxazole (compound 18 of Table 1 and FIG. 18);

S. 2-({[2-(4-Fluorophenyl)-5-pyrimidinyl]oxy}methyl)-2-methyl-6-nitro-2,3-dihydroimidazo[2,1-b][1,3]oxazole (compound 19 of Table 1 and FIG. 18);

T. 2-Methyl-6-nitro-2-[({2-[4-(trifluoromethoxy)phenyl]-5-pyrimidinyl}oxy)methyl]-2,3-dihydroimidazo[2,1-b][1,3]oxazole (compound 20 of Table 1 and FIG. 18);

U. 2-({[5-(4-Fluorophenyl)-2-pyrazinyl]oxy}methyl)-2-methyl-6-nitro-2,3-dihydroimidazo[2,1-b][1.3]oxazole (compound 21 of Table 1 and FIG. 19);

V. 2-Methyl-6-nitro-2-[({5-[4-(trifluoromethoxy)phenyl]-2-pyrazinyl}oxy)methyl]-2,3-dihydroimidazo[2,1-b][1,3]oxazole (compound 22 of Table 1 and FIG. 19);

W. 6-Nitro-2-({[4-(trifluoromethoxy)benzyl]oxy}methyl)-2,3-dihydroimidazo[2,1-b][1,3]oxazole (compound 23 of Table 1 and FIG. 19);

X. 2-({[4-(Benzyloxy)benzyl]oxy}methyl)-6-nitro-2,3-dihydroimidazo[2,1-b][1,3]oxazole (compound 24 of Table 1 and FIG. 19);

Y. 2-Methyl-6-nitro-2-({[4-(trifluoromethoxy)benzyl]oxy}methyl)-2,3-dihydroimidazo[2,1-b][1,3]oxazole (compound 25 of Table 1 and FIG. 19);

Z. 2-({[4-(Benzyloxy)benzyl]oxy}methyl)-2-methyl-6-nitro-2,3-dihydroimidazo[2,1-b][1,3]oxazole (compound 26 of Table 1 and FIG. 19);

AA. 2-Nitro-7-{[4-(trifluoromethoxy)phenoxy]methyl}-6,7-dihydro-5H-imidazo[2,1-b][1,3]oxazine (compound 27 of Table 1 and FIG. 19);

BB. 7-{[4-(Benzyloxy)phenoxy]methyl}-2-nitro-6,7-dihydro-5H-imidazo[2,1-b][1,3]oxazine (compound 28 of Table 1 and FIG. 19);

CC. 7-{[(4'-Fluoro[1,1'-biphenyl]-4-yl)oxy]methyl}-2-nitro-6,7-dihydro-5H-imidazo[2,1-b][1,3]oxazine (compound 29 of Table 1 and FIG. 19);

DD. 2-Nitro-7-({[4'-(trifluoromethyl)[1,1'-biphenyl]-4-yl]oxy}methyl)-6,7-dihydro-5H-imidazo[2,1-b][1,3]oxazine (compound 30 of Table 1 and FIG. 19);

EE. 2-Nitro-7-({[4'-(trifluoromethoxy)[1,1'-biphenyl]-4-yl]oxy}methyl)-6,7-dihydro-5H-imidazo[2,1-b][1,3]oxazine (compound 31 of Table 1 and FIG. 19);

FF. 7-({[5-(4-Fluorophenyl)-2-pyridinyl]oxy}methyl)-2-nitro-6,7-dihydro-5H-imidazo[2,1-b][1,3]oxazine (compound 32 of Table 1 and FIG. 19);

GG. 2-Nitro-7-[({1-[4-(trifluoromethoxy)phenyl]-2-pyridinyl}oxy)methyl]-6,7-dihydro-5H-imidazo[2,1-b][1,3]oxazine (compound 33 of Table 1 and FIG. 19);

HH. 7-({[6-(4-Fluorophenyl)-3-pyridinyl]oxy}methyl)-2-nitro-6,7-dihydro-5H-imidazo[2,1-b][1,3]oxazine (compound 34 of Table 1 and FIG. 19);

II. 2-Nitro-7-[({6-[4-(trifluoromethoxy)phenyl]-3-pyridinyl}oxy)methyl]-6,7-dihydro-5H-imidazo[2,1-b][1,3]oxazine (compound 35 of Table 1 and FIG. 19);

JJ. 7-Methyl-2-nitro-7-{[4-(trifluoromethoxy)phenoxy]methyl}-6,7-dihydro-5H-imidazo[2,1-b][1,3]oxazine (compound 36 of Table 1 and FIG. 19);

KK. 7-{[4-(Benzyloxy)phenoxy]methyl}-7-methyl-2-nitro-6,7-dihydro-5H-imidazo[2,1-b][1,3]oxazine (compound 37 of Table 1 and FIG. 19);

LL. 7-{[(4'-Fluoro[1,1'-biphenyl]-4-yl)oxy]methyl}-7-methyl-2-nitro-6,7-dihydro-5H-imidazo[2,1-b][1,3]oxazine (compound 38 of Table 1 and FIG. 19);

MM. 7-Methyl-2-nitro-7-({[4'-(trifluoromethyl)[1,1'-biphenyl]-4-yl]oxy}methyl)-6,7-dihydro-5H-imidazo[2,1-b][1,3]oxazine (compound 39 of Table 1 and FIG. 20);

NN. 7-Methyl-2-nitro-7-({[4'-(trifluoromethoxy)[1,1'-biphenyl]-4-yl]oxy}methyl)-6,7-dihydro-5H-imidazo[2,1-b][1,3]oxazine (compound 40 of Table 1 and FIG. 20);

OO. 7-({[5-(4-Fluorophenyl)-2-pyridinyl]oxy}methyl)-7-methyl-2-nitro-6,7-dihydro-5H-imidazo[2,1-b][1,3]oxazine (compound 41 of Table 1 and FIG. 20);

PP. 7-Methyl-2-nitro-7-[({5-[4-(trifluoromethyl)phenyl]-2-pyridinyl}oxy)methyl]-6,7-dihydro-5H-imidazo[2,1-b][1,3]oxazine (compound 42 of Table 1 and FIG. 20);

QQ. 7-Methyl-2-nitro-7-[({5-[4-(trifluoromethoxy)phenyl]-2-pyridinyl}oxy)methyl]-6,7-dihydro-5H-imidazo[2,1-b][1,3]oxazine (compound 43 of Table 1 and FIG. 20);

RR. 7-({[6-(4-Fluorophenyl)-3-pyridinyl]oxy}methyl)-7-methyl-2-nitro-6,7-dihydro-5H-imidazo[2,1-b][1,3]oxazine (compound 44 of Table 1 and FIG. 20);

SS. 7-Methyl-2-nitro-7-[({6-[4-(trifluoromethyl)phenyl]-3-pyridinyl}oxy)methyl]-6,7-dihydro-5H-imidazo[2,1-b][1,3]oxazine (compound 45 of Table 1 and FIG. 20);

TT. 7-Methyl-2-nitro-7-[({6-[4-(trifluoromethoxy)phenyl]-3-pyridinyl}oxy)methyl]-6,7-dihydro-5H-imidazo[2,1-b][1,3]oxazine (compound 46 of Table 1 and FIG. 20);

UU. 2-Nitro-7-({[3-(trifluoromethoxy)benzyl]oxy}methyl)-6,7-dihydro-5H-imidazo[2,1-b][1,3]oxazine (compound 47 of Table 1 and FIG. 20);

VV. 2-Nitro-7-({[4-(trifluoromethoxy)benzyl]oxy}methyl)-6,7-dihydro-5H-imidazo[2,1-b][1,3]oxazine (compound 48 of Table 1 and FIG. 20);

WW. 7-({[4-(Benzyloxy)benzyl]oxy}methyl)-2-nitro-6,7-dihydro-5H-imidazo[2,1-b][1,3]oxazine (compound 49 of Table 1 and FIG. 20);

XX. 2-Nitro-7-({[4'-(trifluoromethoxy)[1,1'-biphenyl]-3-yl]methoxy}methyl)-6,7-dihydro-5H-imidazo[2,1-b][1,3]oxazine (compound 50 of Table 1 and FIG. 20);

YY. 2-Nitro-7-({[4'-(trifluoromethoxy)[1,1'-biphenyl]-4-yl]methoxy}methyl)-6,7-dihydro-5H-imidazo[2,1-b][1,3]oxazine (compound 51 of Table 1 and FIG. 20);

ZZ. 7-Methyl-2-nitro-7-({[3-(trifluoromethoxy)benzyl]oxy}methyl)-6,7-dihydro-5H-imidazo[2,1-b][1,3]oxazine (compound 52 of Table 1 and FIG. 20);

AAA. 7-Methyl-2-nitro-7-({[4-(trifluoromethoxy)benzyl]oxy}methyl)-6,7-dihydro-5H-imidazo[2,1-b][1,3]oxazine (compound 53 of Table 1 and FIG. 20);

BBB. 7-({[4-(Benzyloxy)benzyl]oxy}methyl)-7-methyl-2-nitro-6,7-dihydro-5H-imidazo[2,1-b][1,3]oxazine (compound 54 of Table 1 and FIG. 20);

CCC. 7-Methyl-2-nitro-7-({[4'-(trifluoromethoxy)[1,1'-biphenyl]-3-yl]methoxy}methyl)-6,7-dihydro-5H-imidazo[2,1-b][1,3]oxazine (compound 55 of Table 1 and FIG. 20);

DDD. 7-Methyl-2-nitro-7-({[4'-(trifluoromethoxy)[1,1'-biphenyl]-4-yl]methoxy}methyl)-6,7-dihydro-5H-imidazo[2,1-b][1.3]oxazine (compound 56 of Table 1 and FIG. 20);

EEE. (7R)-7-Methyl-2-nitro-7-({[4'-(trifluoromethoxy)[1,1'-biphenyl]-4-yl]methoxy}methyl)-6,7-dihydro-5H-imidazo[2,1-b][1,3]oxazine (compound 57 of Table 1 and FIG. 20);

FFF. (7S)-7-Methyl-2-nitro-7-({[4'-(trifluoromethoxy)[1,1'-biphenyl]-4-yl]methoxy}methyl)-6,7-dihydro-5H-imidazo[2,1-b][1,3]oxazine (compound 58 of Table 1 and FIG. 20);

GGG. 2-Nitro-6-{[4-(trifluoromethoxy)phenoxy]methyl}-6,7-dihydro-5H-imidazo[2,1-b][1,3]oxazine (compound 59 of Table 1 and FIG. 21);

HHH. (6R)-2-Nitro-6-{[4-(trifluoromethoxy)phenoxy]methyl}-6,7-dihydro-5H-imidazo[2,1-b][1,3]oxazine (compound 60 of Table 1 and FIG. 21);

III. (6S)-2-Nitro-6-{[4-(trifluoromethoxy)phenoxy]methyl}-6,7-dihydro-5H-imidazo[2,1-b][1,3]oxazine (compound 61 of Table 1 and FIG. 21);

JJJ. 6-{[(4'-Fluoro[1,1'-biphenyl]-4-yl)oxy]methyl}-2-nitro-6,7-dihydro-5H-imidazo[2,1-b][1,3]oxazine (compound 62 of Table 1 and FIG. 21);

KKK. 2-Nitro-6-({[4'-(trifluoromethyl)[1,1'-biphenyl]-4-yl]oxy}methyl)-6,7-dihydro-5H-imidazo[2,1-b][1,3]oxazine (compound 63 of Table 1 and FIG. 21);

LLL. 2-Nitro-6-({[4'-(trifluoromethoxy)[1,1'-biphenyl]-4-yl]oxy}methyl)-6,7-dihydro-5H-imidazo[2,1-b][1,3]oxazine (compound 64 of Table 1 and FIG. 21);

MMM. 6-({[5-(4-Fluorophenyl)-2-pyridinyl]oxy}methyl)-2-nitro-6,7-dihydro-5H-imidazo[2,1-b][1,3]oxazine (compound 65 of Table 1 and FIG. 21);

NNN. 2-Nitro-6-[({5-[4-(trifluoromethyl)phenyl]-2-pyridinyl}oxy)methyl]-6,7-dihydro-5H-imidazo[2,1-b][1,3]oxazine (compound 66 of Table 1 and FIG. 21);

OOO. 2-Nitro-6-[({5-[4-(trifluoromethoxy)phenyl]-2-pyridinyl}oxy)methyl]-6,7-dihydro-5H-imidazo[2,1-b][1,3]oxazine (compound 67 of Table 1 and FIG. 21);

PPP. 6-({[6-(4-Fluorophenyl)-3-pyridinyl]oxy}methyl)-2-nitro-6,7-dihydro-5H-imidazo[2,1-b][1,3]oxazine (compound 68 of Table 1 and FIG. 21);

QQQ. 2-Nitro-6-[({6-[4-(trifluoromethyl)phenyl]-3-pyridinyl}oxy)methyl]-6,7-dihydro-5H-imidazo[2,1-b][1,3]oxazine (compound 69 of Table 1 and FIG. 21);

RRR. 2-Nitro-6-[({6-[4-(trifluoromethoxy)phenyl]-3-pyridinyl}oxy)methyl]-6,7-dihydro-5H-imidazo[2,1-b][1,3]oxazine (compound 70 of Table 1 and FIG. 21);

SSS. 2-Nitro-6-({[3-(trifluoromethoxy)benzyl]oxy}methyl)-6,7-dihydro-5H-imidazo[2,1-b][1,3]oxazine (compound 71 of Table 1 and FIG. 21);

TTT. 2-Nitro-6-({[4-(trifluoromethoxy)benzyl]oxy}methyl)-6,7-dihydro-5H-imidazo[2,1-b][1,3]oxazine (compound 72 of Table 1 and FIG. 21);

UUU. 6-({[4-(Benzyloxy)benzyl]oxy}methyl)-2-nitro-6,7-dihydro-5H-imidazo[2,1-b][1,3]oxazine (compound 73 of Table 1 and FIG. 21);

VVV. 2-Nitro-6-({[4'-(trifluoromethoxy)[1,1'-biphenyl]-3-yl]methoxy}methyl)-6,7-dihydro-5H-imidazo[2,1-b][1,3]oxazine (compound 74 of Table 1 and FIG. 21); and WWW. 2-Nitro-6-({[4'-(trifluoromethoxy)[1,1'-biphenyl]-4-yl]methoxy}methyl)-6,7-dihydro-5H-imidazo[2,1-b][1,3]oxazine (compound 75 of Table 1 and FIG. 21).

Compounds of Formula I may occur in different geometric and enantiomeric forms, and both pure forms and mixtures of these separate isomers are included in the scope of this invention, as well as any physiologically functional or pharmacologically acceptable salt derivatives or prodrugs thereof. Production of these alternate forms would be well within the capabilities of one skilled in the art.

The current invention also pertains to methods of prevention or therapy for tubercular, protozoal, and other microbial infections, such as *Mycobacterium tuberculosis, Trypanosoma cruzi*, and *Leishmania donovani*, including the step of administering a compound of Formula I.

In another aspect of the present invention there is provided a pharmaceutical composition including a therapeutically effective amount of a compound of Formula I as defined above and a pharmaceutically acceptable excipient, adjuvant, carrier, buffer or stabiliser. A "therapeutically effective amount" is to be understood as an amount of a compound of Formula I that is sufficient to show anti-bacterial or anti-microbial effects. The actual amount, rate and time-course of administration will depend on the nature and severity of the disease being treated. Prescription of treatment is within the responsibility of general practitioners and other medical doctors. The pharmaceutically acceptable excipient, adjuvant, carrier, buffer or stabiliser should be non-toxic and should not interfere with the efficacy of the active ingredient. The precise nature of the carrier or other material will depend on the route of administration, which may be oral, or by injection, such as cutaneous, subcutaneous, intravenous injection, or by dry powder inhaler.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such as gelatin. For intravenous, cutaneous or subcutaneous injection, the active ingredient will be in the form of a parenterally acceptable aqueous solution which is pyrogen-free and has a suitable pH, isotonicity and stability. Those of relevant skill in the art are well able to prepare suitable solutions using, for example, isotonic vehicles such as Sodium Chloride injection, Ringer's injection, Lactated Ringer's injection. Preservatives, stabilisers, buffers, antioxidants and/or other additives may be included as required.

The pharmaceutical composition can further comprise one or more additional anti-infective treatments. These anti-infective treatments can be any suitable treatment available commercially or from other sources that are known to effectively prevent or treat microbial infections, such as *Mycobacterium tuberculosis, Trypanosoma cruzi*, and/or *Leishmania donovani*.

In another aspect, there is provided the use in the manufacture of a medicament of a therapeutically effective amount of a compound of Formula I as defined above for administration to a subject. There is also provided a method of making a compound of Formula I.

The term "pharmacologically acceptable salt" used throughout the specification is to be taken as meaning any acid or base derived salt formed from hydrochloric, sulfuric, phosphoric, acetic, citric, oxalic, malonic, salicylic, malic, fumaric, succinic, ascorbic, maleic, methanesulfonic, isotonic acids and the like, and potassium carbonate, sodium or potassium hydroxide, ammonia, triethylamine, triethanolamine and the like.

The term "prodrug" means a pharmacological substance that is administered in an inactive, or significantly less active, form. Once administered, the prodrug is metabolised in vivo into an active metabolite.

The term "therapeutically effective amount" means a non-toxic but sufficient amount of the drug to provide the desired therapeutic effect. The amount that is "effective" will vary from subject to subject, depending on the age and general condition of the individual, the particular concentration and composition being administered, and the like. Thus, it is not always possible to specify an exact effective amount. However, an appropriate effective amount in any individual case may be determined by one of ordinary skill in the art using routine experimentation. Furthermore, the effective amount is the concentration that is within a range sufficient to permit ready application of the formulation so as to deliver an amount of the drug that is within a therapeutically effective range.

The term "aza" means —CH= replaced by —N= within the compound. The term "diaza" means —CH=CH— replaced by —N=N—, —CH=CH—CH= replaced by —N=CH—N=, or —CH=CH—CH=CH— replaced by —N=CH—CH=N— within the compound.

Further aspects of the present invention will become apparent from the following description given by way of example only and with reference to the accompanying synthetic schemes.

EXAMPLE 1

General Synthetic Schemes

The compounds can be prepared by the general methods outlined in Schemes 1-15, shown in FIGS. 3-17, or by any other suitable method. In the description of Schemes 1-15 below, reference is made to representative compounds shown in Table 1 below and in FIGS. 2 and 18-21.

TABLE 1

Representative Compounds

Figure 2:
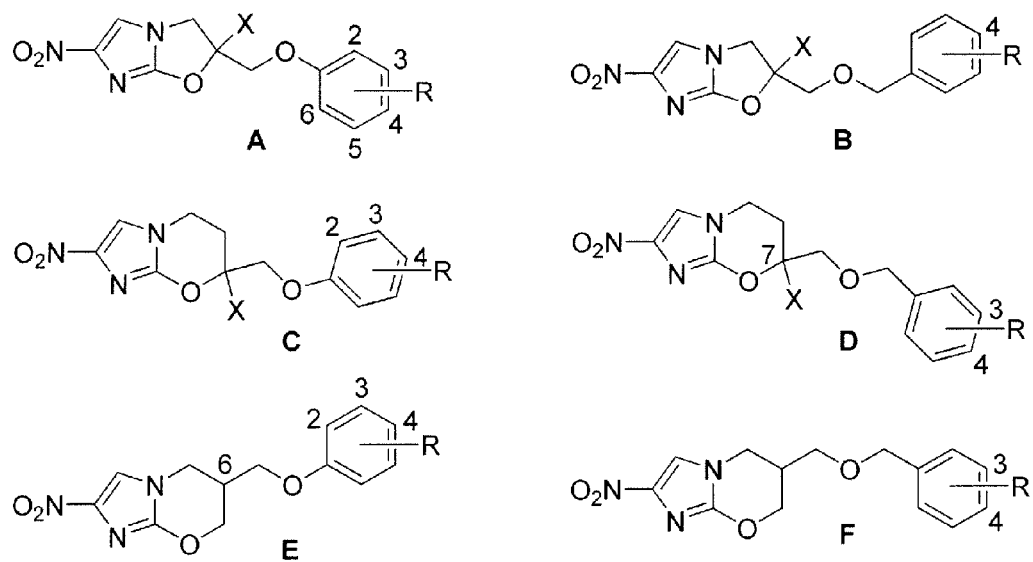
FIG. 2 shows the general structures of representative compounds referred to in Table 1.

| No | FIG. 2 Struct | R | Formula | Mp (° C.) | Analysis |
|---|---|---|---|---|---|
| 1 | A | 4-OCF$_3$ (X = H) | C$_{13}$H$_{10}$F$_3$N$_3$O$_5$ | 170-172 | C, H, N |
| 2 | A | 4-OCH$_2$Ph (X = H) | C$_{19}$H$_{17}$N$_3$O$_5$ | 208-210 | C, H, N |
| 3 | A | 4-[(4-F)phenyl] (X = H) | C$_{18}$H$_{14}$FN$_3$O$_4$ | 224-226 | |
| 4 | A | 4-[(4-CF$_3$)phenyl] (X = H) | C$_{19}$H$_{14}$F$_3$N$_3$O$_4$ | 210-211 | |
| 5 | A | 4-[(4-OCF$_3$)phenyl] (X = H) | C$_{19}$H$_{14}$F$_3$N$_3$O$_5$ | 200-201 | C, H, N |
| 6 | A | 2-aza, 4-[(4-OCF$_3$)phenyl] (X = H) | C$_{18}$H$_{13}$F$_3$N$_4$O$_5$ | 127-130 | |
| 7 | A | 4-OCH$_2$Ph (X = Me) | C$_{20}$H$_{19}$N$_3$O$_5$ | 162-165 | C, H, N |
| 8 | A | 4-[(6-OMe)3-pyridyl] (X = Me) | C$_{19}$H$_{18}$N$_4$O$_5$ | 217-219 | C, H, N |
| 9 | A | 4-[(4-CN)phenyl] (X = Me) | C$_{20}$H$_{16}$N$_4$O$_4$ | 180-181 | C, H, N |
| 10 | A | 4-[(4-F)phenyl] (X = Me) | C$_{19}$H$_{16}$FN$_3$O$_4$ | 180-181 | C, H, N |
| 11 | A | 4-[(4-CF$_3$)phenyl] (X = Me) | C$_{20}$H$_{16}$F$_3$N$_3$O$_4$ | 219-220 | C, H, N |
| 12 | A | 4-[(4-OCF$_3$)phenyl] (X = Me) | C$_{20}$H$_{16}$F$_3$N$_3$O$_5$ | 209-211 | C, H, N |
| 13 | A | 2-aza, 4-[(4-F)phenyl] (X = Me) | C$_{18}$H$_{15}$FN$_4$O$_4$ | 162-164 | |
| 14 | A | 2-aza, 4-[(4-OCF$_3$)phenyl] (X = Me) | C$_{19}$H$_{15}$F$_3$N$_4$O$_5$ | 172-174 | C, H, N |
| 15 | A | 3-aza, 4-[(4-F)phenyl] (X = Me) | C$_{18}$H$_{15}$FN$_4$O$_4$ | 180-181 | |
| 16 | A | 3-aza, 4-[(4-OCF$_3$)phenyl] (X = Me) | C$_{19}$H$_{15}$F$_3$N$_4$O$_5$ | 209-211 | C, H, N |
| 17 | A | 2,6-diaza, 4-[(4-F)phenyl] (X = Me) | C$_{17}$H$_{14}$FN$_5$O$_4$ | 196 dec | C, H, N |
| 18 | A | 2,6-diaza, 4-[(4-OCF$_3$)phenyl] (X = Me) | C$_{18}$H$_{14}$F$_3$N$_5$O$_5$ | 227 dec | C, H, N |
| 19 | A | 3,5-diaza, 4-[(4-F)phenyl] (X = Me) | C$_{17}$H$_{14}$FN$_5$O$_4$ | 201-203 | |
| 20 | A | 3,5-diaza, 4-[(4-OCF$_3$)phenyl] (X = Me) | C$_{18}$H$_{14}$F$_3$N$_5$O$_5$ | 223-225 | C, H, N |
| 21 | A | 2,5-diaza, 4-[(4-F)phenyl] (X = Me) | C$_{17}$H$_{14}$FN$_5$O$_4$ | 200-201 | C, H, N |
| 22 | A | 2,5-diaza, 4-[(4-OCF$_3$)phenyl)] (X = Me) | C$_{18}$H$_{14}$F$_3$N$_5$O$_5$ | 222-224 | C, H, N |
| 23 | B | 4-OCF$_3$ (X = H) | C$_{14}$H$_{12}$F$_3$N$_3$O$_5$ | 134-135 | C, H, N |
| 24 | B | 4-OCH$_2$Ph (X = H) | C$_{20}$H$_{19}$N$_3$O$_5$ | 123-124 | C, H, N |
| 25 | B | 4-OCF$_3$ (X = Me) | C$_{15}$H$_{14}$F$_3$N$_3$O$_5$ | 110-111 | C, H, N |
| 26 | B | 4-OCH$_2$Ph (X = Me) | C$_{21}$H$_{21}$N$_3$O$_5$ | 130-131 | C, H, N |
| 27 | C | 4-OCF$_3$ (X = H) | C$_{14}$H$_{12}$F$_3$N$_3$O$_5$ | 138-140 | C, H, N |
| 28 | C | 4-OCH$_2$Ph (X = H) | C$_{20}$H$_{19}$N$_3$O$_5$·0.25H$_2$O | 222-224 | C, H, N |
| 29 | C | 4-[(4-F)phenyl] (X = H) | C$_{19}$H$_{16}$FN$_3$O$_4$ | 217-219 | C, H, N |
| 30 | C | 4-[(4-CF$_3$)phenyl] (X = H) | C$_{20}$H$_{16}$F$_3$N$_3$O$_4$ | 242-245 | C, H, N |
| 31 | C | 4-[(4-OCF$_3$)phenyl] (X = H) | C$_{20}$H$_{16}$F$_3$N$_3$O$_5$ | 197-199 | C, H, N |
| 32 | C | 2-aza, 4-[(4-F)phenyl] (X = H) | C$_{18}$H$_{15}$FN$_4$O$_4$ | 180-181 | |
| 33 | C | 2-aza, 4-[(4-OCF$_3$)phenyl] (X = H) | C$_{19}$H$_{15}$F$_3$N$_4$O$_5$ | 161-163 | C, H, N |
| 34 | C | 3-aza, 4-[(4-F)phenyl] (X = H) | C$_{18}$H$_{15}$FN$_4$O$_4$ | 204-206 | |
| 35 | C | 3-aza, 4-[(4-OCF$_3$)phenyl] (X = H) | C$_{19}$H$_{15}$F$_3$N$_4$O$_5$ | 161-163 | C, H, N |
| 36 | C | 4-OCF$_3$ (X = Me) | C$_{15}$H$_{14}$F$_3$N$_3$O$_5$ | 134-136 | C, H, N |
| 37 | C | 4-OCH$_2$Ph (X = Me) | C$_{21}$H$_{21}$N$_3$O$_5$ | 174-176 | C, H, N |
| 38 | C | 4-[(4-F)phenyl] (X = Me) | C$_{20}$H$_{18}$FN$_3$O$_4$ | 160-162 | C, H, N |
| 39 | C | 4-[(4-CF$_3$)phenyl] (X = Me) | C$_{21}$H$_{18}$F$_3$N$_3$O$_4$ | 196-198 | C, H, N |
| 40 | C | 4-[(4-OCF$_3$)phenyl] (X = Me) | C$_{21}$H$_{18}$F$_3$N$_3$O$_5$ | 186-188 | C, H, N |
| 41 | C | 2-aza, 4-[(4-F)phenyl] (X = Me) | C$_{19}$H$_{17}$FN$_4$O$_4$ | 145-147 | C, H, N |

TABLE 1-continued

Representative Compounds

| No | FIG. 2 Struct | R | Formula | Mp (° C.) | Analysis |
|----|---------------|---|---------|-----------|----------|
| 42 | C | 2-aza, 4-[(4-CF$_3$)phenyl] (X = Me) | C$_{20}$H$_{17}$F$_3$N$_4$O$_4$ | 212-214 | C, H, N |
| 43 | C | 2-aza, 4-[(4-OCF$_3$)phenyl] (X = Me) | C$_{20}$H$_{17}$F$_3$N$_4$O$_5$ | 195-198 | C, H, N |
| 44 | C | 3-aza, 4-[(4-F)phenyl] (X = Me) | C$_{19}$H$_{17}$FN$_4$O$_4$ | 203-204 | C, H, N |
| 45 | C | 3-aza, 4-[(4-CF$_3$)phenyl] (X = Me) | C$_{20}$H$_{17}$F$_3$N$_4$O$_4$ | 215-217 | C, H, N |
| 46 | C | 3-aza, 4-[(4-OCF$_3$)phenyl] (X = Me) | C$_{20}$H$_{17}$F$_3$N$_4$O$_5$ | 202-203 | C, H, N |
| 47 | D | 3-OCF$_3$ (X = H) | C$_{15}$H$_{14}$F$_3$N$_3$O$_5$ | 100-112 | C, H, N |
| 48 | D | 4-OCF$_3$ (X = H) | C$_{15}$H$_{14}$F$_3$N$_3$O$_5$ | 158-160 | C, H, N |
| 49 | D | 4-OCH$_2$Ph (X = H) | C$_{21}$H$_{21}$N$_3$O$_5$ | 151-153 | C, H, N |
| 50 | D | 3-[(4-OCF$_3$)phenyl] (X = H) | C$_{21}$H$_{18}$F$_3$N$_3$O$_5$ | 117-119 | C, H, N |
| 51 | D | 4-[(4-OCF$_3$)phenyl] (X = H) | C$_{21}$H$_{18}$F$_3$N$_3$O$_5$ | 159-161 | C, H, N |
| 52 | D | 3-OCF$_3$ (X = Me) | C$_{16}$H$_{16}$F$_3$N$_3$O$_5$ | 108-110 | C, H, N |
| 53 | D | 4-OCF$_3$ (X = Me) | C$_{16}$H$_{16}$F$_3$N$_3$O$_5$ | 100-101 | C, H, N |
| 54 | D | 4-OCH$_2$Ph (X = Me) | C$_{22}$H$_{23}$N$_3$O$_5$ | 109-111 | C, H, N |
| 55 | D | 3-[(4-OCF$_3$)phenyl] (X = Me) | C$_{22}$H$_{20}$F$_3$N$_3$O$_5$ | 80-82 | C, H, N |
| 56 | D | 4-[(4-OCF$_3$)phenyl] (X = Me) (rac) | C$_{22}$H$_{20}$F$_3$N$_3$O$_5$ | 150-152 | C, H, N |
| 57 | D | 4-[(4-OCF$_3$)phenyl] (X = Me) (7-R) | C$_{22}$H$_{20}$F$_3$N$_3$O$_5$ | 165-167 | C, H, N |
| 58 | D | 4-[(4-OCF$_3$)phenyl] (X = Me) (7-S) | C$_{22}$H$_{20}$F$_3$N$_3$O$_5$ | 162-164 | C, H, N |
| 59 | E | 4-OCF$_3$ (rac) | C$_{14}$H$_{12}$F$_3$N$_3$O$_5$ | 141-143 | C, H, N |
| 60 | E | 4-OCF$_3$ (6-R) | C$_{14}$H$_{12}$F$_3$N$_3$O$_5$ | 138-139 | C, H, N |
| 61 | E | 4-OCF$_3$ (6-S) | C$_{14}$H$_{12}$F$_3$N$_3$O$_5$ | 139-140 | C, H, N |
| 62 | E | 4-[(4-F)phenyl] | C$_{19}$H$_{16}$FN$_3$O$_4$ | 201-203 | C, H, N |
| 63 | E | 4-[(4-CF$_3$)phenyl] | C$_{20}$H$_{16}$F$_3$N$_3$O$_4$ | 218-221 | C, H, N |
| 64 | E | 4-[(4-OCF$_3$)phenyl] | C$_{20}$H$_{16}$F$_3$N$_3$O$_5$ | 192-194 | C, H, N |
| 65 | E | 2-aza, 4-[(4-F)phenyl] | C$_{18}$H$_{15}$FN$_4$O$_4$ | 160-161 | C, H, N |
| 66 | E | 2-aza, 4-[(4-CF$_3$)phenyl] | C$_{19}$H$_{15}$F$_3$N$_4$O$_4$ | 180-182 | C, H, N |
| 67 | E | 2-aza, 4-[(4-OCF$_3$)phenyl] | C$_{19}$H$_{15}$F$_3$N$_4$O$_5$ | 182-183 | C, H, N |
| 68 | E | 3-aza, 4-[(4-F)phenyl] | C$_{18}$H$_{15}$FN$_4$O$_4$ | 214-216 | C, H, N |
| 69 | E | 3-aza, 4-[(4-CF$_3$)phenyl] | C$_{19}$H$_{15}$F$_3$N$_4$O$_4$ | 233-235 | C, H, N |
| 70 | E | 3-aza, 4-[(4-OCF$_3$)phenyl] | C$_{19}$H$_{15}$F$_3$N$_4$O$_5$ | 180-181 | C, H, N |
| 71 | F | 3-OCF$_3$ | C$_{15}$H$_{14}$F$_3$N$_3$O$_5$ | 60-61 | C, H, N |
| 72 | F | 4-OCF$_3$ | C$_{15}$H$_{14}$F$_3$N$_3$O$_5$ | 92-93 | C, H, N |
| 73 | F | 4-OCH$_2$Ph | C$_{21}$H$_{21}$N$_3$O$_5$ | 150-151 | C, H, N |
| 74 | F | 3-[(4-OCF$_3$)phenyl] | C$_{21}$H$_{18}$F$_3$N$_3$O$_5$ | 78-80 | C, H, N |
| 75 | F | 4-[(4-OCF$_3$)phenyl] | C$_{21}$H$_{18}$F$_3$N$_3$O$_5$ | 135-138 | C, H, N |

Figure 3:
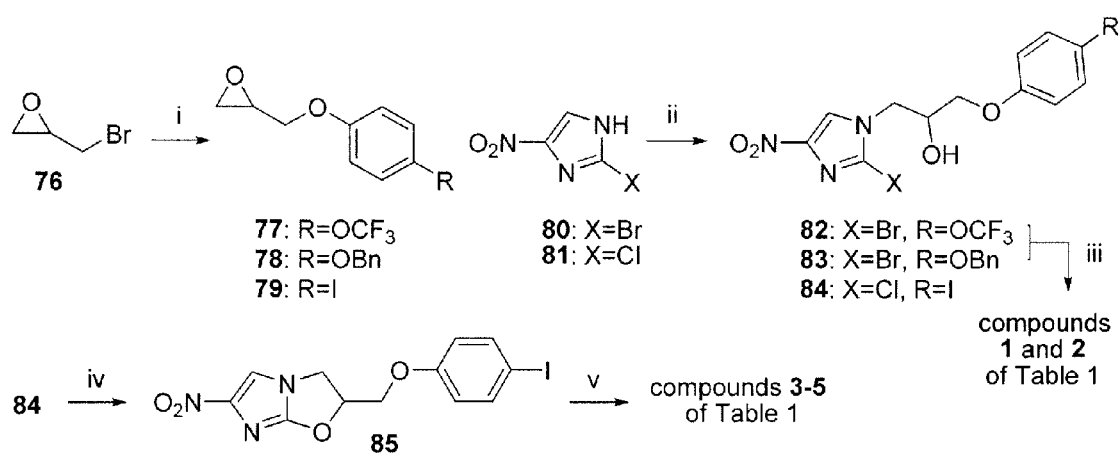
FIG. 3 shows a general synthetic scheme for preparing representative compounds.

In Scheme 1, shown in FIG. 3, reagents and conditions were (i) RPhOH, K$_2$CO$_3$, acetone, reflux, 36-52 h; (ii) 77, 78, or 79, DIPEA, 105° C., 6.5-12 h; (iii) NaH, DMF, 0° C., 45 min; (iv) NaH, DMF, 0° C., 80 min, then 17° C., 60 min; (v) ArB(OH)$_2$, 2M Na$_2$CO$_3$, toluene, EtOH, DMF, Pd(dppf)Cl$_2$ under N$_2$, 88-90° C., 50-90 min. Base-catalysed reactions of 2-bromo-4(5)-nitroimidazole (80) or 2-chloro-4(5)-nitroimidazole (81) with epoxides 77-79 [prepared by alkylation of the appropriate 4-substituted phenols with 2-(bromomethyl)oxirane (76)] gave alcohols 82-84, which underwent NaH-assisted ring closure reactions to give compounds 1 and 2 of Table 1, and iodide 85, respectively. Suzuki couplings of 85 with arylboronic acids then gave compounds 3-5 of Table 1.

Figure 4:
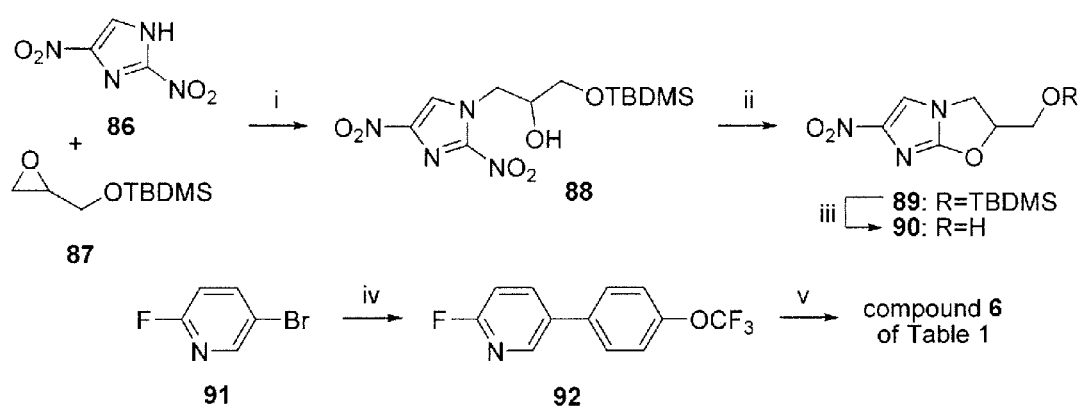
FIG. 4 shows a general synthetic scheme for preparing representative compounds.

In Scheme 2, shown in FIG. 4, reagents and conditions were (i) 70° C., 16 h; (ii) NaH, DMF, −20 to −10° C., 50 min; (iii) 1% HCl in 95% EtOH, 20° C., 6 h, then 4° C., 2.5 d; (iv) 4-OCF$_3$PhB(OH)$_2$, 2M Na$_2$CO$_3$, toluene, EtOH, Pd(dppf)Cl$_2$ under N$_2$, 85-88° C., 3 h; (v) 90, NaH, DMF, 0-20° C., 2.5 h. Reaction of 2,4-dinitroimidazole (86) with epoxide 87 gave alcohol 88, which underwent NaH-assisted ring closure, followed by acid-catalysed desilylation, to give alcohol 90. NaH-assisted alkylation of 90 with fluoropyridine 92 [prepared by Suzuki coupling of 5-bromo-2-fluoropyridine (91) with 4-(trifluoromethoxy)phenylboronic acid] then gave compound 6 of Table 1.

Figure 5:
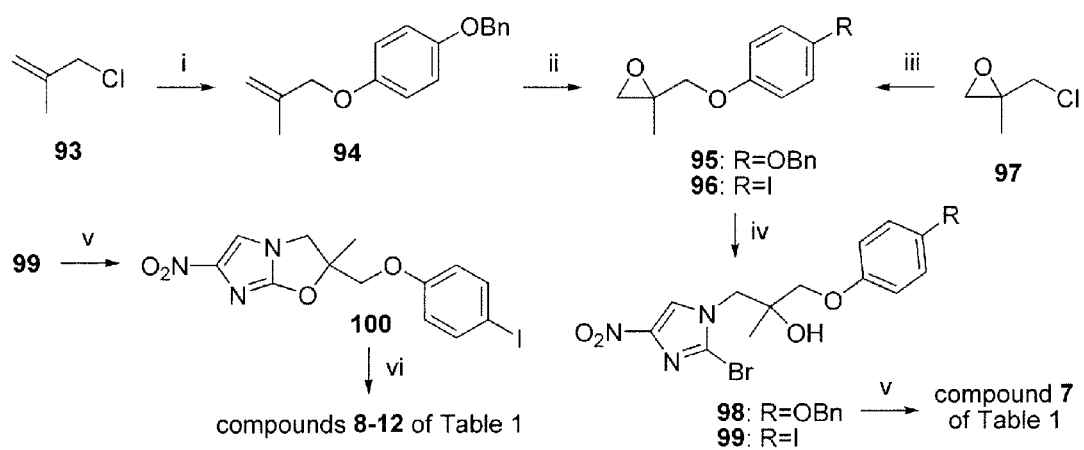
FIG. 5 shows a general synthetic scheme for preparing representative compounds.

In Scheme 3, shown in FIG. 5, reagents and conditions were (i) 4-BnOPhOH, K$_2$CO$_3$, acetone, reflux, 24 h; (ii) m-CPBA, Na$_2$HPO$_4$, CH$_2$Cl$_2$, 0-20° C., 3.5 h; (iii) 4-IPhOH, K$_2$CO$_3$, NaI, DMF, 70-73° C., 32 h; (iv) 80, DIPEA, 107° C., 14-15 h; (v) NaH, DMF, 0° C., 50-75 min; (vi) ArB(OH)$_2$, 2M Na$_2$CO$_3$, toluene, EtOH, Pd(dppf)Cl$_2$ under N$_2$, 90° C., 45 min. Base-catalysed reactions of 2-bromo-4(5)-nitroimidazole (80) with epoxides 95 and 96 [prepared by methallylation of 4-(benzyloxy)phenol with chloride 93, followed by epoxidation, or by alkylation of 4-iodophenol with 2-(chloromethyl)-2-methyloxirane (97)] gave alcohols 98 and 99, which underwent NaH-assisted ring closure reactions to give compound 7 of Table 1, and iodide 100, respectively. Suzuki couplings of 100 with arylboronic acids then gave compounds 8-12 of Table 1.

Figure 6:
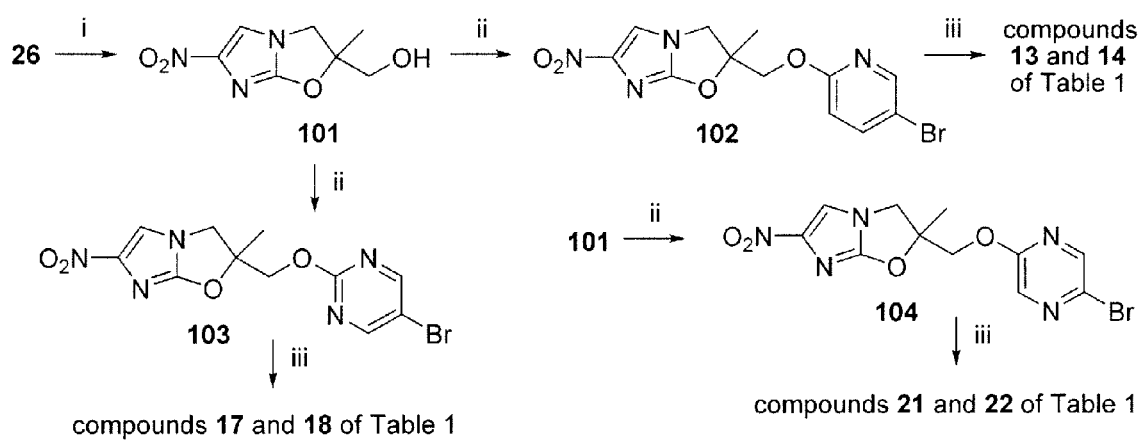
FIG. 6 shows a general synthetic scheme for preparing representative compounds.

In Scheme 4, shown in FIG. 6, reagents and conditions were (i) TFA, anisole, CH$_2$Cl$_2$, 20° C., 4 h; (ii) 91 or 5-Br,2-Clpyrimidine or 2,5-diBrpyrazine, NaH, DMF, 0-20° C., 2-3 h; (iii) ArB(OH)$_2$, 2M Na$_2$CO$_3$, toluene, EtOH, (DMF), Pd(dppf)Cl$_2$ under N$_2$, 89-90° C., 1.8-3 h. NaH-assisted alkylations of alcohol 101 [prepared from compound 26 by acid-catalysed cleavage of the 4-(benzyloxy)benzyl ether side chain] with 5-bromo-2-fluoropyridine (91), 5-bromo-2-chloropyrimidine, and 2,5-dibromopyrazine gave bromides 102-104, which underwent Suzuki couplings with arylboronic acids to give compounds 13, 14, 17, 18, 21 and 22 of Table 1.

Figure 7:
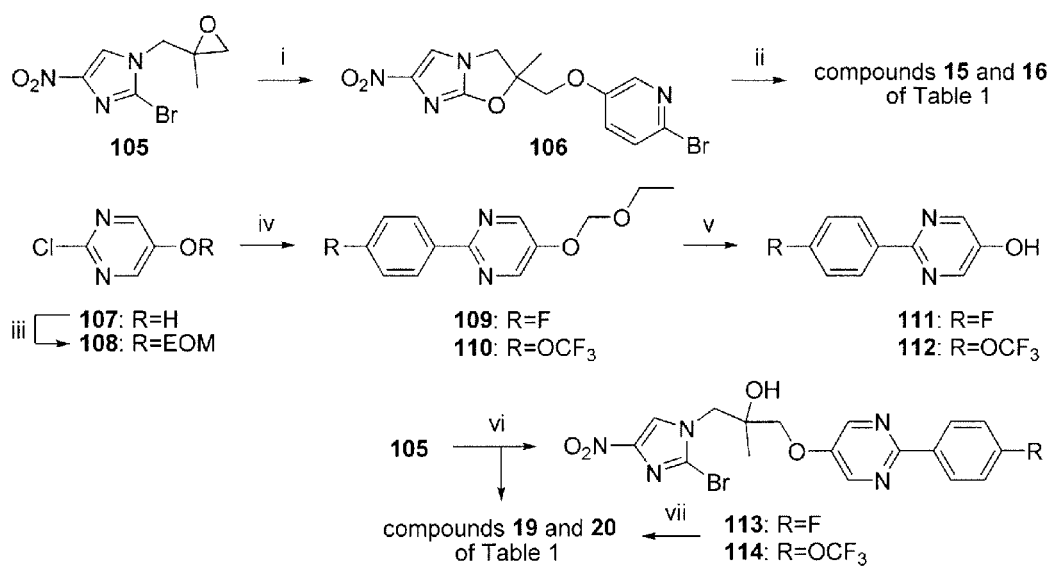
FIG. 7 shows a general synthetic scheme for preparing representative compounds.

In Scheme 5, shown in FIG. 7, reagents and conditions were (i) 6-Br-3-pyridinol, NaH, DMF, 0-20° C., 10 min, then 50° C., 4 h; (ii) ArB(OH)$_2$, 2M Na$_2$CO$_3$, toluene, EtOH, DMF, Pd(dppf)Cl$_2$ under N$_2$, 90° C., 3 h; (iii) EtOCH$_2$Cl, K$_2$CO$_3$, DMF, 20° C., 16 h; (iv) ArB(OH)$_2$, 2M Na$_2$CO$_3$, toluene, EtOH, Pd(dppf)Cl$_2$ under N$_2$, 86° C., 2-2.5 h; (v) 1.25M HCl in MeOH, 20° C., 0-12 h, then 53° C., 2-4 h; (vi) 111 or 112, NaH, DMF, 0-20° C., 10-30 min, then 50-60° C., 3 h; (vii) NaH, DMF, 0° C., 35-80 min. Base-catalysed reaction of epoxide 105 (obtained in 2 steps from 80, via epoxidation of the corresponding alkene, as reported by Ding et al., WO 2008008480A2) with 6-bromo-3-pyridinol gave bromide 106, which underwent Suzuki couplings with arylboronic acids to give compounds 15 and 16 of Table 1. Similar reactions of 105 with arylpyrimidinols 111 and 112 [prepared from 2-chloro-5-pyrimidinol (107) via successive ethoxymethyl protection of the hydroxyl group, Suzuki couplings with arylboronic acids, followed by acid-catalysed removal of the protecting group] gave mixtures of the precursor alcohols (113 or 114) and final compounds 19 or 20 of Table 1. NaH-assisted ring closure of these mixtures (or preferably of the purified alcohols 113 or 114) then gave compounds 19 and 20 of Table 1.

Figure 8:
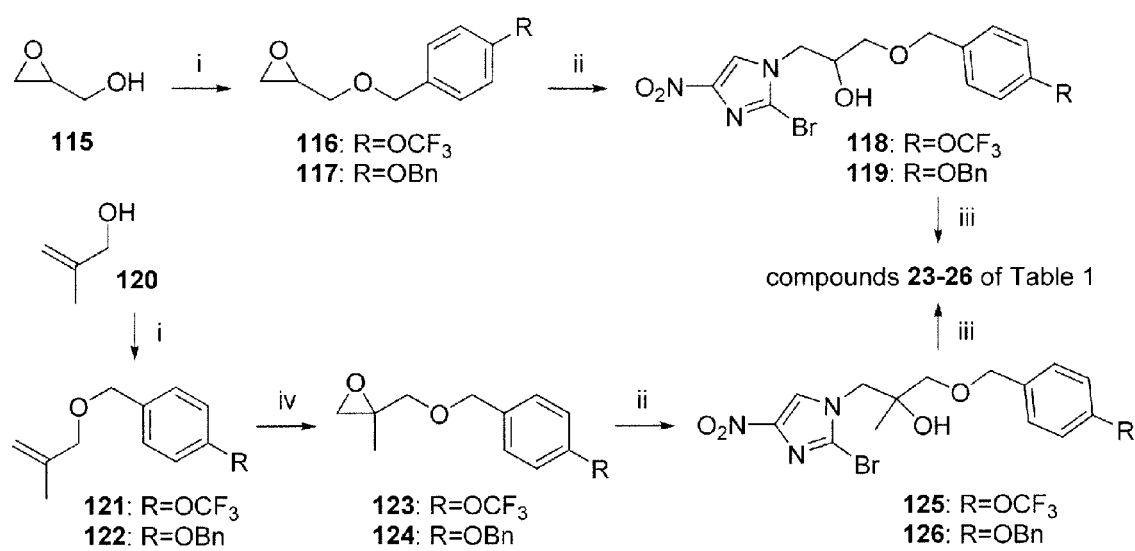
FIG. 8 shows a general synthetic scheme for preparing representative compounds.

In Scheme 6, shown in FIG. 8, reagents and conditions were (i) 4-OCF$_3$BnBr or 4-BnOBnCl, NaH, DMF, 0-20° C., 7-21 h; (ii) 80, DIPEA, 107-108° C., 13-16 h; (iii) NaH, DMF, 0° C., 65-80 min; (iv) m-CPBA, Na$_2$HPO$_4$, CH$_2$Cl$_2$, 0-20° C., 2.5-3.5 h. NaH-assisted alkylations of glycidol (115) with substituted benzyl halides gave epoxides 116 and 117, which underwent successive base-catalysed reaction with 2-bromo-4(5)-nitroimidazole (80), followed by NaH-assisted ring closure of the intermediate alcohols (118 and 119), to give compounds 23 and 24 of Table 1. Similar reactions of epoxides 123 and 124 [prepared from 2-methyl-2-propen-1-ol (120) via alkylation with substituted benzyl halides, followed by epoxidation] with 80 gave the alcohols 125 and 126, which also underwent NaH-assisted ring closure reactions to give compounds 25 and 26 of Table 1.

Figure 9:
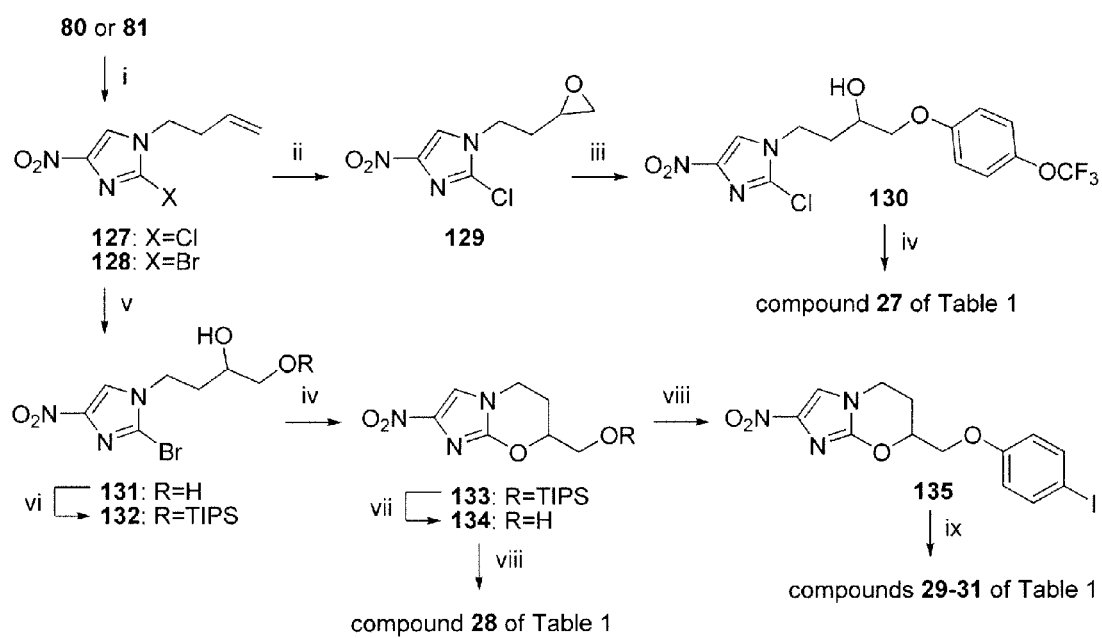
FIG. 9 shows a general synthetic scheme for preparing representative compounds.

In Scheme 7, shown in FIG. 9, reagents and conditions were (i) Br(CH$_2$)$_2$CH=CH$_2$, K$_2$CO$_3$, DMF, 66-73° C., 4.5-12 h; (ii) m-CPBA, Na$_2$HPO$_4$, CH$_2$Cl$_2$, 0-20° C., 50 h; (iii) 4-OCF$_3$PhOH, K$_2$CO$_3$, MEK, 81° C., 12 h; (iv) NaH, DMF, 0-20° C., 2-2.5 h; (v) OsO$_4$, NMO, CH$_2$Cl$_2$, 20° C., 4 h; (vi) TIPSCl, imidazole, DMF, 20° C., 18 h; (vii) 1% HCl in 95% EtOH, 20° C., 35 h; (viii) 4-BnOPhOH or 4-IPhOH, DEAD, PPh$_3$, THF, 0-20° C., 32-51 h; (ix) ArB(OH)$_2$, 2M Na$_2$CO$_3$, toluene, EtOH, DMF, Pd(dppf)Cl$_2$ under N$_2$, 90° C., 90 min. Base-catalysed reaction of epoxide 129 [prepared from 2-chloro-4(5)-nitroimidazole (81) via alkylation with 4-bromo-1-butene, followed by epoxidation] with 4-trifluoromethoxyphenol gave alcohol 130, which underwent NaH-assisted ring closure to give compound 27 of Table 1. Similar ring closure of mono-protected diol 132 [prepared from 2-bromo-4(5)-nitroimidazole (80) via alkylation with 4-bromo-1-butene, followed by dihydroxylation and TIPS protection of the primary alcohol] and acid-catalysed desilylation yielded alcohol 134. Mitsunobu reactions of 134 with the appropriate phenols gave compound 28 of Table 1 and iodide 135. Suzuki couplings of 135 with arylboronic acids then gave compounds 29-31 of Table 1.

Figure 10:
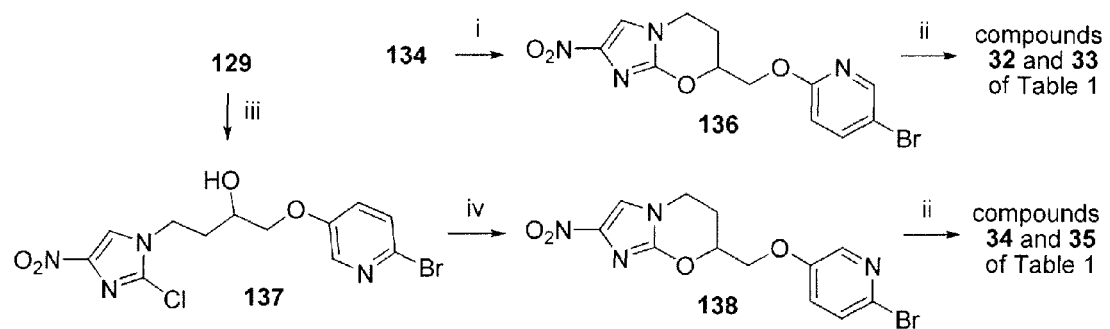
FIG. 10 shows a general synthetic scheme for preparing representative compounds.

In Scheme 8, shown in FIG. 10, reagents and conditions were (i) 91, NaH, DMF, 0-20° C., 2.5 h; (ii) ArB(OH)$_2$, 2M Na$_2$CO$_3$, toluene, EtOH, DMF, Pd(dppf)Cl$_2$ under N$_2$, 90° C., 2.5 h; (iii) 6-Br-3-pyridinol, K$_2$CO$_3$, MEK, 82-85° C., 28 h; (iv) NaH, DMF, 0-20° C., 2.5 h. NaH-assisted alkylation of alcohol 134 with 5-bromo-2-fluoropyridine (91) gave bromide 136, which underwent Suzuki couplings with arylboronic acids to give compounds 32 and 33 of Table 1. Alternatively, base-catalysed reaction of epoxide 129 with 6-bromo-3-pyridinol, followed by NaH-assisted ring closure of the resulting alcohol 137, gave bromide 138, which also underwent Suzuki couplings with arylboronic acids to give compounds 34 and 35 of Table 1.

Figure 11:
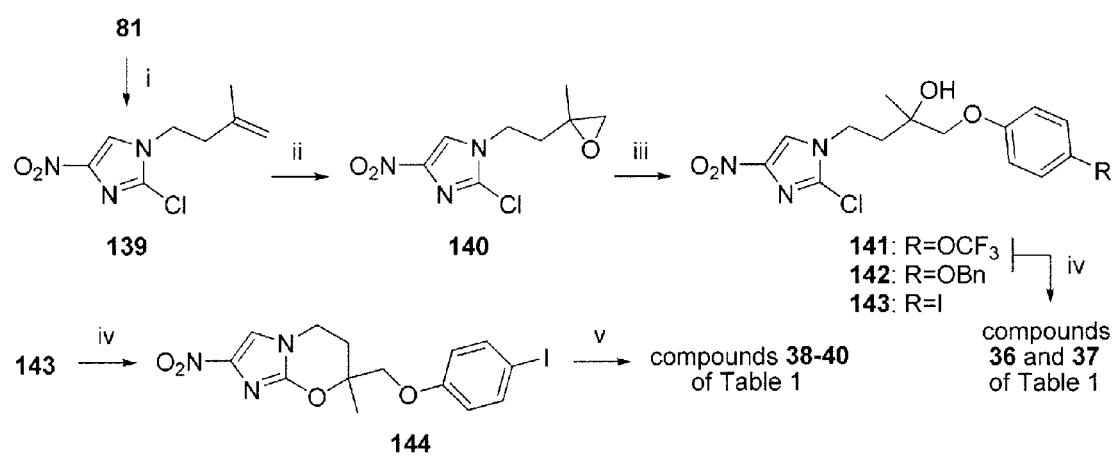
FIG. 11 shows a general synthetic scheme for preparing representative compounds.

In Scheme 9, shown in FIG. 11, reagents and conditions were (i) I(CH$_2$)$_2$C(C$_3$)=CH$_2$, K$_2$CO$_3$, DMF, 61° C., 20 h; (ii) m-CPBA, Na$_2$HPO$_4$, CH$_2$Cl$_2$, 0-20° C., 4 h; (iii) RPhOH, K$_2$CO$_3$, MEK, 82-83° C., 8-10 h; (iv) NaH, DMF, 0-20° C., 2-2.5 h; (v) ArB(OH)$_2$, 2M Na$_2$CO$_3$, toluene, EtOH, DMF, Pd(dppf)Cl$_2$ under N$_2$, 90° C., 100-105 min. Base-catalysed reactions of epoxide 140 [prepared from 2-chloro-4(5)-nitroimidazole (81) via alkylation with 4-iodo-2-methyl-1-butene (obtained by iodination of 3-methyl-3-buten-1-ol, as reported by Helmboldt et al., 2006), followed by epoxidation] with the appropriate phenols gave alcohols 141-143, which underwent NaH-assisted ring closure reactions to give compounds 36 and 37 of Table 1 and iodide 144, respectively. Suzuki couplings of 144 with arylboronic acids then gave compounds 38-40 of Table 1.

Figure 12:
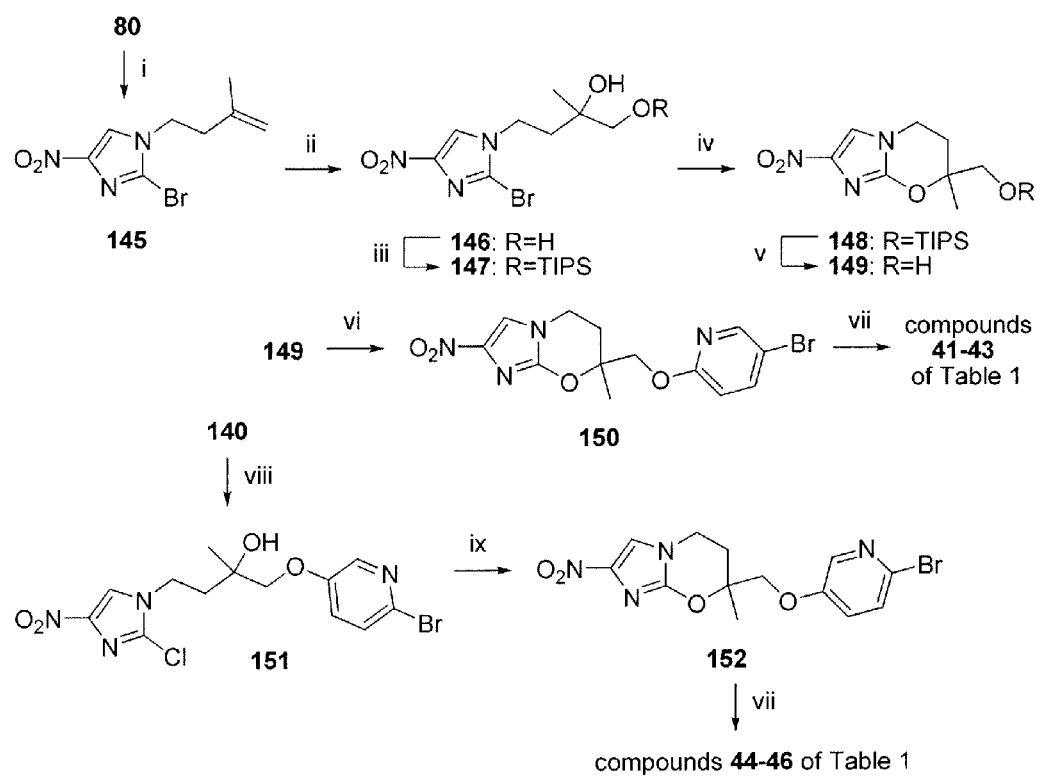
FIG. 12 shows a general synthetic scheme for preparing representative compounds.

In Scheme 10, shown in FIG. 12, reagents and conditions were (i) I(CH$_2$)$_2$C(CH$_3$)=CH$_2$, K$_2$CO$_3$, DMF, 60° C., 11 h; (ii) OsO$_4$, NMO, CH$_2$Cl$_2$, 20° C., 4 h; (iii) TIPSCl, imidazole, DMF, 20° C., 6 d; (iv) NaH, DMF, 0-20° C., 2.5 h, then 46° C., 3.2 h; (v) 1% HCl in 95% EtOH, 44° C., 3 d; (vi) 91, NaH, DMF, 0-20° C., 2.5 h; (vii) ArB(OH)$_2$, 2M Na$_2$CO$_3$, toluene, EtOH, DMF, Pd(dppf)Cl$_2$ under N$_2$, 90° C., 120-135 min; (viii) 6-Br-3-pyridinol, K$_2$CO$_3$, MEK, 84° C., 18.5 h; (ix) NaH, DMF, 0-20° C., 2.5 h. NaH-assisted ring closure of mono-protected diol 147 [prepared from 2-bromo-4(5)-nitroimidazole (80) via alkylation with 4-iodo-2-methyl-1-butene (obtained by iodination of 3-methyl-3-buten-1-ol, as reported by Helmboldt et al., 2006), followed by dihydroxylation and TIPS protection of the primary alcohol] and acid-catalysed desilylation yielded alcohol 149. NaH-assisted alkylation of 149 with 5-bromo-2-fluoropyridine (91) gave bromide 150, which underwent Suzuki couplings with arylboronic acids to give compounds 41-43 of Table 1. Alternatively, base-catalysed reaction of epoxide 140 with 6-bromo-3-pyridinol, followed by NaH-assisted ring closure of the resulting alcohol 151, gave bromide 152, which also underwent Suzuki couplings with arylboronic acids to give compounds 44-46 of Table 1.

Figure 13:
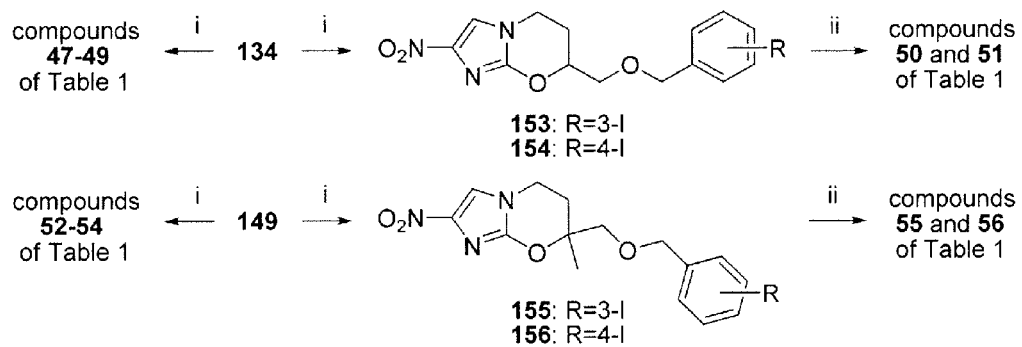
FIG. 13 shows a general synthetic scheme for preparing representative compounds.

In Scheme 11, shown in FIG. 13, reagents and conditions were (i) RBnBr or 4-BnOBnCl, NaH, DMF, 0-20° C., 2.5-7 h; (ii) 4-OCF$_3$PhB(OH)$_2$, 2M Na$_2$CO$_3$, toluene, EtOH, Pd(dppf)Cl$_2$ under N$_2$, 90° C., 20-25 min. NaH-assisted alkylations of alcohols 134 and 149 with substituted benzyl halides gave compounds 47-49 and 52-54 of Table 1 and iodides 153-156. Suzuki couplings of 153-156 with 4-trifluoromethoxyphenylboronic acid then gave compounds 50, 51, 55 and 56 of Table 1.

Figure 14:
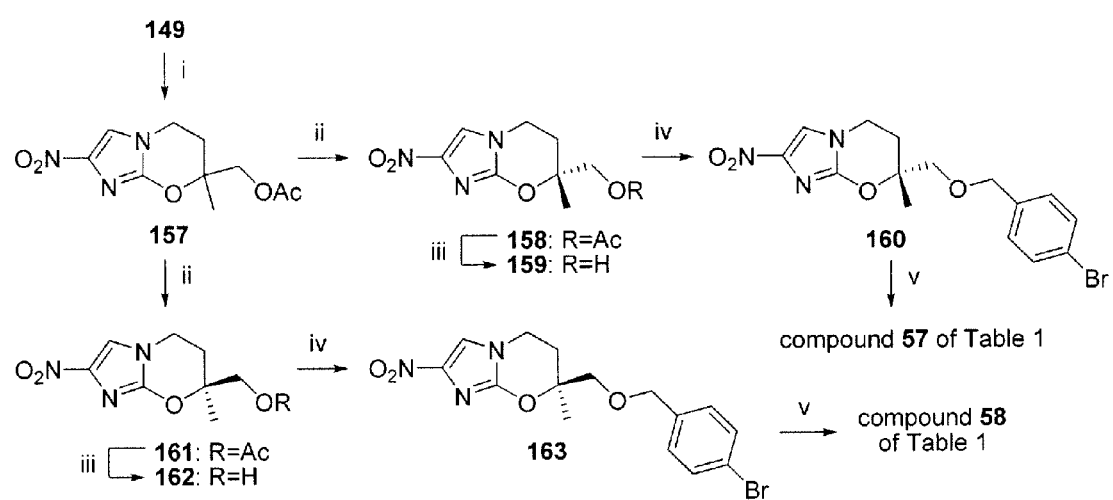
FIG. 14 shows a general synthetic scheme for preparing representative compounds.

In Scheme 12, shown in FIG. 14, reagents and conditions were (i) Ac$_2$O, pyridine, 20° C., 38 h; (ii) preparative chiral HPLC (ChiralPak IA, 40% EtOH/hexane); (iii) K$_2$CO$_3$, aq MeOH, 20° C., 4 h; (iv) 4-BrBnBr, NaH, DMF, 0-20° C., 3 h; (v) 4-OCF$_3$PhB(OH)$_2$, 2M Na$_2$CO$_3$, toluene, EtOH, Pd(dppf)Cl$_2$ under N$_2$, 88° C., 75 min. Preparative chiral HPLC of racemic acetate 157 [obtained from alcohol 149 by acetylation] gave the enantiomers 158 and 161, which were hydrolysed to the enantiomeric alcohols 159 and 162. NaH-assisted alkylations of these alcohols with 4-bromobenzyl bromide gave the bromides 160 and 163, which were Suzuki coupled with 4-trifluoromethoxyphenylboronic acid to give compounds 57 and 58 of Table 1.

Figure 15:
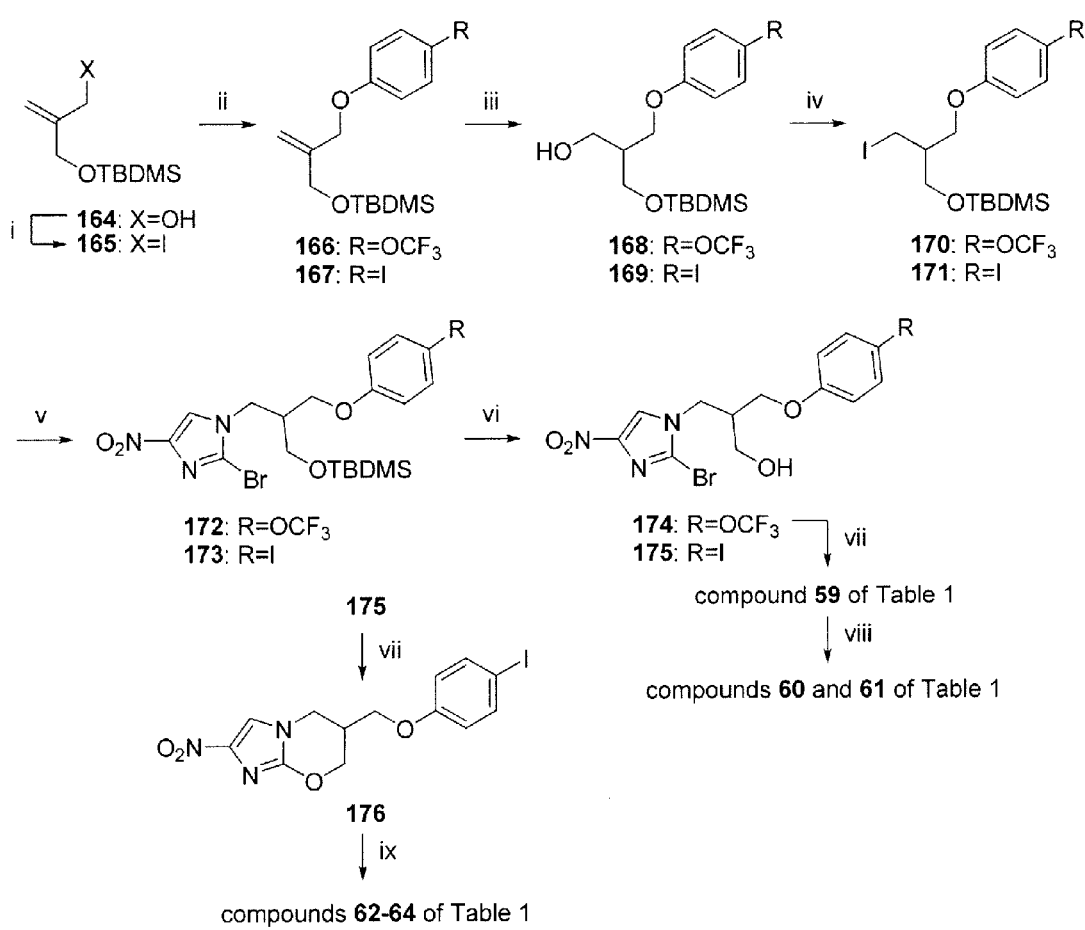
FIG. 15 shows a general synthetic scheme for preparing representative compounds.

In Scheme 13, shown in FIG. 15, reagents and conditions were (i) I$_2$, PPh$_3$, imidazole, CH$_2$Cl$_2$, 0-8° C., 5 h; (ii) RPhOH, K$_2$CO$_3$, acetone, 50° C., 6-11 h; (iii) I$_2$, NaBH$_4$, THF, 0° C., 3-4 h, then 20° C., 13 h, then 30% H$_2$O$_2$, 3N NaOH, 0-20° C., 3 h; (iv) I$_2$, PPh$_3$, imidazole, CH$_2$Cl$_2$, 20° C., 12-15 h; (v) 80, K$_2$CO$_3$, DMF, 84-88° C., 33-37 h; (vi) 1% HCl in 95% EtOH, 20° C., 7-10 h; (vii) NaH, DMF, 0-20° C., 4-5 h; (viii) preparative chiral HPLC (ChiralPak IA, 27% EtOH/hexane); (ix) ArB(OH)$_2$, 2M Na$_2$CO$_3$, toluene, EtOH, DMF, Pd(dppf)Cl$_2$ under N$_2$, 90° C., 90 min. Hydroboration of alkenes 166 and 167 [prepared by alkylation of the appropriate phenols with iodide 165, obtained by iodination of 2-({[tert-butyl(dimethyl)silyl]oxy}methyl)-2-propen-1-ol (164) (reported by Chen et al., US 2007213341 A1, by monosilylation of 2-methylene-1,3-propanediol)] gave the alcohols 168 and 169, which were converted into iodides 170 and 171. Alkylation of 2-bromo-4(5)-nitroimidazole (80) with these iodides, acid-catalysed desilylation, and NaH-assisted ring closure of the resulting alcohols 174 and 175 then gave compound 59 of Table 1 and iodide 176, respectively. Suzuki couplings of 176 with arylboronic acids also gave compounds 62-64 of Table 1.

Figure 16:
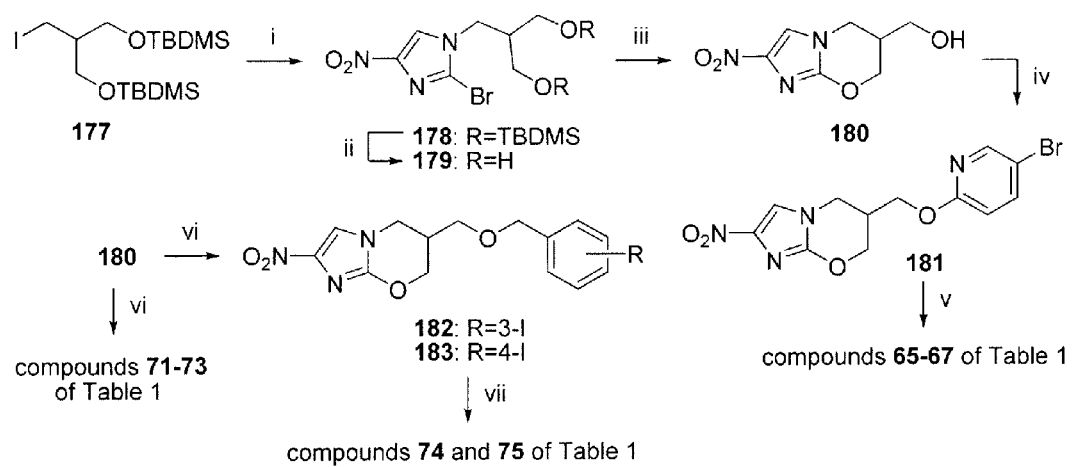
FIG. 16 shows a general synthetic scheme for preparing representative compounds.

In Scheme 14, shown in FIG. 16, reagents and conditions were (i) 80, $K_2CO_3$, DMF, 82° C., 24 h; (ii) 1% HCl in 95% EtOH, 20° C., 4 h, then 4° C., 12 h; (iii) NaH, DMF, 0-20° C., 3.5 h; (iv) 91, NaH, DMF, 0-20° C. 3 h; (v) ArB(OH)$_2$, 2M $Na_2CO_3$, toluene, EtOH, DMF, Pd(dppf)Cl$_2$ under $N_2$, 90° C., 2-2.5 h; (vi) RBnBr or 4-BnOBnI, NaH, DMF, 0-20° C., 0.5-3 h; (vii) 4-OCF$_3$PhB(OH)$_2$, 2M $Na_2CO_3$, toluene, EtOH, Pd(dppf)Cl$_2$ under $N_2$, 90° C., 20 min. Alkylation of 2-bromo-4(5)-nitroimidazole (80) with known iodide 177 (reported by Curran et al., 1998 in 4 steps from 2-methylene-1,3-propanediol) and acid-catalysed desilylation of the product (178) gave the diol 179, which underwent NaH-assisted ring closure to give alcohol 180. NaH-assisted alkylation of 180 with 5-bromo-2-fluoropyridine (91) gave bromide 181, which underwent Suzuki couplings with arylboronic acids to give compounds 65-67 of Table 1. Similar alkylations of alcohol 180 with the appropriately substituted benzyl halides gave compounds 71-73 of Table 1, as well as iodobenzyl ethers 182 and 183. Suzuki couplings of 182 and 183 with 4-(trifluoromethoxy)phenylboronic acid then gave compounds 74 and 75 of Table 1.

Figure 17:
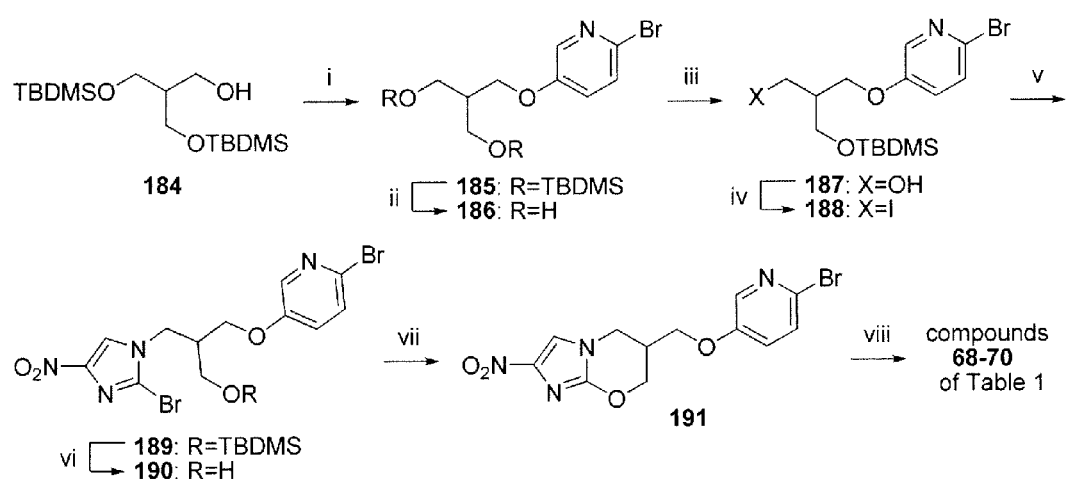
FIG. 17 shows a general synthetic scheme for preparing representative compounds.

In Scheme 15, shown in FIG. 17, reagents and conditions were (i) 6-Br-3-pyridinol, DEAD, PPh$_3$, THF, 0° C., 1 h, then 20° C., 41 h; (ii) 1% HCl in 95% EtOH, 20° C., 13 h; (iii) NaH, THF, 20° C., 1 h, then TBDMSCl, 20° C., 100 min; (iv) I$_2$, PPh$_3$, imidazole, CH$_2$Cl$_2$, 20° C., 18 h; (v) 80, $K_2CO_3$, DMF, 87° C., 42 h; (vi) TBAF, THF, 20° C., 4 h; (vii) NaH, DMF, 0-20° C., 200 min; (viii) ArB(OH)$_2$, 2M $Na_2CO_3$, toluene, EtOH, DMF, Pd(dppf)Cl$_2$ under $N_2$, 90° C., 140 min. Mitsunobu reaction of 6-bromo-3-pyridinol with known alcohol 184 (reported by Kim et al., 2001, via silylation and hydroboration of 2-methylene-1,3-propanediol), and acid-catalysed desilylation of the product (185) gave the diol 186. Monosilylation of 186 gave alcohol 187, which was converted into iodide 188. Alkylation of 2-bromo-4(5)-nitroimidazole (80) with 188, desilylation, and NaH-assisted ring closure of the resulting alcohol 190 gave bromide 191. Suzuki couplings of 191 with arylboronic acids then gave compounds 68-70 of Table 1.

EXAMPLE 2

Methods of Preparation

A. Synthesis of 6-nitro-2-{[4-(trifluoromethoxy)phenoxy]methyl}-2,3-dihydroimidazo[2,1-b][1,3]oxazole (Compound 1 of Table 1) by the Method of Scheme 1

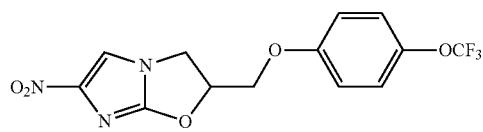

1

A mixture of 4-trifluoromethoxyphenol (0.152 mL, 1.17 mmol), $K_2CO_3$ (260 mg, 1.17 mmol) and 2-(bromomethyl)oxirane (76) (0.30 mL, 3.51 mmol) in anhydrous acetone (3 mL) was stirred in a sealed vial at 59° C. for 36 h. The resulting mixture was filtered, washing with CH$_2$Cl$_2$, and then the filtrate was evaporated to dryness and the residue was chromatographed on silica gel. Elution with 0-15% CH$_2$Cl$_2$/pentane firstly gave foreruns, and then further elution with 20-25% CH$_2$Cl$_2$/pentane gave 2-{[4-(trifluoromethoxy)phenoxy]methyl}oxirane (77) (similarly prepared by Cao et al., WO 2008112483A2 using epichlorohydrin) (260 mg, 95%) as an oil; $^1$H NMR (CDCl$_3$) δ 7.14 (br dd, J=9.0, 0.6 Hz, 2H), 6.91 (dt, J=9.1, 3.0 Hz, 2H), 4.23 (dd, J=11.1, 3.1 Hz, 1H), 3.94 (dd, J=11.1, 5.7 Hz, 1H), 3.34 (m, 1H), 2.91 (dd, J=4.8, 4.2 Hz, 1H), 2.75 (dd, J=4.9, 2.6 Hz, 1H).

A mixture of epoxide 77 (200 mg, 0.854 mmol), 2-bromo-4(5)-nitroimidazole (80) (180 mg, 0.938 mmol) and diisopropylethylamine (0.75 mL, 4.31 mmol) was stirred in a sealed vial at 105° C. for 6.5 h, and then cooled. The product was dissolved in CH$_2$Cl$_2$ (15 mL), washed with aqueous NaHCO$_3$ (15 mL) and the aqueous portion was further extracted with CH$_2$Cl$_2$ (4×15 mL). The combined organic extracts were evaporated to dryness and the residue was chromatographed on silica gel. Elution with CH$_2$Cl$_2$ firstly gave foreruns, and then further elution with 0-1% EtOAc/CH$_2$Cl$_2$ gave 1-(2-bromo-4-nitro-1H-imidazol-1-yl)-3-[4-(trifluoromethoxy)phenoxy]-2-propanol (82) (255 mg, 70%) as a white solid: mp (MeOH/CH$_2$Cl$_2$/hexane) 139-141° C.; $^1$H NMR [(CD$_3$)$_2$SO] δ 8.52 (s, 1H), 7.30 (br dd, J=9.1, 0.7 Hz, 2H), 7.05 (dt, J=9.2, 3.1 Hz, 2H), 5.66 (br s, 1H), 4.28 (dd, J=13.3, 3.3 Hz, 1H), 4.21 (m, 1H), 4.13 (dd, J=13.3, 8.0 Hz, 1H), 4.01 (d, J=5.0 Hz, 2H). Anal. (C$_{13}$H$_{11}$BrF$_3$N$_3$O$_5$) C, H, N.

A solution of alcohol 82 (242 mg, 0.568 mmol) in anhydrous DMF (5 mL) under N$_2$ at 0° C. was treated with 60% NaH (36 mg, 0.90 mmol), then quickly degassed and resealed under N$_2$. After stirring at 0° C. for 45 min, the reaction was cooled (CO$_2$/acetone), quenched with ice/aqueous NaHCO$_3$ (15 mL), added to brine (40 mL), and extracted with CH$_2$Cl$_2$ (6×50 mL). The combined extracts were evaporated to dryness and the residue was chromatographed on silica gel, eluting with CH$_2$Cl$_2$, to give 1 (171 mg, 87%) as a cream solid: mp (MeOH/CH$_2$Cl$_2$/hexane) 170-172° C.; $^1$H NMR [(CD$_3$)$_2$SO] δ 8.16 (s, 1H), 7.31 (br dd, J=9.1, 0.8 Hz, 2H), 7.05 (dt, J=9.2, 3.1 Hz, 2H), 5.74 (m, 1H), 4.50 (dd, J=10.8, 8.9 Hz, 1H), 4.46 (dd, J=11.5, 2.8 Hz, 1H), 4.39 (dd, J=11.5, 5.2 Hz, 1H), 4.22 (dd, J=10.8, 6.5 Hz, 1H). Anal. (C$_{13}$H$_{10}$F$_3$N$_3$O$_5$) C, H, N.

B. Synthesis of 2-{[4-(benzyloxy)phenoxy]methyl}-6-nitro-2,3-dihydroimidazo[2,1-b][1,3]oxazole (Compound 2 of Table 1) by the Method of Scheme 1

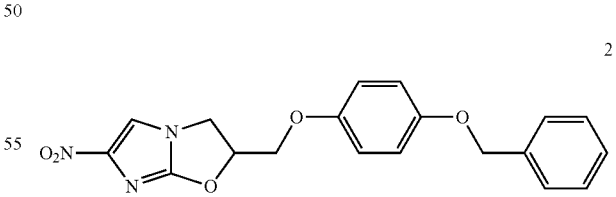

2

Alkylation of 4-(benzyloxy)phenol with 2-(bromomethyl)oxirane (76) as in Example 2A, followed by chromatography of the product on silica gel, eluting with 0-25% CH$_2$Cl$_2$/petroleum ether (foreruns) and then with 25% CH$_2$Cl$_2$/petroleum ether, gave 2-{[4-(benzyloxy)phenoxy]methyl}oxirane (78) (reported by Kopka et al., 2003 using epichlorohydrin) (79%) as a white solid: mp (CH$_2$Cl$_2$/pentane) 61-62° C.; $^1$H NMR (CDCl$_3$) δ 7.44-7.28 (m, 5H), 6.90 (dt, J=9.3, 2.8 Hz, 2H), 6.85 (dt, J=9.3, 2.8 Hz, 2H), 4.16 (dd, J=11.1, 3.3 Hz, 1H), 3.92 (dd, J=11.1, 5.6 Hz, 1H), 3.32 (m, 1H), 2.89 (dd, J=4.8, 4.3 Hz, 1H), 2.73 (dd, J=5.0, 2.7 Hz, 1H).

Reaction of epoxide 78 with 2-bromo-4(5)-nitroimidazole (80) as in Example 2A for 12 h, followed by chromatography of the product on silica gel, eluting with $CH_2Cl_2$ (foreruns) and then with 1-2% $EtOAc/CH_2Cl_2$, gave 1-[4-(benzyloxy) phenoxy]-3-(2-bromo-4-nitro-1H-imidazol-1-yl)-2-propanol (83) (74%) as a pale yellow solid: mp ($MeOH/CH_2Cl_2$/hexane) 160-162° C.; $^1H$ NMR [$(CD_3)_2SO$] δ 8.50 (s, 1H), 7.46-7.28 (m, 5H), 6.94 (dt, J=9.2, 2.9 Hz, 2H), 6.88 (dt, J=9.2, 2.9 Hz, 2H), 5.60 (br d, J=4.6 Hz, 1H), 5.04 (s, 2H), 4.27 (dd, J=13.0, 2.7 Hz, 1H), 4.16 (m, 1H), 4.11 (dd, J=13.1, 8.2 Hz, 1H), 3.93 (dd, J=10.0, 4.8 Hz, 1H), 3.89 (dd, J=10.1, 5.3 Hz, 1H). Anal. ($C_{19}H_{18}BrN_3O_5$) C, H, N.

Ring closure of alcohol 83 with NaH as in Example 2A, followed by chromatography of the product on silica gel, eluting with $CH_2Cl_2$ (foreruns) and then with 1-2% $MeOH/CH_2Cl_2$, gave 2 (94%) as a cream solid: mp ($CH_2Cl_2$/hexane) 208-210° C.; $^1H$ NMR [$(CD_3)_2SO$] δ 8.15 (s, 1H), 7.45-7.28 (m, 5H), 6.95 (dt, J=9.2, 3.0 Hz, 2H), 6.88 (dt, J=9.2, 3.0 Hz, 2H), 5.70 (m, 1H), 5.05 (s, 2H), 4.48 (dd, J=10.7, 8.9 Hz, 1H), 4.35 (dd, J=11.6, 2.8 Hz, 1H), 4.28 (dd, J=11.6, 5.1 Hz, 1H), 4.20 (dd, J=10.8, 6.5 Hz, 1H). Anal. ($C_{19}H_{17}N_3O_5$) C, H, N.

C. Synthesis of 2-{[(4'-fluoro[1,1'-biphenyl]-4-yl)oxy]methyl}-6-nitro-2,3-dihydroimidazo[2,1-b][1,3]oxazole (Compound 3 of Table 1) by the Method of Scheme 1

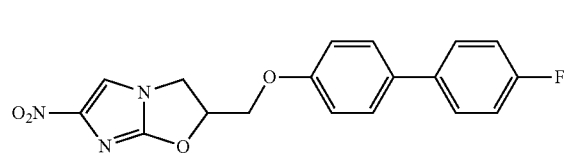

3

Alkylation of 4-iodophenol with 2-(bromomethyl)oxirane (76) as in Example 2A for 52 h, followed by chromatography of the product on silica gel, eluting with 0-10% $CH_2Cl_2$/petroleum ether (foreruns) and then with 20-25% $CH_2Cl_2$/petroleum ether, gave 2-[(4-iodophenoxy)methyl]oxirane (79) (reported by Apparu et al., 2000 using glycidyl tosylate) (89%) as a white solid: mp ($CH_2Cl_2$/petroleum ether) 67-68° C.; $^1H$ NMR ($CDCl_3$) δ 7.56 (dt, J=9.0, 2.7 Hz, 2H), 6.70 (dt, J=9.0, 2.7 Hz, 2H), 4.20 (dd, J=11.1, 3.1 Hz, 1H), 3.92 (dd, J=11.1, 5.7 Hz, 1H), 3.33 (m, 1H), 2.90 (dd, J=4.8, 4.3 Hz, 1H), 2.74 (dd, J=4.9, 2.6 Hz, 1H).

Reaction of epoxide 79 with 2-chloro-4(5)-nitroimidazole (81) and diisopropylethylamine as in Example 2A (but extracting the aqueous wash 6 times with 10% $MeOH/CH_2Cl_2$), followed by chromatography of the product on silica gel, eluting with 0-0.5% $MeOH/CH_2Cl_2$ (foreruns) and then with 0.5-1% $MeOH/CH_2Cl_2$, gave 1-(2-chloro-4-nitro-1H-imidazol-1-yl)-3-(4-iodophenoxy)-2-propanol (84) (83%) as a yellow solid: mp ($MeOH/H_2O$) 174-176° C.; $^1H$ NMR [$(CD_3)_2SO$] δ 8.49 (s, 1H), 7.60 (dt, J=8.9, 2.7 Hz, 2H), 6.81 (dt, J=9.0, 2.7 Hz, 2H), 5.66 (br s, 1H), 4.28 (dd, J=12.8, 2.6 Hz, 1H), 4.19 (m, 1H), 4.14 (dd, J=12.9, 8.0 Hz, 1H), 3.97 (d, J=4.6 Hz, 2H); HRESIMS calcd for $C_{12}H_{11}ClIN_3NaO_4$ m/z [M+Na]$^+$ 447.9346, 445.9375. found 447.9322, 445.9366.

Ring closure of alcohol 84 with NaH as in Example 2A at 0° C. for 80 min and then at 17° C. for 60 min, followed by chromatography of the product on silica gel, eluting with 0-40% EtOAc/petroleum ether (foreruns) and then with 40% EtOAc/petroleum ether and 0-0.5% $MeOH/CH_2Cl_2$, gave 2-[(4-iodophenoxy)methyl]-6-nitro-2,3-dihydroimidazo[2,1-b][1,3]oxazole (85) (77%) as a pale yellow solid: mp ($MeOH/CH_2Cl_2$/hexane) 198-199° C.; $^1H$ NMR [$(CD_3)_2SO$] δ 8.15 (s, 1H), 7.61 (dt, J=8.9, 2.6 Hz, 2H), 6.80 (dt, J=9.0, 2.6 Hz, 2H), 5.72 (m, 1H), 4.49 (dd, J=10.7, 9.0 Hz, 1H), 4.41 (dd, J=11.6, 2.7 Hz, 1H), 4.35 (dd, J=11.6, 5.2 Hz, 1H), 4.20 (dd, J=10.8, 6.5 Hz, 1H). Anal. ($C_{12}H_{10}IN_3O_4$) C, H, N.

A stirred mixture of iodide 85 (250 mg, 0.646 mmol), 4-fluorophenylboronic acid (163 mg, 1.16 mmol) and Pd(dppf)$Cl_2$ (95 mg, 0.13 mmol) in DMF (5.6 mL), toluene (4.4 mL) and EtOH (2.5 mL) was degassed for 11 min (vacuum pump) and then $N_2$ was added. An aqueous solution of 2M $Na_2CO_3$ (1.3 mL, 2.6 mmol) was added by syringe and the stirred mixture was again degassed for 11 min, and then $N_2$ was added. The resulting mixture was stirred at 88° C. for 70 min, and then cooled, diluted with aqueous $NaHCO_3$ (50 mL) and extracted with $CH_2Cl_2$ (6×50 mL). The extracts were evaporated to dryness and the residue was chromatographed on silica gel, eluting with 0-0.5% $MeOH/CH_2Cl_2$ (foreruns) and then with 0.5% $MeOH/CH_2Cl_2$, to give 3 (191 mg, 83%) as a pale brown solid: mp ($MeOH/CH_2Cl_2$/hexane) 224-226° C.; $^1H$ NMR [$(CD_3)_2SO$] δ 8.18 (s, 1H), 7.65 (ddt, J=8.9, 5.4, 2.7 Hz, 2H), 7.59 (dt, J=8.8, 2.6 Hz, 2H), 7.25 (tt, J=8.9, 2.7 Hz, 2H), 7.03 (dt, J=8.8, 2.6 Hz, 2H), 5.76 (m, 1H), 4.51 (dd, J=10.8, 9.0 Hz, 1H), 4.47 (dd, J=11.6, 2.8 Hz, 1H), 4.41 (dd, J=11.6, 5.3 Hz, 1H), 4.23 (dd, J=10.8, 6.5 Hz, 1H); APCI MS m/z 356 [M+H]$^+$.

D. Synthesis of 6-nitro-2-({[4'-(trifluoromethyl)[1,1'-biphenyl]-4-yl]oxy}methyl)-2,3-dihydroimidazo[2,1-b][1,3]oxazole (Compound 4 of Table 1) by the Method of Scheme 1

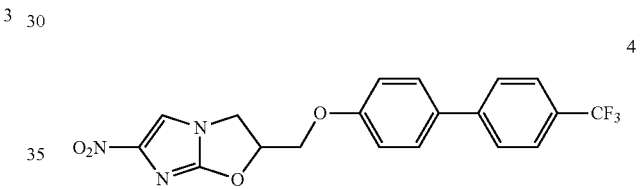

4

Suzuki coupling of iodide 85 and 4-(trifluoromethyl)phenylboronic acid as in Example 2C for 90 min, followed by chromatography of the product on silica gel, eluting with 0-0.5% $MeOH/CH_2Cl_2$ (foreruns) and then with 0.5% $MeOH/CH_2Cl_2$, gave 4 (77%) as a cream solid: mp ($MeOH/CH_2Cl_2$/hexane) 210-211° C.; $^1H$ NMR [$(CD_3)_2SO$] δ 8.19 (s, 1H), 7.86 (br d, J=8.2 Hz, 2H), 7.77 (br d, J=8.4 Hz, 2H), 7.71 (dt, J=8.8, 2.5 Hz, 2H), 7.09 (dt, J=8.9, 2.6 Hz, 2H), 5.77 (m, 1H), 4.52 (dd, J=10.7, 9.0 Hz, 1H), 4.50 (dd, J=11.6, 2.8 Hz, 1H), 4.43 (dd, J=11.6, 5.3 Hz, 1H), 4.24 (dd, J=10.8, 6.5 Hz, 1H); APCI MS m/z 406 [M+H]$^+$.

E. Synthesis of 6-nitro-2-({[4'-(trifluoromethoxy)[1,1'-biphenyl]-4-yl]oxy}methyl)-2,3-dihydroimidazo[2,1-b][1,3]oxazole (Compound 5 of Table 1) by the Method of Scheme 1

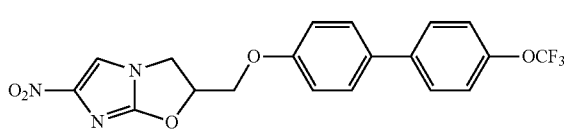

5

Suzuki coupling of iodide 85 and 4-(trifluoromethoxy)phenylboronic acid as in Example 2C for 50 min, followed by chromatography of the product on silica gel, eluting with $CH_2Cl_2$, gave 5 (83%) as a pale pink solid: mp ($CH_2Cl_2$/hexane) 200-201° C.; $^1H$ NMR [$(CD_3)_2SO$] δ 8.18 (s, 1H), 7.74 (br d, J=8.8 Hz, 2H), 7.64 (br d, J=8.8 Hz, 2H), 7.41 (br d, J=8.1 Hz, 2H), 7.06 (br d, J=8.8 Hz, 2H), 5.76 (m, 1H), 4.52

F. Synthesis of 6-nitro-2-[({5-[4-(trifluoromethoxy)
phenyl]-2-pyridinyl}oxy)methyl]-2,3-dihydroimi-
dazo[2,1-b][1,3]oxazole (Compound 6 of Table 1) by
the Method of Scheme 2

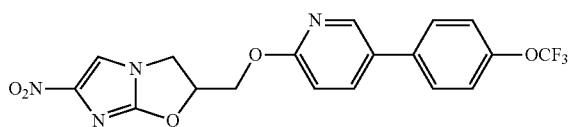

A mixture of 2,4-dinitroimidazole (86) (2.02 g, 12.8 mmol) and tert-butyl(dimethyl)silyl 2-oxiranylmethyl ether (87) (3.84 g, 20.4 mmol) was stirred at 70° C. for 16 h. The resulting cooled mixture was diluted with EtOAc (300 mL) and washed with aqueous $NaHCO_3$ (3×50 mL), water (2×50 mL) and brine (50 mL), and then the solvent was removed. Chromatography of the residue on silica gel, eluting with 10-20% EtOAc/petroleum ether, gave 1-{[tert-butyl(dimethyl)silyl]oxy}-3-(2,4-dinitro-1H-imidazol-1-yl)-2-propanol (88) (reported by Otera et al., US 2006063929A1, starting from 2,4-dinitroimidazole and glycidol) (2.63 g, 60%) as a yellow oil; $^1H$ NMR ($CDCl_3$) δ 8.01 (s, 1H), 4.78 (dd, J=13.9, 2.9 Hz, 1H), 4.46 (dd, J=14.0, 8.3 Hz, 1H), 4.08 (m, 1H), 3.76 (dd, J=10.4, 4.6 Hz, 1H), 3.67 (dd, J=10.5, 5.0 Hz, 1H), 2.60 (br s, 1H), 0.92 (s, 9H), 0.11 (s, 6H); APCI MS m/z 300 $[M+H-HNO_2]^+$.

A solution of alcohol 88 (2.04 g, 5.89 mmol) in anhydrous DMF (20 mL) under $N_2$ at −20° C. was treated with 60% NaH (0.34 g, 8.50 mmol). After stirring at −20 to −10° C. for 50 min, the reaction was quenched with EtOAc and water (150 mL), and extracted with EtOAc (500 mL). The extract was washed with water (2×100 mL) and brine (100 mL), backextracting with EtOAc (100 mL), and then the solvent was removed. Chromatography of the residue on silica gel, eluting with 40-67% EtOAc/petroleum ether, gave 2-({[tert-butyl(dimethyl)silyl]oxy}methyl)-6-nitro-2,3-dihydroimidazo[2,1-b][1,3]oxazole (89) (1.13 g, 64%) as a pale yellow solid: mp (EtOAc/petroleum ether) 142-144° C.; $^1H$ NMR ($CDCl_3$) δ 7.52 (s, 1H), 5.33 (m, 1H), 4.29 (d, J=7.2 Hz, 2H), 4.05 (dd, J=11.9, 3.5 Hz, 1H), 3.86 (dd, J=11.9, 2.8 Hz, 1H), 0.81 (s, 9H), 0.08, 0.03 (2 s, 2×3H). Anal. ($C_{12}H_{21}N_3O_4Si$) C, H, N.

A suspension of silyl ether 89 (503 mg, 1.68 mmol) in a solution of 1% HCl in 95% EtOH (desilylation conditions described by Cunico et al., 1980) (27 mL) was stirred at room temperature for 6 h, and then stored at 4° C. for 2.5 d. The resulting solution was neutralised by dropwise addition of 7M $NH_3$ in MeOH (2 mL) with stirring, and then concentrated to dryness and the residue was chromatographed on silica gel. Elution with 0-2% $MeOH/CH_2Cl_2$ firstly gave foreruns, and then further elution with 2-5% $MeOH/CH_2Cl_2$ gave (6-nitro-2,3-dihydroimidazo[2,1-b][1,3]oxazol-2-yl)methanol (90) (reported by Sehgal et al., 1981 via reaction of 2,4-dinitroimidazole and glycidol) (299 mg, 97%) as a white solid (after trituration with $CH_2Cl_2$): mp ($CH_2Cl_2$) 166-169° C.; $^1H$ NMR [$(CD_3)_2SO$] δ 8.10 (s, 1H), 5.40 (m, 1H), 5.27 (t, J=5.6 Hz, 1H), 4.36 (dd, J=10.5, 8.8 Hz, 1H), 4.11 (dd, J=10.5, 6.4 Hz, 1H), 3.80 (ddd, J=12.8, 5.4, 3.0 Hz, 1H), 3.65 (dd, J=12.8, 5.8, 3.9 Hz, 1H). Anal. ($C_6H_7N_3O_4$) C, H, N.

A stirred mixture of 4-(trifluoromethoxy)phenylboronic acid (1.55 g, 7.53 mmol) and $Pd(dppf)Cl_2$ (367 mg, 0.502 mmol) in toluene (50 mL) and EtOH (25 mL) was degassed for 15 min (vacuum pump) and then $N_2$ was added. An aqueous solution of 2M $Na_2CO_3$ (12.5 mL, 25.0 mmol) was added by syringe and the stirred mixture was again degassed for 15 min, and then $N_2$ was added, followed by 5-bromo-2-fluoropyridine (91) (0.53 mL, 5.15 mmol). The resulting mixture was stirred at 85-88° C. for 3 h, and then cooled, diluted with aqueous $NaHCO_3$ (100 mL) and extracted with $CH_2Cl_2$ (4×100 mL). The extracts were evaporated to dryness and the residue was chromatographed on silica gel. Elution with 0-10% $CH_2Cl_2$/petroleum ether firstly gave foreruns, and then further elution with 10-20% $CH_2Cl_2$/petroleum ether gave 2-fluoro-5-[4-(trifluoromethoxy)phenyl]pyridine (92) (1.32 g, 100%) as a white solid: mp ($CH_2Cl_2$/petroleum ether) 58-60° C.; $^1H$ NMR ($CDCl_3$) δ 8.40 (d, J=2.5 Hz, 1H), 7.94 (ddd, J=8.4, 7.6, 2.6 Hz, 1H), 7.55 (dt, J=8.8, 2.5 Hz, 2 ft), 7.33 (br d, J=8.0 Hz, 2H), 7.02 (dd, J=8.5, 3.0 Hz, 1H); HRESIMS calcd for $C_{12}H_8F_4NO$ m/z ($MH^+$) 258.0537. found 258.0531.

A mixture of alcohol 90 (300 mg, 1.62 mmol) and fluoropyridine 92 (1.255 g, 4.88 mmol) in anhydrous DMF (6 mL) under $N_2$ at 0° C. was treated with 60% NaH (96 mg, 2.40 mmol), then quickly degassed and resealed under $N_2$. After stirring at room temperature for 2.5 h, the reaction was cooled ($CO_2$/acetone), quenched with ice/aqueous $NaHCO_3$ (10 mL), added to brine (40 mL), and extracted with $CH_2Cl_2$ (6×50 mL). The combined extracts were evaporated to dryness and the residue was chromatographed on silica gel. Elution with 0-20% $CH_2Cl_2$/petroleum ether firstly gave foreruns (including recovered 92), and then further elution with $CH_2Cl_2$ gave 6 (5.5 mg, 0.8%) as a cream solid: mp ($CH_2Cl_2$/pentane) 127-130° C.; $^1H$ NMR ($CDCl_3$) δ 8.32 (dd, J=2.5, 0.7 Hz, 1H), 7.80 (dd, J=8.5, 2.5 Hz, 1H), 7.58 (s, 1H), 7.53 (dt, J=8.8, 2.5 Hz, 2H), 7.31 (br dd, J=8.7, 0.8 Hz, 2H), 6.83 (dd, J=8.6, 0.7 Hz, 1H), 5.69 (m, 1H), 4.80 (dd, J=12.4, 4.0 Hz, 1H), 4.75 (dd, J=12.4, 4.1 Hz, 1H), 4.45 (dd, J=10.2, 8.7 Hz, 1H), 4.35 (dd, J=10.2, 6.5 Hz, 1H); APCI MS m/z 423 $[M+H]^+$.

G. Synthesis of 2-{[4-(benzyloxy)phenoxy]methyl}-
2-methyl-6-nitro-2,3-dihydroimidazo[2,1-b][1,3]
oxazole (Compound 7 of Table 1) by the Method of
Scheme 3

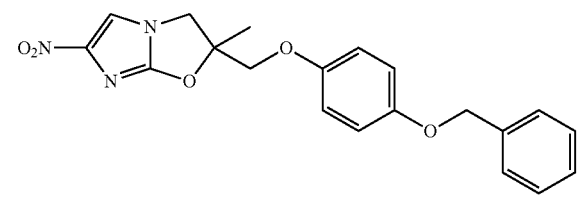

A mixture of 4-(benzyloxy)phenol (2.01 g, 10.1 mmol), $K_2CO_3$ (1.60 g, 11.6 mmol) and 3-chloro-2-methylpropene (93) (2.00 mL, 20.4 mmol) in anhydrous acetone (2.5 mL) was stirred in a sealed vial at 58° C. for 24 h. The resulting mixture was filtered, washing with $CH_2Cl_2$, and then the filtrate was evaporated to dryness and the residue was chromatographed on silica gel. Elution with petroleum ether firstly gave foreruns, and then further elution with 25% $CH_2Cl_2$/petroleum ether gave 1-(benzyloxy)-4-[(2-methyl-2-propenyl)oxy]benzene (94) (Karrer, F. DE 2312518) (1.74 g, 68%) as a white solid: mp ($CH_2Cl_2$/hexane) 62-64° C.; $^1H$ NMR ($CDCl_3$) δ 7.45-7.29 (m, 5H), 6.90 (dt, J=9.3, 2.8 Hz, 2H), 6.85 (dt, J=9.3, 2.8 Hz, 2H), 5.08 (m, 1H), 5.01 (s, 2H), 4.79 (m, 1H), 4.38 (s, 2H), 1.82 (s, 3H).

3-Chloroperbenzoic acid (1.43 g of 50%, 4.14 mmol) was added to an ice-cooled mixture of 94 (500 mg, 1.97 mmol) and powdered $Na_2HPO_4$ (974 mg, 6.86 mmol) in $CH_2Cl_2$ (20 mL), and the resulting mixture was stirred at room temperature for 3.5 h. Cold aqueous $Na_2SO_3$ (50 mL of 10%) was added, and the mixture was extracted with $CH_2Cl_2$ (3×50 mL). The extracts were sequentially washed with cold aqueous $Na_2SO_3$ (50 mL of 10%), aqueous $NaHCO_3$ (50 mL) and brine (50 mL). The combined extracts were then evaporated to dryness and the residue was chromatographed on silica gel. Elution with 25% $CH_2Cl_2$/petroleum ether firstly gave foreruns, and then further elution with 25-33% $CH_2Cl_2$/petroleum ether gave 2-{[4-(benzyloxy)phenoxy]methyl}-2-methyloxirane (95) (460 mg, 87%) as a white solid: mp ($CH_2Cl_2$/pentane) 105-107° C.; $^1H$ NMR ($CDCl_3$) δ 7.44-7.28 (m, 5H), 6.90 (dt, J=9.3, 2.9 Hz, 2H), 6.85 (dt, J=9.3, 2.9 Hz, 2H), 5.01 (s, 2H), 3.97 (d, J=10.5 Hz, 1H), 3.90 (d, J=10.5 Hz, 1H), 2.85 (d, J=4.8 Hz, 1H), 2.71 (d, J=4.8 Hz, 1H), 1.47 (s, 3H). Anal. ($C_{17}H_{18}O_3$) C, H, N.

Reaction of epoxide 95 with 2-bromo-4(5)-nitroimidazole (80) as in Example 2A at 107° C. for 14 h, followed by chromatography of the product on silica gel, eluting with $CH_2Cl_2$ (foreruns) and then with 0-1% $EtOAc/CH_2Cl_2$, gave 1-[4-(benzyloxy)phenoxy]-3-(2-bromo-4-nitro-1H-imidazol-1-yl)-2-methyl-2-propanol (98) (86%) as a pale yellow solid: mp (MeOH/$CH_2Cl_2$/hexane) 148-150° C.; $^1H$ NMR [$(CD_3)_2SO$] δ 8.31 (s, 1H), 7.45-7.28 (m, 5H), 6.94 (dt, J=9.2, 3.0 Hz, 2H), 6.87 (dt, J=9.2, 3.0 Hz, 2H), 5.41 (s, 1H), 5.04 (s, 2H), 4.22 (d, J=14.3 Hz, 1H), 4.15 (d, J=14.3 Hz, 1H), 3.76 (d, J=9.5 Hz, 1H), 3.72 (d, J=9.4 Hz, 1H), 1.19 (s, 3H). Anal. ($C_{20}H_{20}BrN_3O_5$) C, H, N.

Ring closure of alcohol 98 with NaH as in Example 2A for 50 min, followed by chromatography of the product on silica gel, eluting with $CH_2Cl_2$ (foreruns) and then with 0-1% $EtOAc/CH_2Cl_2$, gave 7 (92%) as a pale yellow solid: mp ($CH_2Cl_2$/hexane) 162-165° C.; $^1H$ NMR ($CDCl_3$) δ 7.54 (s, 1H), 7.43-7.28 (m, 5H), 6.89 (dt, J=9.1, 3.0 Hz, 2H), 6.78 (dt, J=9.1, 3.1 Hz, 2H), 5.01 (s, 2H), 4.48 (d, J=10.2 Hz, 1H), 4.17 (d, J=10.1 Hz, 1H), 4.03 (d, J=10.2 Hz, 1H), 4.00 (d, J=10.2 Hz, 1H), 1.76 (s, 3H). Anal. ($C_{20}H_{19}N_3O_5$) C, H, N.

H. Synthesis of 2-{[4-(6-methoxy-3-pyridinyl)phenoxy]methyl}-2-methyl-6-nitro-2,3-dihydroimidazo[2,1-b][1,3]oxazole (Compound 8 of Table 1) by the Method of Scheme 3

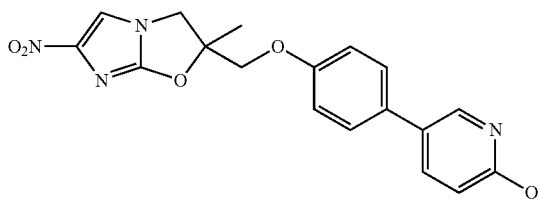

8

A mixture of 4-iodophenol (2.00 g, 9.09 mmol), powdered $K_2CO_3$ (2.54 g, 18.4 mmol), NaI (364 mg, 2.43 mmol) and 2-(chloromethyl)-2-methyloxirane (97) (0.90 mL, 9.31 mmol) in anhydrous DMF (5 mL) was stirred in a sealed vial at 70° C. for 15 h. Further 2-(chloromethyl)-2-methyloxirane (97) (0.18 mL, 1.86 mmol) was added and the mixture was then stirred at 73° C. for 17 h. The cooled mixture was added to ice/aqueous $NaHCO_3$ (100 mL) and extracted with $Et_2O$ (5×100 mL). The extracts were washed with water (100 mL) and then evaporated to dryness and the residue was chromatographed on silica gel. Elution with 0-15% $CH_2Cl_2$/petroleum ether firstly gave foreruns, and then further elution with 15-20% $CH_2Cl_2$/petroleum ether gave 2-[(4-iodophenoxy)methyl]-2-methyloxirane (96) (1.81 g, 69%) as a white solid: mp ($CH_2Cl_2$/pentane) 40-41° C.; $^1H$ NMR ($CDCl_3$) δ 7.55 (dt, J=9.0, 2.7 Hz, 2H), 6.70 (dt, J=9.0, 2.7 Hz, 2H), 4.01 (d, J=10.5 Hz, 1H), 3.90 (d, J=10.5 Hz, 1H), 2.85 (d, J=4.7 Hz, 1H), 2.72 (d, J=4.7 Hz, 1H), 1.47 (s, 3H). Anal. ($C_{10}H_{11}IO_2$) C, H, N.

Reaction of epoxide 96 with 2-bromo-4(5)-nitroimidazole (80) as in Example 2A at 107° C. for 15 h, followed by chromatography of the product on silica gel, eluting with $CH_2Cl_2$ (foreruns) and then with 0-1% $EtOAc/CH_2Cl_2$, gave 1-(2-bromo-4-nitro-1H-imidazol-1-yl)-3-(4-iodophenoxy)-2-methyl-2-propanol (99) (85%) as a foam (after trituration in $Et_2O$/pentane); $^1H$ NMR ($CDCl_3$) δ 8.04 (s, 1H), 7.59 (dt, J=9.0, 2.7 Hz, 2H), 6.66 (dt, J=9.0, 2.7 Hz, 2H), 4.27 (d, J=14.5 Hz, 1H), 4.16 (d, J=14.5 Hz, 1H), 3.86 (d, J=9.2 Hz, 1H), 3.82 (d, J=9.2 Hz, 1H), 2.44 (s, 1H), 1.35 (s, 3H). Anal. ($C_{13}H_{13}BrIN_3O_4$·0.1$Et_2O$) C, H, N.

Ring closure of alcohol 99 with NaH as in Example 2A for 75 min, followed by chromatography of the product on silica gel, eluting with $CH_2Cl_2$, gave 2-[(4-iodophenoxy)methyl]-2-methyl-6-nitro-2,3-dihydroimidazo[2,1-b][1,3]oxazole (100) (92%) as a cream solid: mp (MeOH/$CH_2Cl_2$/hexane) 181-183° C.; $^1H$ NMR ($CDCl_3$) δ 7.57 (dt, J=9.0, 2.7 Hz, 2H), 7.54 (s, 1H), 6.63 (dt, J=9.0, 2.7 Hz, 2H), 4.46 (d, J=10.2 Hz, 1H), 4.20 (d, J=10.1 Hz, 1H), 4.05 (d, J=9.9 Hz, 1H), 4.03 (d, J=10.1 Hz, 1H), 1.78 (s, 3H). Anal. ($C_{13}H_{12}IN_3O_4$) C, H, N.

A stirred mixture of iodide 100 (40.1 mg, 0.100 mmol), 6-methoxy-3-pyridinylboronic acid (23.8 mg, 0.156 mmol) and Pd(dppf)$Cl_2$ (7.3 mg, 9.98 μmol) in toluene (1.7 mL) and EtOH (0.6 mL) was degassed for 4 min (vacuum pump) and then $N_2$ was added. An aqueous solution of 2M $Na_2CO_3$ (0.30 mL, 0.60 mmol) was added by syringe and the stirred mixture was again degassed for 4 min, and then $N_2$ was added. The resulting mixture was stirred at 90° C. for 45 min, and then cooled, diluted with aqueous $NaHCO_3$ (50 mL) and extracted with $CH_2Cl_2$ (4×50 mL). The extracts were evaporated to dryness and the residue was chromatographed on silica gel. Elution with 0-3% $EtOAc/CH_2Cl_2$ firstly gave foreruns, and then further elution with 4% $EtOAc/CH_2Cl_2$ gave 8 (32 mg, 84%) as a cream solid: mp (MeOH/$CH_2Cl_2$/pentane) 217-219° C.; $^1H$ NMR ($CDCl_3$) δ 8.32 (br d, J=2.2 Hz, 1H), 7.72 (dd, J=8.6, 2.6 Hz, 1H), 7.56 (s, 1H), 7.44 (dt, J=8.8, 2.5 Hz, 2H), 6.92 (dt, J=8.8, 2.5 Hz, 2H), 6.79 (d, J=8.5 Hz, 1H), 4.51 (d, J=10.2 Hz, 1H), 4.27 (d, J=10.1 Hz, 1H), 4.13 (d, J=10.1 Hz, 1H), 4.05 (d, J=10.2 Hz, 1H), 3.97 (s, 3H), 1.80 (s, 3H). Anal. ($C_{19}H_{18}N_4O_5$) C, H, N.

I. Synthesis of 4'-[(2-methyl-6-nitro-2,3-dihydroimidazo[2,1-b][1,3]oxazol-2-yl)methoxy][1,1'-biphenyl]-4-carbonitrile (Compound 9 of Table 1) by the Method of Scheme 3

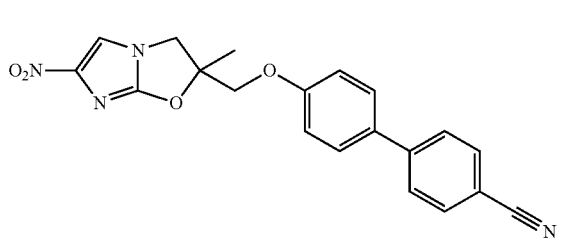

9

Suzuki coupling of iodide 100 and 4-cyanophenylboronic acid as in Example 2H, followed by chromatography of the product on silica gel, eluting with 0-0.5% $EtOAc/CH_2Cl_2$ (foreruns) and then with 0.5-1% $EtOAc/CH_2Cl_2$, gave 9

(45%) as a cream solid: mp (CH$_2$Cl$_2$/pentane) 180-181° C.; $^1$H NMR (CDCl$_3$) δ 7.70 (dt, J=8.6, 1.8 Hz, 2H), 7.62 (dt, J=8.6, 1.8 Hz, 2H), 7.56 (s, 1H), 7.53 (dt, J=8.9, 2.6 Hz, 2H), 6.95 (dt, J=8.9, 2.6 Hz, 2H), 4.51 (d, J=10.2 Hz, 1H), 4.30 (d, J=10.2 Hz, 1H), 4.15 (d, J=10.2 Hz, 1H), 4.06 (d, J=10.2 Hz, 1H), 1.81 (s, 3H). Anal. (C$_{20}$H$_{16}$N$_4$O$_4$) C, H, N.

J. Synthesis of 2-{[(4'-fluoro[1,1'-biphenyl]-4-yl)oxy]methyl}-2-methyl-6-nitro-2,3-dihydroimidazo[2,1-b][1,3]oxazole (Compound 10 of Table 1) by the Method of Scheme 3

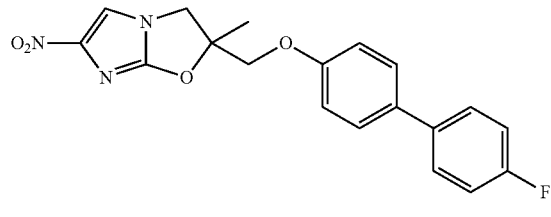

10

Suzuki coupling of iodide 100 and 4-fluorophenylboronic acid as in Example 2H, followed by chromatography of the product on silica gel, eluting with CH$_2$Cl$_2$ (foreruns) and then with 0-1% EtOAc/CH$_2$Cl$_2$, gave 10 (84%) as a cream solid: mp (MeOH/CH$_2$Cl$_2$/pentane) 180-181° C.; $^1$H NMR (CDCl$_3$) δ 7.56 (s, 1H), 7.50-7.43 (m, 4H), 7.10 (tt, J=8.7, 2.6 Hz, 2H), 6.91 (dt, J=8.8, 2.6 Hz, 2H), 4.51 (d, J=10.2 Hz, 1H), 4.27 (d, J=10.1 Hz, 1H), 4.13 (d, J=10.1 Hz, 1H), 4.05 (d, J=10.2 Hz, 1H), 1.80 (s, 3H). Anal. (C$_{19}$H$_{16}$FN$_3$O$_4$) C, H, N.

K. Synthesis of 2-methyl-6-nitro-2-({[4'-(trifluoromethyl)[1,1'-biphenyl]-4-yl]oxy}methyl)-2,3-dihydroimidazo[2,1-b][1,3]oxazole (Compound 11 of Table 1) by the Method of Scheme 3

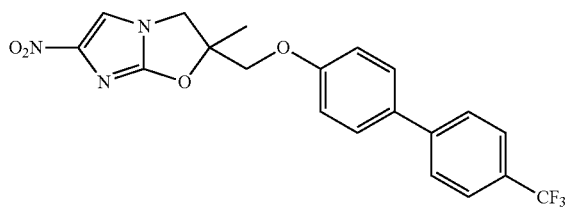

11

Suzuki coupling of iodide 100 and 4-(trifluoromethyl)phenylboronic acid as in Example 2H, followed by chromatography of the product on silica gel, eluting with 0-0.5% EtOAc/CH$_2$Cl$_2$ (foreruns) and then with 0.5% EtOAc/CH$_2$Cl$_2$, gave 11 (88%) as a cream solid: mp (CH$_2$Cl$_2$/pentane) 219-220° C.; $^1$H NMR (CDCl$_3$) δ 7.67 (d, J=8.5 Hz, 2H), 7.63 (d, J=8.5 Hz, 2H), 7.56 (s, 1H), 7.53 (dt, J=8.8, 2.5 Hz, 2H), 6.95 (dt, J=8.8, 2.5 Hz, 2H), 4.51 (d, J=10.2 Hz, 1H), 4.29 (d, J=10.1 Hz, 1H), 4.14 (d, J=10.1 Hz, 1H), 4.06 (d, J=10.2 Hz, 1H), 1.81 (s, 3H). Anal. (C$_{20}$H$_{16}$F$_3$N$_3$O$_4$) C, H, N.

L. Synthesis of 2-methyl-6-nitro-2-({[4'-(trifluoromethoxy)[1,1'-biphenyl]-4-yl]oxy}methyl)-2,3-dihydroimidazo[2,1-b][1,3]oxazole (Compound 12 of Table 1) by the Method of Scheme 3

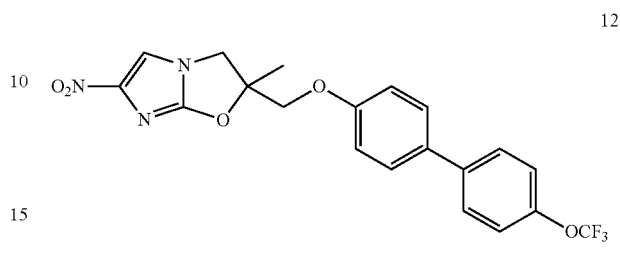

12

Suzuki coupling of iodide 100 and 4-(trifluoromethoxy)phenylboronic acid as in Example 2H, followed by chromatography of the product on silica gel, eluting with CH$_2$Cl$_2$, gave 12 (90%) as a cream solid: mp (MeOH/CH$_2$Cl$_2$/pentane) 209-211° C.; $^1$H NMR (CDCl$_3$) δ 7.56 (s, 1H), 7.53 (dt, J=8.8, 2.5 Hz, 2H), 7.48 (dt, J=8.8, 2.5 Hz, 2H), 7.26 (m, 2H), 6.92 (dt, J=8.8, 2.5 Hz, 2H), 4.51 (d, J=10.2 Hz, 1H), 4.28 (d, J=10.1 Hz, 1H), 4.13 (d, J=10.1 Hz, 1H), 4.05 (d, J=10.2 Hz, 1H), 1.81 (s, 3H). Anal. (C$_{20}$H$_{16}$F$_3$N$_3$O$_5$) C, H, N.

M. Synthesis of 2-({[5-(4-fluorophenyl)-2-pyridinyl]oxy}methyl)-2-methyl-6-nitro-2,3-dihydroimidazo[2,1-b][1,3]oxazole (Compound 13 of Table 1) by the Method of Scheme 4

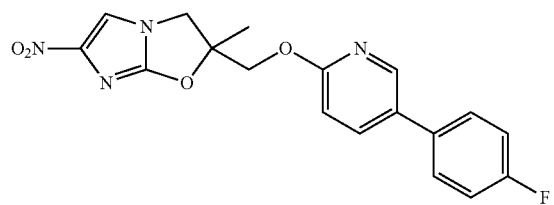

13

Trifluoroacetic acid (25.4 mL, 0.342 mol) was added dropwise to a stirred mixture of 2-({[4-(benzyloxy)benzyl]oxy}methyl)-2-methyl-6-nitro-2,3-dihydroimidazo[2,1-b][1,3]oxazole (26) (see Example 2Z) (2.53 g, 6.40 mmol) and anisole (7.0 mL, 64 mmol) in CH$_2$Cl$_2$ (100 mL) (water bath cooling). After stirring at room temperature for 4 h, the solvents were removed by blowing under a stream of N$_2$. The oily residue was treated with excess solid NaHCO$_3$, then diluted with 15% MeOH/CH$_2$Cl$_2$ (100 mL), and the mixture was stirred at room temperature for 30 min and then filtered. The filtrate was evaporated to dryness and the residue was chromatographed on silica gel. Elution with 0-1% MeOH/CH$_2$Cl$_2$ firstly gave foreruns, and then further elution with 1-2% MeOH/CH$_2$Cl$_2$ gave (2-methyl-6-nitro-2,3-dihydroimidazo[2,1-b][1,3]oxazol-2-yl)methanol (101) (reported by Tsubouchi et al., WO 2004033463A1 via 3 steps, starting from 2-chloro-4(5)-nitroimidazole (81) and 2-[(methoxymethoxy)methyl]-2-methyloxirane) (1.215 g, 95%) as a cream solid: mp (MeOH/CH$_2$Cl$_2$/hexane) 174-176° C.; $^1$H NMR [(CD$_3$)$_2$SO] δ 8.09 (s, 1H), 5.41 (t, J=5.7 Hz, 1H), 4.24 (d, J=10.6 Hz, 1H), 4.03 (d, J=10.7 Hz, 1H), 3.64 (dd, J=12.2, 5.6 Hz, 1H), 3.54 (dd, J=12.2, 5.9 Hz, 1H), 1.51 (s, 3H). Anal. (C$_7$H$_9$N$_3$O$_4$) C, H, N.

5-Bromo-2-fluoropyridine (91) (0.25 mL, 2.43 mmol) was added to a solution of alcohol 101 (200 mg, 1.01 mmol) in anhydrous DMF (4.5 mL) under $N_2$ at 0° C. The resulting mixture was treated with 60% NaH (64 mg, 1.60 mmol), then quickly degassed and resealed under $N_2$. Further 5-bromo-2-fluoropyridine (91) (0.25 mL, 2.43 mmol) was added and the mixture was stirred at room temperature for 2 h, and then cooled ($CO_2$/acetone), quenched with ice/aqueous $NaHCO_3$ (15 mL), added to brine (40 mL) and extracted with $CH_2Cl_2$ (8×40 mL). The combined extracts were evaporated to dryness and the residue was chromatographed on silica gel. Elution with $CH_2Cl_2$ firstly gave foreruns, and then further elution with 0-1.5% EtOAc/$CH_2Cl_2$ gave 2-{[(5-bromo-2-pyridinyl)oxy]methyl}-2-methyl-6-nitro-2,3-dihydroimidazo[2,1-b][1,3]oxazole (102) (130 mg, 36%) as a cream solid: mp ($CH_2Cl_2$/hexane) 151-153° C.; $^1$H NMR ($CDCl_3$) δ 8.17 (dd, J=2.5, 0.5 Hz, 1H), 7.68 (dd, J=8.8, 2.5 Hz, 1H), 7.52 (s, 1H), 6.60 (dd, J=8.7, 0.6 Hz, 1H), 4.58 (d, J=12.0 Hz, 1H), 4.50 (d, J=12.0 Hz, 1H), 4.41 (d, J=10.2 Hz, 1H), 4.01 (d, J=10.2 Hz, 1H), 1.76 (s, 3H). Anal. ($C_{12}H_{11}BrN_4O_4$) C, H, N.

A stirred mixture of bromide 102 (77.2 mg, 0.217 mmol), 4-fluorophenylboronic acid (58 mg, 0.415 mmol) and Pd(dppf)$Cl_2$ (43.5 mg, 59.4 µmol) in DMF (2.3 mL), toluene (1.6 mL) and EtOH (1.1 mL) was degassed for 9 min (vacuum pump) and then $N_2$ was added. An aqueous solution of 2M $Na_2CO_3$ (0.55 mL, 1.1 mmol) was added by syringe and the stirred mixture was again degassed for 9 min, and then $N_2$ was added. The resulting mixture was stirred at 90° C. for 3 h, and then cooled, diluted with aqueous $NaHCO_3$ (50 mL) and extracted with $CH_2Cl_2$ (6×50 mL). The extracts were evaporated to dryness and the residue was chromatographed on silica gel. Elution with 0-1% EtOAc/$CH_2Cl_2$ firstly gave foreruns, and then further elution with 1-2% EtOAc/$CH_2Cl_2$ gave 13 (60 mg, 74%) as a cream solid: mp ($CH_2Cl_2$/hexane) 162-164° C.; $^1$H NMR ($CDCl_3$) δ 8.28 (dd, J=2.5, 0.6 Hz, 1H), 7.76 (dd, J=8.5, 2.5 Hz, 1H), 7.55 (s, 1H), 7.46 (ddt, J=8.9, 5.2, 2.6 Hz, 2H), 7.14 (tt, J=8.7, 2.6 Hz, 2H), 6.75 (dd, J=8.5, 0.7 Hz, 1H), 4.67 (d, J=11.9 Hz, 1H), 4.58 (d, J=11.9 Hz, 1H), 4.47 (d, J=10.2 Hz, 1H), 4.04 (d, J=10.2 Hz, 1H), 1.79 (s, 3H); APCI MS m/z 371 [M+H]$^+$.

N. Synthesis of 2-methyl-6-nitro-2-[({5-[4-(trifluoromethoxy)phenyl]-2-pyridinyl}oxy)methyl]-2,3-dihydroimidazo[2,1-b][1,3]oxazole (Compound 14 of Table 1) by the Method of Scheme 4

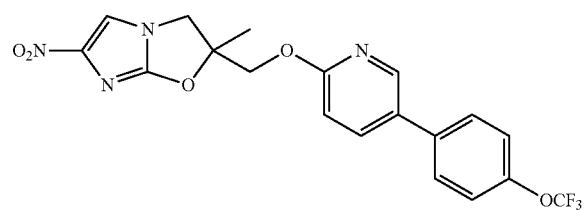

14

Suzuki coupling of bromide 102 and 4-(trifluoromethoxy)phenylboronic acid as in Example 2M, followed by chromatography of the product on silica gel, eluting with $CH_2Cl_2$, gave 14 (80%) as a cream solid: mp ($CH_2Cl_2$/pentane) 172-174° C.; $^1$H NMR ($CDCl_3$) δ 8.31 (d, J=2.1 Hz, 1H), 7.78 (dd, J=8.6, 2.5 Hz, 1H), 7.55 (s, 1H), 7.52 (br d, J=8.8 Hz, 2H), 7.30 (br d, J=8.2 Hz, 2H), 6.76 (d, J=8.7 Hz, 1H), 4.68 (d, J=11.9 Hz, 1H), 4.58 (d, J=11.9 Hz, 1H), 4.47 (d, J=10.2 Hz, 1H), 4.04 (d, J=10.2 Hz, 1H), 1.80 (s, 3H). Anal. ($C_{19}H_{15}F_3N_4O_5$) C, H, N.

O. Synthesis of 2-({[6-(4-fluorophenyl)-3-pyridinyl]oxy}methyl)-2-methyl-6-nitro-2,3-dihydroimidazo[2,1-b][1,3]oxazole (Compound 15 of Table 1) by the Method of Scheme 5

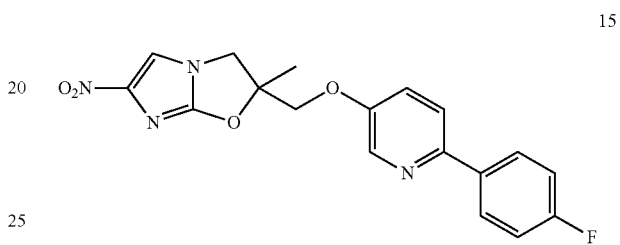

15

A mixture of 2-bromo-1-[(2-methyl-2-oxiranyl)methyl]-4-nitro-1H-imidazole (105) (obtained in 2 steps from 80, via epoxidation of the corresponding alkene, as reported by Ding et al., WO 2008008480A2) (1.011 g, 3.86 mmol) and 6-bromo-3-pyridinol (615 mg, 3.53 mmol) in anhydrous DMF (12 mL) under $N_2$ at 0° C. was treated with 60% NaH (180 mg, 4.50 mmol), then quickly degassed and resealed under $N_2$. After stirring at room temperature for 10 min, and then at 50° C. for 4 h, the reaction was cooled ($CO_2$/acetone), quenched with ice/aqueous $NaHCO_3$ (20 mL), added to brine (100 mL), and extracted with $CH_2Cl_2$ (6×100 mL). The combined extracts were evaporated to dryness and the residue was chromatographed on silica gel. Elution with 0-50% EtOAc/petroleum ether firstly gave foreruns, and then further elution with 50-75% EtOAc/petroleum ether and EtOAc gave a crude solid, which was further chromatographed on silica gel. Elution with $CH_2Cl_2$ firstly gave foreruns, and then further elution with 0.3-0.5% MeOH/$CH_2Cl_2$ gave 2-{[(6-bromo-3-pyridinyl)oxy]methyl}-2-methyl-6-nitro-2,3-dihydroimidazo[2,1-b][1,3]oxazole (106) (reported by Ding et al., WO 2009120789A1 from 105 via a similar procedure) (564 mg, 45%) as a cream solid: mp (MeOH/$CH_2Cl_2$/hexane) 148-150° C.; $^1$H NMR [($CD_3$)$_2$SO] δ 8.14 (s, 1H), 8.10 (dd, J=3.2, 0.3 Hz, 1H), 7.56 (dd, J=8.7, 0.4 Hz, 1H), 7.39 (dd, J=8.8, 3.2 Hz, 1H), 4.42 (d, J=11.1 Hz, 1H), 4.39 (d, J=11.1 Hz, 1H), 4.38 (d, J=11.0 Hz, 1H), 4.19 (d, J=11.0 Hz, 1H), 1.68 (s, 3H). Anal. ($C_{12}H_{11}BrN_4O_4$) C, H, N.

Suzuki coupling of bromide 106 and 4-fluorophenylboronic acid as in Example 2M, followed by chromatography of the product on silica gel, eluting with 0-0.5% MeOH/$CH_2Cl_2$ (foreruns) and then with 0.5% MeOH/$CH_2Cl_2$, gave 15 (74%) as a cream solid: mp (MeOH/$CH_2Cl_2$/hexane) 180-181° C.; $^1$H NMR [($CD_3$)$_2$SO] δ 8.32 (d, J=2.8 Hz, 1H), 8.18 (s, 1H), 8.05 (ddt, J=8.9, 5.6, 2.6 Hz, 2H), 7.91 (d, J=8.8 Hz, 1H), 7.48 (dd, J=8.8, 3.0 Hz, 1H), 7.27 (tt, J=8.9, 2.6 Hz, 2H), 4.47 (d, J=11.0 Hz, 1H), 4.43 (d, J=11.1 Hz, 1H), 4.41 (d, J=11.0 Hz, 1H), 4.22 (d, J=11.0 Hz, 1H), 1.71 (s, 3H); APCI MS m/z 371 [M+H]$^+$.

P. Synthesis of 2-methyl-6-nitro-2-[({6-[4-(trifluoromethoxy)phenyl]-3-pyridinyl}oxy)methyl]-2,3-dihydroimidazo[2,1-b][1,3]oxazole (Compound 16 of Table 1) by the Method of Scheme 5

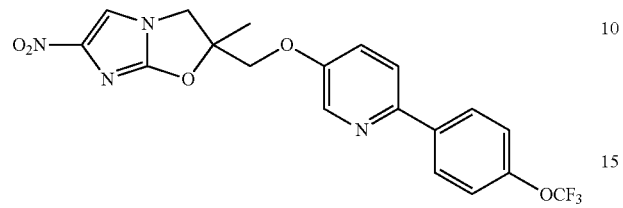

Suzuki coupling of bromide 106 and 4-(trifluoromethoxy)phenylboronic acid as in Example 2M, followed by chromatography of the product on silica gel, eluting with 0-0.33% MeOH/CH$_2$Cl$_2$ (foreruns) and then with 0.33% MeOH/CH$_2$Cl$_2$, gave 16 (67%) as a cream solid: mp (MeOH/CH$_2$Cl$_2$/hexane) 209-211° C.; $^1$H NMR [(CD$_3$)$_2$SO] δ 8.35 (d, J=2.9 Hz, 1H), 8.18 (s, 1H), 8.13 (br d, J=8.9 Hz, 2H), 7.97 (d, J=8.8 Hz, 1H), 7.51 (dd, J=8.8, 3.0 Hz, 1H), 7.44 (br d, J=8.2 Hz, 2H), 4.48 (d, J=11.1 Hz, 1H), 4.44 (d, J=11.2 Hz, 1H), 4.42 (d, J=11.1 Hz, 1H), 4.22 (d, J=11.0 Hz, 1H), 1.71 (s, 3H). Anal. (C$_{19}$H$_{15}$F$_3$N$_4$O$_5$) C, H, N.

Q. Synthesis of 7-({[5-(4-fluorophenyl)-2-pyrimidinyl]oxy}methyl)-2-nitro-6,7-dihydro-5H-imidazo[2,1-b][1,3]oxazine (Compound 17 of Table 1) by the Method of Scheme 4

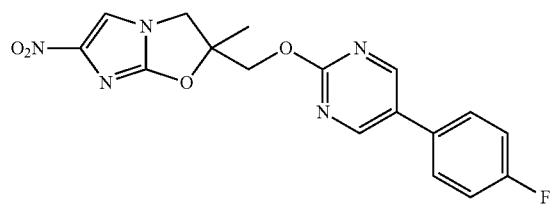

A mixture of alcohol 101 (see Example 2M) (100 mg, 0.502 mmol) and 5-bromo-2-chloropyrimidine (156 mg, 0.806 mmol) in anhydrous DMF (2.5 mL) under N$_2$ at 0° C. was treated with 60% NaH (32 mg, 0.80 mmol), then quickly degassed and resealed under N$_2$. After stirring at room temperature for 140 min, the reaction was cooled (CO$_2$/acetone), quenched with ice/aqueous NaHCO$_3$ (10 mL), added to brine (40 mL), and extracted with CH$_2$Cl$_2$ (6×50 mL). The combined extracts were evaporated to dryness and the residue was chromatographed on silica gel. Elution with 0-0.25% MeOH/CH$_2$Cl$_2$ firstly gave foreruns, and then further elution with 0.25-0.5% MeOH/CH$_2$Cl$_2$ gave 2-{[(5-bromo-2-pyrimidinyl)oxy]methyl}-2-methyl-6-nitro-2,3-dihydroimidazo[2,1-b][1,3]oxazole (103) (reported by Ding et al., WO 2009120789A1 from 101 via a similar procedure) (163 mg, 91%) as a cream solid: mp (MeOH/CH$_2$Cl$_2$/hexane) 224-226° C.; $^1$H NMR [(CD$_3$)$_2$SO] δ 8.77 (s, 2H), 8.14 (s, 1H), 4.61 (s, 2H), 4.41 (d, J=11.0 Hz, 1H), 4.20 (d, J=11.1 Hz, 1H), 1.70 (s, 3H). Anal. (C$_{11}$H$_{10}$BrN$_5$O$_4$) C, H, N.

Suzuki coupling of bromide 103 and 4-fluorophenylboronic acid as in Example 2M, followed by chromatography of the product on silica gel, eluting with CH$_2$Cl$_2$ (foreruns) and then with 0.5% MeOH/CH$_2$Cl$_2$, gave 17 (22%) as a pale yellow solid: mp (CH$_2$Cl$_2$/pentane) 196° C. dec; $^1$H NMR [(CD$_3$)$_2$SO] δ 8.92 (s, 2H), 8.18 (s, 1H), 7.79 (br dd, J=8.8, 5.4 Hz, 2H), 7.34 (br t, J=8.9 Hz, 2H), 4.69 (d, J=12.0 Hz, 1H), 4.65 (d, J=12.0 Hz, 1H), 4.44 (d, J=11.0 Hz, 1H), 4.22 (d, J=11.0 Hz, 1H), 1.72 (s, 3H). Anal. (C$_{17}$H$_{14}$FN$_5$O$_4$) C, H, N.

R. Synthesis of 2-methyl-6-nitro-2-[({5-[4-(trifluoromethoxy)phenyl]-2-pyrimidinyl}oxy)methyl]-2,3-dihydroimidazo[2,1-b][1,3]oxazole (Compound 18 of Table 1) by the Method of Scheme 4

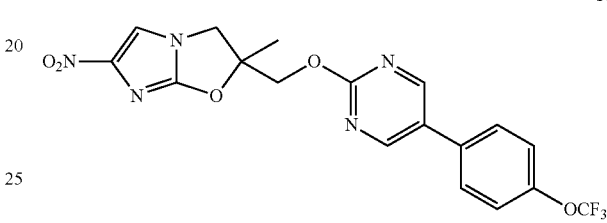

Suzuki coupling of bromide 103 and 4-(trifluoromethoxy)phenylboronic acid as in Example 2M for 2 h, followed by chromatography of the product on silica gel, eluting with CH$_2$Cl$_2$ (foreruns) and then with 0.25% MeOH/CH$_2$Cl$_2$, gave 18 (80%) as a cream solid: mp (CH$_2$Cl$_2$/hexane) 227° C. dec; $^1$H NMR [(CD$_3$)$_2$SO] δ 8.96 (s, 2H), 8.18 (s, 1H), 7.87 (br d, J=8.7 Hz, 2H), 7.50 (br d, J=8.2 Hz, 2H), 4.70 (d, J=12.0 Hz, 1H), 4.67 (d, J=12.0 Hz, 1H), 4.44 (d, J=11.0 Hz, 1H), 4.22 (d, J=11.0 Hz, 1H), 1.72 (s, 3H). Anal. (C$_{18}$H$_{14}$F$_3$N$_5$O$_5$) C, H, N.

S. Synthesis of 2-({[2-(4-fluorophenyl)-5-pyrimidinyl]oxy}methyl)-2-methyl-6-nitro-2,3-dihydroimidazo[2,1-b][1,3]oxazole (Compound 19 of Table 1) by the Method of Scheme 5

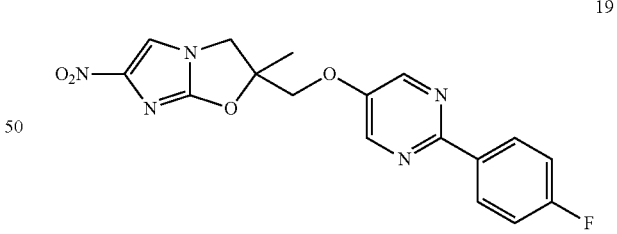

A stirred mixture of 2-chloro-5-pyrimidinol (107) (1.00 g, 7.66 mmol) and chloromethyl ethyl ether (1.75 mL, 18.9 mmol) in anhydrous DMF (2.5 mL) was treated with K$_2$CO$_3$ (2.15 g, 15.6 mmol). After stirring at room temperature for 16 h, the mixture was added to ice/aqueous NaHCO$_3$ (100 mL) and extracted with 50% Et$_2$O/petroleum ether (5×100 mL). The combined extracts were evaporated to dryness and the residue was chromatographed on silica gel. Elution with 0-1% Et$_2$O/petroleum ether firstly gave foreruns, and then further elution with 1-10% Et$_2$O/petroleum ether gave 2-chloro-5-(ethoxymethoxy)pyrimidine (108) (1.27 g, 88%) as an oil; $^1$H NMR (CDCl$_3$) δ 8.43 (s, 2H), 5.27 (s, 2H), 3.74

(q, J=7.1 Hz, 2H), 1.23 (t, J=7.1 Hz, 3 H); HRESIMS calcd for $C_7H_{10}ClN_2O_2$ m/z $[M+H]^+$ 191.0396, 189.0425. found 191.0397, 189.0426.

A stirred mixture of 4-fluorophenylboronic acid (282 mg, 2.02 mmol) and Pd(dppf)Cl$_2$ (199 mg, 0.272 mmol) in toluene (14 mL) and EtOH (7 mL) was degassed for 10 min (vacuum pump) and then N$_2$ was added. An aqueous solution of 2M Na$_2$CO$_3$ (3.3 mL, 6.6 mmol) was added by syringe and the stirred mixture was again degassed for 10 min, and then N$_2$ was added, followed by chloropyrimidine 108 (260 mg, 1.38 mmol). The resulting mixture was stirred at 86° C. for 2.5 h, and then cooled, diluted with aqueous NaHCO$_3$ (50 mL) and extracted with CH$_2$Cl$_2$ (5×50 mL). The extracts were evaporated to dryness and the residue was chromatographed on silica gel. Elution with 0-2% Et$_2$O/petroleum ether firstly gave foreruns, and then further elution with 2% Et$_2$O/petroleum ether gave 5-(ethoxymethoxy)-2-(4-fluorophenyl)pyrimidine (109) (312 mg, 91%) as a white solid: mp (petroleum ether) 42-44° C.; $^1$H NMR (CDCl$_3$) δ 8.58 (s, 2H), 8.36 (ddt, J=9.0, 5.6, 2.5 Hz, 2H), 7.14 (tt, J=8.8, 2.5 Hz, 2H), 5.30 (s, 2H), 3.77 (q. J=7.1 Hz, 2H), 1.25 (t, J=7.1 Hz, 3H); HRESIMS calcd for $C_{13}H_{13}FN_2O_2$ m/z $[M+H]^+$ 249.1034. found 249.1039.

Ether 109 (301 mg, 1.21 mmol) was treated with 1.25M HCl in MeOH (10 mL) and the mixture was stirred at 53° C. for 4 h. The resulting cooled solution was diluted with ice-water (100 mL) and extracted with CH$_2$Cl$_2$ (5×80 mL). The combined extracts were evaporated to dryness and the residue was triturated in pentane to give 2-(4-fluorophenyl)-5-pyrimidinol (111) (225 mg, 98%) as a white solid: mp (pentane) 200-202° C.; $^1$H NMR [(CD$_3$)$_2$SO] δ 10.55 (v br s, 1H), 8.42 (s, 2H), 8.29 (ddt, J=9.1, 5.7, 2.6 Hz, 2H), 7.28 (ft, J=9.0, 2.6 Hz, 2H); HRESIMS calcd for $C_{10}H_8FN_2O$ m/z $[M+H]^+$ 191.0615. found 191.0616.

A mixture of 2-bromo-1-[(2-methyl-2-oxiranyl)methyl]-4-nitro-1H-imidazole (105) (obtained in 2 steps from 80, via epoxidation of the corresponding alkene, as reported by Ding et al., WO 2008008480A2) (279.5 mg, 1.07 mmol) and pyrimidinol 111 (201 mg, 1.06 mmol) in anhydrous DMF (3 mL) under N$_2$ at 0° C. was treated with 60% NaH (54 mg, 1.35 mmol), then quickly degassed and resealed under N$_2$. After stirring at room temperature for 30 min, and then at 60° C. for 3 h, the reaction was cooled (CO$_2$/acetone), quenched with ice/aqueous NaHCO$_3$ (5 mL), added to brine (50 mL), and extracted with CH$_2$Cl$_2$ (8×50 mL). The combined extracts were evaporated to dryness and the residue was chromatographed on silica gel. Elution with 0-33% EtOAc/petroleum ether firstly gave foreruns, and then further elution with 50% EtOAc/petroleum ether gave 1-(2-bromo-4-nitro-1H-imidazol-1-yl)-3-{[2-(4-fluorophenyl)-5-pyrimidinyl]oxy}-2-methyl-2-propanol (113) (76 mg, 16%) as an oil; $^1$H NMR (CDCl$_3$) δ 8.46 (s, 2H), 8.36 (ddt, J=9.0, 5.5, 2.5 Hz, 2H), 8.09 (s, 1H), 7.15 (tt, J=8.7, 2.5 Hz, 2H), 4.32 (d, J=14.6 Hz, 1H), 4.21 (d, J=14.5 Hz, 1H), 4.03 (d, J=9.2 Hz, 1H), 3.99 (d, J=9.1 Hz, 1H), 2.59 (s, 1H), 1.43 (s, 3H); HRESIMS calcd for $C_{17}H_{16}BrFN_5O_4$ m/z $[M+H]^+$ 454.0345, 452.0364. found 454.0342, 452.0358.

Further elution of the above column with EtOAc gave a crude solid, which was further chromatographed over silica gel. Elution with 0-2% EtOAc/CH$_2$Cl$_2$ firstly gave foreruns, and then further elution with 2-5% EtOAc/CH$_2$Cl$_2$ gave 19 (135 mg, 34%) as a cream solid: mp (MeOH/CH$_2$Cl$_2$/hexane) 201-203° C.; $^1$H NMR 8.63 (s, 2H), 8.33 (ddt, J=9.0, 5.7, 2.6 Hz, 2H), 8.18 (s, 1H), 7.32 (tt, J=8.9, 2.6 Hz, 2H), 4.57 (d, J=11.1 Hz, 1H), 4.53 (d, J=11.1 Hz, 1H), 4.42 (d, J=11.0 Hz, 1H), 4.22 (d, J=11.0 Hz, 1H), 1.71 (s, 3H); APCI MS m/z 372 $[M+H]^+$.

Ring closure of alcohol 113 with NaH (1.8 equiv.) as in Example 2A for 35 min, followed by chromatography of the product on silica gel, eluting with 0-2% EtOAc/CH$_2$Cl$_2$ (foreruns) and then with 2-5% EtOAc/CH$_2$Cl$_2$, gave additional 19 (67%).

T. Synthesis of 2-methyl-6-nitro-2-[({2-[4-(trifluoromethoxy)phenyl]-5-pyrimidinyl}oxy)methyl]-2,3-dihydroimidazo[2,1-b][1,3]oxazole (Compound 20 of Table 1) by the Method of Scheme 5

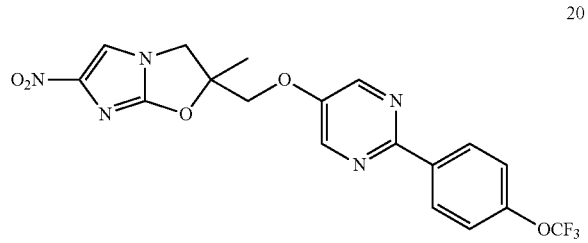

20

Suzuki coupling of chloropyrimidine 108 (see Example 2S) and 4-(trifluoromethoxy)phenylboronic acid as in Example 2S above for 2 h, followed by chromatography of the product on silica gel, eluting with 0-2% Et$_2$O/petroleum ether (foreruns) and then with 2% Et$_2$O/petroleum ether, gave 5-(ethoxymethoxy)-2-[4-(trifluoromethoxy)phenyl]pyrimidine (110) (91%) as a white solid: mp (petroleum ether) 41-43° C.; $^1$H NMR (CDCl$_3$) δ 8.60 (s, 2H), 8.41 (dt, J=9.0, 2.4 Hz, 2H), 7.30 (br dd, J=9.0, 0.9 Hz, 2H), 5.31 (s, 2H), 3.77 (q, J=7.1 Hz, 2H), 1.25 (t, J=7.1 Hz, 3H); HRESIMS calcd for $C_{14}H_{14}F_3N_2O_3$ m/z $[M+H]^+$ 315.0951. found 315.0944.

Ether 110 (379 mg, 1.21 mmol) was treated with 1.25M HCl in MeOH (11 mL) and the mixture was stirred at room temperature for 12 h, and then at 53° C. for 2 h. The resulting cooled solution was diluted with water (50 mL) and extracted with CH$_2$Cl$_2$ (5×50 mL). The combined extracts were evaporated to dryness and the residue was triturated in pentane to give 2-[4-(trifluoromethoxy)phenyl]-5-pyrimidinol (112) (305 mg, 99%) as a white solid: mp (pentane) 156-157° C.; $^1$H NMR (CDCl$_3$) δ 8.45 (s, 2H), 8.38 (dt, J=8.9, 2.4 Hz, 2H), 7.29 (br dd, J=8.9, 0.7 Hz, 2H), 5.60 (br s, 1H); HRESIMS calcd for $C_{11}H_8F_3N_2O_2$ m/z $[M+H]^+$ 257.0532. found 257.0526.

A mixture of 2-bromo-1-[(2-methyl-2-oxiranyl)methyl]-4-nitro-1H-imidazole (105) (obtained in 2 steps from 80, via epoxidation of the corresponding alkene, as reported by Ding et al., WO 2008008480A2) (165 mg, 0.630 mmol) and pyrimidinol 112 (160 mg, 0.625 mmol) in anhydrous DMF (2 mL) under N$_2$ at 0° C. was treated with 60% NaH (33.5 mg, 0.838 mmol), then quickly degassed and resealed under N$_2$. After stirring at room temperature for 10 min, and then at 50° C. for 3 h, the reaction was cooled (CO$_2$/acetone), quenched with ice/aqueous NaHCO$_3$ (5 mL), added to brine (50 mL), and extracted with CH$_2$Cl$_2$ (6×50 mL). The combined extracts were evaporated to dryness and the residue was chromatographed on silica gel. Elution with 0-33% EtOAc/petroleum ether firstly gave foreruns, and then further elution with EtOAc gave a crude mixture of 20 and the non ring-closed alcohol 114 (95 mg). A solution of this mixture in anhydrous DMF (2 mL) under N$_2$ at 0° C. was treated with 60% NaH (6.3 mg, 0.158 mmol), then degassed and resealed under N$_2$, and stirred at 0° C. for 80 min. The reaction was quenched and worked up as before, and then chromatography of the product on silica gel, eluting with 0-2% EtOAc/CH$_2$Cl$_2$ (foreruns) and then with 3-5% EtOAc/CH$_2$Cl$_2$, gave 20 (62 mg, 23%) as a cream solid: mp (MeOH/CH$_2$Cl$_2$/hexane) 223-225° C.; $^1$H NMR [(CD$_3$)$_2$SO] δ 8.66 (s, 2H), 8.40 (dt, J=8.9, 2.4 Hz, 2H), 8.18 (s, 1H), 7.49 (br d, J=8.2 Hz, 2H), 4.59 (d, J=11.1 Hz, 1H), 4.55 (d, J=11.1 Hz, 1H), 4.43 (d, J=11.1 Hz, 1H), 4.23 (d, J=11.0 Hz, 1H), 1.72 (s, 3H). Anal. (C$_{18}$H$_{14}$F$_3$N$_5$O$_5$) C, H, N.

U. Synthesis of 2-({[5-(4-fluorophenyl)-2-pyrazinyl]oxy}methyl)-2-methyl-6-nitro-2,3-dihydroimidazo[2,1-b][1,3]oxazole (Compound 21 of Table 1) by the Method of Scheme 4

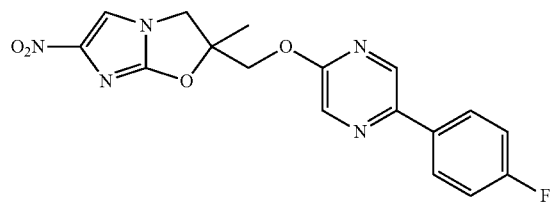

21

A solution of alcohol 101 (see Example 2M) (350 mg, 1.76 mmol) in anhydrous DMF (7 mL) under N$_2$ at 0° C. was treated with 60% NaH (104 mg, 2.60 mmol) and 2,5-dibromopyrazine (837 mg, 3.52 mmol), then quickly degassed and resealed under N$_2$. After stirring at room temperature for 3 h, the reaction was cooled (CO$_2$/acetone), quenched with ice/aqueous NaHCO$_3$ (20 mL), added to brine (80 mL), and extracted with CH$_2$Cl$_2$ (6×100 mL). The combined extracts were evaporated to dryness and the residue was chromatographed on silica gel. Elution with CH$_2$Cl$_2$ firstly gave foreruns, and then further elution with 0-2% EtOAc/CH$_2$Cl$_2$ gave 2-{[(5-bromo-2-pyrazinyl)oxy]methyl}-2-methyl-6-nitro-2,3-dihydroimidazo[2,1-b][1,3]oxazole (104) (428 mg, 68%) as a white solid: mp (MeOH/CH$_2$Cl$_2$/hexane) 198-200° C.; $^1$H NMR [(CD$_3$)$_2$SO] δ 8.44 (d, J=1.3 Hz, 1H), 8.16 (d, J=1.3 Hz, 1H), 8.14 (s, 1H), 4.62 (s, 2H), 4.40 (d, J=11.0 Hz, 1H), 4.19 (d, J=11.0 Hz, 1H), 1.70 (s, 3H). Anal. (C$_{11}$H$_{10}$BrN$_5$O$_4$) C, H, N.

A stirred mixture of bromide 104 (140.2 mg, 0.394 mmol), 4-fluorophenylboronic acid (104 mg, 0.743 mmol) and Pd(dppf)Cl$_2$ (29.8 mg, 40.7 mol) in toluene (6 mL) and EtOH (2.4 mL) was degassed for 8 min (vacuum pump) and then N$_2$ was added. An aqueous solution of 2M Na$_2$CO$_3$ (1.0 mL, 2.0 mmol) was added by syringe and the stirred mixture was again degassed for 8 min, and then N$_2$ was added. The resulting mixture was stirred at 89° C. for 110 min, and then cooled, diluted with aqueous NaHCO$_3$ (50 mL) and extracted with CH$_2$Cl$_2$ (5×50 mL). The extracts were evaporated to dryness and the residue was chromatographed on silica gel. Elution with CH$_2$Cl$_2$ firstly gave foreruns, and then further elution with 2-3% EtOAc/CH$_2$Cl$_2$ gave 21 (112 mg, 77%) as a cream solid: mp (MeOH/CH$_2$Cl$_2$/hexane) 200-201° C.; $^1$H NMR [(CD$_3$)$_2$SO] δ 8.80 (d, J=1.2 Hz, 1H), 8.33 (d, J=1.3 Hz, 1H), 8.17 (s, 1H), 8.08 (br dd, J=8.8, 5.5 Hz, 2H), 7.33 (br t, J=8.9 Hz, 2H), 4.70 (d, J=12.5 Hz, 1H), 4.66 (d, J=12.5 Hz, 1H), 4.43 (d, J=11.1 Hz, 1H), 4.22 (d, J=11.0 Hz, 1H), 1.72 (s, 3H). Anal. (C$_{17}$H$_{14}$FN$_5$O$_4$) C, H, N.

V. Synthesis of 2-methyl-6-nitro-2-[({5-[4-(trifluoromethoxy)phenyl]-2-pyrazinyl}oxy)methyl]-2,3-dihydroimidazo[2,1-b][1,3]oxazole (Compound 22 of Table 1) by the Method of Scheme 4

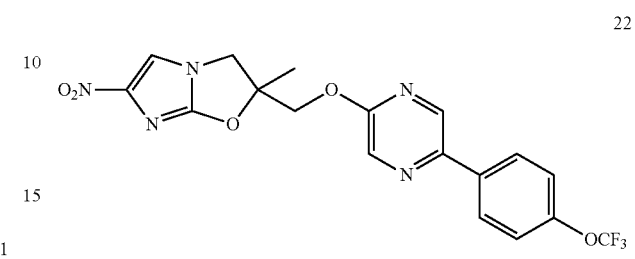

22

Suzuki coupling of bromide 104 and 4-(trifluoromethoxy)phenylboronic acid as in Example 2U, followed by chromatography of the product on silica gel, eluting with CH$_2$Cl$_2$ (foreruns) and then with 1-2.5% EtOAc/CH$_2$Cl$_2$ gave 22 (81%) as a cream solid: mp (MeOH/CH$_2$Cl$_2$/hexane) 222-224° C.; $^1$H NMR [(CD$_3$)$_2$SO] δ 8.85 (d, J=1.3 Hz, 1H), 8.36 (d, J=1.4 Hz, 1H), 8.17 (s, 1H), 8.16 (br d, J=9.1 Hz, 2H), 7.49 (br d, J=8.2 Hz, 2H), 4.69 (s, 2H), 4.44 (d, J=11.0 Hz, 1H), 4.22 (d, J=11.0 Hz, 1H), 1.73 (s, 3H). Anal. (C$_{18}$H$_{14}$F$_3$N$_5$O$_5$) C, H, N.

W. Synthesis of 6-nitro-2-({[4-(trifluoromethoxy)benzyl]oxy}methyl)-2,3-dihydroimidazo[2,1-b][1,3]oxazole (Compound 23 of Table 1) by the Method of Scheme 6

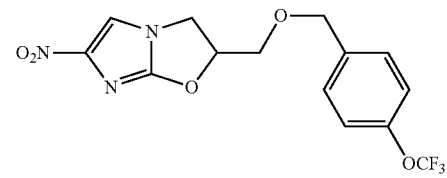

23

A mixture of glycidol (115) (303 mg, 4.09 mmol) and 4-(trifluoromethoxy)benzyl bromide (0.810 mL, 5.06 mmol) in anhydrous DMF (6 mL) under N$_2$ at 0° C. was treated with 60% NaH (246 mg, 6.15 mmol), then quickly degassed and resealed under N$_2$. After stirring at room temperature for 7 h, the mixture was cooled (CO$_2$/acetone), quenched with ice/aqueous NaHCO$_3$ (20 mL), added to water (100 mL) and extracted with EtOAc (4×100 mL). The extracts were washed with brine (100 mL) and evaporated to dryness and the residue was chromatographed on silica gel. Elution with 0-5% Et$_2$O/petroleum ether firstly gave foreruns, and then further elution with 5-10% Et$_2$O/petroleum ether gave 2-({[4-(trifluoromethoxy)benzyl]oxy}methyl)oxirane (116) (625 mg, 62%) as an oil; $^1$H NMR (CDCl$_3$) δ 7.38 (dt, J=8.7, 2.3 Hz, 2H), 7.20 (br dd, J=8.7, 0.7 Hz, 2H), 4.62 (d, J=12.0 Hz, 1H), 4.56 (d, J=12.0 Hz, 1H), 3.82 (dd, J=11.5, 2.8 Hz, 1H), 3.43 (dd, J=11.5, 6.0 Hz, 1H), 3.21 (m, 1H), 2.82 (dd, J=4.9, 4.2 Hz, 1H), 2.63 (dd, J=5.0, 2.7 Hz, 1H); HRESIMS calcd for C$_{11}$H$_{11}$F$_3$NaO$_3$ m/z [M+Na]$^+$ 271.0552. found 271.0557.

Reaction of epoxide 116 with 2-bromo-4(5)-nitroimidazole (80) as in Example 2A at 107° C. for 13 h, followed by chromatography of the product on silica gel, eluting with 0-1% EtOAc/CH$_2$Cl$_2$ (foreruns) and then with 1-2% EtOAc/CH$_2$Cl$_2$, gave 1-(2-bromo-4-nitro-1H-imidazol-1-yl)-3-{[4-(trifluoromethoxy)benzyl]oxy}-2-propanol (118) (61%) as a white solid: mp (CH$_2$Cl$_2$/pentane) 80-81° C.; $^1$H NMR (CDCl$_3$) δ 7.95 (s, 1H), 7.35 (dt, J=8.7, 2.3 Hz, 2H), 7.23 (br d, J=8.7 Hz, 2H), 4.57 (s, 2H), 4.20 (dd, J=13.6, 2.9 Hz, 1H), 4.14 (m, 1H), 4.07 (dd, J=13.4, 7.1 Hz, 1H), 3.59 (dd, J=9.6, 4.2 Hz, 1H), 3.46 (dd, J=9.6, 5.3 Hz, 1H), 2.61 (d, J=5.0 Hz, 1H); HRESIMS calcd for C$_{14}$H$_{14}$BrF$_3$N$_3$O$_5$ m/z [M+H]$^+$ 442.0044, 440.0063. found 442.0044, 440.0061. Anal. (C$_{14}$H$_{13}$BrF$_3$N$_3$O$_5$) H, N, C: calcd, 38.20. found, 38.61.

Ring closure of alcohol 118 with NaH as in Example 2A for 65 min, followed by chromatography of the product on silica gel, eluting with CH$_2$Cl$_2$, gave 23 (90%) as a cream solid: mp (CH$_2$Cl$_2$/hexane) 134-135° C.; $^1$H NMR (CDCl$_3$) δ 7.53 (s, 1H), 7.29 (dt, J=8.7, 2.1 Hz, 2H), 7.20 (br d, J=8.0 Hz, 2H), 5.42 (m, 1H), 4.32 (dd, J=10.0, 8.6 Hz, 1H), 4.26 (dd, J=10.0, 6.5 Hz, 1H), 3.89 (dd, J=11.3, 3.9 Hz, 1H), 3.78 (dd, J=11.3, 3.5 Hz, 1H). Anal. (C$_{14}$H$_{12}$F$_3$N$_3$O$_5$) C, H, N.

X. Synthesis of 2-({[4-(benzyloxy)benzyl]oxy}methyl)-6-nitro-2,3-dihydroimidazo[2,1-b][1,3]oxazole (Compound 24 of Table 1) by the Method of Scheme 6

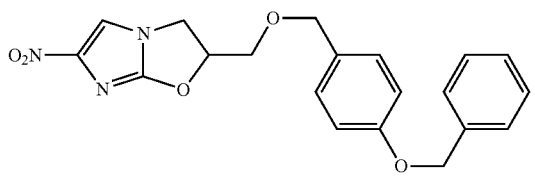

24

Alkylation of glycidol (115) with 4-(benzyloxy)benzyl chloride as in Example 2W for 10 h, followed by chromatography of the product on silica gel, eluting with 0-7.5% Et$_2$O/petroleum ether (foreruns) and then with 7.5-10% Et$_2$O/petroleum ether, gave a crude oil, which was further chromatographed on silica gel. Elution with 0-50% CH$_2$Cl$_2$/petroleum ether firstly gave foreruns, and then further elution with 50-66% CH$_2$Cl$_2$/petroleum ether gave 2-({[4-(benzyloxy)benzyl]oxy}methyl)oxirane (117) (32%) (reported by Cousse et al., EP 187096A1 from epichlorohydrin and 4-(benzyloxy)benzyl alcohol) as an oil; $^1$H NMR (CDCl$_3$) δ 7.45-7.29 (m, 5H), 7.27 (dt, J=8.8, 2.3 Hz, 2H), 6.95 (dt, J=8.7, 2.5 Hz, 2H), 4.54 (d, J=11.6 Hz, 1H), 4.48 (d, J=11.6 Hz, 1H), 3.72 (dd, J=11.5, 3.2 Hz, 1H), 3.42 (dd, J=11.4, 5.8 Hz, 1H), 3.17 (m, 1H), 2.79 (dd, J=5.0, 4.2 Hz, 1H), 2.60 (dd, H=5.1, 2.7 Hz, 1H); HRESIMS calcd for C$_{17}$H$_{18}$NaO$_3$ m/z [M+Na]$^+$ 293.1148. found 293.1143.

Reaction of epoxide 117 with 2-bromo-4(5)-nitroimidazole (80) as in Example 2A at 108° C. for 14 h, followed by chromatography of the product on silica gel, eluting with 0-1% EtOAc/CH$_2$Cl$_2$ (foreruns) and then with 2-4% EtOAc/CH$_2$Cl$_2$, gave 1-{[4-(benzyloxy)benzyl]oxy}-3-(2-bromo-4-nitro-1H-imidazol-1-yl)-2-propanol (119) (73%) as a white solid: mp (CH$_2$Cl$_2$/hexane) 122-123° C.; $^1$H NMR (CDCl$_3$) δ 7.88 (s, 1H), 7.46-7.30 (m, 5H), 7.24 (dt, J=8.6, 2.4 Hz, 2H), 6.98 (dt, J=8.7, 2.4 Hz, 2H), 5.08 (s, 2H), 4.52 (d, J=11.5 Hz, 1H), 4.48 (d, J=11.5 Hz, 1H), 4.18-4.01 (m, 3H), 3.55 (dd, J=9.7, 4.0 Hz, 1H), 3.39 (dd, J=9.6, 5.1 Hz, 1H), 2.48 (d, J=5.3 Hz, 1H). Anal. (C$_{20}$H$_{20}$BrN$_3$O$_5$) C, H, N.

Ring closure of alcohol 119 with NaH as in Example 2A for 80 min, followed by chromatography of the product on silica gel, eluting with CH$_2$Cl$_2$ (foreruns) and then with 1-2% EtOAc/CH$_2$Cl$_2$, gave 24 (88%) as a cream solid: mp (CH$_2$Cl$_2$/hexane) 123-124° C.; $^1$H NMR (CDCl$_3$) δ 7.50 (s, 1H), 7.45-7.29 (m, 5H), 7.19 (dt, J=8.7, 2.4 Hz, 2H), 6.95 (dt, J=8.6, 2.4 Hz, 2H), 5.37 (m, 1H), 4.54 (d, J=11.7 Hz, 1H), 4.50 (d, J=11.7 Hz, 1H), 4.27 (dd, J=10.0, 8.5 Hz, 1H), 4.22 (dd, J=10.0, 6.5 Hz, 1H), 3.82 (dd, J=11.2, 4.2 Hz, 1H), 3.73 (dd, J=11.2, 3.6 Hz, 1H). Anal. (C$_{20}$H$_{19}$N$_3$O$_5$) C, H, N.

Y. Synthesis of 2-methyl-6-nitro-2-({[4-(trifluoromethoxy)benzyl]oxy}methyl)-2,3-dihydroimidazo[2,1-b][1,3]oxazole (Compound 25 of Table 1) by the Method of Scheme 6

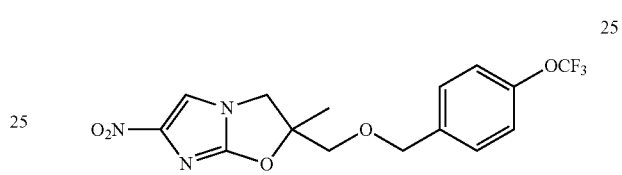

25

A solution of 2-methyl-2-propen-1-ol (120) (2.34 mL, 27.8 mmol) in anhydrous DMF (10 mL, then 2×2 mL to rinse) was added to a suspension of 60% NaH (1.32 g, 33.1 mmol) in anhydrous DMF (10 mL) under N$_2$ at 0° C. and the mixture was stirred at 0° C. for 30 min. 4-(Trifluoromethoxy)benzyl bromide (5.1 mL, 31.9 mmol) was added and the mixture was stirred at room temperature for 21 h. The resulting mixture was added to ice/aqueous NaHCO$_3$ (200 mL) and extracted with 25% EtOAc/petroleum ether (2×200 mL) and 50% EtOAc/petroleum ether (3×200 mL). The extracts were washed with water (200 mL), the volatile solvents were removed, and the residual oil was chromatographed on silica gel. Elution with petroleum ether firstly gave foreruns, then further elution with 0-15% CH$_2$Cl$_2$/petroleum ether gave 1-{[(2-methyl-2-propenyl)oxy]methyl}-4-(trifluoromethoxy)benzene (121) (6.57 g, 96%) as an oil that was used directly in the next step; $^1$H NMR (CDCl$_3$) δ 7.37 (dt, J=8.7, 2.3 Hz, 2H), 7.19 (br d, J=8.0 Hz, 2H), 5.00 (m, 1H), 4.94 (m, 1H), 4.48 (s, 2H), 3.94 (s, 2H), 1.77 (s, 3H).

Epoxidation of alkene 121 with 3-chloroperbenzoic acid as in Example 2G, followed by chromatography of the product on silica gel, eluting with 0-15% CH$_2$Cl$_2$/petroleum ether (foreruns) and then with 15-75% CH$_2$Cl$_2$/petroleum ether and CH$_2$Cl$_2$, gave 2-methyl-2-({[4-(trifluoromethoxy)benzyl]oxy}methyl)oxirane (123) (93%) as an oil; $^1$H NMR (CDCl$_3$) δ 7.37 (dt, J=8.7, 2.4 Hz, 2H), 7.19 (br d, J=7.9 Hz, 2H), 4.59 (d, J=12.1 Hz, 1H), 4.54 (d, J=12.1 Hz, 1H), 3.61 (d, J=11.1 Hz, 1H), 3.44 (d, J=11.1 Hz, 1H), 2.75 (d, J=4.9 Hz, 1H), 2.64 (d, J=4.9 Hz, 1H), 1.40 (s, 3H); HRCIMS (NH$_3$) calcd for C$_{12}$H$_{17}$F$_3$O$_3$N m/z [M+H+NH$_3$]$^+$ 280.1161. found 280.1144.

Reaction of epoxide 123 with 2-bromo-4(5)-nitroimidazole (80) as in Example 2A at 108° C. for 15 h, followed by chromatography of the product on silica gel, eluting with CH$_2$Cl$_2$, gave 1-(2-bromo-4-nitro-1H-imidazol-1-yl)-2-methyl-3-{[4-(trifluoromethoxy)benzyl]oxy}-2-propanol (125) (94%) as a pale yellow oil; $^1$H NMR (CDCl$_3$) δ 8.00 (s, 1H), 7.33 (dt, J=8.6, 2.3 Hz, 2H), 7.22 (br d, J=8.0 Hz, 2H), 4.56 (s, 2H), 4.15 (d, J=14.8 Hz, 1H), 4.04 (d, J=14.5 Hz, 1H), 3.39 (s, 2H), 2.51 (s, 1H), 1.22 (s, 3H); HRESIMS calcd for $C_{15}H_{16}BrF_3N_3O_5$ m/z [M+H]$^+$ 456.0200, 454.0220. found 456.0197, 454.0221.

Ring closure of alcohol 125 with NaH as in Example 2A for 80 min, followed by chromatography of the product on silica gel, eluting with $CH_2Cl_2$ (foreruns) and then with 0-1% EtOAc/$CH_2Cl_2$, gave 25 (87%) as a pale yellow solid: mp ($CH_2Cl_2$/hexane) 110-111° C.; $^1$H NMR (CDCl$_3$) δ 7.50 (s, 1H), 7.26 (br d, J=8.4 Hz, 2H), 7.19 (br d, J=8.3 Hz, 2H), 4.59 (d, J=12.3 Hz, 1H), 4.56 (d, J=12.3 Hz, 1H), 4.36 (d, J=10.0 Hz, 1H), 3.91 (d, J=10.0 Hz, 1H), 3.72 (d, J=10.7 Hz, 1H), 3.59 (d, J=10.6 Hz, 1H), 1.65 (s, 3H). Anal. ($C_{15}H_{14}F_3N_3O_5$) C, H, N.

Z. Synthesis of 2-({[4-(benzyloxy)benzyl]oxy}methyl)-2-methyl-6-nitro-2,3-dihydroimidazo[2,1-b][1,3]oxazole (Compound 26 of Table 1) by the Method of Scheme 6

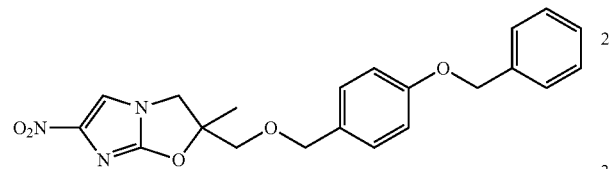

26

A solution of 2-methyl-2-propen-1-ol (120) (1.17 mL, 13.9 mmol) in anhydrous DMF (5 mL, then 2×1 mL to rinse) was added to a suspension of 60% NaH (674 mg, 16.9 mmol) in anhydrous DMF (5 mL) under N$_2$ at 0° C. and the mixture was stirred at 0° C. for 30 min. A solution of 4-(benzyloxy)benzyl chloride (3.87 g, 16.6 mmol) in anhydrous DMF (6 mL, then 2×2 mL to rinse) was added and the mixture was stirred at room temperature for 16 h. The resulting mixture was added to ice/aqueous NaHCO$_3$ (100 mL) and extracted with EtOAc (4×100 mL). The extracts were washed with water (100 mL), the EtOAc was removed, and the residual oil was chromatographed on silica gel. Elution with petroleum ether firstly gave foreruns, then further elution with 0-25% $CH_2Cl_2$/petroleum ether gave 1-(benzyloxy)-4-{[(2-methyl-2-propenyl)oxy]methyl}benzene (122) (reported by Wennerberg et al., 1999 via alkylation of 4-(benzyloxy)benzyl alcohol) (3.48 g, 93%) as an oil that was used directly in the next step; $^1$H NMR (CDCl$_3$) δ 7.45-7.28 (m, 5H), 7.27 (dt, J=8.5, 2.4 Hz, 2H), 6.95 (dt, J=8.7, 2.4 Hz, 2H), 5.07 (s, 2H), 4.99 (m, 1H), 4.91 (m, 1H), 4.42 (s, 2H), 3.91 (s, 2H), 1.76 (s, 3H).

Epoxidation of alkene 122 with 3-chloroperbenzoic acid as in Example 2G for 2.5 h, followed by chromatography of the product on silica gel, eluting with 50% $CH_2Cl_2$/petroleum ether (foreruns) and then with 50-80% $CH_2Cl_2$/petroleum ether and $CH_2Cl_2$, gave 2-({[4-(benzyloxy)benzyl]oxy}methyl)-2-methyloxirane (124) (95%) as an oil: $^1$H NMR (CDCl$_3$) δ 7.45-7.29 (m, 5H), 7.26 (dt, J=8.7, 2.4 Hz, 2H), 6.95 (dt, J=8.7, 2.5 Hz, 2H), 5.07 (s, 2H), 4.52 (d, J=11.6 Hz, 1H), 4.47 (d, J=11.6 Hz, 1H), 3.54 (d, J=11.0 Hz, 1H), 3.42 (d, J=11.0 Hz, 1H), 2.73 (d, J=4.9 Hz, 1H), 2.62 (d, J=4.9 Hz, 1H), 1.39 (s, 3H); HREIMS calcd for $C_{18}H_{20}O_3$ m/z (M$^+$) 284.1412. found 284.1416.

Reaction of epoxide 124 with 2-bromo-4(5)-nitroimidazole (80) as in Example 2A at 108° C. for 16 h, followed by chromatography of the product on silica gel, eluting with $CH_2Cl_2$ (foreruns) and then with 0-2% EtOAc/$CH_2Cl_2$ gave 1-{[4-(benzyloxy)benzyl]oxy}-3-(2-bromo-4-nitro-1H-imidazol-1-yl)-2-methyl-2-propanol (126) (100%) as a light yellow oil; $^1$H NMR (CDCl$_3$) δ 7.94 (s, 1H), 7.46-7.30 (m, 5H), 7.22 (dt, J=8.6, 2.4 Hz, 2H), 6.98 (dt, J=8.7, 2.5 Hz, 2H), 5.08 (s, 2H), 4.50 (d, J=11.5 Hz, 1H), 4.47 (d, J=11.5 Hz, 1H), 4.11 (d, J=14.4 Hz, 1H), 4.00 (d, J=14.4 Hz, 1H), 3.34 (s, 2H), 2.55 (s, 1H), 1.17 (s, 3H); HRESIMS calcd for $C_{21}H_{23}BrN_3O_5$ m/z [M+H]$^+$ 478.0796, 476.0816. found 478.0792, 476.0809.

Ring closure of alcohol 126 with NaH (1.5 equiv.) as in Example 2A for 80 min, followed by chromatography of the product on silica gel, eluting with $CH_2Cl_2$, gave 26 (97%) as a cream solid: mp ($CH_2Cl_2$/hexane) 130-131° C.; $^1$H NMR (CDCl$_3$) δ 7.48 (s, 1H), 7.45-7.29 (m, 5H), 7.16 (dt, J=8.7, 2.4 Hz, 2H), 6.94 (dt, J=8.7, 2.4 Hz, 2H), 5.06 (s, 2H), 4.52 (d, J=11.7 Hz, 1H), 4.47 (d, J=11.7 Hz, 1H), 4.32 (d, J=10.0 Hz, 1H), 3.86 (d, J=10.0 Hz, 1H), 3.67 (d, J=10.6 Hz, 1H), 3.53 (d, J=10.6 Hz, 1H), 1.62 (s, 3H). Anal. ($C_{21}H_{21}N_3O_5$) C, H, N.

AA. Synthesis of 2-nitro-7-{[4-(trifluoromethoxy)phenoxy]methyl}-6,7-dihydro-5H-imidazo[2,1-b][1,3]oxazine (Compound 27 of Table 1) by the Method of Scheme 7

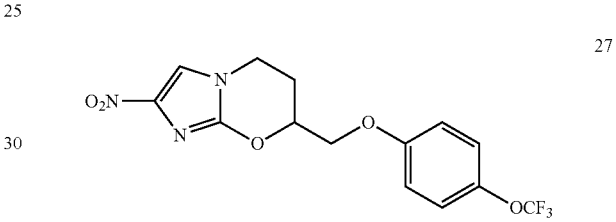

27

4-Bromo-1-butene (2.65 mL, 26.1 mmol) was added to a mixture of 2-chloro-4(5)-nitroimidazole (81) (2.50 g, 17.0 mmol) and K$_2$CO$_3$ (7.88 g, 57.0 mmol) in anhydrous DMF (12 mL) under N$_2$, and the mixture was stirred at 66° C. for 12 h. The resulting cooled mixture was added to ice/aqueous NaHCO$_3$ (140 mL) and extracted with 50% EtOAc/petroleum ether (5×100 mL). The extracts were washed with water (100 mL) and then evaporated to dryness and the residue was chromatographed on silica gel. Elution with 0-10% EtOAc/petroleum ether firstly gave foreruns, and then further elution with 10-20% EtOAc/petroleum ether gave 1-(3-butenyl)-2-chloro-4-nitro-1H-imidazole (127) (2.82 g, 82%) as a cream solid: mp (Et$_2$O/pentane) 56-58° C.; $^1$H NMR (CDCl$_3$) δ 7.72 (s, 1H), 5.74 (ddt, J=17.1, 10.2, 6.9 Hz, 1H), 5.18 (dq, J=10.3, 1.0 Hz, 1H), 5.12 (dq, J=17.1, 1.3 Hz, 1H), 4.09 (t, J=6.9 Hz, 2H), 2.58 (qt, J=6.9, 1.1 Hz, 2H); HRESIMS calcd for $C_7H_9ClN_3O_2$ m/z [M+H]$^+$ 204.0349, 202.0378. found 204.0350, 202.0377.

Epoxidation of alkene 127 with 3-chloroperbenzoic acid as in Example 2G for 50 h, followed by chromatography of the product on silica gel, eluting with 0-10% EtOAc/petroleum ether (foreruns) and then with 20-30% EtOAc/petroleum ether, firstly gave recovered alkene 127 (0.49 g, 17%). Elution with 0-5% Et$_2$O/CH$_2$Cl$_2$ gave a crude product, which was further chromatographed on silica gel, eluting with $CH_2Cl_2$ (foreruns) and then with 0-5% Et$_2$O/CH$_2$Cl$_2$, to give 2-chloro-4-nitro-1-[2-(2-oxiranyl)ethyl]-1H-imidazole (129) (73%) as a pale yellow solid: mp ($CH_2Cl_2$/hexane) 51-52° C.; $^1$H NMR (CDCl$_3$) δ 7.81 (s, 1H), 4.28-4.16 (m, 2H), 2.98-2.92 (m, 1H), 2.85 (dd, J=4.7, 4.0 Hz, 1H), 2.53 (dd, J=4.8, 2.6 Hz, 1H), 2.35-2.25 (m, 1H), 1.87-1.77 (m, 1H); HRESIMS calcd for $C_7H_9ClN_3O_3$ m/z [M+H]$^+$ 220.0298, 218.0327. found 220.0297, 218.0322.

4-Trifluoromethoxyphenol (0.375 mL, 2.89 mmol) was added to a mixture of epoxide 129 (250 mg, 1.15 mmol) and powdered K$_2$CO$_3$ (558 mg, 4.04 mmol) in anhydrous 2-butanone (3 mL) under N$_2$, and the mixture was stirred at 81° C. for 12 h. The resulting cooled mixture was diluted with water (50 mL) and extracted with CH$_2$Cl$_2$ (4×50 mL). The extracts were evaporated to dryness and the residue was chromatographed on silica gel. Elution with 0-25% EtOAc/petroleum ether firstly gave foreruns, and then further elution with 25-33% EtOAc/petroleum ether gave 4-(2-chloro-4-nitro-1H-imidazol-1-yl)-1-[4-(trifluoromethoxy)phenoxy]-2-butanol (130) (306 mg, 67%) as a pale yellow oil; $^1$H NMR (CDCl$_3$) δ 7.85 (s, 1H), 7.16 (br dd, J=9.1, 0.8 Hz, 2H), 6.88 (dt, J=9.2, 3.0 Hz, 2H), 4.37-4.24 (m, 2H), 4.02-3.93 (m, 2H), 3.86 (dd, J=10.0, 7.8 Hz, 1H), 2.47 (dd, J=4.2, 1.1 Hz, 1H), 2.13-1.98 (m, 2H); HRESIMS calcd for C$_{14}$H$_{14}$ClF$_3$N$_3$O$_3$ m/z [M+H]$^+$ 398.0540, 396.0569. found 398.0538, 396.0567.

Further elution of the above column with 66% EtOAc/petroleum ether gave a crude solid (72 mg), which was further chromatographed on silica gel. Elution with CH$_2$Cl$_2$ gave foreruns and then further elution with 0-3% EtOAc/CH$_2$Cl$_2$ gave 27 (61 mg, 15%) as a cream solid: mp (CH$_2$Cl$_2$/hexane) 138-140° C.; $^1$H NMR (CDCl$_3$) δ 7.45 (s, 1H), 7.17 (br dd, J=9.1, 0.7 Hz, 2H), 6.91 (dt, J=9.2, 3.0 Hz, 2H), 4.75 (m, 1H), 4.31 (dd, J=10.2, 4.3 Hz, 1H), 4.26-4.09 (m, 3H), 2.52-2.32 (m, 2H). Anal. (C$_{14}$H$_{12}$F$_3$N$_3$O$_5$) C, H, N.

A stirred solution of alcohol 130 (305 mg, 0.771 mmol) in anhydrous DMF (5 mL) under N$_2$ at 0° C. was treated with 60% NaH (49 mg, 1.23 mmol), then quickly degassed and resealed under N$_2$. After stirring at room temperature for 2.5 h, the reaction was cooled (CO$_2$/acetone), quenched with ice/aqueous NaHCO$_3$ (10 mL), added to brine (40 mL), and extracted with CH$_2$Cl$_2$ (6×50 mL). The combined extracts were evaporated to dryness and the residue was chromatographed on silica gel. Elution with 25-40% EtOAc/petroleum ether firstly gave foreruns, and then further elution with 50-66% EtOAc/petroleum ether gave additional 27 (217 mg, 78%) as a pale yellow solid (see data above).

BB. Synthesis of 7-{[4-(benzyloxy)phenoxy]methyl}-2-nitro-6,7-dihydro-5H-imidazo[2,1-b][1,3]oxazine (Compound 28 of Table 1) by the Method of Scheme 7

28

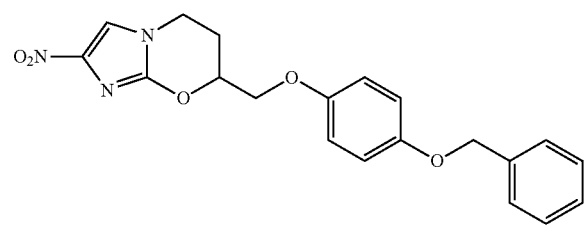

A mixture of 2-bromo-4(5)-nitroimidazole (80) (2.50 g, 13.0 mmol), 4-bromo-1-butene (2.00 mL, 19.7 mmol) and K$_2$CO$_3$ (5.39 g, 39.0 mmol) in anhydrous DMF (25 mL) under N$_2$ was stirred at 73° C. for 4.5 h. The resulting cooled mixture was added to ice/aqueous NaHCO$_3$ (200 mL) and extracted with EtOAc (4×200 mL). The extracts were washed with water (200 mL) and then evaporated to dryness and the residue was chromatographed on silica gel. Elution with 0-10% EtOAc/petroleum ether firstly gave foreruns, and then further elution with 20% EtOAc/petroleum ether gave 2-bromo-1-(3-butenyl)-4-nitro-1H-imidazole (128) (2.96 g, 92%) as a pale yellow waxy solid: mp 28-30° C.; $^1$H NMR (CDCl$_3$) δ 7.77 (s, 1H), 5.75 (ddt, J=17.1, 10.2, 6.9 Hz, 1H), 5.18 (dq, J=10.2, 1.1 Hz, 1H), 5.12 (dq, J=17.1, 1.4 Hz, 1H), 4.09 (t, J=7.0 Hz, 2H), 2.59 (qt, J=6.9, 1.2 Hz, 2H); HRFABMS calcd for C$_7$H$_9$BrN$_3$O$_2$ m/z [M+H]$^+$ 247.9858, 245.9878. found 247.9860, 245.9882.

Osmium tetroxide (3.75 mL of a 4% aqueous solution, 0.614 mmol) was added to a solution of alkene 128 (3.00 g, 12.2 mmol) and 4-methylmorpholine N-oxide (2.16 g, 18.4 mmol) in CH$_2$Cl$_2$ (75 mL), and then the mixture was stirred at room temperature for 4 h. The resulting precipitate was isolated by filtration, washed with CH$_2$Cl$_2$ and water, and then dried to give 4-(2-bromo-4-nitro-1H-imidazol-1-yl)-1,2-butanediol (131) (2.39 g, 70%) as a cream solid: mp (THF/Et$_2$O/pentane) 99-101° C.; $^1$H NMR [(CD$_3$)$_2$SO] δ 8.55 (s, 1H), 4.77 (d, J=5.0 Hz, 1H), 4.58 (t, J=5.6 Hz, 1H), 4.14 (m, 2H), 3.42 (m, 1H), 3.34 (dt, J=10.7, 5.4 Hz, 1H), 3.24 (dt, J=10.7, 5.9 Hz, 1H), 1.98 (dtd, J=13.7, 7.9, 3.2 Hz, 1H), 1.69 (dddd, J=13.6, 9.1, 7.4, 6.0 Hz, 1H). Anal. (C$_7$H$_{10}$BrN$_3$O$_4$) C, H, N.

The filtrate above was added to ice/aqueous Na$_2$SO$_3$ (100 mL) and extracted with EtOAc (3×100 mL). The aqueous portion was saturated with salt and further extracted with EtOAc (7×100 mL). The combined extracts were evaporated to dryness and the residue was chromatographed on silica gel. Elution with 50-67% EtOAc/petroleum ether firstly gave foreruns, and then further elution with 67% EtOAc/petroleum ether and EtOAc gave additional diol 131 (728 mg, 21%).

Triisopropylsilyl chloride (2.50 mL, 11.7 mmol) was added to a solution of diol 131 (3.11 g, 11.1 mmol) and imidazole (1.66 g, 24.4 mmol) in anhydrous DMF (30 mL) under N$_2$ and then the mixture was stirred at room temperature for 18 h. The resulting mixture was added to ice-water (200 mL) and extracted with EtOAc (4×200 mL). The extracts were washed with water (200 mL) and then evaporated to dryness and the residue was chromatographed on silica gel. Elution with 0-20% EtOAc/petroleum ether firstly gave foreruns, and then further elution with 20-33% EtOAc/petroleum ether gave 4-(2-bromo-4-nitro-1H-imidazol-1-yl)-1-[(triisopropylsilyl)oxy]-2-butanol (132) (4.60 g, 95%) as a white solid: mp (CH$_2$Cl$_2$/pentane) 90-91° C.; $^1$H NMR (CDCl$_3$) δ 7.89 (s, 1H), 4.24 (dd, J=7.7, 6.2 Hz, 2H), 3.74 (dd, J=9.6, 3.5 Hz, 1H), 3.62 (m, 1H), 3.53 (dd, J=9.6, 6.8 Hz, 1H), 2.59 (d, J=3.8 Hz, 1H), 1.95-1.82 (m, 2H), 1.17-1.03 (m, 21H). Anal. (C$_{16}$H$_{30}$BrN$_3$O$_4$Si) C, H, N.

A stirred solution of alcohol 132 (2.45 g, 5.61 mmol) in anhydrous DMF (25 mL) under N$_2$ at 0° C. was treated with 60% NaH (388 mg, 9.70 mmol), then quickly degassed and resealed under N$_2$. After stirring at room temperature for 2 h, the reaction was cooled (CO$_2$/acetone), quenched with ice/aqueous NaHCO$_3$ (20 mL), diluted with ice-water (150 mL) and extracted with EtOAc (8×80 mL). The extracts were washed with brine (100 mL) and then evaporated to dryness and the residue was chromatographed on silica gel. Elution with 0-25% EtOAc/petroleum ether firstly gave foreruns, and then further elution with 25% EtOAc/petroleum ether gave 2-nitro-7-{[(triisopropylsilyl)oxy]methyl}-6,7-dihydro-5H-imidazo[2,1-b][1,3]oxazine (133) (1.77 g, 89%) as a pale yellow solid: mp (CH$_2$Cl$_2$/pentane) 121-123° C.; $^1$H NMR (CDCl$_3$) δ 7.42 (s, 1H), 4.45 (m, 1H), 4.17 (ddd, J=12.3, 5.8, 3.7 Hz, 1H), 4.06 (ddd, J=12.3, 10.3, 5.4 Hz, 1H), 4.03 (dd, J=10.7, 4.1 Hz, 1H), 3.95 (dd, J=10.7, 5.8 Hz, 1H), 2.37 (dddd, J=14.5, 5.5, 3.6, 2.8 Hz, 1H), 2.27 (dtd, J=14.5, 10.1, 5.8 Hz, 1H), 1.17-1.03 (m, 21H). Anal. (C$_{16}$H$_{29}$N$_3$O$_4$Si) C, H, N.

A suspension of silyl ether 133 (1.627 g, 4.58 mmol) in a solution of 1% HCl in 95% EtOH (desilylation conditions described by Cunico et al., 1980) (58 mL) was stirred at room temperature for 35 h. The resulting solution was cooled ($CO_2$/acetone), neutralised by dropwise addition of 7 M $NH_3$ in MeOH (7 mL) with stirring, and then concentrated to dryness and the residue was chromatographed on silica gel. Elution with 0-2% MeOH/$CH_2Cl_2$ firstly gave foreruns, and then further elution with 2% MeOH/$CH_2Cl_2$ gave (2-nitro-6,7-dihydro-5H-imidazo[2,1-b][1,3]oxazin-7-yl)methanol (134) (877 mg, 96%) as a pale yellow solid: mp (THF/MeOH/$CH_2Cl_2$/hexane) 179-181° C.; $^1$H NMR [$(CD_3)_2SO$] δ 8.04 (s, 1H), 5.12 (t, J=5.8 Hz, 1H), 4.48 (dtd, J=10.2, 4.7, 2.5 Hz, 1H), 4.13 (ddd, J=12.5, 5.8, 3.0 Hz, 1H), 4.04 (ddd, J=12.4, 11.0, 5.1 Hz, 1H), 3.64 (m, 2H), 2.18 (dtd, J=14.4, 5.0, 2.8 Hz, 1H), 2.03 (dtd, J=14.4, 10.6, 5.7 Hz, 1H). Anal. ($C_7H_9N_3O_4$) C, H, N.

Diethylazodicarboxylate (0.070 mL, 0.45 mmol) was added dropwise to a suspension of alcohol 134 (52.4 mg, 0.263 mmol), triphenylphosphine (104 mg, 0.397 mmol), and 4-(benzyloxy)phenol (79.5 mg, 0.397 mmol) in anhydrous THF (1.0 mL) and the resulting mixture was stirred at room temperature for 51 h. The solvent was removed and the residue was chromatographed on silica gel. Elution with 0-1% EtOAc/$CH_2Cl_2$ firstly gave foreruns, and then further elution with 4% EtOAc/$CH_2Cl_2$ gave a crude solid, which was further chromatographed on silica gel. Elution with 0-33% EtOAc/petroleum ether firstly gave foreruns, and then further elution with 4% MeOH/$CH_2Cl_2$ gave 28 (36 mg, 36%) as a cream solid: mp (MeOH/$CH_2Cl_2$/hexane) 222-224° C.; $^1$H NMR [$(CD_3)_2SO$] δ 8.07 (s, 1H), 7.46-7.28 (m, 5H), 6.99-6.89 (m, 4H), 4.86 (m, 1H), 4.27-4.14 (m, 3H), 4.09 (ddd, J=12.5, 10.9, 5.2 Hz, 1H), 2.35-2.25 (m, 1H), 2.25-2.12 (m, 1H). Anal. ($C_{20}H_{19}N_3O_5 \cdot 0.25H_2O$) C, H, N.

CC. Synthesis of 7-{[(4'-fluoro[1,1'-biphenyl]-4-yl)oxy]methyl}-2-nitro-6,7-dihydro-5H-imidazo[2,1-b][1,3]oxazine (Compound 29 of Table 1) by the Method of Scheme 7

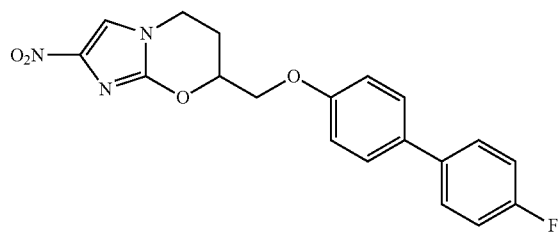

29

Diethylazodicarboxylate (0.070 mL, 0.45 mmol) was added dropwise to a suspension of oxazine alcohol 134 (see Example 2BB above) (251 mg, 1.26 mmol), triphenylphosphine (448 mg, 1.71 mmol), and 4-iodophenol (377 mg, 1.71 mmol) in anhydrous THF (3.0 mL) at 0° C. under $N_2$, and the resulting mixture was stirred at room temperature for 32 h. The solvent was removed and the residue was chromatographed on silica gel. Elution with $CH_2Cl_2$ firstly gave foreruns, and then further elution with 0-2% EtOAc/$CH_2Cl_2$ gave a crude solid, which was further chromatographed on silica gel. Elution with 0-50% EtOAc/petroleum ether firstly gave foreruns, and then further elution with 10% MeOH/$CH_2Cl_2$ gave 7-[(4-iodophenoxy)methyl]-2-nitro-6,7-dihydro-5H-imidazo[2,1-b][1,3]oxazine (135) (433 mg, 86%) as a cream solid: mp (MeOH/$CH_2Cl_2$/hexane) 224-227° C.; $^1$H NMR [$(CD_3)_2SO$] δ 8.08 (s, 1H), 7.62 (dt, J=9.0, 2.7 Hz, 2H), 6.86 (dt, J=9.0, 2.7 Hz, 2H), 4.89 (m, 1H), 4.31 (dd, J=11.1, 3.4 Hz, 1H), 4.25 (dd, J=11.1, 5.8 Hz, 1H), 4.18 (ddd, J=12.6, 5.8, 3.0 Hz, 1H), 4.09 (ddd, J=12.5, 10.8, 5.2 Hz, 1H), 2.35-2.26 (m, 1H), 2.25-2.12 (m, 1H). Anal. ($C_{13}H_{12}IN_3O_4$) C, H, N.

A stirred mixture of iodide 135 (50.1 mg, 0.125 mmol), 4-fluorophenylboronic acid (31.5 mg, 0.225 mmol) and Pd(dppf)$Cl_2$ (14.1 mg, 0.019 mmol) in toluene (1 mL), EtOH (0.6 mL) and DMF (1.5 mL) was degassed for 5 min (vacuum pump) and then $N_2$ was added. An aqueous solution of 2M $Na_2CO_3$ (0.40 mL, 0.80 mmol) was added by syringe and the stirred mixture was again degassed for 5 min, and then $N_2$ was added. The resulting mixture was stirred at 90° C. for 90 min, and then cooled, diluted with aqueous $NaHCO_3$ (50 mL) and extracted with $CH_2Cl_2$ (4×50 mL). The extracts were evaporated to dryness and the residue was chromatographed on silica gel. Elution with 0-1% EtOAc/$CH_2Cl_2$ firstly gave foreruns, and then further elution with 1-2% EtOAc/$CH_2Cl_2$ gave 29 (42 mg, 91%) as a cream solid: mp (MeOH/$CH_2Cl_2$/pentane) 217-219° C.; $^1$H NMR [$(CD_3)_2SO$] δ 8.09 (s, 1H), 7.66 (ddt, J=8.9, 5.4, 2.7 Hz, 2H), 7.60 (dt, J=8.8, 2.6 Hz, 2H), 7.25 (tt, J=8.9, 2.7 Hz, 2H), 7.09 (dt, J=8.8, 2.6 Hz, 2H), 4.93 (m, 1H), 4.37 (dd, J=11.1, 3.4 Hz, 1H), 4.32 (dd, J=11.1, 5.7 Hz, 1H), 4.20 (ddd, J=12.6, 5.8, 3.0 Hz, 1H), 4.11 (ddd, J=12.5, 10.8, 5.2 Hz, 1H), 2.38-2.30 (m, 1H), 2.29-2.16 (m, 1H). Anal. ($C_{19}H_{16}FN_3O_4$) C, H, N.

DD. Synthesis of 2-nitro-7-({[4'-(trifluoromethyl)[1,1'-biphenyl]-4-yl]oxy}methyl)-6,7-dihydro-5H-imidazo[2,1-b][1,3]oxazine (Compound 30 of Table 1) by the Method of Scheme 7

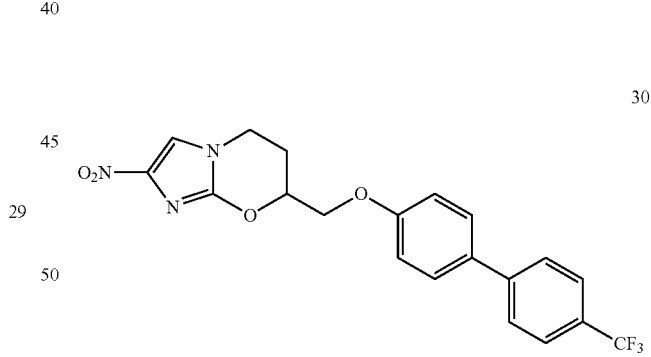

30

Suzuki coupling of iodide 135 and 4-(trifluoromethyl)phenylboronic acid as in Example 2CC above, followed by chromatography of the product on silica gel, eluting with 0-1% EtOAc/$CH_2Cl_2$ (foreruns) and then with 1-2% EtOAc/$CH_2Cl_2$, gave 30 (88%) as a cream solid: mp (MeOH/$CH_2Cl_2$/pentane) 242-245° C.; $^1$H NMR [$(CD_3)_2SO$] δ 8.09 (s, 1H), 7.86 (br d, J=8.2 Hz, 2H), 7.77 (br d, J=8.3 Hz, 2H), 7.72 (dt, J=8.9, 2.5 Hz, 2H), 7.14 (dt, J=8.8, 2.5 Hz, 2H), 4.94 (m, 1H), 4.40 (dd, J=11.1, 3.4 Hz, 1H), 4.34 (dd, J=11.1, 5.8 Hz, 1H), 4.21 (ddd, J=12.5, 5.8, 3.0 Hz, 1H), 4.12 (ddd, J=12.5, 10.9, 5.2 Hz, 1H), 2.39-2.30 (m, 1H), 2.29-2.17 (m, 1H). Anal. ($C_{20}H_{16}F_3N_3O_4$) C, H, N.

EE. Synthesis of 2-nitro-7-({[4'-(trifluoromethoxy) [1,1'-biphenyl]-4-yl]oxy}methyl)-6,7-dihydro-5H-imidazo[2,1-b][1,3]oxazine (Compound 31 of Table 1) by the Method of Scheme 7

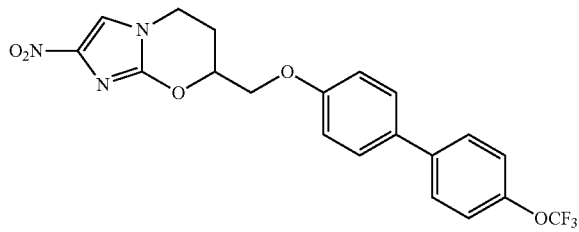

Suzuki coupling of iodide 135 and 4-(trifluoromethoxy) phenylboronic acid as in Example 2CC above, followed by chromatography of the product on silica gel, eluting with 0-1% EtOAc/CH$_2$Cl$_2$ (foreruns) and then with 1-2% EtOAc/CH$_2$Cl$_2$, gave 31 (89%) as a cream solid: mp (CH$_2$Cl$_2$/pentane) 197-199° C.; $^1$H NMR [(CD$_3$)$_2$SO] δ 8.12 (s, 1H), 7.75 (dt, J=8.8, 2.5 Hz, 2H), 7.65 (dt, J=8.9, 2.5 Hz, 2H), 7.42 (br d, J=8.0 Hz, 2H), 7.11 (dt, J=8.9, 2.5 Hz, 2H), 4.94 (m, 1H), 4.38 (dd, J=11.1, 3.3 Hz, 1H), 4.32 (dd, J=11.1, 5.8 Hz, 1H), 4.20 (ddd, J=12.5, 5.7, 2.8 Hz, 1H), 4.11 (ddd, J=12.4, 11.0, 5.1 Hz, 1H), 2.38-2.29 (m, 1H), 2.28-2.15 (m, 1H). Anal. (C$_{20}$H$_{16}$F$_3$N$_3$O$_5$) C, H, N.

FF. Synthesis of 7-({[5-(4-fluorophenyl)-2-pyridinyl]oxy}methyl)-2-nitro-6,7-dihydro-5H-imidazo[2,1-b][1,3]oxazine (Compound 32 of Table 1) by the Method of Scheme 8

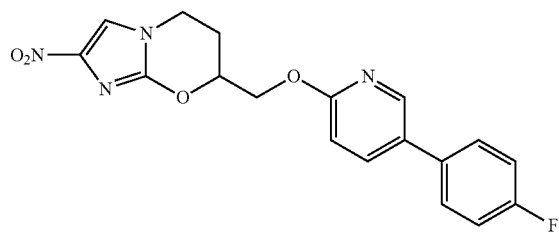

5-Bromo-2-fluoropyridine (91) (0.52 mL, 5.05 mmol) was added to a solution of oxazine alcohol 134 (see Example 2BB) (500 mg, 2.51 mmol) in anhydrous DMF (10 mL) under N$_2$ at 0° C. The resulting mixture was treated with 60% NaH (151 mg, 3.78 mmol), then quickly degassed and resealed under N$_2$. Further 5-bromo-2-fluoropyridine (91) (0.52 mL, 5.05 mmol) was added and the mixture was stirred at room temperature for 2.5 h, and then cooled (CO$_2$/acetone), quenched with ice/aqueous NaHCO$_3$ (30 mL), added to brine (100 mL) and extracted with CH$_2$Cl$_2$ (8×100 mL). The combined extracts were evaporated to dryness and the residue was chromatographed on silica gel. Elution with 0-1% EtOAc/CH$_2$Cl$_2$ firstly gave foreruns, and then further elution with 2-4% EtOAc/CH$_2$Cl$_2$ gave 7-{[(5-bromo-2-pyridinyl)oxy]methyl}-2-nitro-6,7-dihydro-5H-imidazo[2,1-b][1,3]oxazine (136) (778 mg, 87%) as a white solid: mp (MeOH/CH$_2$Cl$_2$/hexane) 182-184° C.; $^1$H NMR [(CD$_3$)$_2$SO] δ 8.30 (dd, J=2.6, 0.5 Hz, 1H), 8.07 (s, 1H), 7.95 (dd, J=8.8, 2.6 Hz, 1H), 6.91 (dd, J=8.8, 0.6 Hz, 1H), 4.90 (m, 1H), 4.58 (dd, J=12.0, 3.3 Hz, 1H), 4.52 (dd, J=12.0, 6.0 Hz, 1H), 4.17 (ddd, J=12.6, 5.8, 2.8 Hz, 1H), 4.09 (ddd, J=12.5, 11.0, 5.2 Hz, 1H), 2.34-2.26 (m, 1H), 2.23-2.11 (m, 1H). Anal. (C$_{12}$H$_{11}$BrN$_4$O$_4$) C, H, N.

Suzuki coupling of bromide 136 and 4-fluorophenylboronic acid (2.0 equiv.) as in Example 2M for 2.5 h, followed by chromatography of the product on silica gel, eluting with 0-3% EtOAc/CH$_2$Cl$_2$ (foreruns) and then with 3% EtOAc/CH$_2$Cl$_2$, gave 32 (91%) as a cream solid: mp (MeOH/CH$_2$Cl$_2$/hexane) 180-181° C.; $^1$H NMR [(CD$_3$)$_2$SO] δ 8.47 (dd, J=2.5, 0.5 Hz, 1H), 8.09 (s, 1H), 8.05 (dd, J=8.6, 2.6 Hz, 1H), 7.72 (ddt, J=8.9, 5.4, 2.7 Hz, 2H), 7.30 (tt, J=8.9, 2.7 Hz, 2H), 6.98 (dd, J=8.6, 0.6 Hz, 1H), 4.94 (m, 1H), 4.64 (dd, J=12.0, 3.4 Hz, 1H), 4.58 (dd, J=12.0, 6.1 Hz, 1H), 4.19 (ddd, J=12.6, 5.8, 2.7 Hz, 1H), 4.10 (ddd, J=12.4, 11.1, 5.1 Hz, 1H), 2.37-2.28 (m, 1H), 2.26-2.13 (m, 1H); APCI MS m/z 371 [M+H]$^+$.

GG. Synthesis of 2-nitro-7-[({5-[4-(trifluoromethoxy)phenyl]-2-pyridinyl}oxy)methyl]-6,7-dihydro-5H-imidazo[2,1-b][1,3]oxazine (Compound 33 of Table 1) by the Method of Scheme 8

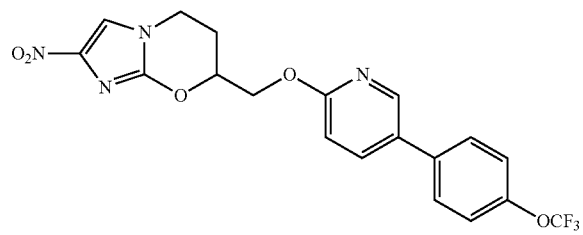

Suzuki coupling of bromide 136 and 4-(trifluoromethoxy) phenylboronic acid as in Example 2M for 2.5 h, followed by chromatography of the product on silica gel, eluting with CH$_2$Cl$_2$ (foreruns) and then with 0-2.5% EtOAc/CH$_2$Cl$_2$, gave 33 (90%) as a cream solid: mp (CH$_2$Cl$_2$/hexane) 161-163° C.; $^1$H NMR (CDCl$_3$) δ 8.32 (d, J=2.0 Hz, 1H), 7.79 (dd, J=8.5, 2.5 Hz, 1H), 7.53 (br d, J=8.7 Hz, 2H), 7.45 (s, 1H), 7.30 (br d, J=8.1 Hz, 2H), 6.86 (d, J=8.6 Hz, 1H), 4.84 (m, 1H), 4.72 (dd, J=11.7, 5.1 Hz, 1H), 4.66 (dd, J=11.7, 4.9 Hz, 1H), 4.21 (ddd, J=12.4, 5.8, 3.4 Hz, 1H), 4.13 (ddd, J=12.4, 10.4, 5.5 Hz, 1H), 2.48-2.30 (m, 2H). Anal. (C$_{19}$H$_{15}$F$_3$N$_4$O$_5$) C, H, N.

HH. Synthesis of 7-({[6-(4-fluorophenyl)-3-pyridinyl]oxy}methyl)-2-nitro-6,7-dihydro-5H-imidazo[2,1-b][1,3]oxazine (Compound 34 of Table 1) by the Method of Scheme 8

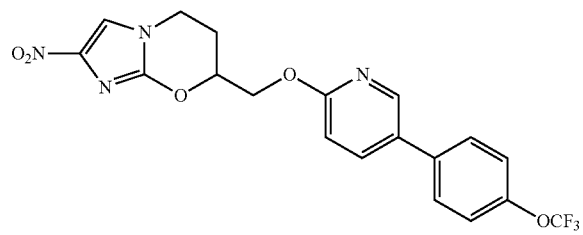

A mixture of epoxide 129 (see Example 2AA) (1.004 g, 4.61 mmol), 6-bromo-3-pyridinol (4.015 g, 23.1 mmol) and powdered K$_2$CO$_3$ (3.319 g, 24.0 mmol) in anhydrous 2-butanone (10 mL) under N₂ was stirred at 82-85° C. for 28 h. The resulting cooled mixture was diluted with water (100 mL) and extracted with 25% EtOAc/CH₂Cl₂ (3×100 mL). The extracts were evaporated to dryness and the residue was chromatographed on silica gel. Elution with 0-40% EtOAc/petroleum ether firstly gave foreruns, and then further elution with 40% EtOAc/petroleum ether gave 1-[(6-bromo-3-pyridinyl)oxy]-4-(2-chloro-4-nitro-1H-imidazol-1-yl)-2-butanol (137) (667 mg, 37%) as a cream solid: mp (MeOH/CH₂Cl₂/pentane) 112-114° C.; $^1$H NMR [(CD₃)₂SO] δ 8.56 (s, 1H), 8.12 (d, J=3.1 Hz, 1H), 7.53 (d, J=8.8 Hz, 1H), 7.39 (dd, J=8.8, 3.2 Hz, 1H), 5.28 (br d, J=4.5 Hz, 1H), 4.24 (dd, J=14.0, 5.8 Hz, 1H), 4.18 (dd, J=14.2, 7.3 Hz, 1H), 3.99 (dd, J=10.0, 4.9 Hz, 1H), 3.96 (dd, J=10.0, 5.5 Hz, 1H), 3.82 (m, 1H), 2.06 (dtd, J=13.9, 7.7, 3.4 Hz, 1H), 1.90 (ddt, J=13.7, 9.2, 6.7 Hz, 1H); HRES-IMS calcd for C₁₂H₁₃BrClN₄O₄ m/z [M+H]⁺ 394.9754, 392.9782, 390.9803. found 394.9753, 392.9777, 390.9797.

Further elution of the above column with EtOAc gave crude ring-closed material, which was further chromatographed on silica gel. Elution with 0-0.5% MeOH/CH₂Cl₂ firstly gave foreruns and then further elution with 0.5% MeOH/CH₂Cl₂ gave 7-{[(6-bromo-3-pyridinyl)oxy]methyl}-2-nitro-6,7-dihydro-5H-imidazo[2,1-b][1,3]oxazine (138) (51 mg, 3%) as a cream solid: mp (MeOH/CH₂Cl₂/hexane) 200-202° C.; $^1$H NMR [(CD₃)₂SO] δ 8.19 (d, J=3.2 Hz, 1H), 8.08 (s, 1H), 7.58 (d, J=8.7 Hz, 1H), 7.47 (dd, J=8.8, 3.2 Hz, 1H), 4.92 (m, 1H), 4.43 (dd, J=11.2, 3.3 Hz, 1H), 4.37 (dd, J=11.2, 5.8 Hz, 1H), 4.19 (ddd, J=12.5, 5.8, 3.0 Hz, 1H), 4.10 (ddd, J=12.5, 10.9, 5.2 Hz, 1H), 2.36-2.27 (m, 1H), 2.26-2.13 (m, 1H). Anal. (C₁₂H₁₁BrN₄O₄) C, H, N.

Ring closure of alcohol 137 with NaH (1.6 equiv.) as in Example 2AA followed by chromatography of the product on silica gel, eluting with 0-0.5% MeOH/CH₂Cl₂ (foreruns) and then with 0.5-0.75% MeOH/CH₂Cl₂, gave additional 138 (87%) as a pale yellow solid (see above).

Suzuki coupling of bromide 138 and 4-fluorophenylboronic acid as in Example 2M for 2.5 h, followed by chromatography of the product on silica gel, eluting with 0-0.5% MeOH/CH₂Cl₂ (foreruns) and then with 0.5% MeOH/CH₂Cl₂, gave 34 (87%) as a cream solid: mp (MeOH/CH₂Cl₂/hexane) 204-206° C.; $^1$H NMR [(CD₃)₂SO] δ 8.43 (br d, J=2.7 Hz, 1H), 8.11 (s, 1H), 8.07 (ddt, J=8.9, 5.6, 2.7 Hz, 2H), 7.94 (br d, J=8.7 Hz, 1H), 7.56 (dd, J=8.8, 3.0 Hz, 1H), 7.28 (tt, J=8.9, 2.6 Hz, 2H), 4.96 (m, 1H), 4.47 (dd, J=11.2, 3.2 Hz, 1H), 4.41 (dd, J=11.2, 5.8 Hz, 1H), 4.20 (ddd, J=12.5, 5.7, 2.9 Hz, 1H), 4.11 (ddd, J=12.4, 11.0, 5.1 Hz, 1H), 2.38-2.30 (m, 1H), 2.29-2.16 (m, 1H); APCI MS m/z 371 [M+H]⁺.

II. Synthesis of 2-nitro-7-[({6-[4-(trifluoromethoxy)phenyl]-3-pyridinyl}oxy)methyl]-6,7-dihydro-5H-imidazo[2,1-b][1,3]oxazine (Compound 35 of Table 1) by the Method of Scheme 8

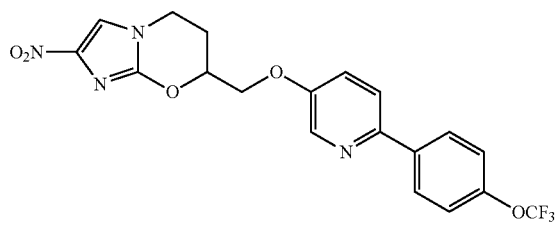

35

Suzuki coupling of bromide 138 and 4-(trifluoromethoxy)phenylboronic acid as in Example 2M for 2.5 h, followed by chromatography of the product on silica gel, eluting with 0-0.33% MeOH/CH₂Cl₂ (foreruns) and then with 0.33% MeOH/CH₂Cl₂, gave 35 (87%) as a cream solid: mp (MeOH/CH₂Cl₂/hexane) 161-163° C.; $^1$H NMR [(CD₃)₂SO] δ 8.46 (d, J=2.9 Hz, 1H), 8.15 (br d, J=8.8 Hz, 2H), 8.11 (s, 1H), 7.99 (d, J=8.8 Hz, 1H), 7.59 (dd, J=8.8, 3.0 Hz, 1H), 7.45 (br d, J=8.2 Hz, 2H), 4.96 (m, 1H), 4.49 (dd, J=11.2, 3.2 Hz, 1H), 4.43 (dd, J=11.2, 5.8 Hz, 1H), 4.20 (ddd, J=12.5, 5.6, 2.7 Hz, 1H), 4.12 (ddd, J=12.4, 11.0, 5.2 Hz, 1H), 2.39-2.30 (m, 1H), 2.29-2.16 (m, 1H). Anal. (C₁₉H₁₅F₃N₄O₅) C, H, N.

JJ. Synthesis of 7-methyl-2-nitro-7-{[4-(trifluoromethoxy)phenoxy]methyl}-6,7-dihydro-5H-imidazo[2,1-b][1,3]oxazine (Compound 36 of Table 1) by the Method of Scheme 9

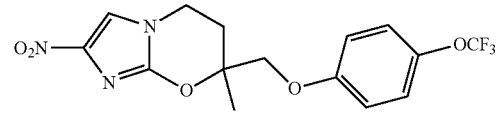

A solution of 4-iodo-2-methyl-1-butene (obtained by iodination of 3-methyl-3-buten-1-ol, as reported by Helmboldt et al., 2006) (2.01 g, 10.3 mmol) in anhydrous DMF (3 mL, then 3×1 mL to rinse) was added to a stirred mixture of 2-chloro-4(5)-nitroimidazole (81) (1.00 g, 6.80 mmol) and powdered K₂CO₃ (2.83 g, 20.5 mmol) in anhydrous DMF (6.5 mL) under N₂, and the mixture was stirred at 61° C. for 20 h. The resulting cooled mixture was added to ice/aqueous NaHCO₃ (100 mL) and extracted with EtOAc (4×100 mL). The extracts were washed with dilute brine (100 mL) and then evaporated to dryness and the residue was chromatographed on silica gel. Elution with 0-10% EtOAc/petroleum ether firstly gave foreruns, and then further elution with 10-15% EtOAc/petroleum ether gave 2-chloro-1-(3-methyl-3-butenyl)-4-nitro-1H-imidazole (139) (1.15 g, 78%) as a white solid: mp (CH₂Cl₂/pentane) 68-69° C.; $^1$H NMR (CDCl₃) δ 7.71 (s, 1H), 4.90 (m, 1H), 4.69 (m, 1H), 4.13 (t, J=7.1 Hz, 2H), 2.52 (br t, J=7.1 Hz, 2H), 1.80 (s, 3H); HRFABMS calcd for C₈H₁₁ClN₃O₂ m/z [M+H]⁺ 218.0510, 216.0540. found 218.0512, 216.0544.

Epoxidation of alkene 139 with 3-chloroperbenzoic acid as in Example 2G for 4 h, followed by chromatography of the product on silica gel, eluting with CH₂Cl₂ (foreruns) and then with 0-5% EtOAc/CH₂Cl₂, gave 2-chloro-1-[2-(2-methyl-2-oxiranyl)ethyl]-4-nitro-1H-imidazole (140) (88%) as a cream solid: mp (CH₂Cl₂/pentane) 82-85° C.; $^1$H NMR (CDCl₃) δ 7.78 (s, 1H), 4.12 (t, J=7.6 Hz, 1H), 2.66 (d, J=4.4 Hz, 1H), 2.62 (d, J=4.4 Hz, 1H), 2.19 (dt, J=14.3, 7.7 Hz, 1H), 2.04 (dt, J=14.3, 7.4 Hz, 1H), 1.39 (s, 3H); HRFABMS calcd for C₈H₁₁ClN₃O₃ m/z [M+H]⁺ 234.0459, 232.0489. found 234.0466, 232.0488.

Reaction of epoxide 140 with 4-trifluoromethoxyphenol as in Example 2AA at 82° C. for 10 h, followed by chromatography of the product on silica gel, eluting with CH₂Cl₂ (foreruns) and then with 0-2% EtOAc/CH₂Cl₂, gave 4-(2-chloro-4-nitro-1H-imidazol-1-yl)-2-methyl-1-[4-(trifluoromethoxy)phenoxy]-2-butanol (141) (77%) as a pale yellow oil; $^1$H NMR (CDCl₃) δ 7.81 (s, 1H), 7.17 (br dd, J=9.1, 0.7 Hz, 2H), 6.90 (dt, J=9.2, 3.1 Hz, 2H), 4.29 (ddd, J=14.1, 9.5, 6.3 Hz, 1H), 4.24 (ddd, J=14.1, 9.6, 6.5 Hz, 1H), 3.85 (d, J=9.0 Hz, 1H), 3.82 (d, J=9.0 Hz, 1H), 2.23 (ddd, J=13.8, 9.3, 6.5 Hz, 1H), 2.21 (s, 1H), 1.40 (s, 3H); HRESIMS calcd for C₁₅H₁₆ClF₃N₃O₅ m/z [M+H]⁺ 412.0697, 410.0725. found 412.0700, 410.0722.

Ring closure of alcohol 141 with NaH as in Example 2AA for 2 h, followed by chromatography of the product on silica gel, eluting with 25-33% EtOAc/petroleum ether (foreruns) and then with 50% EtOAc/petroleum ether, gave 36 (61%) as a cream solid: mp (CH$_2$Cl$_2$/pentane) 134-136° C.; $^1$H NMR (CDCl$_3$) δ 7.45 (s, 1H), 7.16 (br dd, J=9.1, 0.8 Hz, 2H), 6.87 (dt, J=9.2, 3.0 Hz, 2H), 4.21-4.02 (m, 4H), 2.51 (ddd, J=14.5, 7.4, 6.0 Hz, 1H), 2.25 (dt, J=14.5, 6.2 Hz, 1H), 1.60 (s, 3H). Anal. (C$_{15}$H$_{14}$F$_3$N$_3$O$_5$) C, H, N.

KK. Synthesis of 7-{[4-(benzyloxy)phenoxy]methyl}-7-methyl-2-nitro-6,7-dihydro-5H-imidazo[2,1-b][1,3]oxazine (Compound 37 of Table 1) by the Method of Scheme 9

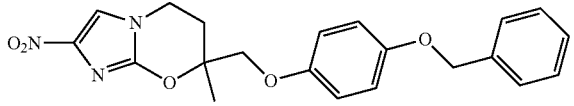

Reaction of epoxide 140 (see Example 2JJ) with 4-(benzyloxy)phenol as in Example 2AA at 82° C. for 10 h, followed by chromatography of the product on silica gel, eluting with CH$_2$Cl$_2$ (foreruns) and then with 2% EtOAc/CH$_2$Cl$_2$, gave 1-[4-(benzyloxy)phenoxy]-4-(2-chloro-4-nitro-1H-imidazol-1-yl)-2-methyl-2-butanol (142) (79%) as an oil; $^1$H NMR (CDCl$_3$) δ 7.79 (s, 1H), 7.44-7.29 (m, 5H), 6.92 (dt, J=9.2, 3.0 Hz, 2H), 6.83 (dt, J=9.2, 3.0 Hz, 2H), 4.28 (ddd, J=14.0, 9.7, 6.1 Hz, 1H), 4.23 (ddd, J=14.0, 9.7, 6.3 Hz, 1H), 3.81 (d, J=9.1 Hz, 1H), 3.77 (d, J=9.0 Hz, 1H), 2.29 (s, 1H), 2.22 (ddd, J=13.8, 9.6, 6.2 Hz, 1H), 2.02 (ddd, J=13.6, 9.7, 6.5 Hz, 1H), 1.38 (s, 3H); HRESIMS calcd for C$_{21}$H$_{23}$ClN$_3$O$_5$ m/z [M+H]$^+$ 434.1293, 432.1321. found 434.1298, 432.1319.

Ring closure of alcohol 142 with NaH (1.4 equiv.) as in Example 2AA, followed by chromatography of the product on silica gel, eluting with 0-33% EtOAc/petroleum ether (foreruns) and then with EtOAc, gave the crude product, which was further chromatographed on silica gel. Elution with 0-2.5% EtOAc/CH$_2$Cl$_2$ firstly gave foreruns, then further elution with 2.5% EtOAc/CH$_2$Cl$_2$ gave 37 (53%) as a cream solid: mp (CH$_2$Cl$_2$/hexane) 174-176° C.; $^1$H NMR [(CD$_3$)$_2$SO] δ 8.07 (s, 1H), 7.45-7.28 (m, 5H), 6.94 (dt, J=9.3, 2.9 Hz, 2H), 6.89 (dt, J=9.3, 2.9 Hz, 2H), 5.04 (s, 2H), 4.21-4.06 (m, 2H), 4.10 (s, 2H), 2.37 (ddd, J=14.5, 7.9, 6.2 Hz, 1H), 2.17 (dt, J=14.4, 5.8 Hz, 1H), 1.48 (s, 3H). Anal. (C$_{21}$H$_{21}$N$_3$O$_5$) C, H, N.

LL. Synthesis of 7-{[(4'-fluoro[1,1'-biphenyl]-4-yl)oxy]methyl}-7-methyl-2-nitro-6,7-dihydro-5H-imidazo[2,1-b][1,3]oxazine (Compound 38 of Table 1) by the Method of Scheme 9

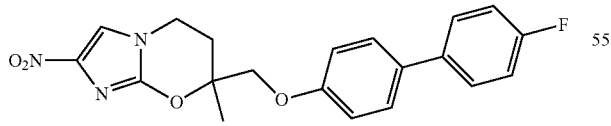

Reaction of epoxide 140 (see Example 2B) with 4-iodophenol as in Example 2AA at 83° C. for 8 h, followed by chromatography of the product on silica gel, eluting with 0-2% EtOAc/CH$_2$Cl$_2$ (foreruns) and then with 5% EtOAc/CH$_2$Cl$_2$, gave 4-(2-chloro-4-nitro-1H-imidazol-1-yl)-1-(4-iodophenoxy)-2-methyl-2-butanol (143) (81%) as a cream solid: mp (CH$_2$Cl$_2$/pentane) 91-93° C.; $^1$H NMR (CDCl$_3$) δ 7.80 (s, 1H), 7.59 (dt, J=8.9, 2.6 Hz, 1H), 6.69 (dt, J=8.9, 2.6 Hz, 1H), 4.28 (ddd, J=14.1, 9.6, 6.3 Hz, 1H), 4.23 (ddd, J=14.1, 9.4, 6.5 Hz, 1H), 3.82 (d, J=9.0 Hz, 1H), 3.79 (d, J=9.0 Hz, 1H), 2.22 (ddd, J=13.8, 9.2, 6.5 Hz, 1 H), 2.20 (s, 1H), 2.02 (ddd, J=13.8, 9.6, 6.6 Hz, 1H), 1.39 (s, 3H); HRESIMS calcd for C$_{14}$H$_{16}$ClIN$_3$O$_4$ m/z [M+H]$^+$ 453.9840, 451.9869. found 453.9832, 451.9857.

Ring closure of alcohol 143 with NaH (1.5 equiv.) as in Example 2AA, followed by chromatography of the product on silica gel, eluting with 0-33% EtOAc/petroleum ether (foreruns) and then with 0-5% EtOAc/CH$_2$Cl$_2$, gave 7-[(4-iodophenoxy)methyl]-7-methyl-2-nitro-6,7-dihydro-5H-imidazo[2,1-b][1,3]oxazine (144) (74%) as a pale yellow solid: mp (CH$_2$Cl$_2$/hexane) 170-172° C.; $^1$H NMR (CDCl$_3$) δ 7.57 (dt, J=9.0, 2.7 Hz, 2H), 7.44 (s, 1H), 6.64 (dt, J=9.0, 2.7 Hz, 2H), 4.19-4.05 (m, 2H), 4.07 (d, J=9.6 Hz, 1H), 4.02 (d, J=9.6 Hz, 1H), 2.49 (ddd, J=14.5, 7.4, 6.0 Hz, 1H), 2.24 (ddd, J=14.5, 6.4, 5.9 Hz, 1H), 1.58 (s, 3H). Anal. (C$_{14}$H$_{14}$IN$_3$O$_4$) C, H, N.

Suzuki coupling of iodide 144 and 4-fluorophenylboronic acid as in Example 2CC for 100 min, followed by chromatography of the product on silica gel, eluting with 0-1% EtOAc/CH$_2$Cl$_2$ (foreruns) and then with 1-2% EtOAc/CH$_2$Cl$_2$, gave 38 (90%) as a pale yellow-orange solid: mp (CH$_2$Cl$_2$/pentane) 160-162° C.; $^1$H NMR (CDCl$_3$) δ 7.51-7.44 (m, 5H), 7.10 (tt, J=8.7, 2.6 Hz, 2H), 6.92 (dt, J=8.8, 2.6 Hz, 2H), 4.23-4.06 (m, 4H), 2.53 (ddd, J=14.4, 7.2, 6.0 Hz, 1H), 2.28 (ddd, J=14.5, 6.8, 5.9 Hz, 1H), 1.62 (s, 3H). Anal. (C$_{20}$H$_{18}$FN$_3$O$_4$) C, H, N.

MM. Synthesis of 7-methyl-2-nitro-7-({[4'-(trifluoromethyl)[1,1'-biphenyl]-4-yl]oxy}methyl)-6,7-dihydro-5H-imidazo[2,1-b][1,3]oxazine (Compound 39 of Table 1) by the Method of Scheme 9

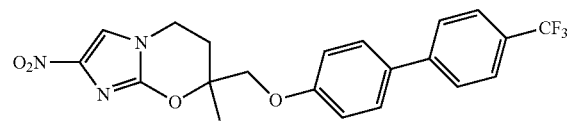

Suzuki coupling of iodide 144 (see Example 2LL) and 4-(trifluoromethyl)phenylboronic acid as in Example 2CC for 100 min, followed by chromatography of the product on silica gel, eluting with 0-1% EtOAc/CH$_2$Cl$_2$ (foreruns) and then with 1% EtOAc/CH$_2$Cl$_2$, gave 39 (87%) as a cream solid: mp (CH$_2$Cl$_2$/pentane) 196-198° C.; $^1$H NMR (CDCl$_3$) δ 7.67 (br d, J=8.5 Hz, 2H), 7.63 (br d, J=8.4 Hz, 2H), 7.54 (dt, J=8.8, 2.6 Hz, 2H), 7.46 (s, 1H), 6.96 (dt, J=8.8, 2.6 Hz, 2H), 4.23-4.08 (m, 4H), 2.54 (ddd, J=14.5, 7.3, 6.0 Hz, 1H), 2.28 (ddd, J=14.5, 6.6, 5.9 Hz, 1H), 1.62 (s, 3H). Anal. (C$_{21}$H$_{18}$F$_3$N$_3$O$_4$) C, H, N.

NN. Synthesis of 7-methyl-2-nitro-7-({[4'-(trifluoromethoxy)[1,1'-biphenyl]-4-yl]oxy}methyl)-6,7-dihydro-5H-imidazo[2,1-b][1,3]oxazine (Compound 40 of Table 1) by the Method of Scheme 9

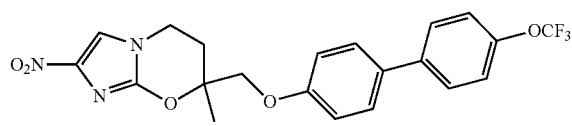

Suzuki coupling of iodide 144 (see Example 2LL) and 4-(trifluoromethoxy)phenylboronic acid as in Example 2CC for 105 min, followed by chromatography of the product on silica gel, eluting with 0-1% EtOAc/CH$_2$Cl$_2$ (foreruns) and then with 1% EtOAc/CH$_2$Cl$_2$, gave 40 (89%) as a pale yellow-pink solid: mp (CH$_2$Cl$_2$/pentane) 186-188° C.; $^1$H NMR (CDCl$_3$) δ 7.53 (dt, J=8.8, 2.5 Hz, 2H), 7.49 (dd, J=8.8, 2.6 Hz, 2H), 7.46 (s, 1H), 7.26 (br dd, J=8.7, 0.8 Hz, 2H), 6.94 (dt, J=8.8, 2.6 Hz, 2H), 4.23-4.07 (m, 4H), 2.53 (ddd, J=14.5, 7.2, 6.0 Hz, 1H), 2.28 (ddd, J=14.5, 6.7, 5.9 Hz, 1H), 1.62 (s, 3H). Anal. (C$_{21}$H$_{18}$F$_3$N$_3$O$_5$) C, H, N.

OO. Synthesis of 7-({[5-(4-fluorophenyl)-2-pyridinyl]oxy}methyl)-7-methyl-2-nitro-6,7-dihydro-5H-imidazo[2,1-b][1,3]oxazine (Compound 41 of Table 1) by the Method of Scheme 10

41

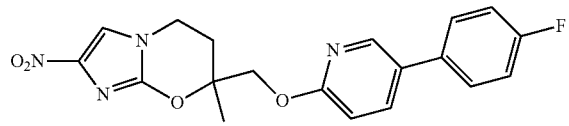

A solution of 4-iodo-2-methyl-1-butene (obtained by iodination of 3-methyl-3-buten-1-ol, as reported by Helmboldt et al., 2006) (2.68 g, 13.7 mmol) in anhydrous DMF (5 mL, then 2×2 mL+1 mL to rinse) was added to a stirred mixture or 2-bromo-4(5)-nitroimidazole (80) (2.00 g, 10.4 mmol) and powdered K$_2$CO$_3$ (4.35 g, 31.5 mmol) in anhydrous DMF (10 mL) under N$_2$, and the resulting mixture was stirred at 60° C. for 11 h. The resulting cooled mixture was added to ice/aqueous NaHCO$_3$ (120 mL) and extracted with EtOAc (3×100 mL). The extracts were washed with dilute brine (100 mL) and then evaporated to dryness and the residue was chromatographed on silica gel. Elution with 0-10% EtOAc/petroleum ether firstly gave foreruns, and then further elution with 20-25% EtOAc/petroleum ether gave 2-bromo-1-(3-methyl-3-butenyl)-4-nitro-1H-imidazole (145) (2.296 g, 85%) as a white solid: mp (CH$_2$Cl$_2$/pentane) 90-92° C.; $^1$H NMR (CDCl$_3$) δ 7.76 (s, 1H), 4.90 (m, 1H), 4.70 (m, 1H), 4.12 (t, J=7.2 Hz, 2H), 2.52 (br t, J=7.1 Hz, 2H), 1.81 (s, 3H). Anal. (C$_8$H$_{10}$BrN$_3$O$_2$) C, H, N.

Osmium tetroxide (2.55 mL of a 4% aqueous solution, 0.417 mmol) was added to a solution of alkene 145 (2.15 g, 8.27 mmol) and 4-methylmorpholine N-oxide (1.49 g, 12.7 mmol) in CH$_2$Cl$_2$ (55 mL), and then the mixture was stirred at room temperature for 4 h. The mixture was cooled (−20° C.), slowly diluted with petroleum ether (70 mL) and recooled (−20° C.) and the resulting precipitate was isolated by filtration, washed with petroleum ether and water, and dried to give 4-(2-bromo-4-nitro-1H-imidazol-1-yl)-2-methyl-1,2-butanediol (146) (1.53 g, 63%) as a pale grey-brown solid: mp (MeOH/CH$_2$Cl$_2$/pentane) 121-123° C.; $^1$H NMR [(CD$_3$)$_2$SO] δ 8.58 (s, 1H), 4.69 (br t, J=5.3 Hz, 1H), 4.41 (br s, 1H), 4.13 (t, J=8.1 Hz, 2H), 3.24 (dd, J=10.6, 5.6 Hz, 1H), 3.18 (dd, J=10.7, 5.6 Hz, 1H), 1.89 (dt, J=13.3, 8.1 Hz, 1H), 1.82 (dt, J=13.3, 8.1 Hz, 1H), 1.09 (s, 3H). Anal. (C$_8$H$_{12}$BrN$_3$O$_3$) C, H, N.

The aqueous portion above was saturated with salt and extracted with EtOAc (6×100 mL). The combined extracts were evaporated to dryness and the residue was chromatographed on silica gel. Elution with 50-67% EtOAc/petroleum ether firstly gave foreruns, and then further elution with 67-80% EtOAc/petroleum ether gave additional 146 (882 mg, 36%).

Triisopropylsilyl chloride (2.00 mL, 9.35 mmol) was added to a solution of diol 146 (2.507 g, 8.52 mmol) and imidazole (1.278 g, 18.8 mmol) in anhydrous DMF (25 mL) under N$_2$ and then the mixture was stirred at room temperature for 3 d. Further triisopropylsilyl chloride (0.50 mL, 2.34 mmol) was added and the mixture was stirred at room temperature for 3 d. The resulting mixture was added to ice-water (130 mL) and extracted with EtOAc (4×100 mL). The extracts were washed with water (100 mL) and then evaporated to dryness and the residue was chromatographed on silica gel. Elution with 0-10% EtOAc/petroleum ether firstly gave foreruns, and then further elution with 33% EtOAc/petroleum ether gave 4-(2-bromo-4-nitro-1H-imidazol-1-yl)-2-methyl-1-[(triisopropylsilyl)oxy]-2-butanol (147) (3.658 g, 95%) as a white solid: mp (CH$_2$Cl$_2$/pentane) 73-75° C.; $^1$H NMR (CDCl$_3$) δ 7.85 (s, 1H), 4.26 (ddd, J=14.1, 10.3, 5.8 Hz, 1H), 4.19 (ddd, J=14.1, 10.3, 6.0 Hz, 1H), 3.56 (s, 2H), 2.52 (s, 1H), 2.11 (ddd, J=13.6, 10.3, 5.8 Hz, 1H), 1.87 (ddd, J=13.6, 10.3, 6.0 Hz, 1H), 1.25 (s, 3H), 1.21-1.04 (m, 21H). Anal. (C$_{17}$H$_{32}$BrN$_3$O$_4$Si) C, H, N.

A stirred solution of alcohol 147 (3.60 g, 8.00 mmol) in anhydrous DMF (35 mL) under N$_2$ at 0° C. was treated with 60% NaH (550 mg, 13.8 mmol), then quickly degassed and resealed under N$_2$. After stirring at room temperature for 2.5 h and then at 46° C. for 190 min, the reaction was cooled (CO$_2$/acetone), quenched with ice/aqueous NaHCO$_3$ (40 mL), diluted with ice-water (140 mL) and extracted with EtOAc (5×80 mL). The combined extracts were washed with brine (80 mL) and then evaporated to dryness and the residue was chromatographed on silica gel. Elution with 0-15% EtOAc/petroleum ether firstly gave foreruns, and then further elution with 15-25% EtOAc/petroleum ether gave 7-methyl-2-nitro-7-{[(triisopropylsilyl)oxy]methyl}-6,7-dihydro-5H-imidazo[2,1-b][1,3]oxazine (148) (2.599 g, 88%) as a pale yellow solid: mp (CH$_2$Cl$_2$/pentane) 112-114° C.; $^1$H NMR (CDCl$_3$) δ 7.41 (s, 1H), 4.14 (ddd, J=12.4, 6.9, 5.8 Hz, 1H), 4.03 (ddd, J=12.4, 7.3, 5.8 Hz, 1H), 3.84 (d, J=10.2 Hz, 1H), 3.77 (d, J=10.2 Hz, 1H), 2.37 (ddd, J=14.4, 7.2, 5.8 Hz, 1H), 2.11 (ddd, J=14.4, 6.9, 5.9 Hz, 1H), 1.45 (s, 3H), 1.16-0.97 (m, 21H). Anal. (C$_{17}$H$_{31}$N$_3$O$_4$Si) C, H, N.

A suspension of silyl ether 148 (2.518 g, 6.81 mmol) in a solution of 1% HCl in 95% EtOH (desilylation conditions described by Cunico et al., 1980) (90 mL) was stirred at 44° C. for 3 days. The resulting solution was cooled (CO$_2$/acetone), neutralised by dropwise addition of 7M NH$_3$ in MeOH (8 mL) and NaHCO$_3$ (0.10 g, 1.19 mmol) with stirring, and then concentrated to dryness and the residue was chromatographed on silica gel. Elution with 0-1% MeOH/CH$_2$Cl$_2$ firstly gave foreruns, and then further elution with 1.5% MeOH/CH$_2$Cl$_2$ gave (7-methyl-2-nitro-6,7-dihydro-5H-imidazo[2,1-b][1,3]oxazin-7-yl)methanol (149) (1.285 g, 88%) as a pale yellow solid: mp (MeOH/CH$_2$Cl$_2$/hexane) 199-201° C.; $^1$H NMR [(CD$_3$)$_2$SO] δ 8.03 (s, 1H), 5.22 (t, J=5.7 Hz, 1H), 4.13 (dt, J=12.9, 6.0 Hz, 1H), 4.05 (ddd, J=13.0, 8.1, 5.6 Hz, 1H), 3.54 (dd, J=11.6, 5.5 Hz, 1H), 3.48 (dd, J=11.6, 5.8 Hz, 1H), 2.21 (ddd, J=14.4, 8.1, 5.9 Hz, 1H), 2.00 (dt, J=14.4, 5.8 Hz, 1H), 1.32 (s, 3H). Anal. (C$_8$H$_{11}$N$_3$O$_4$) C, H, N.

A solution of alcohol 149 (200 mg, 0.938 mmol) in anhydrous DMF (4 mL) under N$_2$ at 0° C. was treated with 60% NaH (53.8 mg, 1.35 mmol), then quickly degassed and resealed under N$_2$. 5-Bromo-2-fluoropyridine (91) (0.245 mL, 2.38 mmol) was added and the mixture was stirred at room temperature for 2.5 h, and then cooled (CO$_2$/acetone), quenched with ice/aqueous NaHCO$_3$ (10 mL), added to brine (40 mL), and extracted with CH$_2$Cl$_2$ (10×50 mL). The combined extracts were evaporated to dryness and the residue was chromatographed on silica gel. Elution with CH$_2$Cl$_2$ firstly gave foreruns, and then further elution with 1-3% EtOAc/

CH₂Cl₂ gave 7-{[(5-bromo-2-pyridinyl)oxy]methyl}-7-methyl-2-nitro-6,7-dihydro-5H-imidazo[2,1-b][1,3]oxazine (150) (269 mg, 78%) as a cream solid: mp (CH₂Cl₂/pentane) 172-174° C.; ¹H NMR (CDCl₃) δ 8.17 (br d, J=2.2 Hz, 1H), 7.67 (dd, J=8.8, 2.5 Hz, 1H), 6.64 (dd, J=8.7, 0.4 Hz, 1H), 4.49 (d, J=11.5 Hz, 1H), 4.42 (d, J=11.4 Hz, 1H), 4.17 (dt, J=12.7, 6.1 Hz, 1H), 4.09 (ddd, J=12.6, 7.7, 5.8 Hz, 1H), 2.45 (ddd, J=14.5, 7.6, 5.9 Hz, 1H), 2.18 (dt, J=14.6, 6.1 Hz, 1H), 1.57 (s, 3H). Anal. ($C_{13}H_{13}BrN_4O_4$) C, H, N.

Suzuki coupling of bromide 150 and 4-fluorophenylboronic acid as in Example 2M for 135 min, followed by chromatography of the product on silica gel, eluting with 0-3% EtOAc/CH₂Cl₂ (foreruns) and then with 3-5% EtOAc/CH₂Cl₂, gave 41 (92%) as a cream solid: mp (CH₂Cl₂/pentane) 145-147° C.; ¹H NMR (CDCl₃) δ 8.28 (d, J=2.5 Hz, 1H), 7.76 (dd, J=8.6, 2.5 Hz, 1H), 7.46 (ddt, J=8.8, 5.1, 2.6 Hz, 2H), 7.45 (s, 1H), 7.14 (tt, J=8.6, 2.6 Hz, 2H), 6.88 (d, J=8.6 Hz, 1H), 4.58 (d, J=11.4 Hz, 1H), 4.50 (d, J=11.4 Hz, 1H), 4.20 (ddd, J=12.6, 6.5, 6.1 Hz, 1H), 4.10 (ddd, J=12.6, 7.3, 5.8 Hz, 1H), 2.49 (ddd, J=14.4, 7.3, 6.0 Hz, 1H), 2.21 (ddd, J=14.4, 6.6, 6.0 Hz, 1H), 1.61 (s, 3H). Anal. ($C_{19}H_{17}FN_4O_4$) C, H, N.

PP. Synthesis of 7-methyl-2-nitro-7-[({5-[4-(trifluoromethyl)phenyl]-2-pyridinyl}oxy)methyl]-6,7-dihydro-5H-imidazo[2,1-b][1,3]oxazine (Compound 42 of Table 1) by the Method of Scheme 10

42

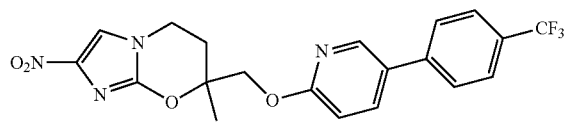

Suzuki coupling of bromide 150 and 4-(trifluoromethyl)phenylboronic acid as in Example 2M for 2 h, followed by chromatography of the product on silica gel, eluting with 0-2% EtOAc/CH₂Cl₂ (foreruns) and then with 3-5% EtOAc/CH₂Cl₂, gave 42 (91%) as a cream solid: mp (CH₂Cl₂/pentane) 212-214° C.; ¹H NMR (CDCl₃) δ 8.35 (dd, J=2.5, 0.4 Hz, 1H), 7.82 (dd, J=8.6, 2.5 Hz, 1H), 7.71 (br d, J=8.2 Hz, 2H), 7.62 (br d, J=8.1 Hz, 2H), 7.46 (s, 1H), 6.82 (dd, J=8.7, 0.4 Hz, 1H), 4.60 (d, J=11.4 Hz, 1H), 4.52 (d, J=11.4 Hz, 1H), 4.21 (ddd, J=12.6, 6.5, 6.0 Hz, 1H), 4.11 (ddd, J=12.7, 7.4, 5.8 Hz, 1H), 2.50 (ddd, J=14.6, 7.4, 5.9 Hz, 1H), 2.22 (ddd, J=14.5, 6.5, 6.0 Hz, 1H), 1.61 (s, 3H). Anal. ($C_{20}H_{17}F_3N_4O_4$) C, H, N.

QQ. Synthesis of 7-methyl-2-nitro-7-[({5-[4-(trifluoromethoxy)phenyl]-2-pyridinyl}oxy)methyl]-6,7-dihydro-5H-imidazo[2,1-b][1,3]oxazine (Compound 43 of Table 1) by the Method of Scheme 10

43

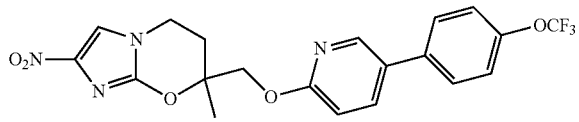

Suzuki coupling of bromide 150 and 4-(trifluoromethoxy)phenylboronic acid as in Example 2M for 2 h, followed by chromatography of the product on silica gel, eluting with 0-2% EtOAc/CH₂Cl₂ (foreruns) and then with 2-3.5% EtOAc/CH₂Cl₂, gave 43 (92%) as a cream solid: mp (CH₂Cl₂/pentane) 195-198° C.; ¹H NMR (CDCl₃) δ 8.31 (dd, J=2.5, 0.7 Hz, 1H), 7.78 (dd, J=8.5, 2.6 Hz, 1H), 7.52 (dt, J=8.8, 2.5 Hz, 2H), 7.45 (s, 1H), 7.30 (br dd, J=8.7, 0.8 Hz, 2H), 6.79 (dd, J=8.6, 0.7 Hz, 1H), 4.59 (d, J=11.4 Hz, 1H), 4.50 (d, J=11.4 Hz, 1H), 4.20 (ddd, J=12.6, 6.7, 5.9 Hz, 1H), 4.10 (ddd, J=12.6, 7.4, 5.8 Hz, 1H), 2.49 (ddd, J=14.5, 7.4, 5.9 Hz, 1H), 2.21 (ddd, J=14.5, 6.6, 5.9 Hz, 1H), 1.61 (s, 3H). Anal. ($C_{20}H_{17}F_3N_4O_5$) C, H, N.

RR. Synthesis of 7-({[6-(4-fluorophenyl)-3-pyridinyl]oxy}methyl)-7-methyl-2-nitro-6,7-dihydro-5H-imidazo[2,1-b][1,3]oxazine (Compound 44 of Table 1) by the Method of Scheme 10

44

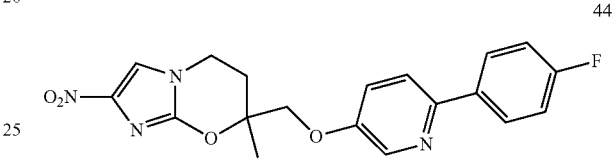

Reaction of epoxide 140 (see Example 2JJ) with 6-bromo-3-pyridinol as in Example 2AA at 84° C. for 18.5 h, followed by chromatography of the product on silica gel, eluting with 25-40% EtOAc/petroleum ether (foreruns) and then with 40-50% EtOAc/petroleum ether, gave 1-[(6-bromo-3-pyridinyl)oxy]-4-(2-chloro-4-nitro-1H-imidazol-1-yl)-2-methyl-2-butanol (151) (70%) as a pale yellow-brown foam; ¹H NMR (CDCl₃) δ 8.09 (dd, J=3.0, 0.3 Hz, 1H), 7.80 (s, 1H), 7.41 (dd, J=8.7, 0.4 Hz, 1H), 7.13 (dd, J=8.7, 3.2 Hz, 1H), 4.29 (ddd, J=14.2, 9.4, 6.4 Hz, 1H), 4.25 (ddd, J=14.1, 9.4, 6.7 Hz, 1H), 3.89 (d, J=8.9 Hz, 1H), 3.86 (d, J=9.0 Hz, 1H), 2.22 (ddd, J=13.9, 9.3, 6.5 Hz, 1H), 2.18 (s, 1H), 2.04 (ddd, J=13.8, 9.4, 6.7 Hz, 1H), 1.42 (s, 3H); HRESIMS calcd for $C_{13}H_{15}BrClN_4O_4$ m/z [M+H]⁺ 408.9910, 406.9939, 404.9960. found 408.9920, 406.9945, 404.9966.

Ring closure of alcohol 151 with NaH (1.5 equiv.) as in Example 2AA, followed by chromatography of the product on silica gel, eluting with 0-50% EtOAc/petroleum ether (foreruns) and then with 0-2% MeOH/CH₂Cl₂, gave 7-{[(6-bromo-3-pyridinyl)oxy]methyl}-7-methyl-2-nitro-6,7-dihydro-5H-imidazo[2,1-b][1,3]oxazine (152) (66%) as a light yellow solid: mp (CH₂Cl₂/hexane) 170-171° C.; ¹H NMR (CDCl₃) δ 8.06 (dd, J=3.1, 0.3 Hz, 1H), 7.46 (s, 1H), 7.40 (dd, J=8.7, 0.3 Hz, 1H), 7.11 (dd, J=8.7, 3.2 Hz, 1H), 4.21-4.07 (m, 4H), 2.52 (ddd, J=14.5, 8.1, 6.3 Hz, 1H), 2.24 (dt, J=14.5, 5.7 Hz, 1H), 1.60 (s, 3H). Anal. ($C_{13}H_{13}BrN_4O_4$) C, H, N.

Suzuki coupling of bromide 152 and 4-fluorophenylboronic acid as in Example 2M for 2 h, followed by chromatography of the product on silica gel, eluting with 0-3% EtOAc/CH₂Cl₂ (foreruns) and then with 3-7% EtOAc/CH₂Cl₂, gave 44 (88%) as a cream solid: mp (CH₂Cl₂/hexane) 203-204° C.; ¹H NMR [(CD₃)₂SO] δ 8.39 (d, J=2.8 Hz, 1H), 8.10 (s, 1H), 8.06 (ddt, J=9.0, 5.6, 2.6 Hz, 2H), 7.92 (d, J=8.8 Hz, 1H), 7.53 (dd, J=8.8, 3.0 Hz, 1H), 7.27 (tt, J=8.9, 2.6 Hz, 2H), 4.33 (s, 2H), 4.25-4.11 (m, 2H), 2.42 (ddd, J=14.5, 8.2, 6.2 Hz, 1H), 2.21 (dt, J=14.4, 5.7 Hz, 1H), 1.52 (s, 3H). Anal. ($C_{19}H_{17}FN_4O_4$) C, H, N.

SS. Synthesis of 7-methyl-2-nitro-7-[({6-[4-(trifluoromethyl)phenyl]-3-pyridinyl}oxy)methyl]-6,7-dihydro-5H-imidazo[2,1-b][1,3]oxazine (Compound 45 of Table 1) by the Method of Scheme 10

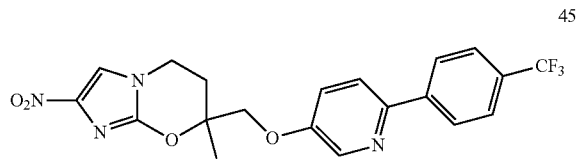

45

Suzuki coupling of bromide 152 (see Example 2RR) and 4-(trifluoromethyl)phenylboronic acid as in Example 2M for 130 min, followed by chromatography of the product on silica gel, eluting with 0-3% EtOAc/CH$_2$Cl$_2$ (foreruns) and then with 4-7% EtOAc/CH$_2$Cl$_2$, gave 45 (65%) as a cream solid: mp (CH$_2$Cl$_2$/hexane) 215-217° C.; $^1$H NMR [(CD$_3$)$_2$SO] δ 8.46 (d, J=2.9 Hz, 1H), 8.25 (br d, J=8.1 Hz, 2H), 8.10 (s, 1H), 8.06 (d, J=8.8 Hz, 1H), 7.81 (br d, J=8.3 Hz, 2H), 7.59 (dd, J=8.8, 3.0 Hz, 1H), 4.36 (s, 2H), 4.26-4.11 (m, 2H), 2.42 (ddd, J=14.5, 8.1, 6.0 Hz, 1H), 2.21 (dt, J=14.4, 5.7 Hz, 1H), 1.53 (s, 3H). Anal. (C$_{20}$H$_{17}$F$_3$N$_4$O$_4$) C, H, N.

TT. Synthesis of 7-methyl-2-nitro-7-[({6-[4-(trifluoromethoxy)phenyl]-3-pyridinyl}oxy)methyl]-6,7-dihydro-5H-imidazo[2,1-b][1,3]oxazine (Compound 46 of Table 1) by the Method of Scheme 10

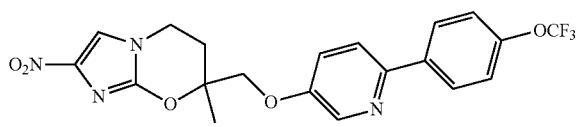

46

Suzuki coupling of bromide 152 (see Example 2RR) and 4-(trifluoromethoxy)phenylboronic acid as in Example 2M for 130 min, followed by chromatography of the product on silica gel, eluting with 0-4% EtOAc/CH$_2$Cl$_2$ (foreruns) and then with 5-7% EtOAc/CH$_2$Cl$_2$, gave 46 (84%) as a cream solid: mp (CH$_2$Cl$_2$/pentane) 202-203° C.; $^1$H NMR [(CD$_3$)$_2$SO] δ 8.42 (d, J=2.8 Hz, 1H), 8.14 (dt, J=8.9, 2.6 Hz, 2H), 8.10 (s, 1H), 7.97 (d, J=8.8 Hz, 1H), 7.56 (dd, J=8.8, 3.0 Hz, 1H), 7.44 (br dd, J=8.9, 0.8 Hz, 2H), 4.34 (s, 2H), 4.25-4.11 (m, 2H), 2.42 (ddd, J=14.5, 8.2, 6.1 Hz, 1H), 2.21 (dt, J=14.4, 5.7 Hz, 1H), 1.52 (s, 3H). Anal. (C$_{20}$H$_{17}$F$_3$N$_4$O$_5$) C, H, N.

UU. Synthesis of 2-nitro-7-({[3-(trifluoromethoxy)benzyl]oxy}methyl)-6,7-dihydro-5H-imidazo[2,1-b][1,3]oxazine (Compound 47 of Table 1) by the Method of Scheme 11

47

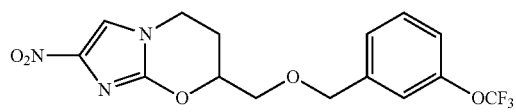

A mixture of oxazine alcohol 134 (see Example 2BB above) (31.8 mg, 0.160 mmol) and 3-(trifluoromethoxy)benzyl bromide (0.040 mL, 0.247 mmol) in anhydrous DMF (3 mL) under N$_2$ at 0° C. was treated with 60% NaH (9.5 mg, 0.238 mmol), then quickly degassed and resealed under N$_2$. After stirring at room temperature for 2.5 h, the mixture was cooled (CO$_2$/acetone), quenched with ice/aqueous NaHCO$_3$ (10 mL), added to brine (40 mL) and extracted with CH$_2$Cl$_2$ (4×50 mL). The combined extracts were evaporated to dryness and the residue was chromatographed on silica gel. Elution with 0-1% EtOAc/CH$_2$Cl$_2$ firstly gave foreruns, and then further elution with 1-2% EtOAc/CH$_2$Cl$_2$ gave 47 (44 mg, 74%) as a cream solid: mp (CH$_2$Cl$_2$/pentane) 110-112° C.; $^1$H NMR (CDCl$_3$) δ 7.41 (s, 1H), 7.41-7.35 (m, 1H), 7.23 (br d, J=7.8 Hz, 1H), 7.19-7.13 (m, 2H), 4.62 (s, 2H), 4.58 (m, 1H), 4.15 (ddd, J=12.4, 5.8, 3.7 Hz, 1H), 4.06 (ddd, J=12.3, 10.1, 5.6 Hz, 1H), 3.84 (dd, J=10.6, 4.3 Hz, 1H), 3.78 (dd, J=10.6, 5.1 Hz, 1H), 2.40-2.21 (m, 2H). Anal. (C$_{15}$H$_{14}$F$_3$N$_3$O$_5$) C, H, N.

VV. Synthesis of 2-nitro-7-({[4-(trifluoromethoxy)benzyl]oxy}methyl)-6,7-dihydro-5H-imidazo[2,1-b][1,3]oxazine (Compound 48 of Table 1) by the Method of Scheme 11

48

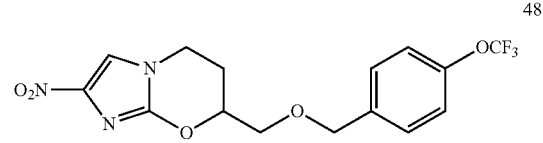

Alkylation of oxazine alcohol 134 (see Example 2BB above) with 4-(trifluoromethoxy)benzyl bromide (1.9 equiv.) and NaH (1.7 equiv.) as in Example 2UU above for 165 min, followed by chromatography of the product on silica gel, eluting with 0-0.5% MeOH/CH$_2$Cl$_2$ (foreruns) and then with 0.5% MeOH/CH$_2$Cl$_2$, gave 48 (69%) as a cream solid: mp (CH$_2$Cl$_2$/hexane) 158-160° C.; $^1$H NMR (CDCl$_3$) δ 7.41 (s, 1H), 7.34 (dt, J=8.8, 2.3 Hz, 2H), 7.20 (br d, J=7.9 Hz, 2H), 4.61 (s, 2H), 4.61-4.54 (m, 1H), 4.14 (ddd, J=12.4, 5.7, 3.7 Hz, 1H), 4.06 (ddd, J=12.3, 10.0, 5.8 Hz, 1H), 3.82 (dd, J=10.7, 4.4 Hz, 1H), 3.78 (dd, J=10.7, 4.9 Hz, 1H), 2.38-2.21 (m, 1H). Anal. (C$_{15}$H$_{14}$F$_3$N$_3$O$_5$) C, H, N.

WW. Synthesis of 7-({[4-(benzyloxy)benzyl]oxy}methyl)-2-nitro-6,7-dihydro-5H-imidazo[2,1-b][1,3]oxazine (Compound 49 of Table 1) by the Method of Scheme 11

49

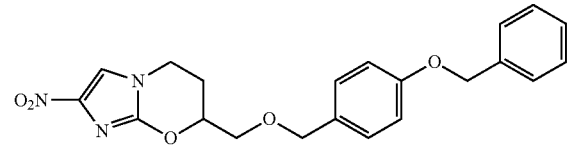

Alkylation of oxazine alcohol 134 (see Example 2BB above) with 4-(benzyloxy)benzyl chloride (3.0 equiv.) and NaH (1.5 equiv.) as in Example 2UU above for 3 h, followed by chromatography of the product on silica gel, eluting with 0-1% EtOAc/CH$_2$Cl$_2$ (foreruns) and then with 1% EtOAc/CH$_2$Cl$_2$, gave 49 (20 mg, 25%) as a cream solid: mp (CH$_2$Cl$_2$/hexane) 151-153° C.; $^1$H NMR (CDCl$_3$) δ 7.45-7.29 (m, 6H), 7.22 (dt, J=8.7, 2.4 Hz, 2H), 6.95 (dt, J=8.7, 2.4 Hz, 2H), 5.07 (s, 2H), 4.54 (m, 1H), 4.52 (s, 2H), 4.11 (ddd, J=12.3, 5.8, 3.9 Hz, 1H), 4.02 (ddd, J=12.3, 10.0, 5.5 Hz, 1H), 3.78 (dd, J=10.5, 4.3 Hz, 1H), 3.71 (dd, J=10.5, 5.5 Hz, 1H), 2.33 (dddd, J=14.5, 5.4, 3.8, 3.0 Hz, 1H), 2.23 (did, J=14.6, 9.8, 5.9 Hz, 1H). Anal. (C$_{21}$H$_{21}$N$_3$O$_5$) C, H, N.

XX. Synthesis of 2-nitro-7-({[4'-(trifluoromethoxy)[1,1'-biphenyl]-3-yl]methoxy}methyl)-6,7-dihydro-5H-imidazo[2,1-b][1,3]oxazine (Compound 50 of Table 1) by the Method of Scheme 11

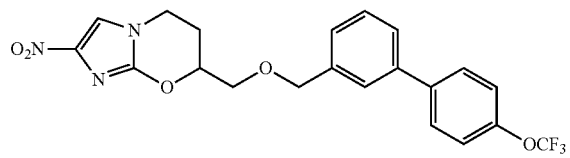

Alkylation of oxazine alcohol 134 (see Example 2BB above) with 3-iodobenzyl bromide (1.36 equiv.) and NaH (1.5 equiv.) as in Example 2UU above for 3 h, followed by chromatography of the product on silica gel, eluting with 0-1% EtOAc/CH$_2$Cl$_2$ (foreruns) and then with 1.5-2% EtOAc/CH$_2$Cl$_2$, gave 7-{[(3-iodobenzyl)oxy]methyl}-2-nitro-6,7-dihydro-5H-imidazo[2, 1-1)][1,3]oxazine (153) (65%) as a cream solid: mp (CH$_2$Cl$_2$/hexane) 131-133° C.; $^1$H NMR (CDCl$_3$) δ 7.65 (br s, 1H), 7.64 (br d, J=7.5 Hz, 1H), 7.41 (s, 1H), 7.26 (m, 1H), 7.09 (td, J=7.4, 1.0 Hz, 1H), 4.57 (m, 1H), 4.54 (s, 2H), 4.15 (ddd, J=12.3, 5.8, 3.8 Hz, 1H), 4.06 (ddd, J=12.3, 10.0, 5.5 Hz, 1H), 3.82 (dd, J=10.6, 4.3 Hz, 1H), 3.76 (dd, J=10.6, 5.1 Hz, 1H), 2.39-2.21 (m, 2H). Anal. (C$_{14}$H$_{14}$IN$_3$O$_4$) C, H, N.

A stirred mixture of iodide 153 (30.2 mg, 0.0727 mmol), 4-(trifluoromethoxy)phenylboronic acid (20.8 mg, 0.101 mmol) and Pd(dppf)Cl$_2$ (2.3 mg, 3.14 μmol) in toluene (1.7 mL) was degassed for 4 min (vacuum pump) and then N$_2$ was added. EtOH (0.6 mL) and aqueous 2M Na$_2$CO$_3$ (0.30 mL, 0.60 mmol) were added by syringe and the resulting mixture was stirred at 90° C. for 20 min, and then cooled, diluted with aqueous NaHCO$_3$ (50 mL) and extracted with CH$_2$Cl$_2$ (4×50 mL). The extracts were evaporated to dryness and the residue was chromatographed on silica gel. Elution with 0-1% EtOAc/CH$_2$Cl$_2$ firstly gave foreruns, and then elution with 1-1.5% EtOAc/CH$_2$Cl$_2$ gave 50 (30 mg, 92%) as a cream solid: mp (CH$_2$Cl$_2$/pentane) 117-119° C.; $^1$H NMR (CDCl$_3$) δ 7.60 (dt, J=8.7, 2.4 Hz, 2H), 7.52-7.47 (m, 2H), 7.44 (t, J=7.8 Hz, 1H), 7.40 (s, 1H), 7.32-7.26 (m, 3H), 4.67 (s, 2H), 4.59 (m, 1H), 4.14 (ddd, J=12.3, 5.7, 3.8 Hz, 1H), 4.05 (ddd, J=12.3, 10.0, 5.6 Hz, 1H), 3.86 (dd, J=10.7, 4.3 Hz, 1H), 3.80 (dd, J=10.7, 5.0 Hz, 1H), 2.40-2.22 (m, 2H). Anal. (C$_{21}$H$_{18}$F$_3$N$_3$O$_5$) C, H, N.

YY. Synthesis of 2-nitro-7-({[4'-(trifluoromethoxy)[1,1'-biphenyl]-4-yl]methoxy}methyl)-6,7-dihydro-5H-imidazo[2,1-b][1,3]oxazine (Compound 51 of Table 1) by the Method of Scheme 11

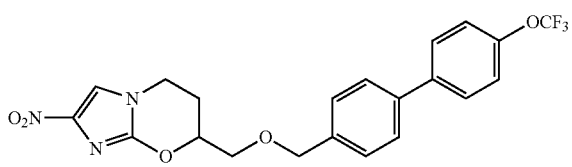

Alkylation of oxazine alcohol 134 (see Example 2BB above) with 4-iodobenzyl bromide (1.35 equiv.) and NaH (1.5 equiv.) as in Example 2UU above, followed by chromatography of the product on silica gel, eluting with CH$_2$Cl$_2$ (foreruns) and then with 1-1.5% EtOAc/CH$_2$Cl$_2$, gave 7-{[(4-iodobenzyl)oxy]methyl}-2-nitro-6,7-dihydro-5H-imidazo[2, 1-1)][1,3]oxazine (154) (61%) as a cream solid: mp (CH$_2$Cl$_2$/hexane) 169-171° C.; $^1$H NMR (CDCl$_3$) δ 7.68 (dt, J=8.3, 2.0 Hz, 2H), 7.41 (s, 1H), 7.05 (br d, J=8.3 Hz, 2H), 4.56 (m, 1H), 4.54 (s, 2H), 4.14 (ddd, J=12.3, 5.7, 3.8 Hz, 1H), 4.05 (ddd, J=12.3, 10.0, 5.6 Hz, 1H), 3.80 (dd, J=10.6, 4.3 Hz, 1H), 3.75 (dd, J=10.6, 5.0 Hz, 1H), 2.37-2.20 (m, 2H); HRFABMS calcd for C$_{14}$H$_{15}$IN$_3$O$_4$ z [M+H]$^+$ 416.0107. found 416.0105.

Suzuki coupling of iodide 154 and 4-(trifluoromethoxy)phenylboronic acid as in Example 2XX above, followed by chromatography of the product on silica gel, eluting with 0-1% EtOAc/CH$_2$Cl$_2$ (foreruns) and then with 1-1.5% EtOAc/CH$_2$Cl$_2$, gave 51 (85%) as a cream solid: mp (CH$_2$Cl$_2$/pentane) 159-161° C.; $^1$H NMR (CDCl$_3$) δ 7.59 (dt, J=8.8, 2.5 Hz, 2H), 7.54 (br d, J=8.2 Hz, 2H), 7.41 (s, 1H), 7.39 (br d, J=8.3 Hz, 2H), 7.29 (br d, J=8.0 Hz, 2H), 4.65 (s, 2H), 4.59 (m, 1H), 4.15 (ddd, J=12.3, 5.8, 3.8 Hz, 1H), 4.06 (ddd, J=12.3, 10.0, 5.6 Hz, 1H), 3.85 (dd, J=10.6, 4.3 Hz, 1H), 3.80 (dd, J=10.6, 5.1 Hz, 1H), 2.41-2.23 (m, 2H). Anal. (C$_{21}$H$_{18}$F$_3$N$_3$O$_5$) C, H, N.

ZZ. Synthesis of 7-methyl-2-nitro-7-({[3-(trifluoromethoxy)benzyl]oxy}methyl)-6,7-dihydro-5H-imidazo[2,1-b][1,3]oxazine (Compound 52 of Table 1) by the Method of Scheme 11

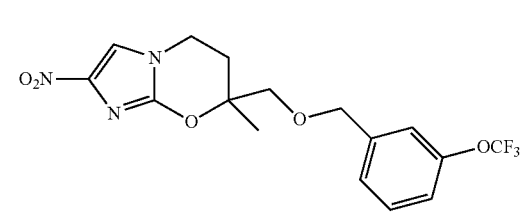

Alkylation of oxazine alcohol 149 (see Example 2OO) with 3-(trifluoromethoxy)benzyl bromide (1.6 equiv.) and NaH (2.0 equiv.) as in Example 2UU above for 3 h, followed by chromatography of the product on silica gel, eluting with 0-1% EtOAc/CH$_2$Cl$_2$ (foreruns) and then with 1-1.5% EtOAc/CH$_2$Cl$_2$, gave 52 (83%) as a cream solid: mp (CH$_2$Cl$_2$/pentane) 108-110° C.; $^1$H NMR (CDCl$_3$) δ 7.38 (s, 1H), 7.36 (t, J=8.0 Hz, 1H), 7.19-7.10 (m, 3H), 4.58 (s, 2H), 4.10 (ddd, J=12.5, 6.9, 5.9 Hz, 1H), 4.02 (ddd, J=12.5, 7.1, 5.9 Hz, 1H), 3.65 (d, J=10.2 Hz, 1H), 3.61 (d, J=10.2 Hz, 1H), 2.38 (ddd, J=14.4, 7.1, 6.0 Hz, 1H), 2.12 (ddd, J=14.5, 6.9, 6.0 Hz, 1H), 1.48 (s, 3H). Anal. (C$_{16}$H$_{16}$F$_3$N$_3$O$_5$) C, H, N.

AAA. Synthesis of 7-methyl-2-nitro-7-({[4-(trifluoromethoxy)benzyl]oxy}methyl)-6,7-dihydro-5H-imidazo[2,1-b][1,3]oxazine (Compound 53 of Table 1) by the Method of Scheme 11

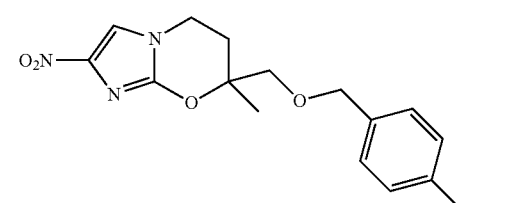

Alkylation of oxazine alcohol 149 (see Example 2OO) with 4-(trifluoromethoxy)benzyl bromide (1.6 equiv.) and NaH (1.8 equiv.) as in Example 2UU above for 3 h, followed by chromatography of the product on silica gel, eluting with CH$_2$Cl$_2$ (foreruns) and then with 1.5% EtOAc/CH$_2$Cl$_2$, gave 53 (83%) as a cream solid: mp (CH$_2$Cl$_2$/pentane) 100-101° C.; $^1$H NMR (CDCl$_3$) δ 7.39 (s, 1H), 7.28 (br d, J=8.7 Hz, 2H), 7.18 (br d, J=8.0 Hz, 2 H), 4.56 (s, 2H), 4.09 (ddd, J=12.5, 6.8, 5.9 Hz, 1H), 4.02 (ddd, J=12.5, 7.3, 5.9 Hz, 1H), 3.64 (d, J=10.2 Hz, 1H), 3.60 (d, J=10.2 Hz, 1H), 2.38 (ddd, J=14.5, 7.2, 5.9 Hz, 1H), 2.11 (ddd, J=14.5, 6.7, 6.0 Hz, 1H), 1.47 (s, 3H). Anal. (C$_{16}$H$_{16}$F$_3$N$_3$O$_5$) C, H, N.

BBB. Synthesis of 7-({[4-(benzyloxy)benzyl]oxy}methyl)-7-methyl-2-nitro-6,7-dihydro-5H-imidazo[2,1-b][1,3]oxazine (Compound 54 of Table 1) by the Method of Scheme 11

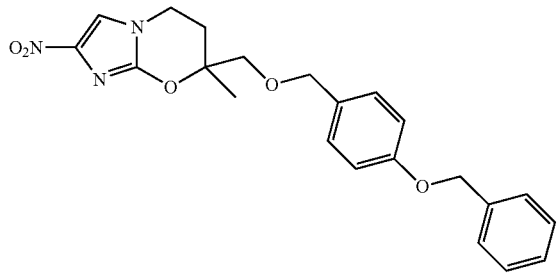

54

Alkylation of oxazine alcohol 149 (see Example 2OO) with 4-(benzyloxy)benzyl chloride (2.8 equiv.) and NaH (1.6 equiv.) as in Example 2UU above for 7 h, followed by chromatography of the product on silica gel, eluting with 0-1% EtOAc/CH$_2$Cl$_2$ (foreruns) and then with 1% EtOAc/CH$_2$Cl$_2$, gave 54 (41%) as a cream solid: mp (CH$_2$Cl$_2$/pentane) 109-111° C.; $^1$H NMR (CDCl$_3$) δ 7.45-7.29 (m, 6H), 7.16 (dt, J=8.6, 2.3 Hz, 2H), 6.93 (dt, J=8.6, 2.4 Hz, 2H), 5.06 (s, 2H), 4.48 (d, J=11.5 Hz, 1H), 4.45 (d, J=11.6 Hz, 1H), 4.03 (ddd, J=12.5, 7.6, 5.8 Hz, 1H), 3.95 (dt, J=12.5, 6.2 Hz, 1H), 3.58 (d, J=10.1 Hz, 1H), 3.54 (d, J=10.1 Hz, 1H), 2.34 (dt, J=14.5, 6.2 Hz, 1H), 2.08 (ddd, J=14.4, 7.6, 6.0 Hz, 1H), 1.45 (s, 3H). Anal. (C$_{22}$H$_{23}$N$_3$O$_5$) C, H, N.

CCC. Synthesis of 7-methyl-2-nitro-7-({[4'-(trifluoromethoxy)[1,1'-biphenyl]-3-yl]methoxy}methyl)-6,7-dihydro-5H-imidazo[2,1-b][1,3]oxazine (Compound 55 of Table 1) by the Method of Scheme 11

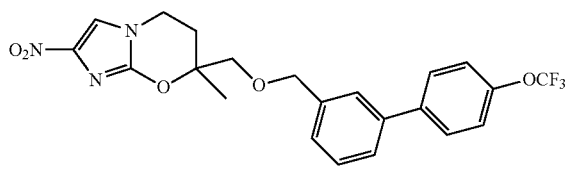

55

Alkylation of oxazine alcohol 149 (see Example 2OO) with 3-iodobenzyl bromide (1.6 equiv.) and NaH (1.8 equiv.) as in Example 2UU above for 3.5 h, followed by chromatography of the product on silica gel, eluting with CH$_2$Cl$_2$ (foreruns) and then with 0-2% EtOAc/CH$_2$Cl$_2$, gave 7-{[(3-iodobenzyl)oxy]methyl}-7-methyl-2-nitro-6,7-dihydro-5H-imidazo[2,1-b][1,3]oxazine (155) (69%) as a cream solid: mp (CH$_2$Cl$_2$/pentane) 122-125° C. (dec); $^1$H NMR (CDCl$_3$) δ 7.63 (br d, J=7.9 Hz, 1H), 7.58 (m, 1H), 7.40 (s, 1H), 7.19 (br d, J=7.7 Hz, 1H), 7.06 (t, J=7.7 Hz, 1H), 4.49 (s, 2H), 4.11 (ddd, J=12.4, 7.3, 5.8 Hz, 1H), 4.01 (ddd, J=12.5, 6.7, 6.0 Hz, 1H), 3.63 (d, J=10.2 Hz, 1H), 3.60 (d, J=10.2 Hz, 1H), 2.37 (ddd, J=14.4, 6.7, 6.0 Hz, 1H), 2.12 (ddd, J=14.4, 7.3, 6.0 Hz, 1H), 1.47 (s, 3H). Anal. (C$_{15}$H$_{16}$IN$_3$O$_4$) C, H, N.

Suzuki coupling of iodide 155 and 4-(trifluoromethoxy)phenylboronic acid as in Example 2H for 25 min, followed by chromatography of the product on silica gel, eluting with 0-0.5% EtOAc/CH$_2$Cl$_2$ (foreruns) and then with 1% EtOAc/CH$_2$Cl$_2$, gave 55 (94%) as a cream solid: mp (CH$_2$Cl$_2$/pentane) 80-82° C.; $^1$H NMR (CDCl$_3$) δ 7.58 (dt, J=8.8, 2.5 Hz, 2H), 7.49 (br dt, J=6.4, 1.5 Hz, 1H), 7.43 (br s, 1H), 7.41 (t, J=7.6 Hz, 1H), 7.37 (s, 1H), 7.30 (br dd, J=8.7, 0.8 Hz, 2H), 7.25 (m, 1H), 4.62 (s, 2H), 4.11 (ddd, J=12.4, 7.1, 5.8 Hz, 1H), 4.00 (ddd, J=12.5, 6.9, 5.9 Hz, 1H), 3.68 (d, J=10.2 Hz, 1H), 3.63 (d, J=10.2 Hz, 1H), 2.39 (ddd, J=14.4, 6.9, 6.0 Hz, 1H), 2.12 (ddd, J=14.4, 7.1, 6.0 Hz, 1H), 1.48 (s, 3H). Anal. (C$_{22}$H$_{20}$F$_3$N$_3$O$_5$) C, H, N.

DDD. Synthesis of 7-methyl-2-nitro-7-({[4'-(trifluoromethoxy)[1,1'-biphenyl]-4-yl]methoxy}methyl)-6,7-dihydro-5H-imidazo[2,1-b][1,3]oxazine (Compound 56 of Table 1) by the Method of Scheme 11

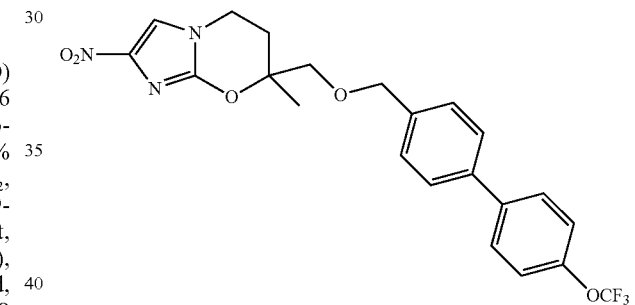

56

Alkylation of oxazine alcohol 149 (see Example 2OO) with 4-iodobenzyl bromide (1.7 equiv.) and NaH (1.9 equiv.) as in Example 2UU above for 3 h, followed by chromatography of the product on silica gel, eluting with CH$_2$Cl$_2$ (foreruns) and then with 1% EtOAc/CH$_2$Cl$_2$, gave 7-{[(4-iodobenzyl)oxy]methyl}-7-methyl-2-nitro-6,7-dihydro-5H-imidazo[2,1-b][1,3]oxazine (156) (54%) as a cream solid: mp (CH$_2$Cl$_2$/pentane) 130-132° C.; $^1$H NMR (CDCl$_3$) δ 7.67 (dt, J=8.3, 2.0 Hz, 2H), 7.39 (s, 1H), 6.99 (br d, J=8.3 Hz, 2H), 4.49 (s, 2H), 4.09 (ddd, J=12.5, 7.0, 5.9 Hz, 1H), 4.01 (ddd, J=12.5, 7.1, 5.9 Hz, 1H), 3.62 (d, J=10.2 Hz, 1H), 3.58 (d, J=10.2 Hz, 1H), 2.37 (ddd, J=14.4, 7.0, 6.0 Hz, 1H), 2.10 (ddd, J=14.4, 6.9, 6.0 Hz, 1H), 1.46 (s, 3H). Anal. (C$_{15}$H$_{16}$IN$_3$O$_4$) C, H, N.

Suzuki coupling of iodide 156 and 4-(trifluoromethoxy)phenylboronic acid as in Example 2H for 25 min, followed by chromatography of the product on silica gel, eluting with 0-0.5% EtOAc/CH$_2$Cl$_2$ (foreruns) and then with 0.5-1% EtOAc/CH$_2$Cl$_2$, gave 56 (92%) as a cream solid: mp (CH$_2$Cl$_2$/pentane) 150-152° C.; $^1$H NMR (CDCl$_3$) δ 7.58 (dt, J=8.8, 2.5 Hz, 2H), 7.52 (dt, J=8.3, 1.9 Hz, 2H), 7.38 (s, 1H), 7.32 (br d, J=8.3 Hz, 2H), 7.28 (br dd, J=8.8, 0.8 Hz, 2H), 4.61 (d, J=12.0 Hz, 1H), 4.58 (d, J=12.0 Hz, 1H), 4.11 (ddd, J=12.4, 7.3, 5.8 Hz, 1H), 4.01 (ddd, J=12.5, 6.7, 6.0 Hz, 1H), 3.67 (d, J=10.2 Hz, 1H), 3.63 (d, J=10.2 Hz, 1H), 2.40 (ddd, J=14.5, 6.7, 6.0 Hz, 1H), 2.13 (ddd. J=14.5, 7.3, 6.0 Hz, 1H), 1.48 (s, 3H). Anal. (C$_{22}$H$_{20}$F$_3$N$_3$O$_5$) C, H, N.

EEE. Synthesis of (7R)-7-methyl-2-nitro-7-({[4'-(trifluoromethoxy)[1,1'-biphenyl]-4-yl]methoxy}methyl)-6,7-dihydro-5H-imidazo[2,1-b][1,3]oxazine (Compound 57 of Table 1) by the Method of Scheme 12

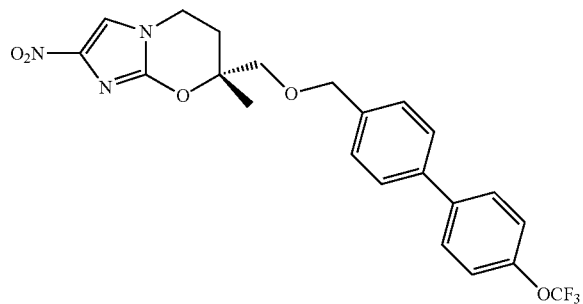

57

Ac$_2$O (3.6 mL, 38.1 mmol) was added to a stirred suspension of alcohol 149 (see Example 2OO) (807 mg, 3.79 mmol) in anhydrous pyridine (7.0 mL). After stirring at room temperature for 38 h, the mixture was diluted with CH$_2$Cl$_2$, added to ice-water (150 mL) and extracted with CH$_2$Cl$_2$ (5×100 mL). The extracts were evaporated to dryness and the residue was chromatographed on silica gel. Elution with CH$_2$Cl$_2$ firstly gave foreruns, and then further elution with 1-6% EtOAc/CH$_2$Cl$_2$ gave 7-methyl-2-nitro-6,7-dihydro-5H-imidazo[2,1-b][1,3]oxazin-7-yl]methyl acetate (157) (962 mg, 100%) as a cream solid: mp (CH$_2$Cl$_2$/hexane) 145-147° C.; $^1$H NMR (CDCl$_3$) δ 7.44 (s, 1H), 4.27 (d, J=11.9 Hz, 1H), 4.20 (d, J=11.9 Hz, 1H), 4.14 (dt, J=12.7, 5.9 Hz, 1H), 4.08 (ddd, J=12.7, 8.3, 5.6 Hz, 1H), 2.32 (ddd, J=14.5, 8.3, 6.1 Hz, 1H), 2.10 (dt, J=14.5, 5.7 Hz, 1H), 2.09 (s, 3H), 1.50 (s, 3H); HRFABMS calcd for C$_{10}$H$_{14}$N$_3$O$_5$ m/z [M+H]$^+$ 256.0934. found 256.0941.

Racemic acetate 157 (990 mg) was separated into pure enantiomers by preparative chiral HPLC, using a ChiralPak IA column and an isocratic solvent system of 40% EtOH in hexane at a flow rate of 6 mL/min, to firstly give [(7S)-7-methyl-2-nitro-6,7-dihydro-5H-imidazo[2,1-b][1,3]oxazin-7-yl]methyl acetate (161) (427 mg, 43%) as a cream solid that was used directly in the next step; $^1$H NMR (CDCl$_3$) δ 7.44 (s, 1H), 4.27 (d, J=11.9 Hz, 1H), 4.20 (d, J=11.9 Hz, 1H), 4.14 (dt, J=12.7, 5.9 Hz, 1H), 4.08 (ddd, J=12.7, 8.3, 5.6 Hz, 1H), 2.32 (ddd, J=14.5, 8.3, 6.1 Hz, 1H), 2.10 (dt, J=14.5, 5.7 Hz, 1H), 2.09 (s, 3H), 1.50 (s, 3H); [α]$_D^{26}$ −6.0° (c 1.00, CHCl$_3$).

The above preparative chiral HPLC of racemic acetate 157 secondly gave [(7R)-7-methyl-2-nitro-6,7-dihydro-5H-imidazo[2,1-b][1,3]oxazin-7-yl]methyl acetate (158) (428 mg, 43%) as a cream solid that was used directly in the next step; $^1$H NMR (CDCl$_3$) δ 7.44 (s, 1H), 4.27 (d, J=11.9 Hz, 1H), 4.20 (d, J=11.8 Hz, 1H), 4.14 (dt, J=12.7, 5.9 Hz, 1H), 4.08 (ddd, J=12.7, 8.3, 5.6 Hz, 1H), 2.32 (ddd, J=14.5, 8.3, 6.1 Hz, 1H), 2.10 (dt, j=14.5, 5.7 Hz, 1H), 2.09 (s, 3H), 1.50 (s, 3H); [α]$_D^{26}$ 6.0° (c 1.00, CHCl$_3$).

Water (4 mL) was added dropwise to a stirred mixture of (R)-acetate 158 (427 mg, 1.67 mmol) and K$_2$CO$_3$ (256 mg, 1.85 mmol) in MeOH (36 mL). After stirring at room temperature for 4 h, the mixture was cooled in ice and treated with 0.1M HCl (37 mL, 3.70 mmol). The solvents were removed under reduced pressure and the residue was chromatographed on silica gel. Elution with 0-1% MeOH/CH$_2$Cl$_2$ firstly gave foreruns, and then further elution with 1-2.5% MeOH/CH$_2$Cl$_2$ gave [(7R)-7-methyl-2-nitro-6,7-dihydro-5H-imidazo[2,1-b][1,3]oxazin-7-yl]methanol (159) (343 mg, 96%) as a pale yellow solid that was used directly in the next step; $^1$H NMR [(CD$_3$)$_2$SO] δ 8.03 (s, 1H), 5.23 (br t, J=5.4 Hz, 1H), 4.13 (dt, J=13.0, 6.0 Hz, 1H), 4.05 (ddd, J=12.9, 8.1, 5.6 Hz, 1H), 3.54 (dd, J=11.6, 4.9 Hz, 1H), 3.48 (dd, J=11.6, 5.2 Hz, 1H), 2.21 (ddd, J=14.4, 8.1, 5.9 Hz, 1H), 2.00 (dt, J=14.4, 5.8 Hz, 1H), 1.32 (s, 3H); [α]$_D^{27}$ −16.0° (c 1.00, DMF).

Alkylation of (R)-alcohol 159 with 4-bromobenzyl bromide (1.3 equiv.) and NaH (1.5 equiv.) as in Example 2UU above for 3 h, followed by chromatography of the product on silica gel, eluting with CH$_2$Cl$_2$ (foreruns) and then with 1% EtOAc/CH$_2$Cl$_2$, gave (7R)-7-{[(4-bromobenzyl)oxy]methyl}-7-methyl-2-nitro-6,7-dihydro-5H-imidazo[2,1-b][1,3]oxazine (160) (349 mg, 57%) as a white solid: mp (CH$_2$Cl$_2$/hexane) 157-159° C.; $^1$H NMR (CDCl$_3$) δ 7.46 (dt, J=8.3, 2.0 Hz, 2H), 7.39 (s, 1H), 7.12 (br d, J=8.3 Hz, 2H), 4.50 (s, 2H), 4.09 (ddd, J=12.5, 6.9, 6.0 Hz, 1H), 4.01 (ddd, J=12.5, 7.0, 6.0 Hz, 1H), 3.62 (d, J=10.2 Hz, 1H), 3.58 (d, J=10.2 Hz, 1H), 2.37 (ddd, J=14.4, 7.0, 6.0 Hz, 1H), 2.10 (ddd, J=14.4, 6.9, 6.1 Hz, 1H), 1.46 (s, 3H); [α]$_D^{27}$ 30.0° (c 1.00, CHCl$_3$); HRFABMS calcd for C$_{15}$H$_{17}$BrN$_3$O$_4$ m/z [M+H]$^+$ 384.0382, 382.0402. found 384.0385, 382.0398.

A stirred mixture of bromide 160 (347.5 mg, 0.909 mmol), 4-(trifluoromethoxy)phenylboronic acid (283 mg, 1.37 mmol) and Pd(dppf)Cl$_2$ (101 mg, 0.138 mmol) in toluene (16 mL) and EtOH (6 mL) was degassed for 10 min (vacuum pump) and then N$_2$ was added. An aqueous solution of 2M Na$_2$CO$_3$ (3.0 mL, 6.00 mmol) was added by syringe and the stirred mixture was again degassed for 10 min, and then N$_2$ was added. The resulting mixture was stirred at 88° C. for 75 min, and then cooled, diluted with aqueous NaHCO$_3$ (100 mL) and extracted with CH$_2$Cl$_2$ (6×100 mL). The extracts were evaporated to dryness and the residue was chromatographed on silica gel. Elution with 0-0.5% EtOAc/CH$_2$Cl$_2$ firstly gave foreruns, and then further elution with 0.5-1.5% EtOAc/CH$_2$Cl$_2$ gave 57 (381 mg, 90%) as a cream solid: mp (CH$_2$Cl$_2$/hexane) 165-167° C.; $^1$H NMR (CDCl$_3$) δ 7.58 (dt, J=8.7, 2.4 Hz, 2H), 7.52 (br d, J=8.2 Hz, 2H), 7.38 (s, 1H), 7.32 (br d, J=8.1 Hz, 2H), 7.28 (br d, J=8.1 Hz, 2H), 4.61 (d, J=12.1 Hz, 1H), 4.58 (d, J=12.1 Hz, 1H), 4.11 (ddd, J=12.4, 7.2, 5.8 Hz, 1H), 4.01 (ddd, J=12.6, 6.5, 6.1 Hz, 1H), 3.67 (d, J=10.2Hz, 1H), 3.63 (d, J=10.2 Hz, 1H), 2.40 (ddd, J=14.4, 6.6, 6.1 Hz, 1H), 2.13 (ddd, J=14.5, 7.3, 6.0 Hz, 1H), 1.48 (s, 3H); [α]$_D^{27}$ 37.0° (c 1.00, CHCl$_3$). Anal. (C$_{22}$H$_{20}$F$_3$N$_3$O$_5$) C, H, N.

FFF. Synthesis of (7S)-7-methyl-2-nitro-7-({[4'-(trifluoromethoxy)[1,1'-biphenyl]-4-yl]methoxy}methyl)-6,7-dihydro-5H-imidazo[2,1-b][1,3]oxazine (Compound 58 of Table 1) by the Method of Scheme 12

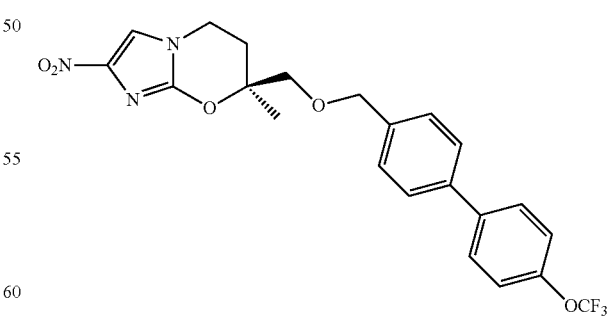

58

Hydrolysis of (S)-acetate 161 (426 mg, 1.67 mmol) with K$_2$CO$_3$ in MeOH/water as in Example 2EEE above, followed by chromatography of the product on silica gel, eluting with 0-1% MeOH/CH$_2$Cl$_2$ (forerun), and then with 1-2.5% MeOH/CH$_2$Cl$_2$, gave [(7S)-7-methyl-2-nitro-6,7-dihydro-5H-imidazo[2,1-b][1,3]oxazin-7-yl]methanol (162) (343 mg, 96%) as a pale yellow solid that was used directly in the next step; $^1$H NMR [(CD$_3$)$_2$SO] δ 8.03 (s, 1H), 5.22 (br t, J=5.7 Hz, 1H), 4.13 (dt, J=13.0, 6.0 Hz, 1H), 4.05 (ddd, J=12.9, 8.1, 5.6 Hz, 1H), 3.54 (dd, J=11.6, 5.4 Hz, 1H), 3.48 (dd, J=11.6, 5.7 Hz, 1H), 2.21 (ddd, J=14.4, 8.1, 5.9 Hz, 1H), 2.00 (dt, J=14.4, 5.8 Hz, 1H), 1.32 (s, 3H); [α]$_D^{27}$ 18.0° (c 1.00, DMF).

Alkylation of (S)-alcohol 162 with 4-bromobenzyl bromide (1.35 equiv.) and NaH (1.55 equiv.) as in Example 2UU above for 3 h, followed by chromatography of the product on silica gel, eluting with CH$_2$Cl$_2$ (foreruns) and then with 1% EtOAc/CH$_2$Cl$_2$, gave (7S)-7-{[(4-bromobenzyl)oxy]methyl}-7-methyl-2-nitro-6,7-dihydro-5H-imidazo[2,1-b][1,3]oxazine (163) (373 mg, 61%) as a white solid: mp (CH$_2$Cl$_2$/hexane) 159-161° C.; $^1$H NMR (CDCl$_3$) δ 7.46 (dt, J=8.4, 2.1 Hz, 2H), 7.39 (s, 1H), 7.12 (dt, J=8.4, 2.1 Hz, 2H), 4.50 (s, 2H), 4.09 (ddd, J=12.5, 7.0, 5.8 Hz, 1H), 4.01 (ddd, J=12.5, 7.1, 5.9 Hz, 1H), 3.62 (d, J=10.2 Hz, 1H), 3.58 (d, J=10.2 Hz, 1H), 2.37 (ddd, J=14.4, 7.1, 5.9 Hz, 1H), 2.10 (ddd, J=14.5, 7.0, 5.9 Hz, 1H), 1.46 (s, 3H); [α]$_D^{27}$ −32.0° (c 1.00, CHCl$_3$); HRFABMS calcd for C$_{15}$H$_{17}$BrN$_3$O$_4$ m/z [M+H]$^+$ 384.0382, 382.0402. found 384.0374, 382.0393.

Suzuki coupling of bromide 163 and 4-(trifluoromethoxy)phenylboronic acid as in Example 2EEE, followed by chromatography of the product on silica gel, eluting with 0-0.5% EtOAc/CH$_2$Cl$_2$ (foreruns) and then with 0.5-1% EtOAc/CH$_2$Cl$_2$, gave 58 (415 mg, 92%) as a cream solid: mp (CH$_2$Cl$_2$/hexane) 162-164° C.; $^1$H NMR (CDCl$_3$) δ 7.58 (dt, J=8.8, 2.5 Hz, 2H), 7.52 (br d, J=8.3 Hz, 2H), 7.38 (s, 1H), 7.32 (br d, J=8.3 Hz, 2H), 7.28 (br dd, J=8.8, 0.8 Hz, 2H), 4.61 (d, J=12.1 Hz, 1H), 4.58 (d, J=12.1 Hz, 1H), 4.11 (ddd, J=12.4, 7.3, 5.8 Hz, 1H), 4.01 (ddd, J=12.5, 6.6, 6.1 Hz, 1H), 3.67 (d, J=10.2 Hz, 1H), 3.63 (d, J=10.2 Hz, 1H), 2.40 (ddd, J=14.4, 6.7, 6.0 Hz, 1H), 2.13 (ddd, J=14.4, 7.3, 6.0 Hz, 1H), 1.48 (s, 3H). [α]$_D^{27}$ −36.0° (c 1.00, CHCl$_3$). Anal. (C$_{22}$H$_{20}$F$_3$N$_3$O$_5$) C, H, N.

GGG. Synthesis of 2-nitro-6-{[4-(trifluoromethoxy)phenoxy]methyl}-6,7-dihydro-5H-imidazo[2,1-b][1,3]oxazine (Compound 59 of Table 1) by the Method of Scheme 13

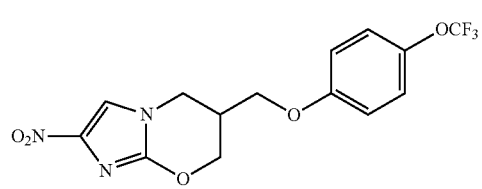

A solution of iodine (1.49 g, 5.85 mmol) in anhydrous CH$_2$Cl$_2$ (3×10 mL, then 4×1 mL to rinse) was added dropwise to a stirred mixture of imidazole (0.441 g, 6.48 mmol) and triphenylphosphine (1.50 g, 5.71 mmol) in anhydrous CH$_2$Cl$_2$ (3 mL) at 0° C. under N$_2$. After stirring at 0° C. for 30 min, a solution of 2-({[tert-butyl(dimethyl)silyl]oxy}methyl)-2-propen-1-ol (164) (reported by Chen et al., US 2007213341 A1, by monosilylation of 2-methylene-1,3-propanediol) (1.00 g, 4.94 mmol) in anhydrous CH$_2$Cl$_2$ (4 mL, then 4×1 mL to rinse) was added, and the mixture was stirred at 0-8° C. for 5 h. The resulting mixture was concentrated carefully under reduced pressure, and the residual oil was chromatographed on silica gel. Elution with pentane firstly gave foreruns, and then further elution with 10% CH$_2$Cl$_2$/pentane gave tert-butyl(dimethyl)silyl 2-(iodomethyl)-2-propenyl ether (165) (1.46 g, 95%) as a volatile pink oil that was used directly in the next step; $^1$H NMR (CDCl$_3$) δ 5.31 (br s, 1H), 5.19 (d, J=1.3 Hz, H), 4.31 (s, 2H), 3.95 (s, 2H), 0.92 (s, 9H), 0.10 (s, 6H).

A mixture of iodide 165 (4.63 g, 14.8 mmol), 4-(trifluoromethoxy)phenol (3.10 mL, 23.9 mmol) and powdered K$_2$CO$_3$ (3.56 g, 25.8 mmol) in acetone (10 mL) was stirred at 50° C. for 11 h. The resulting cooled mixture was diluted with ice-water (100 mL) and extracted with CH$_2$Cl$_2$ (4×100 mL). The combined extracts were evaporated to dryness and the residue was chromatographed on silica gel. Elution with 0-3% CH$_2$Cl$_2$/petroleum ether firstly gave foreruns, and then further elution with 5-10% CH$_2$Cl$_2$/petroleum ether gave tert-butyl(dimethyl)[(2-{[4-(trifluoromethoxy)phenoxy]methyl}-2-propenyl)oxy]silane (166) (3.12 g, 58%) as a colourless oil; $^1$H NMR (CDCl$_3$) δ 7.12 (br d, J=9.0 Hz, 2H), 6.90 (dt, J=9.1, 2.9 Hz, 2H), 5.27 (d, J=0.7 Hz, 1H), 5.20 (d, J=1.1 Hz, 1H), 4.54 (s, 2H), 4.24 (s, 2H), 0.91 (s, 9H), 0.07 (s, 6H); HRFABMS calcd for C$_{17}$H$_{26}$F$_3$O$_3$Si m/z [M+H]$^+$ 363.1603. found 363.1604.

A solution of iodine (825 mg, 3.25 mmol) in anhydrous THF (5 mL, then 2×3 mL to rinse) was added dropwise (over 70 min) to a stirred mixture of alkene 166 (5.21 g, 14.4 mmol) and powdered NaBH$_4$ (257 mg, 6.79 mmol) in anhydrous THF (18 mL) at 0° C. under N$_2$. After stirring at 0° C. for 3 h, and then at room temperature for 13 h, the mixture was again cooled to 0° C., treated with 30% H$_2$O$_2$ (6.8 mL) and 3N NaOH (6.8 mL), and then stirred at room temperature for 3 h. Water (160 mL) was then added, and the mixture was extracted with EtOAc (4×160 mL). The extracts were washed with brine (80 mL) and evaporated to dryness and the residue was chromatographed on silica gel. Elution with 0-3.5% EtOAc/petroleum ether firstly gave foreruns, and then further elution with 4-8% EtOAc/petroleum ether gave 3-{[tert-butyl(dimethyl)silyl]oxy}-2-{[4-(trifluoromethoxy)phenoxy]methyl}-1-propanol (168) (3.32 g, 61%) as a colourless oil; $^1$H NMR (CDCl$_3$) δ 7.13 (br d, J=9.0 Hz, 2H), 6.89 (dt, J=9.1, 3.0 Hz, 2H), 4.08 (dd, J=9.3, 6.6 Hz, 1H), 4.04 (dd, J=9.3, 6.0 Hz, 1H), 3.94-3.81 (m, 4H), 2.36 (dd, J=6.1, 5.2 Hz, 1H), 2.19 (m, 1H), 0.89 (s, 9H), 0.07, 0.05 (2 s, 6H); HRFABMS calcd for C$_{17}$H$_{28}$F$_3$O$_4$Si m/z [M+H]$^+$ 381.1709. found 381.1707.

A solution of iodine (2.89 g, 11.4 mmol) in anhydrous CH$_2$Cl$_2$ (6×10 mL, then 5mL+2 mL to rinse) was added dropwise (over 100 min) to a stirred mixture of alcohol 168 (3.28 g, 8.62 mmol), imidazole (1.50 g, 22.0 mmol) and triphenylphosphine (2.83 g, 10.8 mmol) in anhydrous CH$_2$Cl$_2$ (20 mL) under N$_2$. After stirring at room temperature for 15 h, the resulting mixture was concentrated under reduced pressure, and the residue was chromatographed on silica gel. Elution with petroleum ether firstly gave foreruns, and then further elution with 5-20% CH$_2$Cl$_2$/petroleum ether gave tert-butyl(3-iodo-2-{[4-(trifluoromethoxy)phenoxy]methyl}propoxy)dimethylsilane (170) (3.90 g, 92%) as a pale brown oil; NMR (CDCl$_3$) δ 7.13 (br dd, J=9.1, 0.7 Hz, 2H), 6.89 (dt, J=9.1, 3.0 Hz, 2H), 4.01 (dd, J=9.3, 5.7 Hz, 1H), 3.94 (dd, J=9.3, 6.2 Hz, 1H), 3.75 (dd, J=10.1, 5.6 Hz, 1H), 3.70 (dd, J=10.1, 5.6 Hz, 1H), 3.39 (dd, J=10.1, 5.9 Hz, 1H), 3.37 (dd, J=10.1, 6.0 Hz, 1H), 2.10 (sept, J=5.8 Hz, 1H), 0.89 (s, 9H), 0.07, 0.06 (2 s, 6H); HRCIMS calcd for C$_{17}$H$_{27}$F$_3$IO$_3$Si m/z [M+H]$^+$ 491.0726. found 491.0721.

A mixture of iodide 170 (3.89 g, 7.93 mmol), 2-bromo-4(5)-nitroimidazole (80) (1.68 g, 8.77 mmol) and powdered K$_2$CO$_3$ (1.90 g, 13.7 mmol) in anhydrous DMF (20 mL) was stirred at 84-88° C. for 37 h. The resulting cooled mixture was diluted with ice-water (100 mL) and extracted with EtOAc (5×100 mL). The extracts were washed with brine (100 mL), backextracting with EtOAc (50 mL), and then evaporated to dryness and the residue was chromatographed on silica gel.

Elution with 0-7% EtOAc/petroleum ether firstly gave foreruns, and then further elution with 7-15% EtOAc/petroleum ether gave 2-bromo-1-(3-{[tert-butyl(dimethyl)silyl]oxy}-2-{[4-(trifluoromethoxy)phenoxy]methyl}propyl)-4-nitro-1H-imidazole (172) (3.57 g, 81%) as a pale yellow oil; $^1$H NMR (CDCl$_3$) δ 7.82 (s, 1H), 7.16 (br dd, J=9.1, 0.7 Hz, 2H), 6.85 (dt, J=9.1, 3.0 Hz, 2H), 4.26 (d, J=7.1 Hz, 2H), 3.96 (d, J=5.6 Hz, 2H), 3.77 (dd, J=10.6, 5.1 Hz, 1H), 3.67 (dd, J=10.6, 4.7 Hz, 1H), 2.51 (m, 1H), 0.92 (s, 9H), 0.08, 0.07 (s, 6H); HRFABMS calcd for C$_{20}$H$_{28}$BrF$_3$N$_3$O$_5$Si m/z [M+H]$^+$ 556.0913, 554.0934. found 556.0921, 554.0938.

Silyl ether 172 (3.42 g, 6.17 mmol) was treated with a solution of 1% HCl in 95% EtOH (desilylation conditions described by Cunico et al., 1980) (31 mL), and the mixture was stirred at room temperature for 12 h. The resulting solution was cooled (CO$_2$/acetone), neutralised by dropwise addition of 7M NH$_3$ in MeOH (6.6 mL) with stirring, and then concentrated to dryness and the residue was chromatographed on silica gel. Elution with 0-30% EtOAc/petroleum ether firstly gave foreruns, and then further elution with 40-50% EtOAc/petroleum ether gave 3-(2-bromo-4-nitro-1H-imidazol-1-yl)-2-{[4-(trifluoromethoxy)phenoxy]methyl}-1-propanol (174) (2.48 g, 91%) as a white solid: mp (CH$_2$Cl$_2$/pentane) 97-99° C.; $^1$H NMR (CDCl$_3$) δ 7.88 (s, 1H), 7.17 (br d, J=8.5 Hz, 2H), 6.88 (dt, J=9.1, 3.0 Hz, 2H), 4.34 (dd, J=14.4, 7.4 Hz, 1H), 4.31 (dd, J=14.4, 7.1 Hz, 1H), 4.06 (dd, J=9.6, 5.7 Hz, 1H), 4.03 (dd, J=9.6, 4.8 Hz, 1H), 3.88 (dt, J=10.8, 4.4 Hz, 1H), 3.76 (dt, J=10.8, 4.9 Hz, 1H), 2.54 (m, 1H), 1.72 (t, J=4.4 Hz, 1H); HRFABMS calcd for C$_{14}$H$_{14}$BrF$_3$N$_3$O$_5$ m/z [M+H]$^+$ 442.0049, 440.0069. found 442.0053, 440.0063.

A stirred solution of alcohol 174 (2.48 g, 5.64 mmol) in anhydrous DMF (50 mL) under N$_2$ at 0° C. was treated with 60% NaH (345 mg, 8.63 mmol), then quickly degassed and resealed under N$_2$. After stirring at room temperature for 4 h, the reaction was cooled (CO$_2$/acetone), quenched with ice/aqueous NaHCO$_3$ (30 mL), added to brine (200 mL), and extracted with CH$_2$Cl$_2$ (8×100 mL). The combined extracts were evaporated to dryness and the residue was chromatographed on silica gel. Elution with 0-1% EtOAc/CH$_2$Cl$_2$ firstly gave foreruns, and then further elution with 1.5-2% EtOAc/CH$_2$Cl$_2$ gave 59 (1.407 g, 69%) as a pale yellow solid: mp (CH$_2$Cl$_2$/hexane) 141-143° C.; $^1$H NMR (CDCl$_3$) δ 7.45 (s, 1H), 7.17 (br dd, J=9.1, 0.7 Hz, 2H), 6.88 (dt, J=9.2, 3.0 Hz, 2H), 4.62 (ddd, J=11.5, 3.2, 0.8 Hz, 1H), 4.50 (dd, J=11.6, 7.3 Hz, 1H), 4.27 (ddd, J=12.5, 5.6, 0.7 Hz, 1H), 4.17 (dd, J=12.4, 7.1 Hz, 1H), 4.13 (dd, J=9.6, 5.7 Hz, 1H), 4.07 (dd, J=9.6, 6.7 Hz, 1H), 2.88 (m, 1H). Anal. (C$_{14}$H$_{12}$F$_3$N$_3$O$_5$) C, H, N.

HHH. Synthesis of (6R)-2-nitro-6-{[4-(trifluoromethoxy)phenoxy]methyl}-6,7-dihydro-5H-imidazo[2,1-b][1,3]oxazine (Compound 60 of Table 1) by the Method of Scheme 13

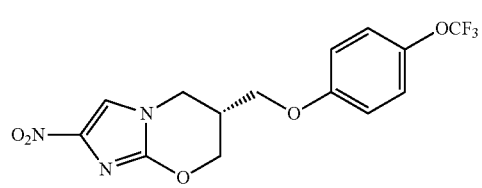

Racemic ether 59 (1.18 g) was separated into pure enantiomers by preparative chiral HPLC, using a ChiralPak IA column and an isocratic solvent system of 27% EtOH in hexane, to firstly give 60 (510 mg, 43%) as a white solid: mp (CH$_2$Cl$_2$/hexane) 138-139° C.; $^1$H NMR (CDCl$_3$) δ 7.45 (s, 1H), 7.17 (br dd, J=9.0, 0.6 Hz, 2H), 6.88 (dt, J=9.2, 3.0 Hz, 2H), 4.62 (ddd, J=11.5, 3.2, 0.7 Hz, 1H), 4.50 (dd, J=11.5, 7.3 Hz, 1H), 4.27 (br dd, J=12.4, 5.6 Hz, 1H), 4.17 (dd, J=12.4, 7.0 Hz, 1H), 4.13 (dd, J=9.6, 5.7 Hz, 1H), 4.07 (dd, J=9.6, 6.7 Hz, 1H), 2.88 (m, 1H); [α]$^{26}$ 14° (c, 1.00, CHCl$_3$). Anal. (C$_{14}$H$_{12}$F$_3$N$_3$O$_5$) C, H, N.

III. Synthesis of (6S)-2-nitro-6-{[4-(trifluoromethoxy)phenoxy]methyl}-6,7-dihydro-5H-imidazo[2,1-b][1,3]oxazine (Compound 61 of Table 1) by the Method of Scheme 13

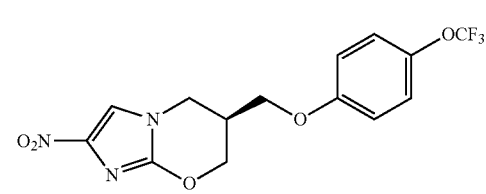

Preparative chiral HPLC of ether 59 (see Example 2HHH above) secondly gave 61 (509 mg, 43%) as a white solid: mp (CH$_2$Cl$_2$/hexane) 139-140° C.; $^1$H NMR (CDCl$_3$) δ 7.45 (s, 1H), 7.17 (br dd, J=9.1, 0.6 Hz, 2H), 6.88 (dt, J=9.1, 3.0 Hz, 2H), 4.62 (ddd, J=11.5, 3.2, 0.6 Hz, 1H), 4.50 (dd, J=11.5, 7.3 Hz, 1H), 4.27 (br dd, J=12.4, 5.2 Hz, 1H), 4.17 (dd, J=12.5, 7.1 Hz, 1H), 4.13 (dd, J=9.6, 5.7 T-Tz, 1H), 4.07 (dd, J=9.6, 6.7 Hz, 1H), 2.88 (m, 1H); [α]$^{26}$ −14° (c, 1.00, CHCl$_3$). Anal. (C$_{14}$H$_{12}$F$_3$N$_3$O$_5$) C, H, N.

JJJ. Synthesis of 6-{[(4'-fluoro[1,1'-biphenyl]-4-yl)oxy]methyl}-2-nitro-6,7-dihydro-5H-imidazo[2,1-b][1,3]oxazine (Compound 62 of Table 1) by the Method of Scheme 13

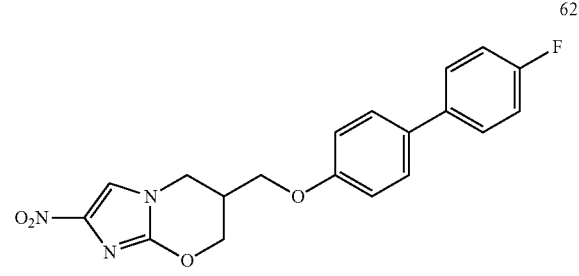

Alkylation of 4-iodophenol with iodide 165 (see Example 2GGG) and K$_2$CO$_3$ as in Example 2GGG above for 6 h, followed by chromatography of the product on silica gel, eluting with petroleum ether (foreruns) and then with 5% CH$_2$Cl$_2$/petroleum ether, gave tert-butyl({2-[(4-iodophenoxy)methyl]-2-propenyl}oxy)dimethylsilane (167) (94%) as an oil; $^1$H NMR (CDCl$_3$) δ 7.54 (dt, J=8.9, 2.7 Hz, 2H), 6.70 (dt, J=8.9, 2.7 Hz, 2H), 5.25 (d, J=1.0 Hz, 1H), 5.19 (d, J=1.2 Hz, 1H), 4.51 (s, 2H), 4.23 (s, 2H), 0.91 (s, 9H), 0.07 (2 s, 6H); HRFABMS calcd for C$_{16}$H$_{26}$H$_{26}$Si m/z [M+H]$^+$ 405.0747. found 405.0739.

A solution of iodine (282 mg, 1.11 mmol) in anhydrous THF (1.5 mL, then 2×0.75 mL to rinse) was added dropwise (over 40 min) to a stirred mixture of alkene 167 (1.71 g, 4.23 mmol) and powdered NaBH$_4$ (90 mg, 2.38 mmol) in anhydrous THF (5.5 mL) at 0° C. under N$_2$. After stirring at 0° C. for 4 h, and then at room temperature for 13 h, the mixture was again cooled to 0° C., treated with 30% H$_2$O$_2$ (2.4 mL) and 3N NaOH (2.4 mL), and then stirred at room temperature for 3 h. Water (50 mL) was then added, and the mixture was extracted with EtOAc (4×50 mL). The extracts were washed with brine (50 mL) and evaporated to dryness and the residue was chromatographed on silica gel. Elution with 0-2% EtOAc/petroleum ether firstly gave foreruns, and then further elution with 4-5% EtOAc/petroleum ether gave 3-{[tert-butyl(dimethyl)silyl]oxy}-2-[(4-iodophenoxy)methyl]-1-propanol (169) (1.26 g, 71%) as a pale yellow oil; $^1$H NMR (CDCl$_3$) δ 7.55 (dt, J=9.0, 2.7 Hz, 2H), 6.69 (dt, J=9.0, 2.7 Hz, 2H), 4.06 (dd, J=9.3, 6.7 Hz, 1H), 4.01 (dd, J=9.3, 5.9 Hz, 1H), 3.93-3.80 (m, 4H), 2.36 (dd, J=6.3, 5.1 Hz, 1H), 2.17 (sept, J=5.4 Hz, 1H), 0.89 (s, 9H), 0.06, 0.05 (2 s, 6H); HRFABMS calcd for C$_{16}$H$_{28}$IO$_3$Si m/z [M+H]$^+$ 423.0853. found 423.0849.

Iodination of alcohol 169 with I$_2$, PPh$_3$ and imidazole as in Example 2GGG above for 12 h, followed by chromatography of the product on silica gel, eluting with 0-5% CH$_2$Cl$_2$/petroleum ether (foreruns) and then with 5-10% CH$_2$Cl$_2$/petroleum ether, gave tert-butyl {3-iodo-2-[(4-iodophenoxy)methyl]propoxy}dimethylsilane (171) (94%) as a colourless oil; $^1$H NMR (CDCl$_3$) δ 7.55 (dt, J=9.0, 2.7 Hz, 2H), 6.68 (dt, J=9.0, 2.7 Hz, 2H), 3.98 (dd, J=9.4, 5.7 Hz, 1H), 3.92 (dd, J=9.4, 6.2 Hz, 1H), 3.74 (dd, J=10.1, 5.6 Hz, 1H), 3.69 (dd, J=10.1, 5.6 Hz, 1H), 3.38 (dd, J=10.0, 5.9 Hz, 1H), 3.35 (dd, J=10.0, 6.1 Hz, 1H), 2.09 (sept, J=5.8 Hz, 1H), 0.89 (s, 9H), 0.06 (2 s, 6H); HRFABMS calcd for C$_{16}$H$_{27}$I$_2$O$_2$Si m/z [M+H]$^+$ 532.9870. found 532 9864.

Alkylation of 2-promo-4(5)-nitroimidazole (80) with iodide 171 and K$_2$CO$_3$ as in Example 2GGG above for 33 h, followed by chromatography of the product on silica gel, eluting with 0-7% EtOAc/petroleum ether (foreruns) and then with 8-15% EtOAc/petroleum ether, gave 2-bromo-1-{3-{[ter 1-butyl(dimethyl)silyl]oxy}-2-[(4-iodophenoxy)methyl]propyl}-4-nitro-1H-imidazole (173) (80%) as a white solid: mp (CH$_2$Cl$_2$/pentane) 81-83° C.; $^1$H NMR (CDCl$_3$) δ 7.81 (s, 1H), 7.57 (dt, J=9.0, 2.7 Hz, 2H), 6.64 (dt, J=9.0, 2.6 Hz, 2H), 4.24 (d, J=7.1 Hz, 1H), 3.93 (d, J=5.6 Hz, 1H), 3.76 (dd, J=10.6, 5.1 Hz, 1H), 3.66 (dd, J=10.6, 4.7 Hz, 1H), 2.50 (m, 1H), 0.91 (s, 9H), 0.07 (2 s, 6H); HRFABMS calcd for C$_{19}$H$_{28}$BrIN$_3$O$_4$Si m/z [M+H]$^+$ 598.0057, 596.0077. found 598.0070, 596.0082.

Hydrolysis of silyl ether 173 with 1% HCl in 95% EtOH as in Example 2GGG above for 7 h, followed by chromatography of the product on silica gel, eluting with 0-30% EtOAc/petroleum ether (foreruns) and then with 40-50% EtOAc/petroleum ether, gave 3-(2-bromo-4-nitro-1H-imidazol-1-yl)-2-[(4-iodophenoxy)methyl]-1-propanol (175) (86%) as a white solid: mp (CH$_2$Cl$_2$/pentane) 109-111° C.; $^1$H NMR (CDCl$_3$) δ 7.87 (s, 1H), 7.58 (dt, J=9.0, 2.7 Hz, 2H), 6.66 (dt, J=9.0, 2.7 Hz, 2H), 4.33 (dd, J=14.4, 7.3 Hz, 1H), 4.29 (dd, J=14.4, 7.1 Hz, 1H), 4.03 (dd, J=9.6, 5.7 Hz, 1H), 4.00 (dd, J=9.6, 7.8 Hz, 1H), 3.86 (ddd, J=10.9, 4.6, 4.3 Hz, 1H), 3.75 (dt, J=10.8, 4.9 Hz, 1H), 2.52 (m, 1H), 1.72 (t, J=4.4 Hz, 1H); HRFABMS calcd for C$_{13}$H$_{14}$BrIN$_3$O$_4$ m/z [M+H]$^+$ 483.9192, 481.9212. found 483.9200, 481.9211.

Ring closure of alcohol 175 with NaH as in Example 2GGG for 5 h, followed by chromatography of the product on silica gel, eluting with 0-1% EtOAc/CH$_2$Cl$_2$ (foreruns) and then with 1.5-2% EtOAc/CH$_2$Cl$_2$, gave 6-[(4-iodophenoxy)methyl]-2-nitro-6,7-dihydro-5H-imidazo[2,1-b][1,3]oxazine (176) (78%) as a pale yellow solid: mp (CH$_2$Cl$_2$/pentane triturate) 239-240° C.; $^1$H NMR [(CD$_3$)$_2$SO] δ 8.09 (s, 1H), 7.60 (dt, J=9.0, 2.7 Hz, 2H), 6.82 (dt, J=9.0, 2.7 Hz, 2H), 4.59 (dd, J=10.9, 2.9 Hz, 1H), 4.44 (dd, J=11.0, 7.2 Hz, 1H), 4.28 (dd, J=12.5, 5.4 Hz, 1H), 4.09 (dd. J=10.0, 6.7 Hz, 1H), 4.06 (dd, J=10.0, 6.7 Hz, 1H), 4.03 (dd, J=12.5, 7.0 Hz, 1H), 2.82 (m, 1H). Anal. (C$_{13}$H$_{12}$IN$_3$O$_4$) C, H, N.

Suzuki coupling of iodide 176 and 4-fluorophenylboronic acid as in Example 2CC above, followed by chromatography of the product on silica gel, eluting with 0-1% EtOAc/CH$_2$Cl$_2$ (foreruns) and then with 1-2% EtOAc/CH$_2$Cl$_2$, gave 62 (92%) as a pale pink solid: mp (CH$_2$Cl$_2$/pentane) 201-203° C.; $^1$H NMR [(CD$_3$)$_2$SO] δ 8.11 (s, 1H), 7.65 (dt, J=8.9, 2.7 Hz, 2H), 7.64 (dt, J=8.8, 2.7 Hz, 2H), 7.59 (dt, J=8.8, 2.5 Hz, 2H), 7.25 (tt, 8.9, 2.7 Hz, 2H), 7.05 (dt, J=8.8, 2.6 Hz, 2H), 4.63 (dd, J=10.9, 2.9 Hz, 1H), 4.48 (dd, J=11.0, 7.3 Hz, 1H), 4.31 (dd, J=12.5, 5.4 Hz, 1H), 4.16 (dd, J=10.0, 6.7 Hz, 1H), 4.12 (dd, J=10.0, 6.7 Hz, 1H), 4.07 (dd, J=12.6, 7.0 Hz, 1H), 2.86 (m, 1H). Anal. (C$_{19}$H$_{16}$FN$_3$O$_4$) C, H, N.

KKK. Synthesis of 2-nitro-6-({[4'-(trifluoromethyl)[1,1'-biphenyl]-4-yl]oxy}methyl)-6,7-dihydro-5H-imidazo[2,1-b][1,3]oxazine (Compound 63 of Table 1) by the Method of Scheme 13

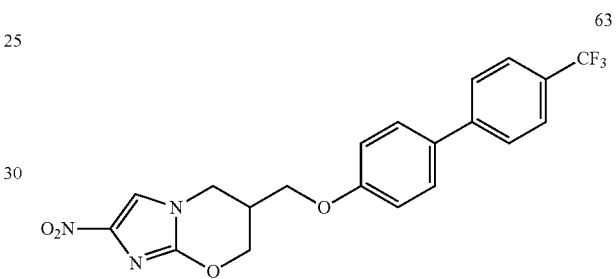

Suzuki coupling of iodide 176 (see Example 2JJJ above) and 4-(trifluoromethyl)phenylboronic acid as in Example 2CC above, followed by chromatography of the product on silica gel, eluting with 0-1% EtOAc/CH$_2$Cl$_2$ (foreruns) and then with 1-2% EtOAc/CH$_2$Cl$_2$, gave 63 (90%) as a cream solid: mp (CH$_2$Cl$_2$/pentane) 218-221° C.; $^1$H NMR [(CD$_3$)$_2$SO] δ 8.11 (s, 1H), 7.85 (br d, 0.1=8.2 Hz, 2H), 7.77 (br d, J=8.3 Hz, 2H), 7.71 (dt, J=8.8, 2.5 Hz, 2H), 7.10 (dt, J=8.8, 2.5 Hz, 2H), 4.63 (dd, J=10.9, 2.9 Hz, 1H), 4.48 (dd, J=11.0, 7.2 Hz, 1H), 4.32 (dd, J=12.5, 5.5 Hz, 1H), 4.18 (dd, J=10.0, 6.7 Hz, 1H), 4.15 (dd, J=10.0, 6.7 Hz, 1H), 4.08 (dd, J=12.6, 7.0 Hz, 1H), 2.87 (m, 1H). Anal. (C$_{20}$H$_{16}$F$_3$N$_3$O$_4$) C, H, N.

LLL. Synthesis of 2-nitro-6-({[4'-(trifluoromethoxy)[1,1'-biphenyl]-4-yl]oxy}methyl)-6,7-dihydro-5H-imidazo[2,1-b][1,3]oxazine (Compound 64 of Table 1) by the Method of Scheme 13

Suzuki coupling of iodide 176 (see Example 2JJJ above) and 4-(trifluoromethoxy)phenylboronic acid as in Example 2CC above, followed by chromatography of the product on silica gel, eluting with CH$_2$Cl$_2$, gave 64 (93%) as a cream solid: mp (CH$_2$Cl$_2$/pentane) 192-194° C.; $^1$H NMR (CDCl$_3$) δ 7.54 (dt, J=8.7, 2.4 Hz, 2H), 7.50 (dt, J=8.7, 2.5 Hz, 2H), 7.46 (s, 1H), 7.26 (m, 2H), 6.96 (dt, J=8.7, 2.4 Hz, 2H), 4.63 (dd, J=11.5, 3.1 Hz, 1H), 4.52 (dd, J=11.5, 7.4 Hz, 1H), 4.28 (dd, J=12.4, 5.6 Hz, 1H), 4.20 (m, 1H), 4.18 (dd, J=10.0, 5.7 Hz, 1H), 4.12 (dd, J=9.7, 6.7 Hz, 1H), 2.91 (m, 1H). Anal. (C$_{20}$H$_{16}$F$_3$N$_3$O$_5$) C, H, N.

MMM. Synthesis of 6-({[5-(4-fluorophenyl)-2-pyridinyl]oxy}methyl)-2-nitro-6,7-dihydro-5H-imidazo[2,1-b][1,3]oxazine (Compound 65 of Table 1) by the Method of Scheme 14

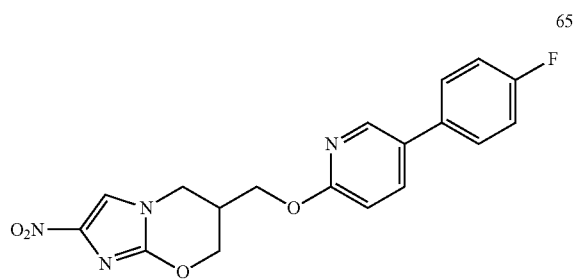

A mixture of 2-bromo-4(5)-nitroimidazole (80) (3.373 g, 17.6 mmol), 6-(iodomethyl)-2,2,3,3,9,9,10,10-octamethyl-4,8-dioxa-3,9-disilaundecane (177) (reported by Curran et al., 1998 in 4 steps from 2-methylene-1,3-propanediol) (6.79 g, 15.3 mmol) and powdered K$_2$CO$_3$ (5.10 g, 36.9 mmol) in anhydrous DMF (40 mL) under N$_2$ was stirred at 82° C. for 24 h. The resulting cooled mixture was added to ice-water (200 mL) and extracted with EtOAc (3×200 mL). The extracts were washed with water (200 mL), back-extracting with EtOAc (200 mL), and then further washed with brine (150 mL). The combined extracts were evaporated to dryness and the residue was chromatographed on silica gel. Elution with 0-2% EtOAc/petroleum ether firstly gave foreruns, and then further elution with 3-5% EtOAc/petroleum ether gave 2-bromo-1-[3-{[tert-butyl(dimethyl)silyl]oxy}-2-({[tert-butyl(dimethyl)silyl]oxy}methyl)propyl]-4-nitro-1H-imidazole (178) (7.35 g, 95%) as a white solid: mp (pentane) 51-53° C.; $^1$H NMR (CDCl$_3$) δ 7.83 (s, 1H), 4.12 (d, J=7.2 Hz, 2H), 3.61 (dd, J=10.4, 5.5 Hz, 2H), 3.56 (dd, J=10.4, 5.0 Hz, 2H), 2.15 (m, 1H), 0.91 (s, 18H), 0.07 (2 s, 2×6H). Anal. (C$_{19}$H$_{38}$BrN$_3$O$_4$Si$_2$) C, H, N.

A suspension of silyl ether 178 (7.35 g, 14.5 mmol) in a solution of 1% HCl in 95% EtOH (desilylation conditions described by Cunico et al., 1980) (150 mL) was stirred at room temperature for 4 h, and then kept at 4° C. for 12 h. The resulting solution was cooled (CO$_2$/acetone), neutralised by dropwise addition of 7M NH$_3$ in MeOH (9.8 mL) with stirring, and then concentrated to dryness and the residue was chromatographed on silica gel. Elution with 33-75% EtOAc/petroleum ether firstly gave foreruns, and then further elution with 75% EtOAc/petroleum ether and EtOAc gave 2-[(2-bromo-4-nitro-1H-imidazol-1-yl)methyl]-1,3-propanediol (179) (3.42, 85%) as a white solid: mp (MeOH/CH$_2$Cl$_2$/hexane) 110-112° C.; $^1$H NMR [(CD$_3$)$_2$SO] δ 8.50 (s, 1H), 4.65 (t, J=5.0 Hz, 2H), 4.07 (d, J=7.3 Hz, 2H), 3.41 (m, 4H), 2.06 (m, 1H). Anal. (C$_7$H$_{10}$BrN$_3$O$_4$) C, H, N.

A stirred solution of diol 179 (3.44 g, 12.3 mmol) in anhydrous DMF (30 mL) under N$_2$ at 0° C. was treated with 60% NaH (1.72 g, 43.0 mmol), then quickly degassed and resealed under N$_2$. After stirring at room temperature for 3.5 h, the reaction was cooled (CO$_2$/acetone), quenched with ice/aqueous NH$_4$Cl (20 mL) and aqueous NaHCO$_3$ (20 mL), added to brine (150 mL) and extracted with CH$_2$Cl$_2$ (3×150 mL), 10% MeOH/CH$_2$Cl$_2$ (6×150 mL), and EtOAc (15×150 mL). The combined extracts were evaporated to dryness and the residue was chromatographed on silica gel. Elution with 0-2% MeOH/CH$_2$Cl$_2$ firstly gave foreruns, and then further elution with 2-3% MeOH/CH$_2$Cl$_2$ gave the crude product (1.88 g), which was further chromatographed on silica gel. Elution with 50-90% EtOAc/petroleum ether firstly gave foreruns, and then further elution with 90% EtOAc/petroleum ether and EtOAc gave (2-nitro-6,7-dihydro-5H-imidazo[2,1-b][1,3]oxazin-6-yl)methanol (180) (1.649 g, 67%) as a pale yellow solid: mp (MeOH/CH$_2$Cl$_2$/hexane) 130-131° C.; $^1$H NMR [(CD$_3$)$_2$SO] δ 8.06 (s, 1H), 4.96 (t, J=5.1 Hz, 1H), 4.49 (ddd, J=10.9, 3.3, 0.9 Hz, 1H), 4.30 (dd, J=10.9, 7.9 Hz, 1H), 4.15 (ddd, J=12.5, 5.4, 0.8 Hz, 1H), 3.90 (dd, J=12.5, 7.7 Hz, 1H), 3.47 (m, 2H), 2.40 (m, 1H). Anal. (C$_7$H$_9$N$_3$O$_4$) C, H, N.

Alkylation of oxazine alcohol 180 with 5-bromo-2-fluoropyridine (91) (2.0 equiv.) and NaH (1.74 equiv.) as in Example 2OO for 3 h, followed by chromatography of the product on silica gel, eluting with 0-0.25% MeOH/CH$_2$Cl$_2$ (foreruns) and then with 0.25-0.5% MeOH/CH$_2$Cl$_2$, gave 6-{[(5-bromo-2-pyridinyl)oxy]methyl}-2-nitro-6,7-dihydro-5H-imidazo[2,1-b][1,3]oxazine (181) (67%) as a white solid: mp (MeOH/CH$_2$Cl$_2$/hexane) 233-235° C.; $^1$H NMR [(CD$_3$)$_2$SO] δ 8.27 (dd, J=2.5, 0.4 Hz, 1H), 8.07 (s, 1H), 7.93 (dd, J=8.8, 2.6 Hz, 1H), 6.85 (dd, J=8.9, 0.5 Hz, 1H), 4.60 (dd, J=11.0, 2.7 Hz, 1H), 4.44 (dd, J=11.1, 7.4 Hz, 1H), 4.36 (dd, J=11.0, 6.7 Hz, 1H), 4.33 (dd, J=11.0, 6.7 Hz, 1H), 4.27 (dd, J=12.5, 5.4 Hz, 1H), 4.04 (dd. J=12.6, 7.1 Hz, 1H), 2.85 (m, 1H). Anal. (C$_{12}$H$_{11}$BrN$_4$O$_4$.) C, H, N.

Suzuki coupling of bromide 181 and 4-fluorophenylboronic acid (2.0 equiv.) as in Example 2M for 2.5 h, followed by chromatography of the product on silica gel, eluting with 0-5% EtOAc/CH$_2$Cl$_2$ (foreruns) and then with 5-6% EtOAc/CH$_2$Cl$_2$, gave 65 (93%) as a cream solid: mp (CH$_2$Cl$_2$/pentane) 160-161° C.; $^1$H NMR (CDCl$_3$) δ 8.29 (dd, J=2.5, 0.6 Hz, 1H), 7.78 (dd, J=8.8, 2.5 Hz, 1H), 7.46 (ddt, J=8.9, 5.2, 2.6 Hz, 2H), 7.44 (s, 1H), 7.14 (tt, J=6.5, 2.6 Hz, 2H), 6.83 (dd, J=8.6, 0.7 Hz, 1H), 4.64 (ddd, J=11.4, 3.3, 1.0 Hz, 1H), 4.54 (dd, J=11.3, 6.2 Hz, 1H), 4.49 (dd, J=11.3, 6.5 Hz, 1H), 4.45 (dd, J=11.5, 7.9 Hz, 1H), 4.26 (ddd, J=12.4, 5.6, 0.9 Hz, 1H), 4.10 (dd, J=12.4, 7.7 Hz, 1H), 2.94 (m, 1H). Anal. (C$_{18}$H$_{15}$FN$_4$O$_4$) C, H, N.

NNN. Synthesis of 2-nitro-6-[({5-[4-(trifluoromethyl)phenyl]-2-pyridinyl}oxy)methyl]-6,7-dihydro-5H-imidazo[2,1-b][1,3]oxazine (Compound 66 of Table 1) by the Method of Scheme 14

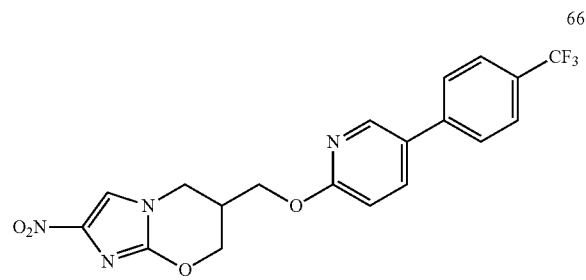

Suzuki coupling of bromide 181 (see Example 2MMM) and 4-(trifluoromethyl)phenylboronic acid as in Example 2M for 130 min, followed by chromatography of the product on silica gel, eluting with 0-4% EtOAc/CH$_2$Cl$_2$ (foreruns) and then with 5-6% EtOAc/CH$_2$Cl$_2$, gave 66 (94%) as a cream solid: mp (CH$_2$Cl$_2$/pentane) 180-182° C.; $^1$H NMR (CDCl$_3$) δ 8.38 (dd, J=2.5, 0.5 Hz, 1H), 7.87 (dd, J=8.6, 2.6 Hz, 1H), 7.73 (br d, J=8.2 Hz, 2H), 7.64 (br d, J=8.1 Hz, 2H), 7.48 (s, 1H), 6.89 (dd, J=8.6, 0.6 Hz, 1H), 4.66 (ddd, 11.4, 3.3, 0.9 Hz, 1H), 4.57 (dd, J=11.3, 6.3 Hz, 1H), 4.52 (dd, J=11.3, 6.4 Hz, 1H), 4.49 (dd, J=11.5, 7.9 Hz, 1H), 4.29 (ddd, J=12.4, 5.6, 0.8 Hz, 1H), 4.13 (dd, J=12.4, 7.6 Hz, 1H), 2.98 (m, 1H). Anal. (C$_{19}$H$_{15}$F$_3$N$_4$O$_4$) C, H, N.

OOO. Synthesis of 2-nitro-6-[({5-[4-(trifluoromethoxy)phenyl]-2-pyridinyl}oxy)methyl]-6,7-dihydro-5H-imidazo[2,1-b][1,3]oxazine (Compound 67 of Table 1) by the Method of Scheme 14

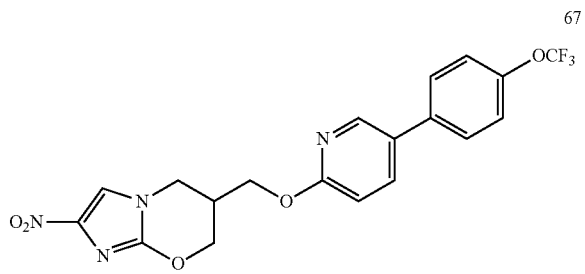

67

Suzuki coupling of bromide 181 (see Example 2MMM) and 4-(trifluoromethoxy)phenylboronic acid as in Example 2M for 2 h, followed by chromatography of the product on silica gel, eluting with 0-4% EtOAc/CH$_2$Cl$_2$ (foreruns) and then with 4-5% EtOAc/CH$_2$Cl$_2$, gave 67 (93%) as a cream solid: mp (CH$_2$Cl$_2$/pentane) 182-183° C.; $^1$H NMR (CDCl$_3$) δ 8.31 (dd, J=2.5, 0.7 Hz, 1H), 7.80 (dd, J=8.6, 2.6 Hz, 1H), 7.52 (dt, J=8.8, 2.6 Hz, 2H), 7.44 (s, 1H), 7.30 (br dd, J=8.7, 0.8 Hz, 2H), 6.84 (dd, J=8.6, 0.6 Hz, 1H), 4.64 (ddd, J=11.5, 3.3, 0.9 Hz, 1H), 4.54 (dd, J=11.3, 6.2 Hz, 1H), 4.50 (dd, J=11.2, 6.4 Hz, 1H), 4.46 (dd, J=11.4, 7.9 Hz, 1H), 4.26 (ddd, J=12.4, 5.6, 0.8 Hz, 1H), 4.10 (dd, J=12.4, 7.6 Hz, 1H), 2.95 (m, 1H). Anal. (C$_{19}$H$_{15}$F$_3$N$_4$O$_5$) C, H, N.

PPP. Synthesis of 6-({[6-(4-fluorophenyl)-3-pyridinyl]oxy}methyl)-2-nitro-6,7-dihydro-5H-imidazo[2,1-b][1,3]oxazine (Compound 68 of Table 1) by the Method of Scheme 15

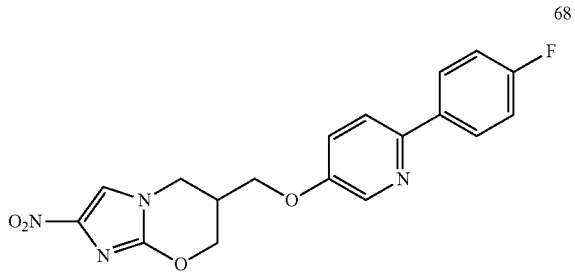

68

Diethylazodicarboxylate (3.445 mL, 22.2 mmol) was added dropwise to a stirred mixture of 3-{[tert-butyl(dimethyl)silyl]oxy}-2-({[tert-butyl(dimethyl)silyl]oxy}methyl)-1-propanol (184) (reported by Kim et al., 2001, via silylation and hydroboration of 2-methylene-1,3-propanediol) (5.706 g, 17.1 mmol), 6-bromo-3-pyridinol (3.571 g, 20.5 mmol) and triphenylphosphine (5.386 g, 20.5 mmol) in anhydrous THF (55 mL) at 0° C. under N$_2$. After stirring at 0° C. for 1 h, and then at room temperature for 41 h, the mixture was concentrated under reduced pressure and the residue was chromatographed on silica gel. Elution with 0-5% Et$_2$O/petroleum ether firstly gave foreruns, and then further elution with 5% Et$_2$O/petroleum ether gave 2-bromo-5-[3-{[tert-butyl(dimethyl)silyl]oxy}-2-({[tert-butyl(dimethyl)silyl]oxy}methyl)propoxy]pyridine (185) (8.09 g, 97%) as a colourless oil; $^1$H NMR (CDCl$_3$) δ 8.06 (d, J=3.0 Hz, 1H), 7.35 (dd, J=8.7, 0.3 Hz, 1H), 7.11 (dd, J=8.7, 3.2 Hz, 1H), 4.03 (d, J=5.9 Hz, 2H), 3.73 (dd, J=10.1, 5.7 Hz, 1H), 3.69 (dd, J=10.0, 6.0 Hz, 1H), 2.16 (sept, J=5.8 Hz, 1H), 0.88 (s, 18H), 0.03 (2 s, 12H); HRESIMS calcd for C$_{21}$H$_{41}$BrNO$_3$Si$_2$ m/z [M+H]$^+$ 492.1783, 490.1803. found 492.1786, 490.1804.

Silyl ether 185 (11.06 g, 22.5 mmol) was treated with a solution of 1% HCl in 95% EtOH (desilylation conditions described by Cunico et al., 1980) (200 mL), and the mixture was stirred at room temperature for 13 h. The resulting solution was cooled (CO$_2$/acetone), neutralised by dropwise addition of 7M NH$_3$ in MeOH (10 mL) with stirring, and then concentrated to dryness and the residue was chromatographed on silica gel. Elution with 0-3% MeOH/CH$_2$Cl$_2$ firstly gave foreruns, and then further elution with 5% MeOH/CH$_2$Cl$_2$ gave 2-{[(6-bromo-3-pyridinyl)oxy]methyl}-1,3-propanediol (186) (5.56 g, 94%) as a white solid: mp (CH$_2$Cl$_2$) 90-91° C.; $^1$H NMR (CDCl$_3$) δ 8.07 (d, J=3.1 Hz, 1H), 7.36 (d, J=8.7 Hz, 1H), 7.12 (dd, J=8.7, 3.1 Hz, 1H), 4.15 (d, J=6.1 Hz, 1H), 3.95 (dt, J=10.8, 4.9 Hz, 1H), 3.92 (dt, J=10.8, 5.3 Hz, 1H), 2.24 (m, 1H), 1.99 (t, J=5.1 Hz, 2H). Anal. (C$_9$H$_{12}$BrNO$_3$) C, H, N.

A suspension of diol 186 (5.25 g, 20.0 mmol) in anhydrous THF (66 mL) under N$_2$ was stirred at room temperature until the solid had completely dissolved (~10 min), and then treated with 60% NaH (0.829 g, 20.7 mmol) and quickly degassed and resealed under N$_2$. After stirring at room temperature for 60 min (to give a white precipitate), tert-butyldimethylsilyl chloride (3.21 g, 21.3 mmol) was added, and the mixture was stirred at room temperature for 100 min. The resulting mixture was concentrated under reduced pressure and the residue was chromatographed on silica gel. Elution with 0-33% Et$_2$O/petroleum ether firstly gave foreruns, and then further elution with 33-50% Et$_2$O/petroleum ether gave 3-[(6-bromo-3-pyridinyl)oxy]-2-({[tert-butyl(dimethyl)silyl]oxy}methyl)-1-propanol (187) (5.97 g, 79%) as a colourless oil; $^1$H NMR (CDCl$_3$) δ 8.07 (d, J=3.1 Hz, 1H), 7.36 (d, J=8.7 Hz, 1H), 7.12 (dd, J=8.7, 3.1 Hz, 1H), 4.12 (dd, J=9.2, 6.6 Hz, 1H), 4.09 (dd, J=9.2, 5.9 Hz, 1H), 3.94-3.80 (m, 4H), 2.27 (dd, J=6.3, 4.8 Hz, 1H), 2.18 (sept, J=5.4 Hz, 1H), 0.89 (s, 9H), 0.06, 0.05 (2 s, 6H); HRESIMS calcd for C$_{15}$H$_{27}$BrNO$_3$Si m/z [M+H]$^+$ 378.0918, 376.0938. found 378.0912, 376.0931.

Iodination of alcohol 187 with I$_2$, PPh$_3$ and imidazole as in Example 2GGG above for 18 h, followed by chromatography of the product on silica gel, eluting with petroleum ether and pentane (foreruns) and then with 5-25% Et$_2$O/pentane, gave 2-bromo-5-[3-{[tert-butyl(dimethyl)silyl]oxy}-2-(iodomethyl)propoxy]pyridine (188) (97%) as a colourless oil; $^1$H NMR (CDCl$_3$) δ 8.07 (d, J=3.0 Hz, 1H), 7.37 (dd, J=8.7, 0.3 Hz, 1H), 7.11 (dd, J=8.7, 3.2 Hz, 1H), 4.06 (dd, J=9.2, 5.7 Hz, 1H), 3.99 (dd, J=9.2, 6.1 Hz, 1H), 3.74 (dd, J=10.1, 5.6 Hz, 1H), 3.70 (dd, J=10.1, 5.5 Hz, 1H), 3.36 (d, J=6.0 Hz, 2H), 2.12 (sept, J=5.8 Hz, 1H), 0.89 (s, 9H), 0.06 (2 s, 6H); HRESIMS calcd for $C_{15}H_{26}BrINO_2Si$ m/z [M+H]$^+$ 487.9935, 485.9955. found 487.9931, 485.9952.

Alkylation of 2-bromo-4(5)-nitroimidazole (80) with iodide 188 and $K_2CO_3$ as in Example 2GGG above for 42 h, followed by chromatography of the product on silica gel, eluting with 0-20% EtOAc/petroleum ether (foreruns) and then with 20-33% EtOAc/petroleum ether, gave 2-bromo-5-[3-(2-bromo-4-nitro-1H-imidazol-1-yl)-2-({[tert-butyl(dimethyl)silyl]oxy}methyl)propoxy]pyridine (189) (73%) as a cream solid: mp ($CH_2Cl_2$/hexane) 132-134° C.; $^1$H NMR ($CDCl_3$) δ 8.05 (d, J=3.0 Hz, 1H), 7.82 (s, 1H), 7.40 (dd, J=8.7, 0.4 Hz, 1H), 7.06 (dd, J=8.7, 3.2 Hz, 1H), 4.25 (d, J=7.2 Hz, 2H), 4.01 (d, J=5.7 Hz, 2H), 3.77 (dd, J=10.7, 4.9 Hz, 1H), 3.66 (dd, J=10.6, 4.6 Hz, 1H), 2.53 (m, 1H), 0.91 (s, 9H), 0.08, 0.07 (2 s, 6H). Anal. ($C_{18}H_{26}Br_2N_4O_4Si$) C, H, N.

Tetra-n-butylammonium fluoride (13.0 mL of a 1M solution in THF, 13.0 mmol) was added dropwise to a stirred solution of silyl ether 189 (6.78 g, 12.3 mmol) in anhydrous THF (140 mL) and the mixture was stirred at room temperature for 4 h. The resulting solution was concentrated under reduced pressure, and then diluted with ice-water (120 mL) and extracted with EtOAc (5×120 mL). The extracts were washed with brine (100 mL) and then evaporated to dryness and the residue was chromatographed on silica gel. Elution with 0-80% $Et_2O$/petroleum ether, petroleum ether and 0-1% MeOH/$CH_2Cl_2$ firstly gave foreruns, and then further elution with 2-3% MeOH/$CH_2Cl_2$ gave 3-(2-bromo-4-nitro-1H-imidazol-1-yl)-2-{[(6-bromo-3-pyridinyl)oxy]methyl}-1-propanol (190) (5.36 g, 100%) as a pale yellow foam; $^1$H NMR ($CDCl_3$) δ 8.07 (d, J=3.0 Hz, 1H), 7.89 (s, 1H), 7.40 (d, J=8.7 Hz, 1H), 7.09 (dd, J=8.7, 3.2 Hz, 1H), 4.32 (d, J=7.2 Hz, 2H), 4.09 (d, J=5.5 Hz, 2H), 3.87 (dd, J=10.7, 4.7 Hz, 1H), 3.75 (dd, J=10.8, 4.8 Hz, 1H), 2.57 (m, 1H); HRESIMS calcd for $C_{12}H_{13}Br_2N_4O_4$ z [M+H]$^+$ 438.9258, 436.9278, 434.9298. found 438.9262, 436.9279, 434.9299.

Ring closure of alcohol 190 with NaH (1.35 equiv.) as in Example 2GGG for 200 min, followed by chromatography of the product on silica gel, eluting with 0-1% MeOH/$CH_2Cl_2$ (foreruns) and then with 1-3% MeOH/$CH_2Cl_2$, gave 6-{[(6-bromo-3-pyridinyl)oxy]methyl}-2-nitro-6,7-dihydro-5H-imidazo[2,1-b][1,3]oxazine (191) (71%) as a pale yellow solid: mp (MeOH/$CH_2Cl_2$/hexane) 197-199° C.; $^1$H NMR [($CD_3$)$_2$SO] δ 8.15 (br d, J=3.0 Hz, 1H), 8.10 (s, 1H), 7.56 (dd, J=8.7, 0.3 Hz, 1H), 7.42 (dd, J=8.8, 3.2 Hz, 1H), 4.60 (dd, J=11.0, 2.7 Hz, 1H), 4.45 (dd, J=11.0, 7.0 Hz, 1H), 4.29 (dd, J=12.5, 5.5 Hz, 1H), 4.20 (dd, J=10.0, 6.8 Hz, 1H), 4.17 (dd, J=10.0, 6.711z, 1H), 4.05 (dd, J=12.6, 6.8 Hz, 1H), 2.85 (m, 1H). Anal. ($C_{12}H_{11}BrN_4O_4$) C, H, N.

Suzuki coupling of bromide 191 and 4-fluorophenylboronic acid as in Example 2M for 140 min, followed by chromatography of the product on silica gel, eluting with 0-4% EtOAc/$CH_2Cl_2$ (foreruns) and then with 5-6% EtOAc/$CH_2Cl_2$, gave 68 (85%) as a pale yellow-brown solid: mp (MeOH/$CH_2Cl_2$/hexane) 214-216° C.; $^1$H NMR [($CD_3$)$_2$SO] δ 8.38 (d, J=2.8 Hz, 1H), 8.11 (s, 1H), 8.06 (ddt, J=8.9, 5.6, 2.6 Hz, 2H), 7.91 (d, J=8.8 Hz, 1H), 7.51 (dd, 8.8, 3.0 Hz, 1H), 7.27 (dt, J=8.9, 2.6 Hz, 2H), 4.63 (dd, J=11.0, 2.9 Hz, 1H), 4.49 (dd, J=11.1, 7.1 Hz, 1H), 4.32 (dd, J=12.5, 5.5 Hz, 1H), 4.25 (dd, J=10.0, 6.8 Hz, 1H), 4.22 (dd, J=−10.0, 6.7 Hz, 1H), 4.08 (dd, J=12.6, 6.9 Hz, 1H), 2.89 (m, 1H). Anal. ($C_{18}H_{15}FN_4O_4$) C, H, N.

QQQ. Synthesis of 2-nitro-6-[({6-[4-(trifluoromethyl)phenyl]-3-pyridinyl}oxy)methyl]-6,7-dihydro-5H-imidazo[2,1-b][1,3]oxazine (Compound 69 of Table 1) by the Method of Scheme 15

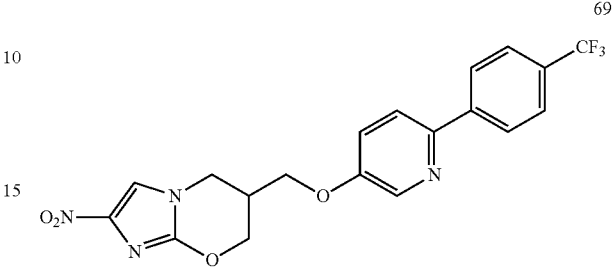

Suzuki coupling of bromide 191 (see Example 2PPP) and 4-(trifluoromethyl)phenylboronic acid as in Example 2M for 140 min, followed by chromatography of the product on silica gel, eluting with 0-4% EtOAc/$CH_2Cl_2$ (foreruns) and then with 4-5% EtOAc/$CH_2Cl_2$, gave 69 (41 mg, 69%) as a pale yellow solid: mp (MeOH/$CH_2Cl_2$/hexane) 233-235° C.; $^1$H NMR [($CD_3$)$_2$SO] δ 8.45 (d, J=2.7 Hz, 1H), 8.24 (br d, J=8.1 Hz, 2H), 8.12 (s, 1H), 8.05 (d, J=8.9 Hz, 1H), 7.81 (br d, J=8.3 Hz, 2H), 7.57 (dd, J=8.8, 3.0 Hz, 1H), 4.64 (dd, J=11.0, 2.9 Hz, 1H), 4.50 (dd, J=11.1, 7.1 Hz, 1H), 4.32 (dd, J=12.5, 5.4 Hz, 1H), 4.28 (dd, J=10.0, 6.7 Hz, 1H), 4.25 (dd, J=10.1, 6.7 Hz, 1H), 4.09 (dd, J=12.6, 6.8 Hz, 1H), 2.90 (m, 1H). Anal. ($C_{19}H_{15}F_3N_4O_4$) C, H, N.

RRR. Synthesis of 2-nitro-6-[({6-[4-(trifluoromethoxy)phenyl]-3-pyridinyl}oxy)methyl]-6,7-dihydro-5H-imidazo[2,1-b][1,3]oxazine (Compound 70 of Table 1) by the Method of Scheme 15

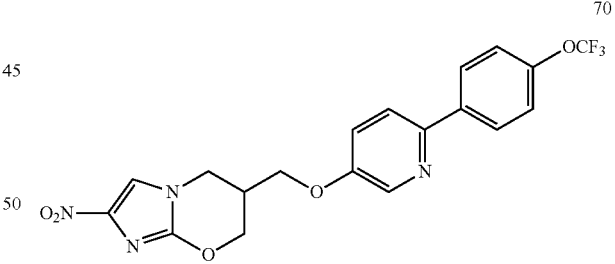

Suzuki coupling of bromide 191 (see Example 2PPP) and 4-(trifluoromethoxy)phenylboronic acid as in Example 2M for 140 min, followed by chromatography of the product on silica gel, eluting with 0-4% EtOAc/$CH_2Cl_2$ (foreruns) and then with 4-5% EtOAc/$CH_2Cl_2$, gave 70 (55 mg, 89%) as a cream solid: mp (MeOH/$CH_2Cl_2$/hexane) 180-181° C.; $^1$H NMR [($CD_3$)$_2$SO] δ 8.41 (d, J=2.7 Hz, 1H), 8.14 (dt, J=8.9, 2.5 Hz, 2H), 8.11 (s, 1H), 7.96 (d, J=8.7 Hz, 1H), 7.54 (dd, J=8.8, 3.0 Hz, 1H), 7.44 (br dd, J=8.8, 0.8 Hz, 2H), 4.64 (dd, J=10.9, 2.9 Hz, 1H), 4.49 (dd, J=11.0, 7.1 Hz, 1H), 4.32 (dd, J=12.5, 5.4 Hz, 1H), 4.26 (dd, J=10.1, 6.7 Hz, 1H), 4.23 (dd, J=10.1, 6.7 Hz, 1H), 4.09 (dd, J=12.6, 6.8 Hz, 1H), 2.89 (m, 1H). Anal. ($C_{19}H_{15}F_3N_4O_5$) C, H, N.

SSS. Synthesis of 2-nitro-6-({[3-(trifluoromethoxy)benzyl]oxy}methyl)-6,7-dihydro-5H-imidazo[2,1-b][1,3]oxazine (Compound 71 of Table 1) by the Method of Scheme 14

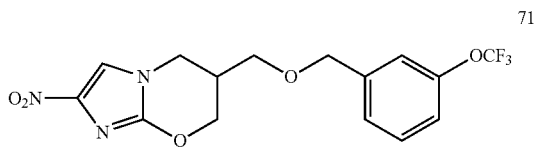

Alkylation of oxazine alcohol 180 (see Example 2MMM) with 3-(trifluoromethoxy)benzyl bromide and NaH (1.6 equiv.) as in Example 2UU above, followed by chromatography of the product on silica gel, eluting with 0-1% EtOAc/CH$_2$Cl$_2$ (foreruns) and then with 1.5% EtOAc/CH$_2$Cl$_2$, gave 71 (56%) as a cream solid: mp (CH$_2$Cl$_2$/pentane) 60-61° C.; $^1$H NMR (CDCl$_3$) δ 7.40 (s, 1H), 7.39 (t, J=7.8 Hz, 1H), 7.21 (br d, J=7.8 Hz, 1H), 7.20-7.14 (m, 2H), 4.54 (s, 2H), 4.51 (ddd, J=11.5, 3.4, 0.9 Hz, 1H), 4.36 (dd, J=11.4, 7.8 Hz, 1H), 4.15 (ddd, J=12.3, 5.6, 0.8 Hz, 1H), 4.03 (dd, J=12.3, 7.5 Hz, 1H), 3.62 (dd, J=9.6, 5.8 Hz, 1H), 3.57 (dd, J=9.6, 6.6 Hz, 1H), 2.68 (m, 1H). Anal. (C$_{15}$H$_{14}$F$_3$N$_3$O$_5$) C, H, N.

TTT. Synthesis of 2-nitro-6-({[4-(trifluoromethoxy)benzyl]oxy}methyl)-6,7-dihydro-5H-imidazo[2,1-b][1,3]oxazine (Compound 72 of Table 1) by the Method of Scheme 14

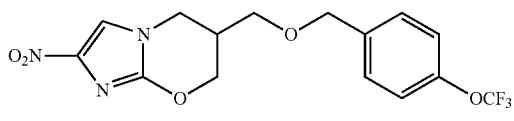

Alkylation of oxazine alcohol 180 (see Example 2MMM) with 4-(trifluoromethoxy)benzyl bromide (1.9 equiv.) and NaH (1.6 equiv.) as in Example 2UU above for 3 h, followed by chromatography of the product on silica gel, eluting with 0-1% EtOAc/CH$_2$Cl$_2$ (foreruns) and then with 2% EtOAc/CH$_2$Cl$_2$, gave 72 (59%) as a cream solid: mp (CH$_2$Cl$_2$/hexane) 92-93° C.; $^1$H NMR (CDCl$_3$) δ 7.40 (s, 1H), 7.32 (dt, J=8.7, 2.3 Hz, 2H), 7.21 (br d, J=8.0 Hz, 2H), 4.52 (s, 2H), 4.51 (ddd, J=11.3, 3.3, 0.9 Hz, 1H), 4.36 (dd, J=11.4, 7.8 Hz, 1H), 4.15 (ddd, J=12.3, 5.6, 0.8 Hz, 1H), 4.02 (dd, J=12.3, 7.5 Hz, 1H), 3.62 (dd, J=9.6, 5.9 Hz, 1H), 3.56 (dd, J=9.6, 6.5 Hz, 1H), 2.67 (m, 1H). Anal. (C$_{15}$H$_{14}$F$_3$N$_3$O$_5$) C, H, N.

UUU. Synthesis of 6-({[4-(benzyloxy)benzyl]oxy}methyl)-2-nitro-6,7-dihydro-5H-imidazo[2,1-b][1,3]oxazine (Compound 73 of Table 1) by the Method of Scheme 14

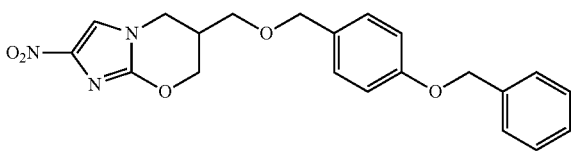

A solution of 4-(benzyloxy)benzyl iodide (reported by Cativiela et al., 1995, via iodination of 4-(benzyloxy)benzyl alcohol) (98 mg, 0.302 mmol) in anhydrous DMF (0.3 mL, then 2×0.4 mL to rinse) was added to a solution of oxazine alcohol 180 (see Example 2MMM) (30.7 mg, 0.154 mmol) in anhydrous DMF (1 mL) under N$_2$ at 0° C. The mixture was treated with 60% NaH (8.8 mg, 0.22 mmol), then quickly degassed and resealed under N$_2$. After stirring at room temperature for 35 min, the mixture was cooled (CO$_2$/acetone), quenched with ice/aqueous NaHCO$_3$ (10 mL), added to brine (40 mL) and extracted with CH$_2$Cl$_2$ (3×50 mL) and EtOAc (3×50 mL). The combined extracts were evaporated to dryness and the residue was chromatographed on silica gel. Elution with 0-2% EtOAc/CH$_2$Cl$_2$ firstly gave foreruns, and then elution with 2-3% EtOAc/CH$_2$Cl$_2$ gave the crude product (20 mg), which was further chromatographed on silica gel. Elution with 25-40% EtOAc/petroleum ether firstly gave foreruns, and then further elution with EtOAc gave 73 (15 mg, 25%) as a white solid: mp (CH$_2$Cl$_2$/hexane) 150-151° C.; $^1$H NMR (CDCl$_3$) δ 7.46-7.29 (m, 6H), 7.20 (dt, J=8.6, 2.4 Hz, 2H), 6.96 (dt, J=8.7, 2.4 Hz, 2H), 5.07 (s, 2H), 4.48 (ddd, J=11.4, 3.3, 0.8 Hz, 1H), 4.46 (d, J=11.6 Hz, 1H), 4.43 (d, J=11.6 Hz, 1H), 4.32 (dd, J=11.4, 7.9 Hz, 1H), 4.09 (br dd, J=12.3, 5.5 Hz, 1H), 3.99 (dd, J=12.3, 7.6 Hz, 1H), 3.56 (dd, J=9.6, 5.7 Hz, 1H), 3.50 (dd, J=9.6, 6.7 Hz, 1H), 2.62 (m, 1H). Anal. (C$_{21}$H$_{21}$N$_3$O$_5$) C, H, N.

VVV. Synthesis of 2-nitro-6-({[4'-(trifluoromethoxy)[1,1'-biphenyl]-3-yl]methoxy}methyl)-6,7-dihydro-5H-imidazo[2,1-b][1,3]oxazine (Compound 74 of Table 1) by the Method of Scheme 14

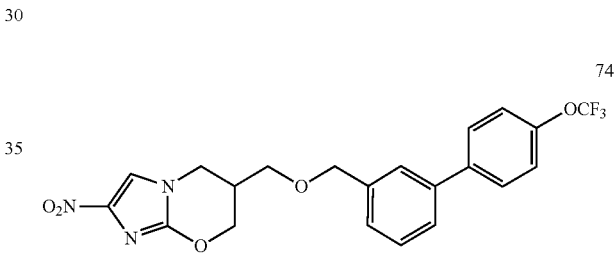

A mixture of oxazine alcohol 180 (see Example 2MMM) (200.3 mg, 1.01 mmol) and 3-iodobenzyl bromide (406 mg, 1.37 mmol) in anhydrous DMF (7.5 mL) under N$_2$ at 0° C. was treated with 60% NaH (57 mg, 1.43 mmol), then quickly degassed and resealed under N$_2$. After stirring at room temperature for 140 min, the mixture was cooled (CO$_2$/acetone), quenched with ice/aqueous NaHCO$_3$ (10 mL) and diluted with water (40 mL) to precipitate a crude solid, which was collected by filtration and washed with water and petroleum ether (0.49 g). The filtrate was extracted with EtOAc (3×80 mL), and then the extracts were washed with brine (50 mL). The combined extracts were evaporated to dryness and the residue was combined with the solid above and chromatographed on silica gel. Elution with 0-1% EtOAc/CH$_2$Cl$_2$ firstly gave foreruns, and then further elution with 1-2% EtOAc/CH$_2$Cl$_2$ gave 6-{[(3-iodobenzyl)oxy]methyl}-2-nitro-6,7-dihydro-5H-imidazo[2,1-b][1,3]oxazine (182) (184 mg, 44%) as a cream solid: mp (CH$_2$Cl$_2$/hexane) 127-130° C.; $^1$H NMR (CDCl$_3$) δ 7.69-7.62 (m, 2H), 7.40 (s, 1H), 7.24 (m, 1H), 7.10 (br t, J=8.0 Hz, 1H), 4.51 (dd, J=11.4, 3.1 Hz, 1H), 4.48 (d, J=12.3 Hz, 1H), 4.44 (d, J=12.2 Hz, 1H), 4.35 (dd, J=11.4, 7.7 Hz, 1H), 4.14 (dd, J=12.3, 5.5 Hz, 1H), 4.02 (dd, J=12.3, 7.4 Hz, 1H), 3.60 (dd, J=9.6, 5.8 Hz, 1H), 3.54 (dd, J=9.6, 6.7 Hz, 1H), 2.66 (m, 1H). Anal. (C$_{14}$H$_{14}$IN$_3$O$_4$) C, H, N.

Suzuki coupling of iodide 182 and 4-(trifluoromethoxy)phenylboronic acid as in Example 2XX above, followed by chromatography of the product on silica gel, eluting with 0-1% EtOAc/CH$_2$Cl$_2$ (foreruns) and then with 1-1.5%

EtOAc/CH$_2$Cl$_2$, gave 74 (92%) as a cream solid: mp (CH$_2$Cl$_2$/pentane) 78-80° C.; $^1$H NMR (CDCl$_3$) δ 7.58 (dt, J=8.8, 2.5 Hz, 2H), 7.51 (dt, J=7.8, 1.5 Hz, 1H), 7.48-7.42 (m, 2H), 7.37 (s, 1H), 7.33-7.26 (m, 3H), 4.61 (d, J=11.9 Hz, 1H), 4.57 (d, J=12.0 Hz, 1H), 4.51 (ddd, J=11.4, 3.2, 0.7 Hz, 1H), 4.37 (dd, J=11.4, 7.6 Hz, 1H), 4.13 (dd, J=12.4, 5.5 Hz, 1H), 4.03 (dd, J=12.3, 7.4 Hz, 1H), 3.64 (dd, J=9.6, 5.8 Hz, 1H), 3.58 (dd, J=9.6, 6.7 Hz, 1H), 2.67 (m, 1H). Anal. (C$_{21}$H$_{18}$F$_3$N$_3$O$_5$) C, H, N.

WWW. Synthesis of 2-nitro-6-({[4'-(trifluoromethoxy) [1,1'-biphenyl]-4-yl]methoxy}methyl)-6,7-dihydro-5H-imidazo[2,1-b][1,3]oxazine (Compound 75 of Table 1) by the Method of Scheme 14

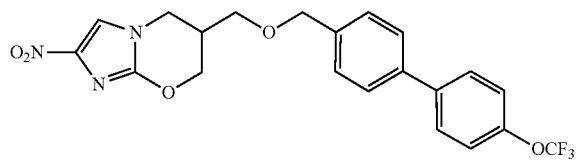

Alkylation of oxazine alcohol 180 (see Example 2MMM) with 4-iodobenzyl bromide and NaH (1.4 equiv.) as in Example 2UU above for 3 h, followed by chromatography of the product on silica gel, eluting with 0-1% EtOAc/CH$_2$Cl$_2$ (foreruns) and then with 3% EtOAc/CH$_2$Cl$_2$, gave 6-{[(4-iodobenzyl)oxy]methyl}-2-nitro-6,7-dihydro-5H-imidazo[2,1-b][1,3]oxazine (183) (42%) as a white solid: mp (CH$_2$Cl$_2$/hexane) 161-163° C.; $^1$H NMR (CDCl$_3$) δ 7.70 (dt, J=8.3, 2.0 Hz, 2H), 7.40 (s, 1H), 7.03 (br d, J=8.3 Hz, 2H), 4.50 (ddd, J=11.4, 3.3, 0.8 Hz, 1H), 4.46 (s, 2H), 4.34 (dd, J=11.4, 7.8 Hz, 1H), 4.13 (ddd, J=12.3, 5.6, 0.8 Hz, 1H), 4.00 (dd, J=12.3, 7.6 Hz, 1H), 3.59 (dd, J=9.6, 5.8 Hz, 1H), 3.53 (dd, J=9.6, 6.5 Hz, 1H), 2.65 (m, 1H); HRFABMS calcd for C$_{14}$H$_{15}$IN$_3$O$_4$ m/z [M+H]$^+$ 416.0107. found 416.0108.

Suzuki coupling of iodide 183 and 4-(trifluoromethoxy) phenylboronic acid as in Example 2XX above, followed by chromatography of the product on silica gel, eluting with 0-1% EtOAc/CH$_2$Cl$_2$ (foreruns) and then with 1-1.5% EtOAc/CH$_2$Cl$_2$, gave 75 (95%) as a cream solid: mp (CH$_2$Cl$_2$/pentane) 135-138° C.; $^1$H NMR (CDCl$_3$) δ 7.59 (dt, J=8.8, 2.5 Hz, 2H), 7.55 (dt, J=8.3, 1.9 Hz, 2H), 7.40 (s, 1H), 7.37 (br d, J=8.3 Hz, 2H), 7.29 (br dd, J=8.7, 0.8 Hz, 2H), 4.57 (s, 2H), 4.52 (ddd, J=11.4, 3.3, 0.8 Hz, 1H), 4.37 (dd, J=11.4, 7.8 Hz, 1H), 4.15 (ddd, J=12.3, 5.6, 0.7 Hz, 1H), 4.04 (dd, J=12.3, 7.5 Hz, 1H), 3.64 (dd, J=9.6, 5.8 Hz, 1H), 3.58 (dd, J=9.6, 6.6 Hz, 1H), 2.68 (m, 1H). Anal. (C$_{21}$H$_{18}$F$_3$N$_3$O$_5$) C, H, N.

EXAMPLE 3

Biological Activities and Stability

The biological activity of the compounds of the invention was evaluated as follows. Results are shown below in Table 2.

(a) Minimum inhibitory concentrations (MICs). Compounds were evaluated for their activity against replicating *Mycobacterium tuberculosis* in an 8 day microplate-based assay using Alamar blue reagent (added on day 7) for determination of growth (MABA) (Collins et al., 1997; Falzari et al., 2005). The lowest compound concentration effecting an inhibition of >90% was considered the MIC. Screening for the activity of the compounds against bacteria in the non-replicating state that models clinical persistence used an 11 day high-throughput, luminescence-based low-oxygen-recovery assay (LORA), where *M. tuberculosis* bacteria containing a plasmid with an acetamidase promoter driving a bacterial luciferase gene were first adapted to low oxygen conditions by extended culture (Cho et al., 2007).

(b) Mammalian cell cytotoxicity assay. This was assessed against VERO cells (CCL-81, American Type Culture Collection) in a 72 h exposure, using a tetrazolium dye assay (Falzari et al., 2005).

(c) Antiprotozoal screening. Compounds were evaluated for their activities against both *Trypanosoma cruzi* amastigotes and *Leishmania donovani* amastigotes (free or encapsulated in macrophages), according to the following protocols:

(i) *Trypanosoma cruzi* assay. L-6 cells (2×10$^3$) in medium (100 μL of RPMI 1640 supplemented with 2 mM L-glutamine plus 10% heat inactivated fetal calf serum) were seeded in 96-well microtitre plates (Costar™) and incubated at 37° C. (5% CO$_2$) for 1d. A suspension (50 μL) of *Trypanosoma cruzi* trypomastigotes (5×10$^3$ of Tulahuen C2C4 strain, containing the β-galactosidase gene) was added, and the cells were incubated at 37° C. (5% CO$_2$) for a further 48 h to establish the infection. The medium was removed and replaced by fresh medium and the infected cells were then incubated at 37° C. (5% CO$_2$) for 96 h in either medium alone or in the presence of serial (3-fold) dilutions of test compounds (initially prepared as 10 mg/mL stock solutions in DMSO and diluted into medium). Benznidazole was employed as a standard in each assay. Following incubation, chlorophenol red glycoside (100 mM) in 0.1% Nonidet P40/PBS (50 μL) was added, and (after 6 h) the absorbance at 540 nm was measured and used to calculate the IC$_{50}$ values.

(ii) Axenic *Leishmania donovani* assay. Axenically grown *L. donovani* amastigotes (MHOM-ET-67/L82) from a healthy culture in log phase were seeded at a density of 1×10$^6$/mL medium (SM, pH 5.4 plus 10% heat inactivated fetal calf serum) in 96-well microtitre plates (Costar™) and incubated at 37° C. (5% CO$_2$) for 70 h in either medium alone or in the presence of serial (3-fold) dilutions of test compounds (initially prepared as 10 mg/mL stock solutions in DMSO and diluted into medium). Miltefosin was employed as a standard in each assay. After incubation, Resazurin fluorescent dye was added to each well, and incubation was continued for an additional 2 h. The IC$_{50}$ values were determined from measurements of the fluorescence data.

(iii) *Leishmania donovani* infected macrophage assay. Freshly harvested mouse macrophages in medium (RPMI 1640 plus 10% heat inactivated fetal calf serum) were incubated at 37° C. (5% CO$_2$) for 24 h and then infected (1:3 macrophages to amastigotes) with an axenic *L. donovani* amastigote culture (MHOM-ET-67/L82) in medium (SM, pH 5.4 plus 10% heat inactivated fetal calf serum). The infected macrophages were seeded at a density of 1.2×10$^6$/mL (by diluting in RPMI+10% FCS) in 16-well slides (Lab-tek™) and incubated at 37° C. (5% CO$_2$) for 24 h. The medium was removed and replaced by fresh medium (RPMI 1640+10% FCS), and this was repeated following mixing. The infected macrophages were then incubated at 37° C. (5% CO$_2$) for 96 h in either medium alone or in the presence of serial (3-fold) dilutions of test compounds (initially prepared as 10 mg/mL stock solutions in DMSO and diluted into medium). Miltefosin was employed as a standard in each assay. After removal of the medium and wells, the slides were fixed (5 min in 100% MeOH) and stained (10% Giemsa, 10 min). The ratio of infected to uninfected macrophages was determined by microscopic examination, and the IC$_{50}$ values were then calculated by linear regression analysis.

TABLE 2

In vitro biological activity of selected compounds of Table 1

| | MIC (μM) | | | IC$_{50}$ (μg/mL) | |
| | MABA | LORA | IC$_{50}$ (μM) | | L. donovani |
| No | (aerobic) | (anaerobic) | VERO | T. cruzi | axen | macro |
|---|---|---|---|---|---|---|
| 7 | 0.53 | 24 | ND | 3.2 | 0.016 | 0.40 |
| 8 | 0.04 | 14 | >128 | 4.1 | 0.017 | 0.38 |
| 9 | 0.04 | 3.7 | >128 | 1.2 | 0.016 | 0.20 |
| 10 | 0.045 | 11 | >128 | 2.0 | 0.040 | 0.23 |
| 11 | 0.08 | >128 | >128 | 18 | 0.028 | 0.47 |
| 12 | 0.087 | 64 | >128 | 9.4 | 0.016 | 0.74 |
| 25 | 0.25 | 34 | >128 | 0.24 | 0.029 | 0.22 |
| 26 | 0.30 | 50 | >128 | 0.34 | 0.013 | 0.36 |
| 47 | 3.8 | 15 | ND | 1.1 | 0.041 | 0.084 |
| 49 | 0.46 | 3.0 | >128 | 0.55 | 0.048 | 0.065 |
| 50 | 0.24 | 5.1 | >128 | 6.3 | 0.041 | 0.15 |
| 51 | 0.055 | 1.5 | >128 | 15 | 0.046 | 0.17 |
| 54 | 0.20 | 1.4 | >128 | 0.74 | 0.047 | 0.095 |
| 71 | 0.33 | 15 | >128 | 0.56 | 0.20 | 0.65 |
| 72 | 2.4 | 7.9 | 46 | 0.62 | 0.089 | 0.55 |
| 73 | 3.1 | 35 | 113 | 2.8 | 0.16 | 0.53 |
| 74 | 0.22 | 2.9 | >128 | 0.94 | 0.16 | 0.54 |
| 75 | 0.30 | >128 | >128 | 0.47 | 0.20 | 0.67 |

The in vitro microsomal stability and in vivo biological activity of selected compounds of the invention was also evaluated as follows, with results shown in Table 3.

(a) Stability of the compounds to human and mouse microsomes. Test compounds (1 μM) were incubated at 37° C. with pooled human or CD-1 mouse liver microsome preparations (0.5 mg/mL final protein concentration) and an NADPH regenerating system (MgCl2, 3.3 mM; G6P, 3.3 mM; G6PD, 0.4 U/mL; NADP+, 1.3 mM) in phosphate buffer (75 mM, pH 7.4), with a final volume of 200 μL. The compounds were dissolved in DMSO such that the final DMSO concentration was 0.5%. Reactions were stopped at 0 and 60 min by the addition of MeCN (100 μL) containing 0.2 μM metoprolol as an internal standard. Samples were diluted 10× and centrifuged prior to analysis by LC-MS/MS using electrospray ionization and SRM monitoring using a gradient LC method. LC peak areas were integrated and expressed as analyte/IS peak area ratios (PAR), and a mean value for each time point was calculated from the duplicates. The percent remaining value was calculated as:

% remaining=100×(Mean PAR$_{T60}$/Mean PAR$_{T0}$).

(b) In vivo mouse acute TB infection assay. BALB/c mice were infected via aerosol with a suspension of ~2×106 colony forming units (CFU) of M. tuberculosis Erdman/mL (Falzari et al., 2005). Each compound was given orally to a group of 7 or 8 mice at 100 mg/kg daily for 5 days a week for 3 weeks, beginning on day 11 post-infection. Compounds were administered as a suspension in 0.5% CMC/0.08% Tween 80 in water. Mice were sacrificed on day 31 and the numbers of CFU in the lungs were determined and compared with the CFU for vehicle alone-treated mice at this time. PA-824 was employed as a positive control in each experiment, and the results are recorded as the ratio of the average reduction in CFU in the compound-treated mice/the average CFU reduction in the mice treated with PA-824. In this assay, PA-824 caused up to 2.5-3 log reductions in CFU.

TABLE 3

Microsomal stability and in vivo biological activity of selected compounds of Table 1

| | Microsomes (% remaining) | | In vivo efficacy vs |
| No | Human | Mouse | PA-824 |
|---|---|---|---|
| PA-824 | 82 | 94 | 1.00 |
| 12 | 82 | 81 | 112 |
| 25 | 68 | 30 | 0.025 |
| 72 | 71 | 41 | ND |

REFERENCES CITED

The content of each of the documents listed below is hereby incorporated by reference.

U.S. Patent Documents

U.S. Pat. No. 5,668,127
U.S. Pat. No. 6,087,358
US 2006063929A1

International Patent Documents

DE 2312518
EP 1555267
JP 2005/330266
WO 2004/033463
WO 2005/042542
WO 2007/075872
WO 2008/112483
WO 2009/120789

Non-Patent Publications

Anderson et al., Org. Biomol. Chem. 6, 1973-1980 (2008).
Apparu et al., Tetrahedron: Asymmetry 11, 2885-2898 (2000).
Ashtekar et al., Antimicrobial Agents Chemother. 37, 183-186 (1993).
Cavalli et al., J. Med. Chem. 52, 7339-7359 (2009).
Cativiela et al., J. Org. Chem. 60, 3074-3083 (1995).
Cho et al., Antimicrob. Agents Chemother. 51, 1380-1385 (2007).
Collins et al., Antimicrob. Agents Chemother. 41, 1004-1009 (1997).
Cunico et al., J. Org. Chem. 45, 4797-4798 (1980).
Curran et al., J. Am. Chem. Soc. 120, 342-351 (1998).
Falzari et al., Antimicrob. Agents Chemother. 49, 1447-1454 (2005).
Ferrara et al., Lancet 367, 1328-1334 (2006).
Helmboldt et al., Org. Lett. 8, 1573-1576 (2006).
Kim et al., J. Med. Chem. 52, 1317-1328 and 1329-1344 (2009).
Kim et al., J. Med. Chem. 44, 3092-3108 (2001).
Kopka et al., Bioorg. Med. Chem. 11, 3513-3527 (2003).
Li et al., Bioorg. Med. Chem. Lett. 18, 2256-2262 (2008).
Manjunatha et al., Proc. Natl. Acad. Sci. USA 103, 431-436 (2006).

Matsumoto et al., *PLoS Medicine* 3, 2131-2143 (2006).
Nagarajan et al., *Eur. J. Med. Chem.* 24, 631-633 (1989).
Sasaki et al., *J. Med. Chem.* 49, 7854-7860 (2006).
Sehgal et al., *J. Med. Chem.* 24, 601-604 (1981).
Singh et al., *Science* 322, 1392-1395 (2008).
Stover et al., *Nature* 405, 962-966 (2000).
Tyagi et al., *Antimicrob. Agents Chemother.* 49, 2289-2293 (2005).
Wennerberg et al., *J. Org. Chem.* 64, 54-59 (1999).

What is claimed is:

1. A compound having a structure of Formula I:

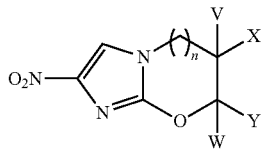

wherein n is 1

V and W are independently H or $CH_3$, and one of X or Y is H and the other is one of Formulae IIa or IIb, wherein Formulae IIa and IIb have general structures of:

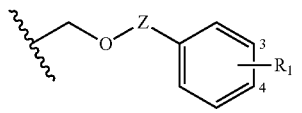

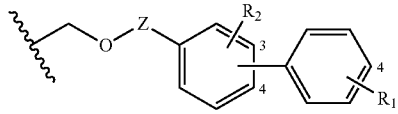

wherein Formula IIa comprises a single ring labeled at a 3-position and a 4-position and having $R_1$ as a substituent, and Formula IIb comprises a first ring labeled at a 3-position and a 4-position and having as substituents both $R_2$ and a terminal ring labeled at a 4-position and having $R_1$ as a substituent, wherein the single ring of Formula IIa and the first ring and the terminal ring of Formula IIb comprise C, CH, or aza at each ring position, wherein the single ring of Formula IIa and the first ring and the terminal ring of Formula IIb independently comprise no more than two aza, Z in Formulae IIa and IIb is $CH_2$ or a direct bond, and $R_1$ and $R_2$ are independently any one or two of H, F, Cl, I, CN, $CF_3$, $OCF_3$, $OCH_3$, or $OCH_2Ph$.

2. The compound of claim 1 wherein:

n is 1,

V and W are independently H or $CH_3$, and one of X or Y is H and the other is one of Formulae IIa or IIb, wherein Formulae IIa and IIb have structures of:

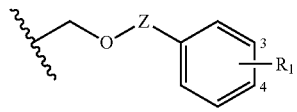

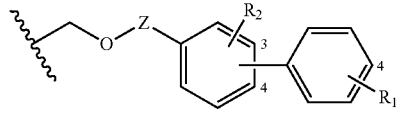

wherein Formula IIa comprises a single ring labeled at a 3-position and a 4-position and having $R_1$ as a substituent, and Formula IIb comprises a first ring labeled at a 3-position and a 4-position and having as substituents both $R_2$ and a terminal ring labeled at a 4-position and having $R_1$ as a substituent, wherein the first ring of Formula IIb comprises C, CH or aza at each ring position, wherein the first ring of Formula IIb comprises no more than two aza, and both the single ring of Formula IIa and the terminal ring of Formula IIb comprise C or CH at each ring position when $R_1$ is not 4-OMe, or comprise aza at the 3-position and C or CH at each remaining ring position when $R_1$ is 4-OMe, Z in Formulae IIa and IIb is $CH_2$, or a direct bond, $R_1$ is 4-F, 4-CN, 4-I, 4-$CF_3$, 3-$OCF_3$, 4-$OCF_3$, 4-$OCH_2Ph$, or 4-OMe, and $R_2$ is H.

3. A pharmaceutical composition comprising a therapeutically effective amount of the compound of claim 1 and a pharmaceutically acceptable excipient, adjuvant, carrier, buffer, stabilizer, or mixture thereof.

4. The pharmaceutical composition of claim 3, further comprising one or more additional anti-infective treatments for microbial infection caused by *Mycobacterium tuberculosis, Trypanosoma cruzi,* or *Leishmania donovani.*

5. A method of treating microbial infection caused by *Mycobacterium tuberculosis, Trypanosoma cruzi,* or *Leishmania donovani* comprising administering the pharmaceutical composition of claim 3.

6. A compound selected from the group consisting of:
A. 2-Nitro-7-{[4-(trifluoromethoxy)phenoxy]methyl}-6,7-dihydro-5H-imidazo[2,1-b][1,3]oxazine;
B. 7-{[4-(Benzyloxy)phenoxy]methyl}-2-nitro-6,7-dihydro-5H-imidazo[2,1-b][1,3]oxazine;
C. 7-{[(4'-Fluoro[1,1'-biphenyl]-4-yl)oxy]methyl}-2-nitro-6,7-dihydro-5H-imidazo[2,1-b][1,3]oxazine;
D. 2-Nitro-7-({[4'-(trifluoromethyl)[1,1'-biphenyl]-4-yl]oxy}methyl)-6,7-dihydro-5H-imidazo[2,1-b][1,3]oxazine;
E. 2-Nitro-7-({[4'-(trifluoromethoxy)[1,1'-biphenyl]-4-yl]oxy}methyl)-6,7-dihydro-5H-imidazo[2,1-b][1,3]oxazine;
F. 7-({[5-(4-Fluorophenyl)-2-pyridinyl]oxy}methyl)-2-nitro-6,7-dihydro-5H-imidazo[2,1-b][1,3]oxazine;
G. 2-Nitro-7-[({5-[4-trifluoromethoxy)phenyl]-2-pyridinyl}oxy)methyl]-6,7-dihydro-5H-imidazo[2,1-b][1,3]oxazine;
H. 7-({[6-(4-Fluorophenyl)-3-pyridinyl]oxy}methyl)-2-nitro-6,7-dihydro-5H-imidazo[2,1-b][1,3]oxazine;
I. 2-Nitro-7-[({6-[4-(trifluoromethoxy)phenyl]-3-pyridinyl}oxy)methyl]-6,7-dihydro-5H-imidazo[2,1-b][1,3]oxazine;

J. 7-Methyl-2-nitro-7-{[4-(trifluoromethoxy)phenoxy]methyl}-6,7-dihydro-5H-imidazo[2,1-b][1,3]oxazine;
K. 7-{[4-(Benzyloxy)phenoxy]methyl}-7-methyl-2-nitro-6,7-dihydro-5H-imidazo[2,1-b][1,3]oxazine;
L. 7-{[(4'-Fluoro[1,1'-biphenyl]-4-yl)oxy]methyl}-7-methyl-2-nitro-6,7-dihydro-5H-imidazo[2,1-b][1,3]oxazine;
M. 7-Methyl-2-nitro-7-({[4'-(trifluoromethyl)[1,1'-biphenyl]-4-yl]oxy}methyl)-6,7-dihydro-5H-imidazo[2,1-b][1,3]oxazine;
N. 7-Methyl-2-nitro-7-({[4'-(trifluoromethoxy)[1,1'-biphenyl]-4-yl]oxy}methyl)-6,7-dihydro-5H-imidazo[2,1-b][1,3]oxazine;
O. 7-({[5-(4-Fluorophenyl)-2-pyridinyl]oxy}methyl)-7-methyl-2-nitro-6,7-dihydro-5H-imidazo[2,1-b][1,3]oxazine;
P. 7-Methyl-2-nitro-7-[({5-[4-(trifluoromethyl)phenyl]-2-pyridinyl}oxy)methyl]-6,7-dihydro-5H-imidazo[2,1-b][1,3]oxazine;
Q. 7-Methyl-2-nitro-7-[({5-[4-(trifluoromethoxy)phenyl]-2-pyridinyl}oxy)methyl]-6,7-dihydro-5H-imidazo[2,1-b][1,3]oxazine;
R. 7-({[6-(4-Fluorophenyl)-3-pyridinyl]oxy}methyl)-7-methyl-2-nitro-6,7-dihydro-5H-imidazo[2,1-b][1,3]oxazine;
S. 7-Methyl-2-nitro-7-[({6-[4-(trifluoromethyl)phenyl]-3-pyridinyl}oxy)methyl]-6,7-dihydro-5H-imidazo[2,1-b][1,3]oxazine;
T. 7-Methyl-2-nitro-7-[({6-[4-(trifluoromethoxy)phenyl]-3-pyridinyl}oxy)methyl]-6,7-dihydro-5H-imidazo[2,1-b][1,3]oxazine;
U. 2-Nitro-7-({[3-(trifluoromethoxy)benzyl]oxy}methyl)-6,7-dihydro-5H-imidazo[2,1-b][1,3]oxazine;
V. 2-Nitro-7-({[4-(trifluoromethoxy)benzyl]oxy}methyl)-6,7-dihydro-5H-imidazo[2,1-b][1,3]oxazine;
W. 7-({[4-(Benzyloxy)benzyl]oxy}methyl)-2-nitro-6,7-dihydro-5H-imidazo[2,1-b][1,3]oxazine;
X. 2-Nitro-7-({[4'-(trifluoromethoxy)[1,1'-biphenyl]-3-yl]methoxy}methyl)-6,7-dihydro-5H-imidazo[2,1-b][1,3]oxazine;
Y. 2-Nitro-7-({[4'-(trifluoromethoxy)[1,1'-biphenyl]-4-yl]methoxy}methyl)-6,7-dihydro-5H-imidazo[2,1-b][1,3]oxazine;
Z. 7-Methyl-2-nitro-7-({[3-(trifluoromethoxy)benzyl]oxy}methyl)-6,7-dihydro-5H-imidazo[2,1-b][1,3]oxazine;
AA. 7-Methyl-2-nitro-7-({[4-(trifluoromethoxy)benzyl]oxy}methyl)-6,7-dihydro-5H-imidazo[2,1-b][1,3]oxazine;
BB. 7-({[4-(Benzyloxy)benzyl]oxy}methyl)-7-methyl-2-nitro-6,7-dihydro-5H-imidazo[2,1-b][1,3]oxazine;
CC. 7-Methyl-2-nitro-7-({[4'-(trifluoromethoxy)[1,1'-biphenyl]-3-yl]methoxy}methyl)-6,7-dihydro-5H-imidazo[2,1-b][1,3]oxazine;
DD. 7-Methyl-2-nitro-7-({[4'-(trifluoromethoxy)[1,1'-biphenyl]-4-yl]methoxy}methyl)-6,7-dihydro-5H-imidazo[2,1-b][1,3]oxazine;
EE. (7R)-7-Methyl-2-nitro-7-({[4'-(trifluoromethoxy)[1,1'-biphenyl]-4-yl]methoxy}methyl)-6,7-dihydro-5H-imidazo[2,1-b][1,3]oxazine;
FF. (7S)-7-Methyl-2-nitro-7-({[4'-(trifluoromethoxy)[1,1'-biphenyl]-4-yl]methoxy}methyl)-6,7-dihydro-5H-imidazo[2,1-b][1,3]oxazine;
GG. 2-Nitro-6-{[4-(trifluoromethoxy)phenoxy]methyl}-6,7-dihydro-5H-imidazo[2,1-b][1,3]oxazine;
HH. (6R)-2-Nitro-6-{[4-(trifluoromethoxy)phenoxy]methyl}-6,7-dihydro-5H-imidazo[2,1-b][1,3]oxazine;
II. (6S)-2-Nitro-6-{[4-(trifluoromethoxy)phenoxy]methyl}-6,7-dihydro-5H-imidazo[2,1-b][1,3]oxazine;
JJ. 6-{[(4'-Fluoro[1,1'-biphenyl]-4-yl)oxy]methyl}-2-nitro-6,7-dihydro-5H-imidazo[2,1-b][1,3]oxazine;
KK. 2-Nitro-6-({[4'-(trifluoromethyl)[1,1'-biphenyl]-4-yl]oxy}methyl)-6,7-dihydro-5H-imidazo[2,1-b][1,3]oxazine;
LL. 2-Nitro-6-({[4'-(trifluoromethoxy)[1,1'-biphenyl]-4-yl]oxy}methyl)-6,7-dihydro-5H-imidazo[2,1-b][1,3]oxazine;
MM. 6-({[5-(4-Fluorophenyl)-2-pyridinyl]oxy}methyl)-2-nitro-6,7-dihydro-5H-imidazo[2,1-b][1,3]oxazine;
NN. 2-Nitro-6-[({5-[4-(trifluoromethyl)phenyl]-2-pyridinyl}oxy)methyl]-6,7-dihydro-5H-imidazo[2,1-b][1,3]oxazine;
OO. 2-Nitro-6-[({5-[4-(trifluoromethoxy)phenyl]-2-pyridinyl}oxy)methyl]-6,7-dihydro-5H-imidazo[2,1-b][1,3]oxazine;
PP. 6-({[6-(4-Fluorophenyl)-3-pyridinyl]oxy}methyl)-2-nitro-6,7-dihydro-5H-imidazo[2,1-b][1,3]oxazine;
QQ. 2-Nitro-6-[({6-[4-(trifluoromethyl)phenyl]-3-pyridinyl}oxy)methyl]-6,7-dihydro-5H-imidazo[2,1-b][1,3]oxazine;
RR. 2-Nitro-6-[({6-[4-(trifluoromethoxy)phenyl]-3-pyridinyl}oxy)methyl]-6,7-dihydro-5H-imidazo[2,1-b][1,3]oxazine;
SS. 2-Nitro-6-({[3-(trifluoromethoxy)benzyl]oxy}methyl)-6,7-dihydro-5H-imidazo[2,1-b][1,3]oxazine;
TT. 2-Nitro-6-({[4-(trifluoromethoxy)benzyl]oxy}methyl)-6,7-dihydro-5H-imidazo[2,1-b][1,3]oxazine;
UU. 6-({[4-(Benzyloxy)benzyl]oxy}methyl-2-nitro-6,7-dihydro-5H-imidazo[2,1-b][1,3]oxazine;
VV. 2-Nitro-6-({[4'-(trifluoromethoxy)[1,1'-biphenyl]-3-yl]methoxy}methyl)-6,7-dihydro-5H-imidazo[2,1-b][1,3]oxazine;
WW. 2-Nitro-6-({[4'-(trifluoromethoxy)[1,1'-biphenyl]-4-yl]methoxy}methyl)-6,7-dihydro-5H-imidazo[2,1-b][1,3]oxazine; and
mixtures, optical or geometric isomers, and pharmacologically acceptable salt derivatives, and prodrugs thereof.

* * * * *